United States Patent
Miyata et al.

(10) Patent No.: US 7,951,806 B2
(45) Date of Patent: May 31, 2011

(54) PLASMINOGEN ACTIVATOR INHIBITOR-1 INHIBITOR

(75) Inventors: Toshio Miyata, Sendai (JP); Nagahisa Yamaoka, Osaka (JP); Hidehiko Kodama, Osaka (JP)

(73) Assignee: Renascience Co., Ltd., Tokyo (JP)

( * ) Notice: Subject to any disclaimer, the term of this patent is extended or adjusted under 35 U.S.C. 154(b) by 277 days.

(21) Appl. No.: 12/046,547

(22) Filed: Mar. 12, 2008

(65) Prior Publication Data

US 2009/0124620 A1   May 14, 2009

Related U.S. Application Data

(60) Provisional application No. 60/951,820, filed on Jul. 25, 2007.

(51) Int. Cl.
*A61K 31/495* (2006.01)
*A61K 31/381* (2006.01)
*C07D 241/04* (2006.01)
*C07D 333/10* (2006.01)

(52) U.S. Cl. ............ 514/252.13; 544/358; 544/359; 544/379; 514/252.12; 514/438

(58) Field of Classification Search .......... 544/358, 544/359, 374, 379; 514/252.12, 252.13, 514/438; 549/29
See application file for complete search history.

(56) References Cited

FOREIGN PATENT DOCUMENTS

| JP | 56-007716 | 1/1981 |
|---|---|---|
| WO | WO 2006/107719 A2 | 10/2006 |
| WO | WO 2007/083689 A1 | 7/2007 |

OTHER PUBLICATIONS

Aya et al, Tissue-Type Plasminogen Activator and its Inhibitor in Human Glomerulonephritis, *Journal of Pathology*, vol. 166: 289-295 (1992).

Yoshida et al, Enhanced Expression of Plasminogen Activator Inhibitor 1 in Patients with Nephrotic Syndrome, *Nephron* 88:24-29 (2001).

Huang et al, A Mutant, Noninhibitory Plasminogen Activator Inhibitor Type 1 Decreases Matrix Accumulation in Experimental Glomerulonephritis, *The Journal of Clinical Investigation* 112(3):379-388 (2003).

Haraguchi et al, t-PA Promotes Glomerular Plasmin Generation and Matrix Degradation in Experimental Glomerulonephritis, *Kidney International* 59:2146-2155 (2001).

Egelund et al, A Regulatory Hydrophobic Area in the Flexible Joint Region of Plasminogen Activator Inhibitor-1, Defined with Fluorescent Activity-Neutralizing Ligands, *The Journal of Biological Chemistry*, 276 (16):13077-13086 (2001).

Matsuo et al, Plasminogen Activator in Bronchoalveolar Fluid, *Haemostasis* 16:43-50 (1986).

Kivirikko et al, Modifications of a Specific Assay for Hydroxyproline in Urine, *Analytical Biochemistry* 19:249-255 (1967).

Ashcroft et al, Simple Method of Estimating Severity of Pulmonary Fibrosis on a Numerical Scale, *Journal of Clinical Pathology* 41:467-470 (1988).

Eitzman et al, Bleomycin-Induced Pulmonary Fibrosis in Transgenic Mice That Either Lack or Overexpress the Murine Plasminogen Activator Inhibitor-1 Gene, *The Journal of Clinical Investigation* 97(1):232-237 (1996).

Milton et al, Biaryl Acids: Novel Non-Nucleoside Inhibitors of HIV Reverse Transcriptase Types 1 and 2, *Bioorganic & Medicinal Chemistry Letters* 8:2623-2628 (1998).

*Primary Examiner* — Golam M Shameem
(74) *Attorney, Agent, or Firm* — Roylance, Abrams, Berdo & Goodman LLP

(57) ABSTRACT

The present invention relates to an inhibitor of plasminogen activator inhibitor-1. The present invention further relates to a pharmaceutical composition that has an inhibitory action on PAI-1 activity and is useful in the prevention and treatment of various diseases whose onset is associated with PAI-1 activity. Furthermore, the present invention relates to a novel compound having PAI-1 inhibitory activity represented by the following general formula (I), and a salt thereof.

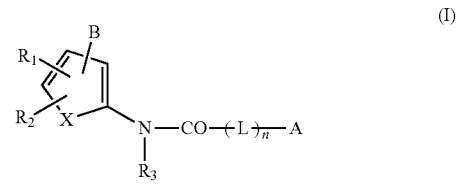

Each symbol is defined as those in the specification.

8 Claims, 15 Drawing Sheets

Fig. 4

| Ex. | Chemical Compound | Formula M.W. | Toxicolor Test (PAI-1 Activity %) | | |
|---|---|---|---|---|---|
| | | | 100 μM | 50 μM | 20 μM |
| 1 | Sodium 2-(6-(3-(tert-butoxycarbonyl)-4-phenylthiophen-2-ylamino)-6-oxohexanamido) benzoate | C28H29N2NaO6S 544.60 | 12.1 | 97.8 | - |
| 2 | Ssodium 2-(6-(3-(tert-butoxycarbonyl)-4-phenylthiophen-2-ylamino)-6-oxohexanamido)-5-chlorobenzoate | C28H28ClN2NaO6S 579.04 | 12.5 | 42.5 | - |
| 3 | 2-(6-(6-Oxo-6-(4-phenylthiophen-2-ylamino)hexanamido)benzoic acid | C23H22N2O4S 422.5 | 41.4 | 99.9 | - |
| 4 | 2-(6-(2-Carboxy-4-chlorophenylamino)-6-oxohexanamido)-4-phenylthiophen-3-carboxylic acid | C24H21ClN2O6S 500.95 | 35.7 | 99.8 | - |
| 5 | 2-(6-Oxo-6-(4-phenylpiperidin-1-yl)hexanamido)-4-phenylthiophen-3-carboxylic acid | C28H30N2O4S 490.61 | 12.0 | 97.7 | - |
| 6 | 2-(6-(4-Chlorophenylamino)-6-oxohexanamido)-4-phenylthiophen-3-carboxylic acid | C23H21ClN2O4S 456.94 | 10.8 | 67.5 | - |
| 7 | 2,2'-(Oxybis((1-oxo-2,1-ethanediyl)imino))bis(5-methyl-4-phenylthiophen-3-carboxylic acid) | C28H24N2O7S2 564.63 | 7.9 | 15.5 | - |
| 8 | 2,2'-(Oxybis((1-oxo-2,1-ethanediyl)imino))bis(5-phenylthiophen-3-carboxylic acid) | C26H20N2O7S2 536.58 | 9.3 | 12.9 | - |
| 9 | 2,2'-(Oxybis((1-oxo-2,1-ethanediyl)imino))bis(4-phenylthiophen-3-carboxylic acid) | C26H20N2O7S2 536.58 | 19.8 | 94.2 | - |
| 10 | 2-(2-(2-(3-(Tert-butoxycarbonyl)-5-methyl-4-phenylthiophen-2-ylamino)-2-oxoethoxy)acetamido)-5-methyl-4-phenylthiophen-3-carboxylic acid | C32H32N2O7S2 620.74 | - | 12.7 | 34.8 |

Note: - indicates Not Measured

Fig. 5

| Ex. | Chemical Compound | Formula M.W. | Toxicolor Test (PAI-1 Activity %) | | |
|---|---|---|---|---|---|
| | | | 100 μM | 50 μM | 20 μM |
| 11 | Sodium 2-(6-(3-(*tert*-butoxycarbonyl)-4-isopropylthiophen-2-ylamino)-6-oxohexanamido)benzoate | C25H31N2NaO6S 510.58 | 20.7 | 99.3 | - |
| 12 | 2-(6-(4-Isopropylthiophen-2-ylamino)-6-oxohexanamido)benzoic acid | C20H24N2O4S 388.48 | 24.5 | 69.6 | - |
| 13 | 2-(2-(2-(4-Benzhydrylpiperazin-1-yl)-2-oxoethoxy)acetamido)-5-methyl-4-(pyridin-3-yl)thiophen-3-carboxylic acid | C32H32N4O5S 584.69 | - | 12.7 | 89.7 |
| 14 | 2-(2-(2-(4-Benzhydrylpiperazin-1-yl)-2-oxoethoxy)acetamido)-5-methyl-4-(pyridin-3-yl)thiophen-3-carboxylic acid | C32H32N4O5S 584.69 | - | 20.5 | 92.3 |
| 15 | Sodium 2-(2-(2-(4-benzhydrylpiperazin-1-yl)-2-oxoethoxy)acetamido)-5-methyl-4-phenylthiophen-3-carboxylate | C33H32N3NaO5S 605.68 | - | 5.8 | 35.6 |
| 16 | 2-(5-(1,3-Dioxoisoindolin-2-yl)pentanamido)-4-phenylthiophen-3-carboxylic acid | C24H20N2O5S 448.49 | 32.8 | 100.0 | - |
| 17 | 2-(5-(3-(*Tert*-butoxycarbonyl)-4-phenylthiophen-2-ylamino)-5-oxopentylcarbamoyl)benzoic acid | C28H30N2O6S 522.61 | 38.2 | 98.9 | - |
| 18 | 2-(2-(Benzyloxycarbonylamino)-5-(4-chlorophenylamino)-5-oxopentanamido)-5-chlorobenzoic acid | C26H23Cl2N3O6 544.38 | 12.3 | 47.7 | - |
| 19 | 2-(2-(Benzyloxycarbonylamino)-5-((4-chlorophenyl)(methyl)amino)-5-oxopentanamido)-5-chlorobenzoic acid | C27H25Cl2N3O6 558.41 | 14.6 | 73.6 | - |
| 20 | 2-(2-(Benzyloxycarbonylamino)-5-oxo-5-(4-phenylpiperazin-1-yl)pentanamido)-5-chlorobenzoic acid | C30H31ClN4O6 579.04 | 14.2 | 45.4 | - |

Note: - indicates Not Measured

Fig. 6

| Ex. | Chemical Compound | Formula M.W. | Toxicolor Test (PAI-1 Activity %) | | |
|---|---|---|---|---|---|
| | | | 100 μM | 50 μM | 20 μM |
| 21 | Sodium 2-(5-(4-benzhydrylpiperazin-1-yl)-2-(benzyloxycarbonylamino)-5-oxopentanamido)-5-chlorobenzoate | C37H36ClN4NaO6 691.15 | 7.1 | 17.9 | - |
| 22 | 2-(5-(4-Benzhydrylpiperazin-1-yl)-4-(benzyloxycarbonylamino)-5-oxopentanamido)-5-chlorobenzoic acid | C37H37ClN4O6 669.17 | - | 13.5 | 88.3 |
| 23 | 2-(5-(4-Benzhydrylpiperazin-1-yl)-2-(tert-butoxycarbonylamino)-5-oxopentanamido)-5-chlorobenzoic acid | C34H39ClN4O6 635.15 | - | 7.0 | 89.6 |
| 24 | 2-(2-Amino-5-(4-benzhydrylpiperazin-1-yl)-5-oxopentanamido)-5-chlorobenzoic acid | C29H31ClN4O4 535.03 | - | 74.3 | 97.7 |
| 25 | 5-Chloro-2-(2-((2-(4-chlorophenylamino)-2-oxoethyl)(methyl)amino)acetamido)benzoic acid | C18H17Cl2N3O4 410.25 | 48.2 | 100.0 | - |
| 26 | 2-(2-((2-(4-Benzhydrylpiperazin-1-yl)-2-oxoethyl)(methyl)amino)acetamido)-5-chlorobenzoic acid | C29H31ClN4O4 535.03 | 14.9 | 99.9 | - |
| 27 | 5-Chloro-2-(6-(4-chlorophenylamino)-6-oxohexanamido)benzoic acid | C19H18Cl2N2O4 409.26 | 37.7 | 99.9 | - |
| 28 | 2-(2-(4-Benzhydrylpiperazin-1-yl)-2-oxoethoxy)acetamido)-5-methoxybenzoic acid | C29H31N3O6 517.57 | - | 86.7 | 99.1 |
| 29 | Sodium 5-chloro-2-(2-(2-(4-(4-chlorophenyl) piperazin-1-yl)-2-oxoethoxy)acetamido)benzoic acid | C21H20Cl2N3NaO5 488.30 | - | 60.5 | 91.4 |
| 30 | Sodium 2-(2-(2-(4-benzhydrylpiperazin-1-yl)-2-oxoethoxy)acetamido)-5-chlorobenzoate | C28H27ClN3NaO5 543.97 | 10.9 | 37.4 | - |

Note: - indicates Not Measured

Fig. 7

| Ex. | Chemical Compound | Formula M.W. | Toxicolor Test (PAI-1 Activity %) | | |
|---|---|---|---|---|---|
| | | | 100 μM | 50 μM | 20 μM |
| 31 | Sodium 2-(2-(4-benzhydryloxy) piperidin-1-yl)-2-oxoethoxy)acetamido-5-chlorobenzoate | C29H28ClN2NaO6 558.99 | - | 9.8 | 90.0 |
| 32 | Sodium 5-chloro-2-(2-(2-(4,4-diphenylpiperidin-1-yl)-2-oxoethoxy)acetamido)benzoate | C28H26ClN2NaO5 528.96 | - | 7.6 | 81.0 |
| 33 | 2-(2-(2-(4-Chloro-2-(methoxycarbonyl)phenylamino)-2-oxoethoxy)acetamido)-5-methyl-4-phenylthiophen-3-carboxylic acid | C24H21ClN2O7S 516.96 | - | 5.0 | 59.0 |
| 34 | 2-(2-(2-(4-(Bis(4-fluorophenyl)methyl)piperadin-1-yl)-2-oxoethoxy)acetamido)-5-chlorobenzoate | C28H26ClF2N3O5 557.97 | - | 15.5 | 98.8 |
| 35 | 2-(2-(2-(1-Adamantylamino)-2-oxoethoxy)acetamido)-5-chlorobenzoate | C21H25ClN2O5 420.89 | - | 49.6 | 89.0 |
| 36 | 2-(2-(2-(4-(9H-Fluoren-9-yl) piperazin-1-yl)-2-oxoethoxy)acetamido)-5-chlorobenzoate | C28H26ClN3O5 519.98 | - | 26.8 | 86.1 |
| 37 | 2-(2-(2-(Benzhydrylamino)-2-oxoethoxy)acetamido)-5-chlorobenzoate | C24H21ClN2O5 452.89 | - | 47.5 | 98.4 |
| 38 | 2-(2-(2-(3-(Tert-butoxycarbonyl)-5-methyl-4-phenylthiophen-2-ylamino)-2-oxoethoxy)acetamido)-5-chlorobenzoic acid | C27H27ClN2O7S 559.03 | - | 14.7 | 79.2 |
| 39 | 5-Chloro-2-(2-(2-(4-chlorophenylamino)-2-oxoethoxy)acetamido) benzoic acid | C17H14Cl2N2O5 397.21 | 36.1 | 100.0 | - |
| 40 | 2-(2-(2-(4-Benzhydrylpiperazin-1-yl)-2-oxoethoxy)acetamido)-5-fluorobenzoic acid | C24H18Cl2N2O6 501.32 | 13.0 | 98.7 | - |

Note: - indicates Not Measured

Fig. 8

| Ex. | Chemical Compound | Formula M.W. | Toxicolor Test (PAI-1 Activity %) | | |
|---|---|---|---|---|---|
| | | | 100 μM | 50 μM | 20 μM |
| 41 | 2-(2-(2-(4-Benzhydrylpiperazin-1-yl)-2-oxoethoxy)acetamido)-5-fluorobenzoic acid | C28H28FN3O5 505.54 | - | 50.4 | 92.3 |
| 42 | 3-(2-(2-(4-Benzhydrylpiperazin-1-yl)-2-oxoethoxy)acetamido)benzoic acid | C28H29N3O5 487.55 | - | 88.2 | 98.7 |
| 43 | 4-(2-(2-(4-Benzhydrylpiperazin-1-yl)-2-oxoethoxy)acetamido)-3-chlorobenzoic acid | C28H28ClN3O5 521.99 | - | 70.9 | 97.4 |
| 44 | Sodium 4-(2-(2-(4-benzhydrylpiperazin-1-yl)-2-oxoethoxy)acetamido)-4'-fluorobiphenyl-3-carboxylate | C34H31FN3NaO5 603.62 | - | 7.5 | 82.9 |
| 45 | Sodium -(2-(2-(4-benzhydrylpiperazin-1-yl)-2-oxoethoxy)acetamido)-2',4'-difluorobiphenyl-3-carboxylate | C34H30F2N3NaO5 621.61 | - | 7.7 | 79.6 |
| 46 | Sodium 4-(2-(2-(4-benzhydrylpiperazin-1-yl)-2-oxoethoxy)acetamido)-4'-cyanobiphenyl-3-carboxylate | C35H31N4NaO5 610.63 | - | 8.4 | 85.4 |
| 47 | Sodium 4-(2-(2-(4-benzhydrylpiperazin-1-yl)-2-oxoethoxy)acetamido)-4'-(dimethylamino)biphenyl-3-carboxylate | C36H37N4NaO5 628.69 | - | 6.4 | 28.9 |
| 48 | Sodium 4-(2-(2-(4-benzhydrylpiperazin-1-yl)-2-oxoethoxy)acetamido)-4'-methoxybiphenyl-3-carboxylate | C35H34N3NaO6 615.65 | − | 12.2 | 96.5 |
| 49 | Sodium 4-(2-(2-(4-benzhydrylpiperazin-1-yl)-2-oxoethoxy)acetamido)-4'-morpholinobiphenyl-3-carboxylate | C38H39N4NaO6 670.73 | − | 12.7 | 97.3 |
| 50 | Sodium 2-(2-(2-(4-benzhydrylpiperazin-1-yl)-2-oxoethoxy)acetamido)-5-(pyridin-4-yl)benzoate | C33H31N4NaO5 586.61 | − | 17.8 | 98.5 |

Note: - indicates Not Measured

Fig. 9

| Ex. | Chemical Compound | Formula M.W. | Toxicolor Test (PAI-1 Activity %) | | |
|---|---|---|---|---|---|
| | | | 100 μM | 50 μM | 20 μM |
| 51 | Sodium 2-(2-(2-(4-benzhydrylpiperazin-1-yl)-2-oxoethoxy)acetamido)-5-bromobenzoate | C28H27BrN3NaO5 588.42 | 10.1 | 23.0 | — |
| 52 | 2-(2-(2-Benzhydrylamino)-2-oxoethoxy)acetamido-5-(pyridin-4-yl)benzoic acid | C29H25N3O5 495.53 | — | 0.9 | 34.0 |
| 53 | 2-(2-(2-(4-Benzhydrylpiperazin-1-yl)-2-oxoethoxy)acetamido)-5-(pyridin-3-yl)benzoic acid | C33H32N4O5 564.63 | — | 11.8 | 86.1 |
| 54 | 2-(2-(2-(4-Benzhydrylpiperazin-1-yl)-2-oxoethoxy)acetamido)-5-(pyridin-4-yl)benzoic acid | C33H32N4O5 564.63 | — | 5.0 | 42.8 |
| 55 | 2-(2-(2-(4-Benzhydrylpiperazin-1-yl)-2-oxoethoxy)acetamido)-5-(1-methyl-1H-pyrazol-4-yl)benzoic acid | C32H33N5O5 567.64 | — | 12.3 | 49.5 |
| 56 | Sodium 2-(2-(2-(4-benzhydrylpiperazin-1-yl)-2-oxoethoxy)acetamido)-5-benzylbenzoate | C35H34N3NaO5 599.65 | — | 9.5 | 98.9 |
| 57 | Sodium 4-(2-(2-(4-benzhydrylpiperazin-1-yl)-2-oxoethoxy)acetamido)biphenyl-3-carboxylate | C34H32N3NaO5 585.62 | — | 16.8 | 83.8 |
| 58 | 4-(2-(2-(4-Chlorophenylamino)-2-oxoethoxy)acetamido)biphenyl-3-carboxylic acid | C23H19ClN2O5 438.86 | — | 19.7 | 92.0 |
| 59 | 2,2'-(Oxybis((1-oxo-2,1-ethanediyl)imino))bis(5-phenylbenzene-1-carboxylic acid) | C30H24N2O7 524.52 | 5.5 | 9.9 | — |
| 60 | 5-Chloro-2-(5-(3-(4-chlorophenyl)ureido)pentanamido)benzoic acid | C19H19Cl2N3O4 424.28 | 20.7 | 99.9 | — |
| 61 | 5-Chloro-2-(5-(4-chlorophenylsulfonamido)pentanamido)benzoic acid | C18H18Cl2N2O5S 445.32 | 66.0 | 99.9 | — |

Note: - indicates Not Measured

Fig. 10

| Ex. | Chemical Compound | Formula M.W. | Toxicolor Test (PAI-1 Activity%) 50 μM | Toxicolor Test (PAI-1 Activity%) 20 μM |
|---|---|---|---|---|
| 62 | Sodium 2-(2-(2-(4-benzhydrylpiperazin-1-yl)-2-oxoethoxy)acetamido)-5-isobutylbenzoate | C32H36N3NaO5 565.64 | 9.4 | 91.6 |
| 63 | Sodium 2-(2-(2-(4-benzhydrylpiperazin-1-yl)-2-oxoethoxy)acetamido)-5-(1H-pyrazol-4-yl)benzoate | C31H30N5NaO5 575.59 | 21.4 | 78.2 |
| 64 | 2-(2-(2-(4-Bnzhydrylpiperazin-1-yl)-2-oxoethoxy)acetamido)-5-(quinolin-3-yl)benzoic acid | C37H34N4O5 614.69 | 7.5 | 62.7 |
| 65 | 2-(2-(2-(4-Benzhydrylpiperazin-1-yl)-2-oxoethoxy)acetamido)-5-(benzo[b]thiophen-2-yl)benzoic acid | C36H33N3O5S 619.73 | 10.8 | 76.9 |
| 66 | 4-(2-(2-(Benzhydrylamino)-2-oxoethoxy)acetamido)-4'-fluorobiphenyl-3-carboxylic acid | C30H25FN2O5 512.53 | 13.1 | 97.7 |
| 67 | 5-Chloro-2-(2-(2-(2,6-diisopropylphenylamino)-2-oxoethoxy)acetamido)benzoic acid | C23H27ClN2O5 446.92 | 75.0 | 99.8 |
| 68 | 5-Chloro-2-(2-(2-(1-(naphthalen-1-yl)ethylamino)-2-oxoethoxy)acetamido)benzoic acid | C23H21ClN2O5 440.88 | 66.3 | 99.8 |
| 69 | 5-Chloro-2-(2-(2-(5-isopropyl-2-methylphenylamino)-2-oxoethoxy)acetamido)benzoic acid | C21H23ClN2O5 418.87 | 52.8 | 99.3 |
| 70 | 5-Chloro-2-(2-(2-oxo-2-(4-phenylbutylamino)ethoxy)acetamido)benzoic acid | C21H23ClN2O5 418.87 | 50.4 | 88.3 |
| 71 | 2-(2-(2-(Bis(4-fluorophenyl)methyl)amino)-2-oxoethoxy)acetamido)-5-chlorobenzoic acid | C24H19ClF2N2O5 488.87 | 30.3 | 83.7 |

Fig. 11

| Ex. | Chemical Compound | Formula M.W. | Toxicolor Test (PAI–1 Activity%) | |
|---|---|---|---|---|
| | | | 50 μM | 20 μM |
| 72 | 2-(2-(2-(Bis(4-(trifluoromethyl)benzyl)amino)-2-oxoethoxy) acetamido)-5-chlorobenzoic acid | C27H21ClF6N2O5 602.91 | 5.0 | 66.0 |
| 73 | Sodium 2-(2-(2-(bis(4-fluorobenzyl)amino)-2-oxoethoxy) acetamido)-5-chlorobenzoate | C25H20ClF2N2NaO5 524.88 | 12.4 | 71.1 |
| 74 | 2-(2-(2-(3,5-Bis(trifluoromethyl)phenylamino)-2-oxoethoxy) acetamido)-5-chlorobenzoic acid | C19H13ClF6N2O5 498.76 | 17.5 | 75.6 |
| 75 | Sodium 2-(2-(2-(4-benzhydrylpiperazin-1-yl)-2-oxoethoxy)acetamido)-4-chlorobenzoate | C28H27ClN3NaO5 543.97 | 13.3 | 91.3 |
| 76 | Sodium 2-(2-(2-(4-benzhydrylpiperazin-1-yl)-2-oxoethoxy) acetamido)-4-bromobenzoate | C28H27BrN3NaO5 588.42 | 10.2 | 79.8 |
| 77 | 2-(2-(2-(4-Benzhydrylpiperazin-1-yl)-2-oxoethoxy) acetamido)-4-(pyridin-4-yl)benzoic acid | C33H32N4O5 564.63 | 9.6 | 48.6 |
| 78 | 3-(2-(2-(4-Benzhydrylpiperazin-1-yl)-2-oxoethoxy) acetamido)-4'-fluorobiphenyl-4-carboxylic acid | C34H32FN3O5 581.63 | 13.5 | 91.0 |
| 79 | 2-(2-(Benzhydrylamino)-2-oxoacetamido)-5-chlorobenzoic acid | C22H17ClN2O4 408.83 | 27.2 | 83.4 |
| 80 | 2-(5-(4-Benzhydrylpiperazin-1-yl)-5-oxopentanamido)-5-chlorobenzoic acid | C29H30ClN3O4 520.02 | 16.4 | 85.1 |
| 81 | Sodium 2-(2-(2-(4-benzhydrylpiperazin-1-yl)-2-oxoethoxy) acetamido)-5-(2,4-dimethylthiazole 5-yl)benzoate | C33H33N4NaO5S 620.69 | 14.5 | 99.8 |

Fig. 12

| Ex. | Chemical Compound | Formula M.W. | Toxicolor Test (PAI-1 Activity%) | |
|---|---|---|---|---|
| | | | 50 μM | 20 μM |
| 82 | 2-(2-(2-(Benzhydrylamino)-2-oxoethoxy)acetamido)-5-methyl-4-phenylthiophen-3-carboxylic acid | C29H26N2O5S 514.59 | 11.1 | 89.3 |
| 83 | Sodium 5-chloro-2-(2-(2-(diphenylamino)-2-oxoethoxy)acetamido)benzoate | C23H18ClN2NaO5 460.84 | 77.8 | 99.8 |
| 84 | 5-Chloro-2-(2-(2-(2,2-diphenylethylamino)-2-oxoethoxy)acetamido)benzoic acid | C25H23ClN2O5 466.91 | 32.2 | 96.1 |
| 85 | 2-(2-(2-((3S*,5R*)-4-Benzhydryl-3,5-dimethyl piperazin-1-yl)-2-oxoethoxyacetamido-5-chlorobenzoic acid hydrochloride | C30H33Cl2N3O5 586.51 | 7.2 | 42.7 |
| 86 | Sodium 2-(2-(2-(4-benzhydrylpiperazin-1-yl)-2-oxoethoxy)acetamido)-5-(benzyloxy)benzoate | C35H34N3NaO6 615.65 | 9.7 | 99.3 |
| 87 | Sodium 2-(2-(2-(4-benzhydrylpiperazin-1-yl)-2-oxoethoxy)acetamido)-5-isobutoxybenzoate | C32H36N3NaO6 581.63 | 12.2 | 99.3 |
| 88 | 2-(2-(4-Benzhydrylpiperazin-1-yl)-2-oxoethoxy)-N-(4-chloro-2-(1H-tetrazol-5-yl)phenyl)acetamide | C28H28ClN7O3 546.02 | 15.1 | 71.6 |
| 89 | 2-(2-(4-Benzhydrylpiperazin-1-yl)-2-oxoethoxy)-N-(4-chloro-2-(5-oxo-4,5-dihydro-1,2,4-oxadiazol-3-yl)phenyl)acetamide | C29H28ClN5O5 562.02 | 9.4 | 78.3 |
| 90 | 2-(2-(4-Benzhydrylpiperazin-1-yl)-2-oxoethoxy)-N-(5-methyl-4-phenyl-3-(1H-tetrazol-5-yl)thiophen-2-yl)acetamide | C33H33N7O3S 607.73 | 7.0 | 63.1 |
| 91 | 2-(2-((2-(Benzhydrylamino)-2-oxoethyl)(methyl)amino)acetamido)-5-chlorobenzoic acid hydrochloride | C25H25Cl2N3O4 502.39 | 42.5 | 96.4 |

Fig. 13

| Ex. | Chemical Compound | Formula M.W. | Toxicolor Test (PAI-1 Activity%) | |
|---|---|---|---|---|
| | | | 50 μM | 20 μM |
| 92 | 2-(2-(2-(4-Benzhydrylpiperazin-1-yl)-2-oxoethylthio)acetamido)-5-chlorobenzoic acid hydrochloride | C28H29Cl2N3O4S 574.52 | 15.9 | 71.2 |
| 93 | 2-(2-(1-(2-(4-Benzhydrylpiperazin-1-yl)-2-oxoethyl)cyclohexyl) acetamido)-5-chlorobenzoic acid hydrochloride | C34H39Cl2N3O4 624.60 | 6.5 | 35.1 |
| 94 | 2-((1S,2S)-2-(4-Benzhydrylpiperazine-1-carbonyl)cyclohexanecarboxamido)-5-chlorobenzoic acid hydrochloride | C32H35Cl2N3O4 596.54 | 5.7 | 26.7 |
| 95 | 2-((1S,2R)-2-(4-benzhydrylpiperazine-1-carbonyl)cyclohexanecarboxamido)-5-chlorobenzoic acid hydrochloride | C32H35Cl2N3O4 596.54 | 17.7 | 53.7 |

Fig. 15
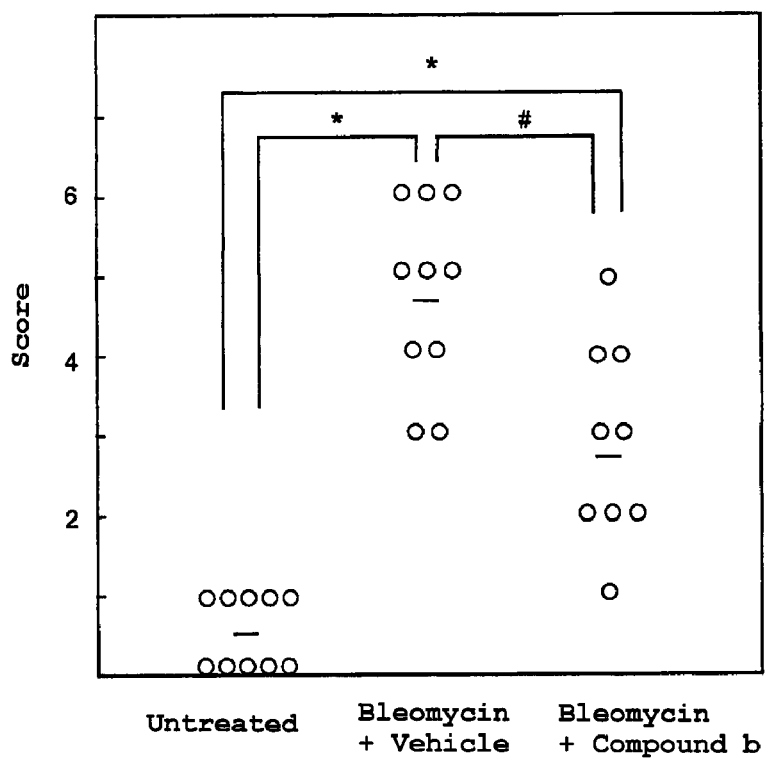
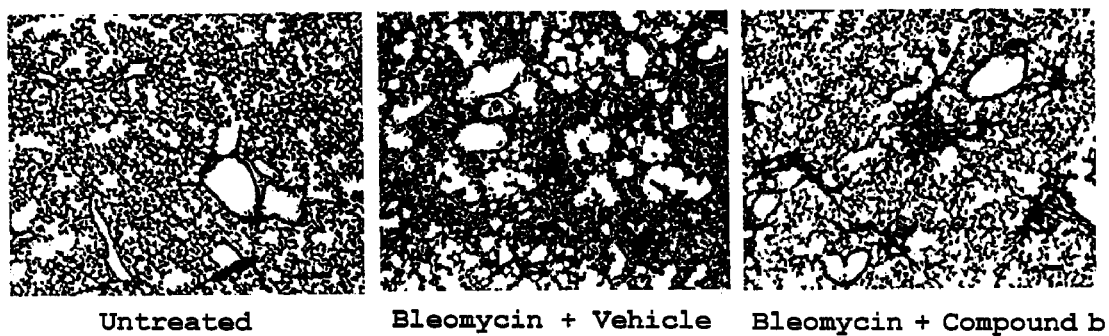

PLASMINOGEN ACTIVATOR INHIBITOR-1 INHIBITOR

TECHNICAL FIELD

The present invention relates to an inhibitor of plasminogen activator inhibitor-1 (hereinafter referred to as "PAI-1"). The present invention further relates to a pharmaceutical composition having an inhibitory action on PAI-1 activity and being efficacious in the prevention and treatment of various diseases whose onset is associated with PAI-1 activity. Furthermore, the present invention relates to a novel compound having PAI-1 inhibitory activity.

BACKGROUND ART

Atrial thrombus caused by atrial fibrillation and thrombi formed by the disruption of atheroma (atherosclerotic vessels) in the aorta or carotid artery may cause ischemic cerebrovascular diseases such as cerebral embolism, cerebral infarction, transient ischemic attack, etc., and ischemic heart diseases such as angina pectoris, myocardial infarction, atrial thrombus caused by atrial fibrillation, cardiac insufficiency, etc. While blood circulation must have good fluidity to deliver oxygen and nutrients to body tissues and remove waste (from the circulatory system), it is required to be coagulative to stop bleeding for the prevention of blood loss due to injury. When the balance between such opposed functions of fluidity and coagulation is lost and shifts to coagulation, an intravascular thrombus is formed, which is thought to cause ischemic cerebrovascular disorders and heart diseases.

The fibrinolytic system plays important roles in thrombolysis, tissue destruction and repair, cell migration, etc. The fibrinolytic system is activated when plasminogen activator (hereinafter referred to as "PA") converts plasminogen to plasmin, whereas plasminogen activator inhibitor-1 (PAI-1) inhibits PA.

Tissue plasminogen activator (hereinafter referred to as "t-PA") converts plasminogen, i.e., the precursor of plasmin, to plasmin. Plasmin converts fibrin to a fibrin degradation product by breaking it down. PAI-1 is a serine protease inhibitor that specifically inhibits t-PA and urokinase plasminogen activator (hereinafter referred to as "u-PA"), suppresses plasmin generation, and as a result inhibits fibrin degradation.

Based on tertiary structural differences, PAI-1 is present in an active form that shows PA inhibitory activity and in a latent form that shows no PA inhibitory activity. In plasma, PAI-1 is known to be typically present in a concentration of 20 ng/mL, and produced in hepatocytes, megakaryocytes and lipocytes in addition to the vascular endothelial cells, which are the primary PAI-1 producing cells.

PAI-1 is an acute phase protein, and is thought to be one of the factors that cause ischemic organ dysfunctions in sepsis and disseminated intravascular coagulation syndrome (DIC) through accelerated production due to various cytokines and growth factors. Further, genetic polymorphism due to single base substitutions in the PAI-1 gene promoter is known, and it has been revealed that plasma PAI-1 concentration increases as a result of such genetic polymorphism.

Furthermore, in diabetes mellitus, accelerating arteriosclerosis and microvascular complications are presumed to be factors in ischemic heart disease, diabetic retinopathy and renal damage, i.e., all are critical complications of diabetes mellitus. For example, in diabetic nephropathy, increased extracellular matrix in the glomerulus and fibrous stroma are observed characteristics, and PAI-1 expression is increased in the glomerulus and renal tubules. In proximal renal tubule incubation, increased PAI-1 production is evident under hyperglycemic conditions. Further, a correlation between PAI-1 expression in renal tissues and macrophage infiltration is confirmed in experiments using a model mouse with renal interstitial fibrosis (non-patent document 1).

Furthermore, PAI-1 concentrations in urine are documented as being high in nephrotic syndrome patients based on the measurement results of PAI-1 levels in urine collected over a 24-hour period from nephrotic syndrome patients (see non-patent document 2).

As a result of administrating an inactive PAI-1 mutant (non-patent document 3) or t-PA (non-patent document 4) as a PAI-1 antagonist to a Thy-1 nephritis model, it is reported that the alleviation of inflammation (cellular infiltration), TGF-$\beta$ suppression, and a decrease in mesangial matrix are observed, whereby Thy-1 nephritis is alleviated.

Reduced fibrinolytic activity due to an increased PAI-1 concentration in plasma is associated with ischemic heart diseases such as angina pectoris, myocardial infarction, cardiac insufficiency; deep-vein thrombosis and pulmonary embolism originated therefrom; and diabetic angiopathy. In addition to reduced fibrinolytic activity, some other thrombogenic abnormalities including hypercoagulation and platelet hyper-aggregation are also seen in diabetic patients. They are caused by microthrombus formation, and play important roles in the progress of diabetic microangiopathy and diabetic macroangiopathy. As described above, PAI-1 is presumably involved in the various pathologic formations and the progress of thromboses, cancers, diabetes mellitus, arteriosclerosis, etc. For this reason, a compound that inhibits PAI-1 activity is useful as a preventive and treatment agent for diseases associated with reduced fibrinolytic activity such as thromboses, cancers, diabetic complications, arteriosclerosis, etc. (non-patent document 5). Tissue fibril formation occurs in many tissues and organs such as the lungs, heart, blood vessels, liver, kidneys, etc.; however, there is no drug available to treat them radically. In reality, adrenocorticotropic hormones such as predonisolone, corticosteroid, etc., and cytotoxic drugs such as cyclophosphamide (alkylating agent) and azathioprine (antimetabolites, immunosuppressants) have been used as palliative therapy based on experience.

Non-patent document 1: Aya N. et al., J. Pathol., 166, 289-295, 1992

Non-patent document 2: Yoshida Y. et al., Nephron, 88, 24-29, 2001

Non-patent document 3: W. A. Border et al., J. Clin. Invest., 112, 379, 2003

Non-patent document 4: W. A. Border et al., Kidney Int, 59, 246, 2001

Non-patent document 5: Egelund R. et al., J. Biol. Chem., 276, 13077-13086, 2001

DISCLOSURE OF THE INVENTION

Problems to be Solved by the Invention

Urokinase, i.e., u-PA, is known as a fibrinolytic-system-promoting drug. This drug is obtained by the purification of human urine, and is not considered to be highly productive or safe. Moreover, urokinase is a high molecular weight compound having a molecular weight of about 54000. Other known fibrinolytic-system-promoting drugs include tisokinase, alteplase (gene recombinant), nasaruplase (cell culture), nateplase (gene recombinant), monteplase (gene recombinant), pamiteplase (gene recombinant), and batroxobin; however, they are all high molecular weight compounds. Considering this fact, a highly safe low-molecularweight compound drug that can be synthesized in large amounts is in demand as a fibrinolytic-system-promoting drug. Also expected is the development of drugs efficacious in radically treating fibrous tissue and the alleviation thereof. In view of the foregoing problems, an object of the present invention is to provide a pharmaceutical composition that can be mass synthesized, has an active component of a low molecular weight compound and is very safe; in particular, to provide a pharmaceutical composition that is useful as a fibrinolytic-system-promoting drug or anti-fibrosis agent. Another object of the present invention is to provide a novel compound effective as an active component for a pharmaceutical composition such as fibrinolytic-system-promoting drug, anti-fibrosis agent, or the like.

Means for Solving the Problem

The present inventors have conducted extensive studies to solve the above problems, and found that a compound represented by the following formula (I) or a salt thereof, or a solvate thereof (hereinafter collectively referred to as "compound (I) of the present invention" or simply referred to as "compound (I)") has high inhibitory activity on plasminogen activator inhibitor-1 (PAI-1). Further, the present inventors have confirmed that such compounds can be useful active components for a fibrinolytic-system-promoting drug as PAI-1 inhibitors. PAI-1 is presumed to be a primary factor in fibrous tissue, particularly in pulmonary fibrosis (see Reference Test Examples). In accordance with compound (I) of the present invention, tissue fibril formation is thought to be significantly alleviated by PAI-1 inhibitory activity. The present invention has been accomplished based on these findings.

More specifically, the present invention encompasses the following embodiments.

1. Aromatic or Heterocyclic Carboxylic Acid, Ester or Bioisoster Thereof 1-1. A compound represented by the general formula (I), or a salt thereof;

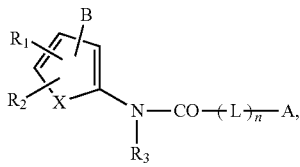

(I)

wherein —$R_1$ and $R_2$, the same or different, each represent a hydrogen atom, halogen atom, alkyl, cycloalkyl, cycloalkylalkyl, alkenyl, cycloalkenyl, alkynyl, hydroxyl, alkoxy, cycloalkoxy, alkenyloxy, cycloalkenyloxy, aryloxy, aralkyl, aralkyloxy, heterocyclic group, heterocyclic-alkyl, heterocyclic-alkyloxy; or substituted or unsubstituted aryl; or amino, carbamoyl, cyano, carboxy or alkoxycarbonyl group that may be substituted or unsubstituted with 1 to 2 substituents, and may adjoin with each other to form a ring;

—$R_3$ is a hydrogen atom, or substituted or unsubstituted alkyl, alkenyl, alkynyl, cycloalkyl, aryl or aralkyl group;

—X is an oxygen atom, sulfur atom, —N($R_4$)—, —C($R_5$)=C($R_6$)—, —C($R_7$)=N—, or —N=C($R_8$)— group, wherein $R_4$ is a hydrogen atom, or a substituted or unsubstituted alkyl group, $R_5$, $R_6$, $R_7$ and $R_8$ each represent a hydrogen atom, halogen atom, or substituted or unsubstituted alkyl or alkoxy group;

—B is a carboxy, alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl;

-L is a substituted or unsubstituted alkylene (some carbon atoms in said alkylene may form a cycloalkyl ring), alkenylene, alkynylene, cycloalkylene, alkyleneoxyalkylene, alkylenethioalkylene, alkylene-SO-alkylene or alkylene-$SO_2$-alkylene, or alkylene-N($R_9$)-alkylene group, wherein $R_9$ is a hydrogen atom, or a substituted or unsubstituted alkyl group;

-n is an integer of 0 or 1;

-A is —$COR_{10}$, —N($R_{11}$)—$COR_{12}$, —N($R_{11}$)—$SO_2$—$R_{12}$, —N($R_{11}$)—CONH—$R_{12}$, or a group represented by the following formula

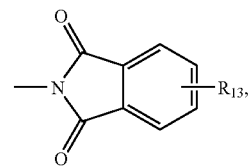

wherein $R_{11}$ is hydrogen or alkyl;

$R_{12}$ is a substituted or unsubstituted alkyl, cycloalkyl, aryl or aralkyl group (including diphenylalkyl);

$R_{13}$ is hydrogen, halogen, alkyl or alkoxy group;

$R_{10}$ is N($R_{14}$)($R_{15}$), wherein $R_{14}$ and $R_{15}$, the same or different, each represent a hydrogen atom, a substituted or unsubstituted alkyl, alkenyl, cycloalkenyl, alkynyl, bicycloalkyl, bicycloalkenyl, adamanthyl, aryl, heterocyclic ring, aralkyl or heterocyclic-alkyl group, or $R_{10}$ is a group represented by the following formula:

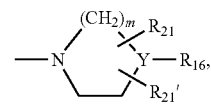

wherein m is an integer of 1 to 4, Y represents a nitrogen atom, CH, C($R_{16}'$)—, C(OH)— or CH—O—; $R_{16}$ and $R_{16}'$, the same or different, each represent a hydrogen atom, or a substituted or unsubstituted alkyl, cycloalkyl, alkenyl, cycloalkenyl, alkynyl, bicycloalkyl, bicycloalkenyl, adamanthyl, aryl or aralkyl group (including diphenylalkyl); and $R_{21}$ and $R_{21}'$, the same or different, each represent a hydrogen atom, a substituted or unsubstituted alkyl, or phenyl group.

1-2. The compound according to 1-1 excluding thiophene compounds represented by the following general formula (I') from the compounds represented by the above general formula (I), or a salt thereof:

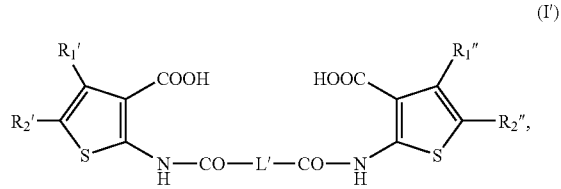

(I')

wherein $R_1'$ and $R_1''$, the same or different, each represent a hydrogen atom, substituted or unsubstituted phenyl or thienyl, or $C_{1-6}$ straight- or branched-chain alkyl group; $R_2'$ and $R_2''$, the same or different, each represent a hydrogen atom, substituted or unsubstituted phenyl, $C_{1-6}$ straight- or branched-chain alkyl group, or a halogen atom; $R_1$ and $R_2'$, and $R_{11}''$ and $R_2''$, may join together to form a 5- or 6-membered ring; and L' represents a $C_{1-7}$ straight- or branched-chain alkylene, alkenylene or alkynylene or $C_{3-8}$ cycloalkylene group.

1-3. The compound or the salt thereof according to 1-1 or 1-2, wherein the above compound (I) is a thiophen-3-carboxylic acid represented by the following general formula (II):

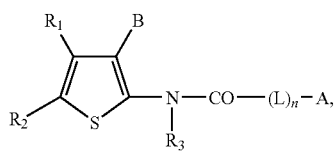

(II)

wherein $R_1$, $R_2$, $R_3$, L, B, n and A are defined as above; or a bioisoster thereof.

1-4. The compound or the salt thereof according to 1-1 or 1-2, wherein the above compound (I) is a benzoic acid represented by the following general formula (III):

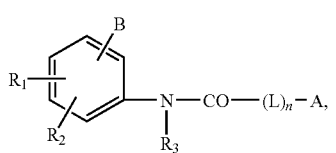

(III)

wherein $R_1$, $R_2$, $R_3$, L, B, n and A are defined as above; or a bioisoster thereof.

1-5. The compound or the salt thereof according to any one of 1-1 to 1-4, wherein the compound (I) is at least one selected from the group consisting of compounds (1) to (95) below:

(1) 2-(6-(3-(tert-butoxycarbonyl)-4-phenylthiophen-2-ylamino)-6-oxo-hexanamido)benzoic acid,
(2) 2-(6-(3-(tert-butoxycarbonyl)-4-phenylthiophen-2-ylamino)-6-oxo-hexanamido)-5-chlorobenzoic acid,
(3) 2-(6-oxo-6-(4-phenylthiophen-2-ylamino) hexanamido) benzoic acid,
(4) 2-(6-(2-carboxy-4-chlorophenylamino)-6-oxo-hexanamido)-4-phenylthiophen-3-carboxylic acid,
(5) 2-(6-oxo-6-(4-phenylpiperidin-1-yl) hexanamido)-4-phenylthiophen-3-carboxylic acid,
(6) 2-(6-(4-chlorophenylamino)-6-oxo-hexanamido)-4-phenylthiophen-3-carboxylic acid,
(7) 2,2'-(oxybis((1-oxo-2,1-ethanediyl)imino))bis(5-methyl-4-phenylthiophen-3-carboxylic acid),
(8) 2,2'-(oxybis((1-oxo-2,1-ethanediyl)imino))bis(5-phenylthiophen-3-carboxylic acid),
(9) 2,2'-(oxybis((1-oxo-2,1-ethanediyl)imino))bis(4-phenylthiophen-3-carboxylic acid),
(10) 2-(2-(2-(3-(tert-butoxycarbonyl)-5-methyl-4-phenylthiophen-2-ylamino)-2-oxoethoxy)acetamido)-5-methyl-4-phenylthiophen-3-carboxylic acid,
(11) 2-(6-(3-(tert-butoxycarbonyl)-4-isopropylthiophen-2-ylamino)-6-oxo-hexanamido)benzoic acid,
(12) 2-(6-(4-isopropylthiophen-2-ylamino)-6-oxo-hexanamido)benzoic acid,
(13) 2-(2-(2-(4-benzhydryl piperazin-1-yl)-2-oxoethoxy)acetamido)-5-methyl-4-(pyridin-4-yl)thiophen-3-carboxylic acid,
(14) 2-(2-(2-(4-benzhydryl piperazin-1-yl)-2-oxoethoxy)acetamido)-5-methyl-4-(pyridin-3-yl)thiophen-3-carboxylic acid,
(15) 2-(2-(2-(4-benzhydryl piperazin-1-yl)-2-oxoethoxy)acetamido)-5-methyl-4-phenylthiophen-3-carboxylic acid,
(16) 2-(5-(1,3-dioxoisoindolin-2-yl)pentanamido)-4-phenylthiophen-3-carboxylic acid,
(17) 2-(5-(3-(tert-butoxycarbonyl)-4-phenylthiophen-2-ylamino)-5-oxopentylcarbamoyl)benzoic acid,
(18) 2-(2-(benzyloxycarbonylamino)-5-(4-chlorophenylamino)-5-oxopentanamido)-5-chlorobenzoic acid,
(19) 2-(2-(benzyloxycarbonylamino)-5-((4-chlorophenyl)(methyl)amino)-5-oxopentanamido)-5-chlorobenzoic acid,
(20) 2-(2-(benzyloxycarbonylamino)-5-oxo-5-(4-phenylpiperazin-1-yl) pentanamido)-5-chlorobenzoic acid,
(21) 2-(5-(4-benzhydryl piperazin-1-yl)-2-(benzyloxycarbonylamino)-5-oxopentanamido)-5-chlorobenzoic acid,
(22) 2-(5-(4-benzhydryl piperazin-1-yl)-4-(benzyloxycarbonylamino)-5-oxopentanamido)-5-chlorobenzoic acid,
(23) 2-(5-(4-benzhydryl piperazin-1-yl)-2-(tert-butoxycarbonylamino)-5-oxopentanamido)-5-chlorobenzoic acid,
(24) 2-(2-amino-5-(4-benzhydryl piperazin-1-yl)-5-oxopentanamido)-5-chlorobenzoic acid,
(25) 5-chloro-2-(2-((2-(4-chlorophenylamino)-2-oxoethyl)(methyl)amino)acetamido)benzoic acid,
(26) 2-(2-((2-(4-benzhydryl piperazinSe-1-yl)-2-oxoethyl)(methyl)amino)acetamido)-5-chlorobenzoic acid,
(27) 5-chloro-2-(6-(4-chlorophenylamino)-6-oxo-hexanamido) benzoic acid,
(28) 2-(2-(2-(4-benzhydryl piperazin-1-yl)-2-oxoethoxy)acetamido)-5-methoxybenzoic acid,
(29) 5-chloro-2-(2-(2-(4-(4-chlorophenyl)piperazin-1-yl)-2-oxoethoxy)acetamido)benzoic acid,
(30) 2-(2-(2-(4-benzhydryl piperazin-1-yl)-2-oxoethoxy)acetamido-5-chlorobenzoic acid,
(31) 2-(2-(2-(4-benzhydryloxy)piperidin-1-yl)-2-oxoethoxy)acetamido-5-chlorobenzoic acid,
(32) 5-chloro-2-(2-(2-(4,4-diphenylpiperidin-1-yl)-2-oxoethoxy)acetamido)benzoic acid,
(33) 2-(2-(2-(4-chloro-2-(methoxycarbonyl)phenylamino)-2-oxoethoxy)acetamido)-5-methyl-4-phenylthiophen-3-carboxylic acid,
(34) 2-(2-(2-(4-(bis(4-fluorophenyl)methyl)piperazin-1-yl)-2-oxoethoxy)acetamido)-5-chlorobenzoic acid,
(35) 2-(2-(2-(1-adamantylamino)-2-oxoethoxy)acetamido)-5-chlorobenzoic acid,
(36) 2-(2-(2-(4-(9H-fluoren-9-yl)piperazin-1-yl)-2-oxoethoxy)acetamido)-5-chlorobenzoic acid,
(37) 2-(2-(2-(benzhydrylamino)-2-oxoethoxy)acetamido)-5-chlorobenzoic acid,
(38) 2-(2-(2-(3-(tert-butoxycarbonyl)-5-methyl-4-phenylthiophen-2-ylamino)-2-oxoethoxy)acetamido)-5-chlorobenzoic acid,
(39) 5-chloro-2-(2-(2-(4-chlorophenylamino)-2-oxoethoxy) acetamido)benzoic acid,
(40) 2-(2-(2-(2-benzoyl-4-chlorophenylamino)-2-oxoethoxy)acetamido)-5-chlorobenzoic acid,
(41) 2-(2-(2-(4-benzhydryl piperazin-1-yl)-2-oxoethoxy)acetamido)-5-fluorobenzoic acid,
(42) 3-(2-(2-(4-benzhydryl piperazin-1-yl)-2-oxoethoxy)acetamido)benzoic acid,
(43) 4-(2-(2-(4-benzhydryl piperazin-1-yl)-2-oxoethoxy)acetamido)-3-chlorobenzoic acid,

(44) 4-(2-(2-(4-benzhydryl piperazin-1-yl)-2-oxoethoxy)acetamido)-4'-fluorobiphenyl-3-carboxylic acid,
(45) 4-(2-(2-(4-benzhydryl piperazin-1-yl)-2-oxoethoxy)acetamido)-2',4'-difluorobiphenyl-3-carboxylic acid,
(46) 4-(2-(2-(4-benzhydryl piperazin-1-yl)-2-oxoethoxy)acetamido)-4'-cyano biphenyl-3-carboxylic acid,
(47) 4-(2-(2-(4-benzhydryl piperazin-1-yl)-2-oxoethoxy)acetamido)-4'-(dimethylamino)biphenyl-3-carboxylic acid,
(48) 4-(2-(2-(4-benzhydryl piperazin-1-yl)-2-oxoethoxy)acetamido)-4'-methoxybiphenyl-3-carboxylic acid,
(49) 4-(2-(2-(4-benzhydryl piperazin-1-yl)-2-oxoethoxy)acetamido)-4'-morpholinobiphenyl-3-carboxylic acid,
(50) 2-(2-(2-(4-benzhydryl piperazin-1-yl)-2-oxoethoxy)acetamido)-5-(pyridine-4-yl)benzoic acid,
(51) 2-(2-(2-(4-benzhydryl piperazin-1-yl)-2-oxoethoxy)acetamido)-5-bromobenzoic acid,
(52) 2-(2-(2-benzhydrylamino)-2-oxoethoxy)acetamido-5-(pyridine-4-yl)benzoic acid,
(53) 2-(2-(2-(4-benzhydryl piperazin-1-yl)-2-oxoethoxy)acetamido)-5-(pyridin-3-yl)benzoic acid,
(54) 2-(2-(2-(4-benzhydryl piperazin-1-yl)-2-oxoethoxy)acetamido)-5-(pyridine-4-yl)benzoic acid,
(55) 2-(2-(2-(4-benzhydryl piperazin-1-yl)-2-oxoethoxy)acetamido)-5-(1-methyl-1H-pyrazol-4-yl)benzoic acid,
(56) 2-(2-(2-(4-benzhydryl piperazin-1-yl)-2-oxoethoxy)acetamido)-5-benzylbenzoic acid,
(57) 4-(2-(2-(4-benzhydryl piperazin-1-yl)-2-oxoethoxy)acetamido)biphenyl-3-carboxylic acid,
(58) 4-(2-(2-(4-chlorophenylamino)-2-oxoethoxy)acetamido) biphenyl-3-carboxylic acid,
(59) 2,2'-(oxybis((1-oxo-2,1-ethanediyl)imino))bis(5-phenylbenzen-1-carboxylic acid),
(60) 5-chloro-2-(5-(3-(4-chlorophenyl)ureido)pentanamido) benzoic acid,
(61) 5-chloro-2-(5-(4-chlorophenylsulfonamido)pentanamido)benzoic acid,
(62) 2-(2-(2-(4-benzhydrylpiperazin-1-yl)-2-oxoethoxy)acetamido)-5-isobutyl benzoic acid,
(63) 2-(2-(2-(4-benzhydrylpiperazin-1-yl)-2-oxoethoxy)acetamido)-5-(1H-pirazol-4-yl)benzoic acid,
(64) 2-(2-(2-(4-benzhydrylpiperazin-1-yl)-2-oxoethoxy)acetamido)-5-(quinolin-3-yl)benzoic acid,
(65) 2-(2-(2-(4-benzhydrylpiperazin-1-yl)-2-oxoethoxy)acetamido)-5-(benzo[b]thiophen-2-yl)benzoic acid,
(66) 4-(2-(2-(benzhydrylamino)-2-oxoethoxy)acetamido)-4'-fluorobiphenyl-3-carboxylic acid,
(67) 5-chloro-2-(2-(2-(2,6-diisopropylphenylamino)-2-oxoethoxy)acetamido)benzoic acid,
(68) 5-chloro-2-(2-(2-(1-(naphthalen-1-yl)ethylamino)-2-oxoethoxy)acetamido)benzoic acid,
(69) 5-chloro-2-(2-(2-(5-isopropyl-2-methylphenylamino)-2-oxoethoxy)acetamido)benzoic acid,
(70) 5-chloro-2-(2-(2-oxo-2-(4-phenylbutylamino)ethoxy) acetamido)benzoic acid,
(71) 2-(2-(2-(bis(4-fluorophenyl)methyl)amino-2-oxoethoxy)acetamido)-5-chlorobenzoic acid,
(72) 2-(2-(2-(bis(4-(trifluoromethyl)benzyl)amino)-2-oxoethoxy)acetamido)-5-chlorobenzoic acid,
(73) 2-(2-(2-(bis(4-fluorobenzyl)amino)-2-oxoethoxy)acetamido)-5-chlorobenzoic acid,
(74) 2-(2-(2-(3,5-bis(trifluoromethyl)phenylamino)-2-oxoethoxy)acetamido)-5-chlorobenzoic acid,
(75) 2-(2-(2-(4-benzhydrylpiperazin-1-yl)-2-oxoethoxy)acetamido)-4-chlorobenzoic acid,
(76) 2-(2-(2-(4-benzhydrylpiperazin-1-yl)-2-oxoethoxy)acetamido)-4-bromobenzoic acid,
(77) 2-(2-(2-(4-benzhydrylpiperazin-1-yl)-2-oxoethoxy)acetamido)-4-(pyridin-4-yl)benzoic acid,
(78) 3-(2-(2-(4-benzhydrylpiperazin-1-yl)-2-oxoethoxy)acetamido)-4'-fluorobiphenyl-4-carboxylic acid,
(79) 2-(2-(benzhydrylamino)-2-oxoacetamido)-5-chlorobenzoic acid,
(80) 2-(5-(4-benzhydrylpiperazin-1-yl)-5-oxopentanamido)-5-chlorobenzoic acid,
(81) 2-(2-(2-(4-benzhydrylpiperazin-1-yl)-2-oxoethoxy)acetamido)-5-(2,4-dimethylthiazol-5-yl)benzoic acid,
(82) 2-(2-(2-(benzhydrylamino)-2-oxoethoxy)acetamido)-5-methyl-4-phenylthiophen-3-carboxylic acid,
(83) 5-chloro-2-(2-(2-(diphenylamino)-2-oxoethoxy)acetamido)benzoic acid,
(84) 5-chloro-2-(2-(2-(2,2-diphenylethylamino)-2-oxoethoxy)acetamido)benzoic acid,
(85) 2-(2-(2-((3S*, 5R*)-4-benzhydryl-3,5-dimethylpiperazin-1-yl)-2-oxoethoxy)acetamido)-5-chlorobenzoic acid,
(86) 2-(2-(2-(4-benzhydrylpiperazin-1-yl)-2-oxoethoxy)acetamido)-5-(benzyloxy)benzoic acid,
(87) 2-(2-(2-(4-benzhydrylpiperazin-1-yl)-2-oxoethoxy)acetamido)-5-isobutoxybenzoic acid,
(88) 2-(2-(4-benzhydrylpiperazin-1-yl)-2-oxoethoxy)-N-(4-chloro-2-(1H-tetrazol-5-yl)phenyl)acetamide,
(89) 2-(2-(4-benzhydrylpiperazin-1-yl)-2-oxoethoxy)-N-(4-chloro-2-(5-oxo-4,5-dihydro-1,2,4-oxadiazol-3-yl)phenyl)acetamide,
(90) 2-(2-(4-benzhydrylpiperazin-1-yl)-2-oxoethoxy)-N-(5-methyl-4-phenyl-3-(1H-tetrazol-5-yl)thiophen-2-yl)acetamide,
(91) 2-(2-((2-(benzhydrylamino)-2-oxoethyl)(methyl)amino)acetamido)-5-chlorobenzoic acid,
(92) 2-(2-(2-(4-benzhydrylpiperazin-1-yl)-2-oxoethylthio)acetamido)-5-chlorobenzoic acid,
(93) 2-(2-(1-(2-(4-benzhydrylpiperazin-1-yl)-2-oxyethyl)cyclohexyl)acetamido)-5-chlorobenzoic acid,
(94) 2-((1S*,2S*)-2-(4-benzhydrylpiperazine-1-carbonyl)cyclohexanecarboxamido)-5-chlorobenzoic acid, and
(95) 2-((1S*,2R*)-2-(4-benzhydrylpiperazine-1-carbonyl)cyclohexanecarboxamido)-5-chlorobenzoic acid 2. Method for Producing Aromatic or Heterocyclic Carboxylic Acid, Ester or Bioisoster Thereof 2-1. A method for producing an aromatic or heterocyclic carboxylic acid represented by the general formula (Ia), the method comprising the following steps (a) and (x) (Production Method 1):

(a) a step of condensing a compound (1) and a compound (2) to form an ester compound (4a), represented by the formulae below; and (x) a step of removing an $R_{17}$ group from the ester compound (4a) formed in the above step (a) to produce an aromatic or heterocyclic carboxylic acid (Ia);

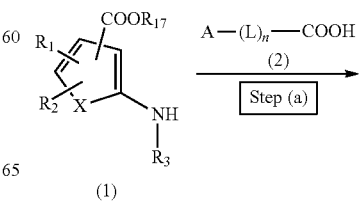

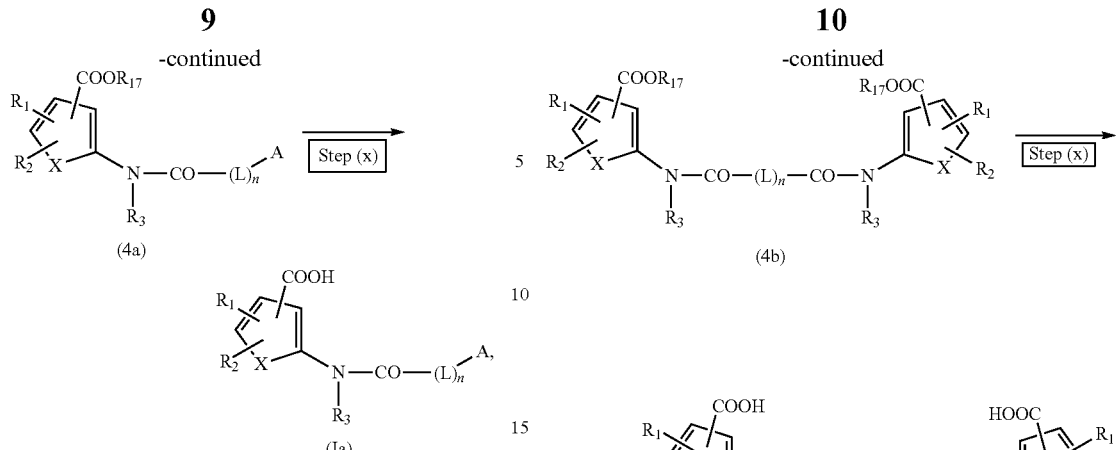

wherein $R_1$, $R_2$, $R_3$, L, X, n and A are defined as above; $R_{17}$ represents alkyl, aryl or aralkyl.

2-2. A method for producing an aromatic or heterocyclic carboxylic acid represented by the general formula (Ib), the method comprising the following steps (b) and (x) (Production Method 2):

(b) a step of condensing the compound (1) and a compound (3) to form an ester compound (4b), represented by the formulae below; and (x) a step of removing the $R_{17}$ group from the ester compound (4b) formed in the above step (b) to produce an aromatic or heterocyclic carboxylic acid (Ib);

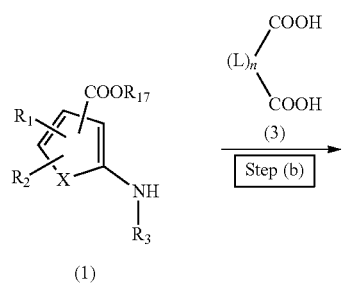

wherein $R_1$, $R_2$, $R_3$, $R_{17}$, L, X and n are defined as above.

2-3. A method for producing an aromatic or heterocyclic carboxylic acid represented by the general formula (Ic), the method comprising the following steps (c), (d) and (x) (Production Method 3):

(c) a step of reacting the compound (1) and an intramolecular anhydride of dicarboxylic acid (5) to form an ester carboxylic acid compound (6a), represented by the formulae below, (d) a step of reacting the ester carboxylic acid compound (6a) formed in the above step (c) and a compound (7) to form an ester compound (4c), and (x) a step of removing the $R_{17}$ group from the ester compound (4c) formed in the above step (d) to produce an aromatic or heterocyclic carboxylic acid (Ic);

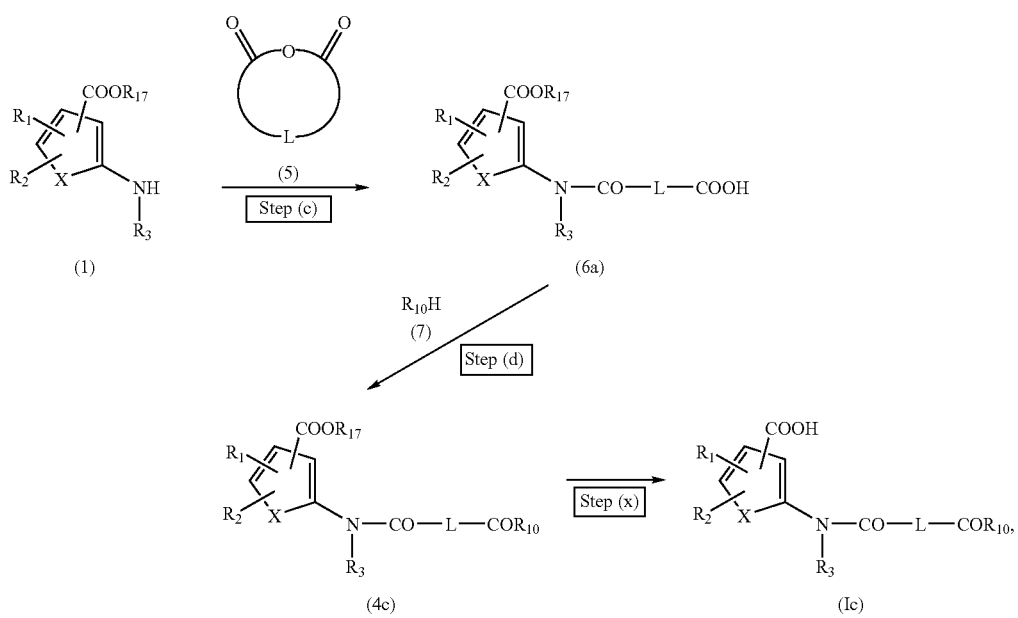

wherein $R_1$, $R_2$, $R_3$, $R_{10}$, $R_{17}$, L and X are defined as above.

2-4. A method for producing an aromatic or heterocyclic carboxylic acid represented by the general formula (Ic) or (Id), the method comprising the following steps (e), (f), (d) and (x) (Production Method 4):

(e) a step of reacting the compound (1) and an ester carboxylic acid (8) to form a compound (9), represented by the formulae below, (f) a step of removing the $R_{18}$ group from the compound (9) formed in the above step (e) to form an ester carboxylic acid (6a) or (6b), (d) a step of reacting the ester carboxylic acid (6a) or (6b) formed in the above step (f) and a compound (7) to produce an ester compound (4c) or (4d), and (x) a step of removing the $R_{17}$ group from the ester compound (4c) or (4d) formed in the above step (d) to produce an aromatic or heterocyclic carboxylic acid (Ic) or (Id);

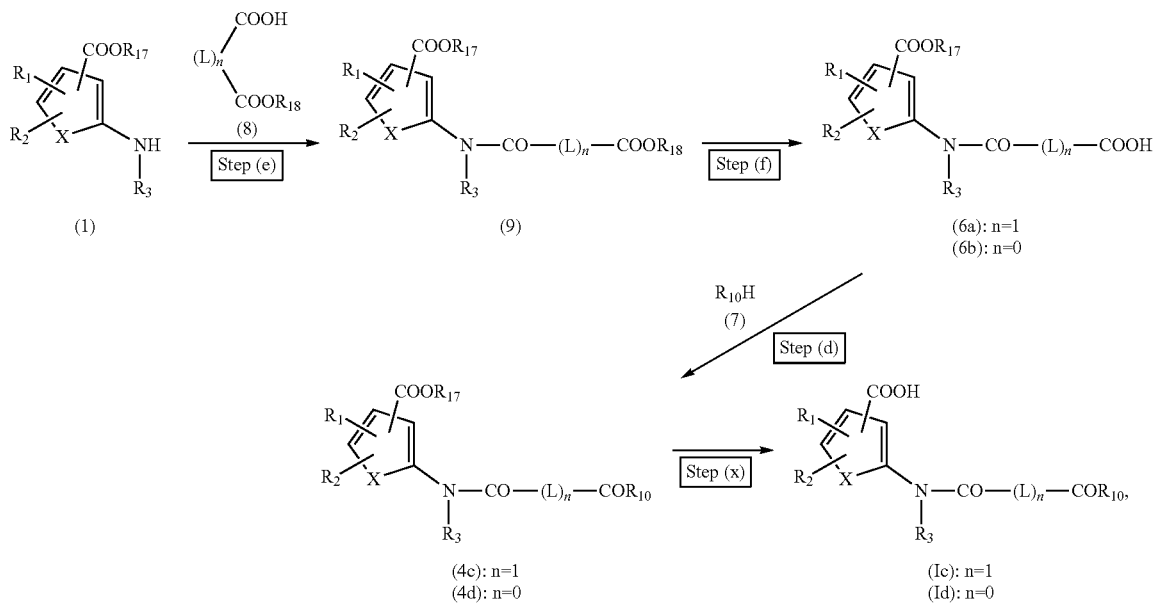

wherein $R_1$, $R_2$, $R_3$ $R_{10}$, $R_{17}$, L, n and X are defined as above, $R_{18}$ represents alkyl, aryl or aralkyl.

2-5. A method for producing an aromatic or heterocyclic carboxylic acid represented by the general formula (Ie) or (If), the method comprising the following steps (g), (h), (i) and (x) (Production Method 5):

(g) a step of reacting the compound (1) and a compound (10) to form a compound (11), represented by the formulae below, (h) a step of removing an amino-protective group from the compound (11) formed in the above step (g) to form an amine compound (12), (i) a step of reacting the amine compound (12) formed in the above step (h) and a sulfonyl chloride compound (13) or an isocyanate compound (14) to form an ester compound (4e) or (4f), and (x) a step of removing the $R_{17}$ group from the ester compound (4e) or (4f) formed in the above step (d) to produce an aromatic or heterocyclic carboxylic acid (Ie) or (If);

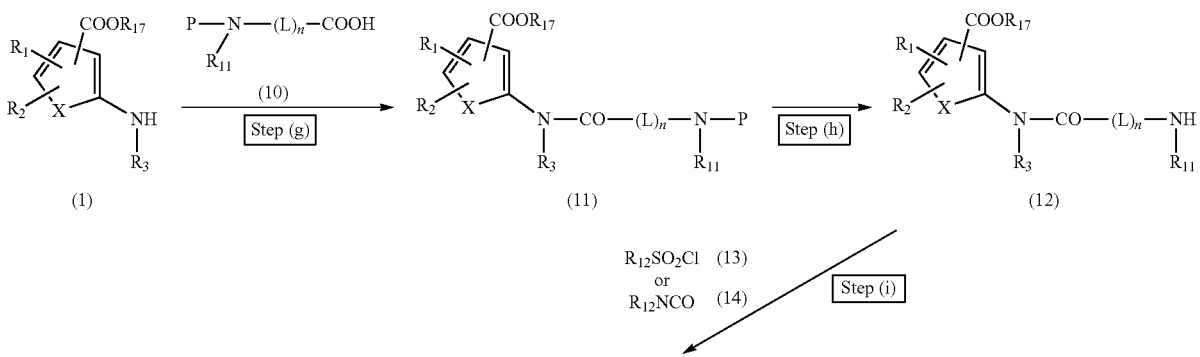

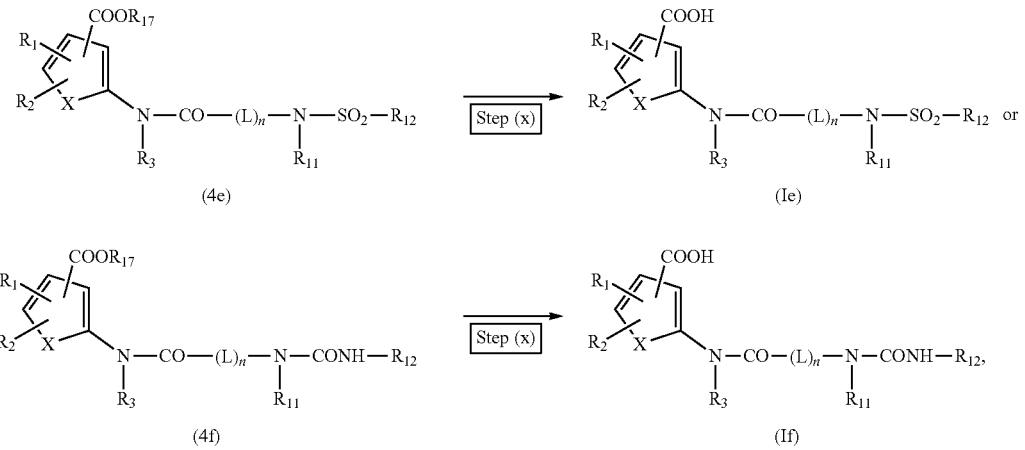

wherein $R_1$, $R_2$, $R_3$, $R_{11}$, $R_{12}$, $R_{17}$, L, n and X are defined as above, and P represents an amino protecting group.

2-6. A method for producing an aromatic or heterocyclic carboxylic acid represented by the general formula (Ig), the method comprising the following steps (j) and (x) (Production Method 6):

(j) a step of reacting the compound (1) and a compound (15) to form a compound (4g), represented by the formulae below, and (x) a step of removing the $R_{17}$ group from the ester compound (4g) formed in the above step (j) to produce an aromatic or heterocyclic carboxylic acid (Ig);

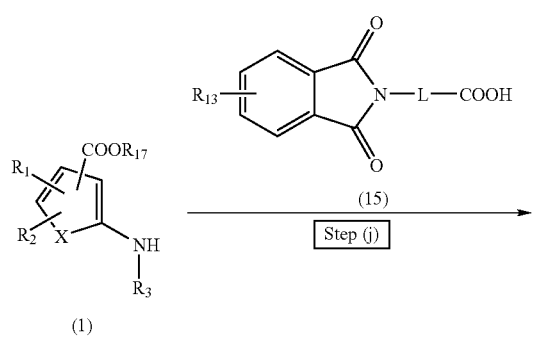

-continued

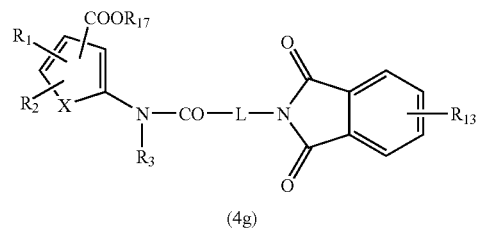

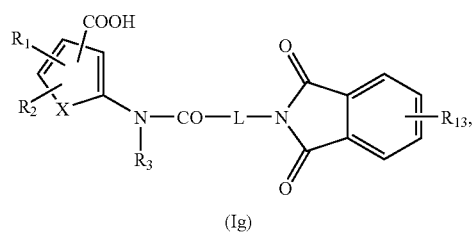

wherein $R_1$, $R_2$, $R_3$, $R_{13}$, $R_{17}$, L and X are defined as above.

2-7. A method for producing an aromatic or heterocyclic dicarboxylic acid represented by the general formula (Ih), the method comprising the following steps (j), (k) and (x) (Production Method 7):

(j) a step of reacting the compounds (1) and (15) to form the ester compound (4g), represented by the formulae below, (k) a step of treating the ester compound (4g) formed in the above step (j) with alkali, hydrolyzing a phthalyl group to form an ester carboxylic acid (4h), and (x) a step of removing the $R_{17}$ group from the obtained ester carboxylic acid (4h) in the above step to produce an aromatic or heterocyclic dicarboxylic acid (Ih);

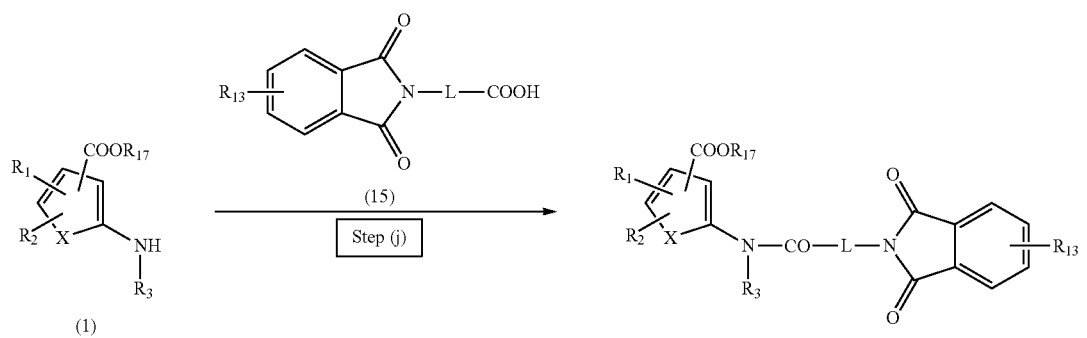

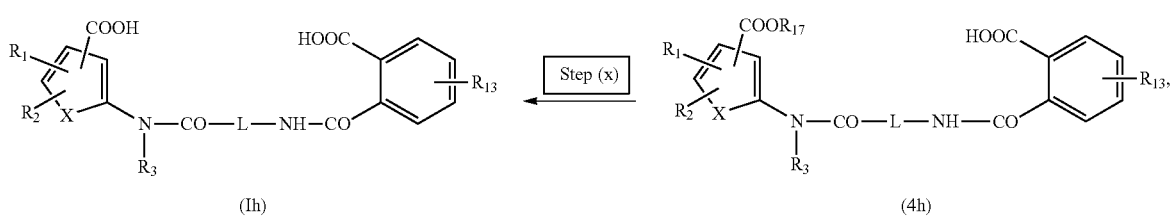

wherein $R_1$, $R_2$, $R_3$, $R_{13}$, $R_{17}$, L and X are defined as above.

2-8. A method for producing the carboxylic acid represented by the general formula (Ii), the method comprising the following steps (x-1) and (x-2) represented by the formulae below are conducted instead of the step (x) in the method for producing the aromatic or heterocyclic carboxylic acid of 2-1 to 2-7 (Production Method 8):

(x-1) a step of reacting a compound (16) and a compound (4') substituted with a halogen atom, and (x-2) a step of removing the $R_{17}$ group from an ester compound (4") formed in the above step (x-1) to produce the carboxylic acid compound (Ii);

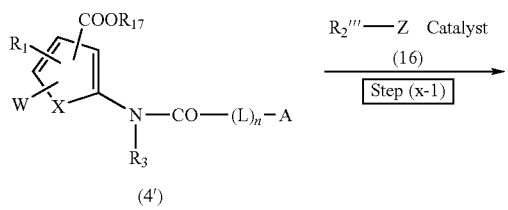

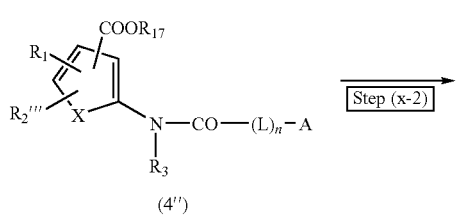

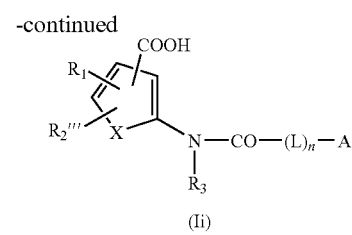

wherein $R_1$, $R_3$, $R_{17}$, L, A, X and n are defined as above; W represents a halogen atom; $R_2'''$ represents an alkyl, cycloalkyl, alkenyl, cycloalkenyl, alkynyl, alkoxy, cycloalkoxy, alkenyloxy, cycloalkenyloxy, aryl, aryloxy, aralkyl, aralkyloxy, heterocyclic ring, heterocyclic-alkyl, heterocyclic-alkyloxy group; Z is a group represented by $-B(OR_{20})OR_{20}$ wherein $R_{20}$ represents a hydrogen atom or alkyl group, when $R_{20}$ represents alkyl, $R_{20}$ may join together to form a ring, or is a group represented by $-ZnW$, wherein W is a halogen atom.

2-9. A method for producing a tetrazole compound (20) which is a bioisoster of the carboxylic acid represented by the general formula (Ic), the method comprising the following steps (c'), (d') and (y) (Production Method 9a):

(c') a step of reacting a compound (17) and the intramolecular anhydride of dicarboxylic acid (5) to form a cyanocarboxylic acid compound (18), (d') a step of reacting the cyanocarboxylic acid compound (18) formed in the above step (c') and the compound (7) to form a nitrile compound (19), and (y) a step of producing the tetrazole compound (20) from the nitrile compound (19) formed in the above step (d') and an azide;

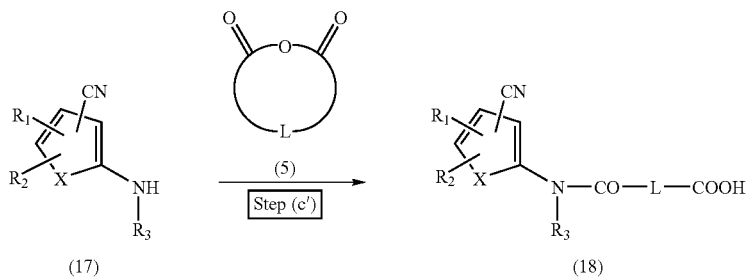

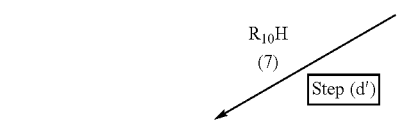

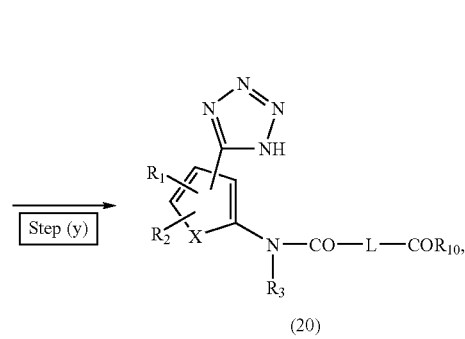

wherein $R_1$, $R_2$, $R_3$, $R_{10}$, X and L are defined as above.

2-10. A method for producing a compound (22) which is a bioisoster of the carboxylic acid represented by the general formula (Ic), the method comprising the following steps (z) and (z-1) (Production Method 10):

(z) a step of reacting the compound (19) and hydroxylamine hydrochloride to form an amidoxime compound (21), as represented by the formulae below, and (z-1) a step of reacting the amidoxime compound (21) formed in the above step (z) and an active carbonyl compound to form 1,2,4-oxadiazol-5-on (22);

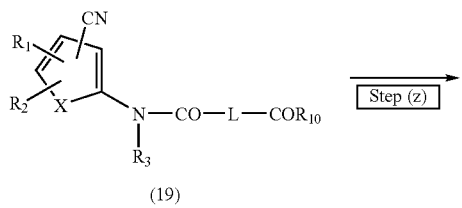

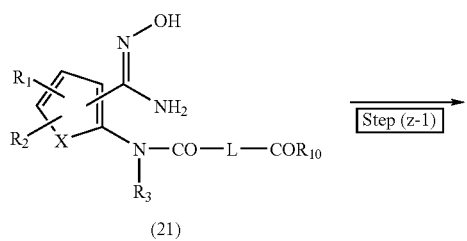

-continued

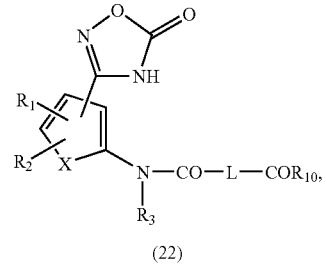

wherein $R_1$, $R_2$, $R_3$, $R_{10}$, L, and X are defined as above.

2-11. A method for producing a compound (23) which is a bioisoster of the carboxylic acid represented by the general formula (Ic), the method comprising the following steps (z) and (z-2) (Production Method 1° a.):

(z) a step of reacting the compound (19) and hydroxylamine hydrochloride to form an amidoxime compound (21), as represented by the formulae below, and (z-2) a step of reacting the amidoxime compound (21) formed in the above step (z) and 1,1'-thiocarbonyldiimidazole to form a 1,2,4-oxadiazol-5-thion compound (23);

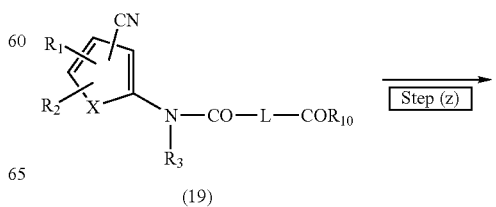

-continued

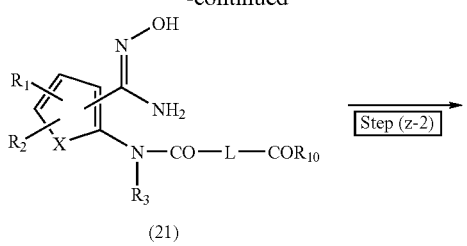
(21)

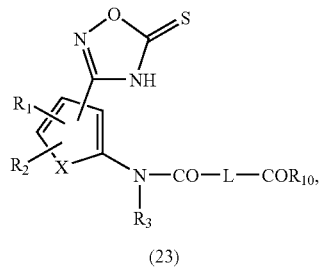
(23)

wherein $R_1$, $R_2$, $R_3$, $R_{10}$, L, and X are defined as above.

2-12. A method for producing a compound (24) which is a bioisoster of the carboxylic acid represented by the general formula (Ic), the method comprising the following steps (z) and (z-3) (Production Method 12a):

(z) a step of reacting the compound (19) and hydroxylamine hydrochloride to form an amidoxime compound (21), as represented by the formulae below, and (z-3) a step of reacting the amidoxime compound (21) formed in the above step (z) and 1,1'-thiocarbonyldiimidazole in the absence of a base, and further reacting with an acid, to form a 1,2,4-thiadiazol-5-on compound (24);

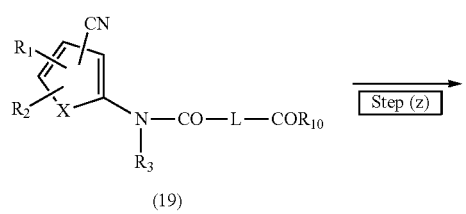
(19)

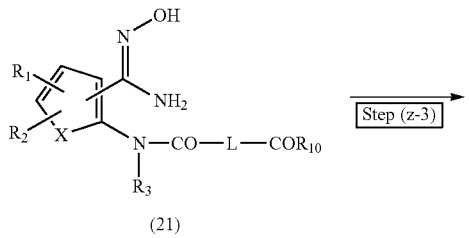
(21)

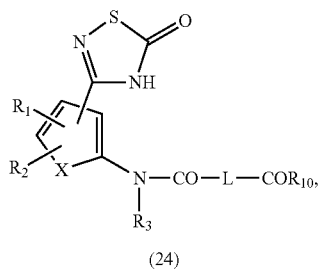
(24)

wherein $R_1$, $R_2$, $R_3$, $R_{10}$, L, and X are defined as above.

2-13. A method for producing a compound (26) which is a bioisoster of the carboxylic acid represented by the general formula (Ia), the method comprising the following steps (a') and (y') (Production Method 9b):

(a') a step of condensing the compound (17) and a compound (2) to form a nitrile compound (25), as represented by the formulae below, and (y') a step of producing a tetrazole compound (26) from the nitrile compound (25) formed in the above step (a') and an azide:

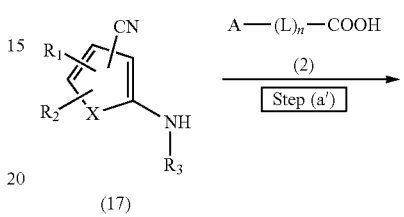
(17)

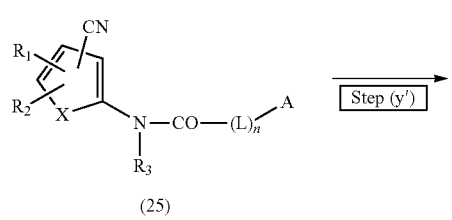
(25)

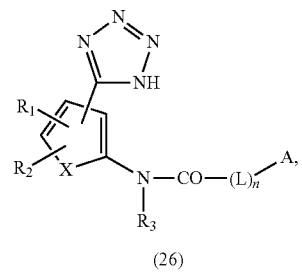
(26)

wherein $R_1$, $R_2$, $R_3$, A, L, n and X are defined as above.

2-14. A method for producing a compound (28) which is a bioisoster of the carboxylic acid represented by the general formula (Ia), the method comprising the following steps (z') and (z-1') (Production Method 10b):

(z') a step of reacting the compound (25) and hydroxylamine hydrochloride to form an amidoxime compound (27), as represented by the formulae below, and (z-1') a step of reacting the amidoxime compound (27) formed in the above step (z') and an active carbonyl compound to form the 1,2,4-oxadiazol-5-on compound (28);

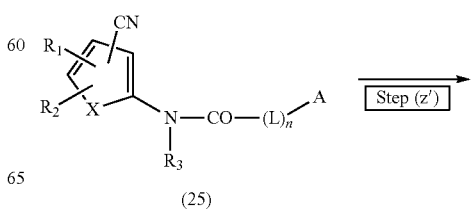
(25)

-continued

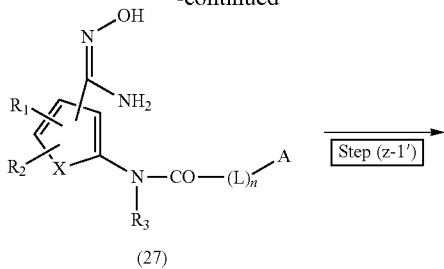

(27)

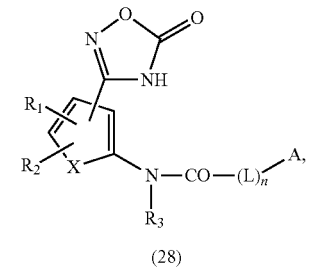

(28)

wherein $R_1$, $R_2$, $R_3$, A, L, n and X are defined as above.

2-15. A method for producing a compound (29) which is a bioisoster of the carboxylic acid represented by the general formula (Ia), the method comprising the following steps (z') and (z-2') (Production Method 11b):

(z') a step of reacting the compound (25) and hydroxylamine hydrochloride to form an amidoxime compound (27), as represented by the formulae below, and (z-2') a step of reacting the amidoxime compound (27) formed in the above step (z') and 1,1'-thiocarbonyldiimidazole to form a 1,2,4-oxadiazol-5-thion compound (29);

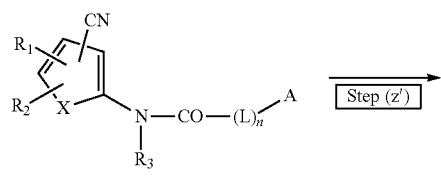

(25)

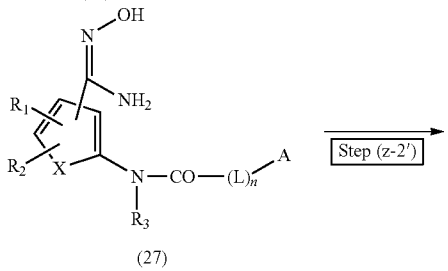

(27)

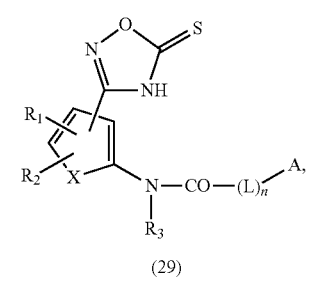

(29)

wherein $R_1$, $R_2$, $R_3$, A, L, n and X are defined as above.

2-16. A method for producing a compound (30) which is a bioisoster of the carboxylic acid represented by the general formula (Ia), the method comprising the following steps (z') and (z-3') (Production Method 12b):

(z') a step of reacting the compound (25) and hydroxylamine hydrochloride to form an amidoxime compound (27), as represented by the formulae below, and (z-3') a step of reacting the amidoxime compound (27) formed in the above step (z') and 1,1'-thiocarbonyldiimidazole in the absence of a base, and further reacting with an acid, to form a 1,2,4-thiadiazol-5-on compound (30);

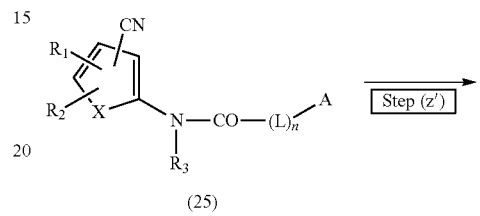

(25)

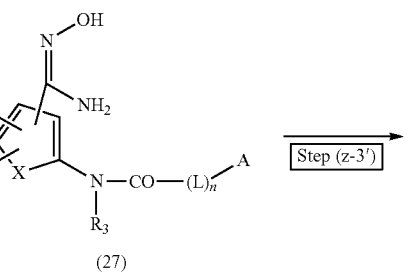

(27)

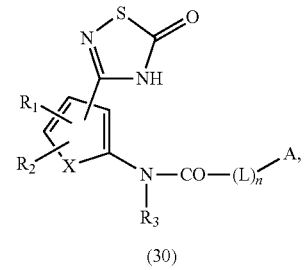

(30)

wherein $R_1$, $R_2$, $R_3$, A, L, n and X are defined as above.

2-17. A method for producing a compound represented by the general formula (III-4-2), the method comprising a step (o) below:

(o) a step of oxidizing a compound (III-4-1) wherein n is 1 and L is alkylenethioalkylene in the general formula (I), to produce a compound (III-4-2) wherein L is an alkylene-SO-alkylene group;

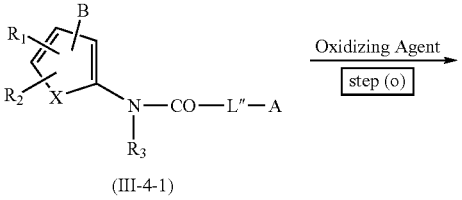

(III-4-1)

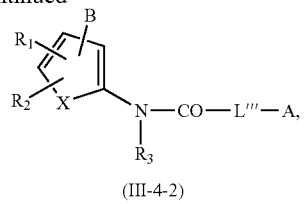

(III-4-2)

wherein $R_1$, $R_2$, $R_3$, B and X are defined as above; L" is alkylenethioalkylene, and L'" is alkylene-SO-alkylene.

2-18. A method for producing a compound represented by the general formula (III-4-3), the method comprising the steps (p) or (q) below:

(p) a step of reacting an excessive amount of an oxidizing agent to the compound (III-4-1) wherein n is 1 and L is alkylenethioalkylene in the general formula (I) to produce the compound (III-4-3) wherein L is alkylene-$SO_2$-alkylene, or (q) a step of further oxidizing the compound (III-4-2) obtained by the method shown in 2-17 to produced the compound (III-4-3) wherein L is alkylene-$SO_2$-alkylene;

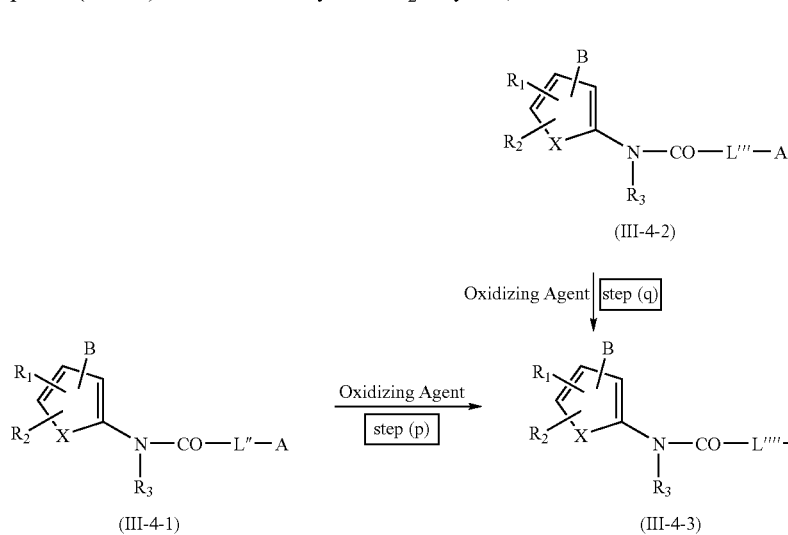

wherein $R_1$, $R_2$, $R_3$, B, X, L" and L'" are defined as above; L"" represents alkylene-$SO_2$-alkylene.

3. PAI-1 Inhibitor 3-1. An inhibitor of plasminogen activator inhibitor-1 (PAI-1) comprising, as an active component, a compound or a salt thereof according to any one of 1-1 to 1-5, or a solvate thereof.

4. Pharmaceutical Composition 4-1. A pharmaceutical composition containing a compound or a salt according to any one of 1-1 to 1-5, or a solvate thereof, and a pharmaceutically acceptable carrier or additive.

4-2. The pharmaceutical composition according to 4-1, the composition being a preventive drug or treatment drug for a disease whose onset is associated with PAI-1 activity.

4-3. The pharmaceutical composition according to 4-1 or 4-2, the composition being a fibrinolytic-system-promoting drug.

4-4. The pharmaceutical composition according to 4-2 or 4-3, wherein the disease whose onset is associated with PAI-1 activity is thrombosis in an artery, thrombosis in an vein, deep-vein thrombosis (DVT) during surgery, disseminated intravascular coagulation syndrome(DIC), angiopathy, neuropathy, retinopathy or nephropathy as a diabetic complication, or restenosis occurring after percutaneous transluminal coronary angioplasty (PTCA).

4-5. The pharmaceutical composition according to 4-4, wherein the thrombosis in an artery is thrombosis in the brain, such as cerebral thrombosis, cerebral embolism, transient ischemic attack; thrombosis in the heart, such as angina pectoris, myocardial infarction; thrombosis in a lower extremity, such as lower extremity acute artery thrombosis; or thrombosis in the upper intestinal tract, such as upper intestinal tract arterial thrombosis; and the thrombosis in a vein is thrombosis in the extremities, such as deep-vein thrombosis; or thrombosis occurring when a blood clot travels to the lung, such as pulmonary embolism.

4-6. The pharmaceutical composition according to 4-2 or 4-3, wherein the disease whose onset is associated with PAI-1 activity is a disease accompanied by tissue fibril formation.

4-7. The pharmaceutical composition according to 4-6, wherein the disease accompanied by tissue fibril formation is pulmonary fibrosis.

4-8. The pharmaceutical composition according to any one of 4-1 to 4-7, the composition being in a form for oral administration.

Effects of the Invention

According to the present invention, a novel low-molecular weight compound having a high inhibitory action against PAI-1 can be provided. The compound is useful as an active component of a pharmaceutical composition such as a preventive agent or treatment agent for various diseases caused by PAI-1 activity.

Further, according to the present invention, a pharmaceutical composition feasible for mass synthesis and having an active component of a low-molecular-weight compound can be provided. As described earlier, the pharmaceutical composition has an active component of a compound having high inhibitory action against PAI-1 (PAI-1 inhibitor), and can hence be effectively used as a preventive or treatment agent for various diseases caused by PAI-1 activity. More specifically, the pharmaceutical composition of the present invention is useful as a fibrinolytic-system-promoting drug for preventing or treating thromboses in an artery, thromboses in a vein, deep-vein thrombosis (DVT) occurring during surgery, disseminated intravascular coagulation syndrome (DIC), angiopathy, neuropathy, retinopathy or nephropathy as a diabetic complication, or restenosis occurred after percutaneous transluminal coronary angioplasty (PTCA), etc. Further, the pharmaceutical composition of the present invention is useful as an anti-fibrosis drug in preventing or treating various diseases associated with tissue fibril formation, particularly, pulmonary fibrosis.

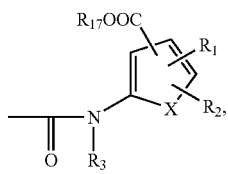

Compound (Ib): A=

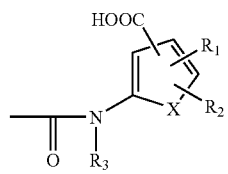

Compound (4c) and (Ic): A: —$COR_{10}$ n:1
Compound (4d) and (Id): A: —$COR_{10}$ n:0
Compound (4e) and (Ie): A: —$N(R_{11})$—$SO_2$—$R_{12}$
Compounds (4f) and (If): A: —$N(R_{11})$—CONH—$R_{12}$
Compounds (4g) and (Ig): A=

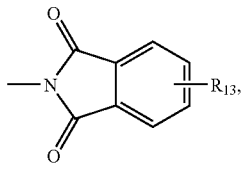

n:1
Compounds (4h) and (Ih): A=

Figure 2:
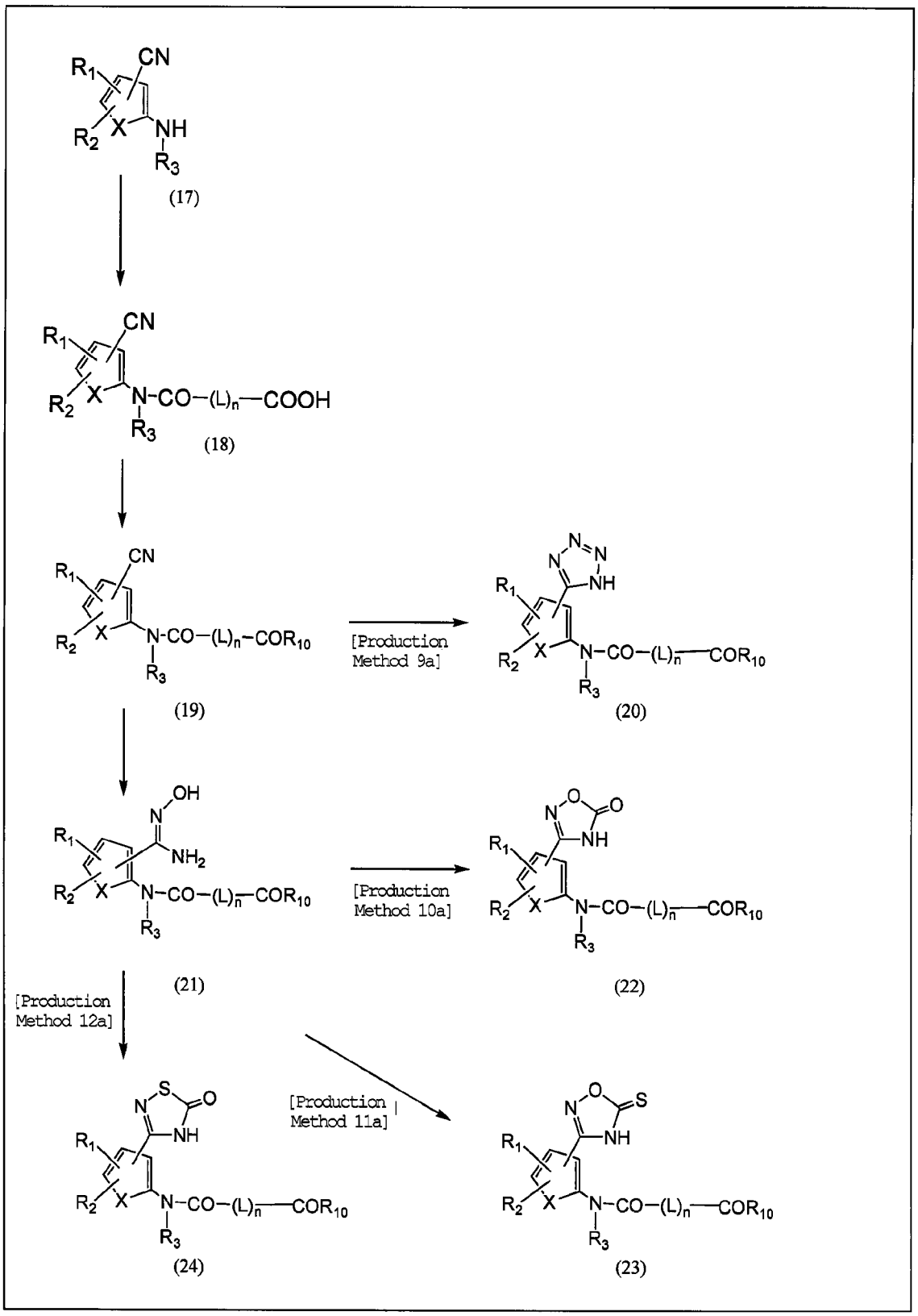
Figure 3:
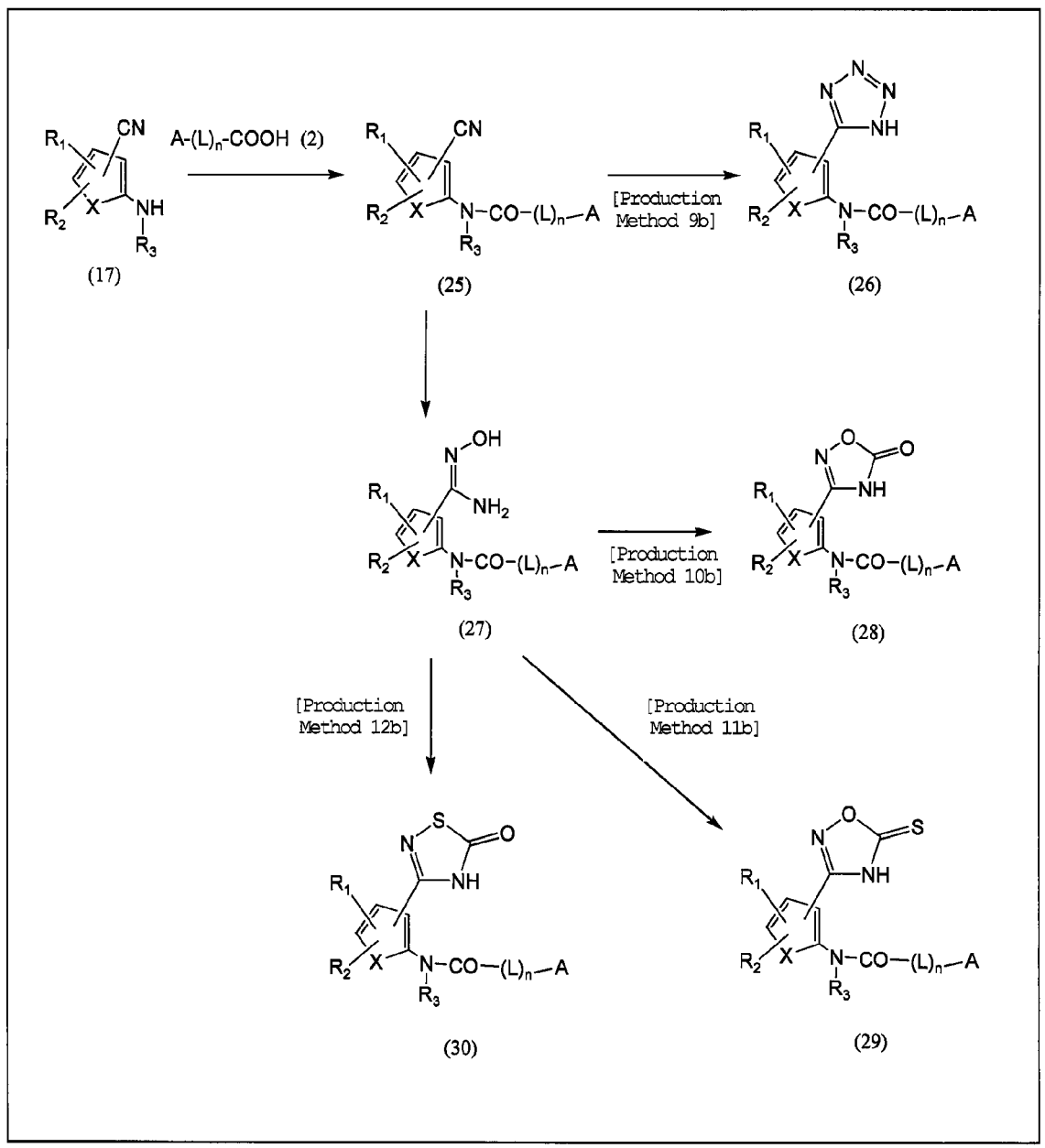

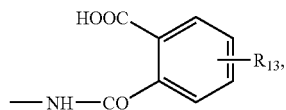

n:1
FIG. 2 shows the production methods of the compound (I) of the present invention. Symbols in the figure are defined as those in the specification.
FIG. 3 shows the production methods of the compound (I) of the present invention. The symbols in the figure are defined as those in the specification.

Figure 14:
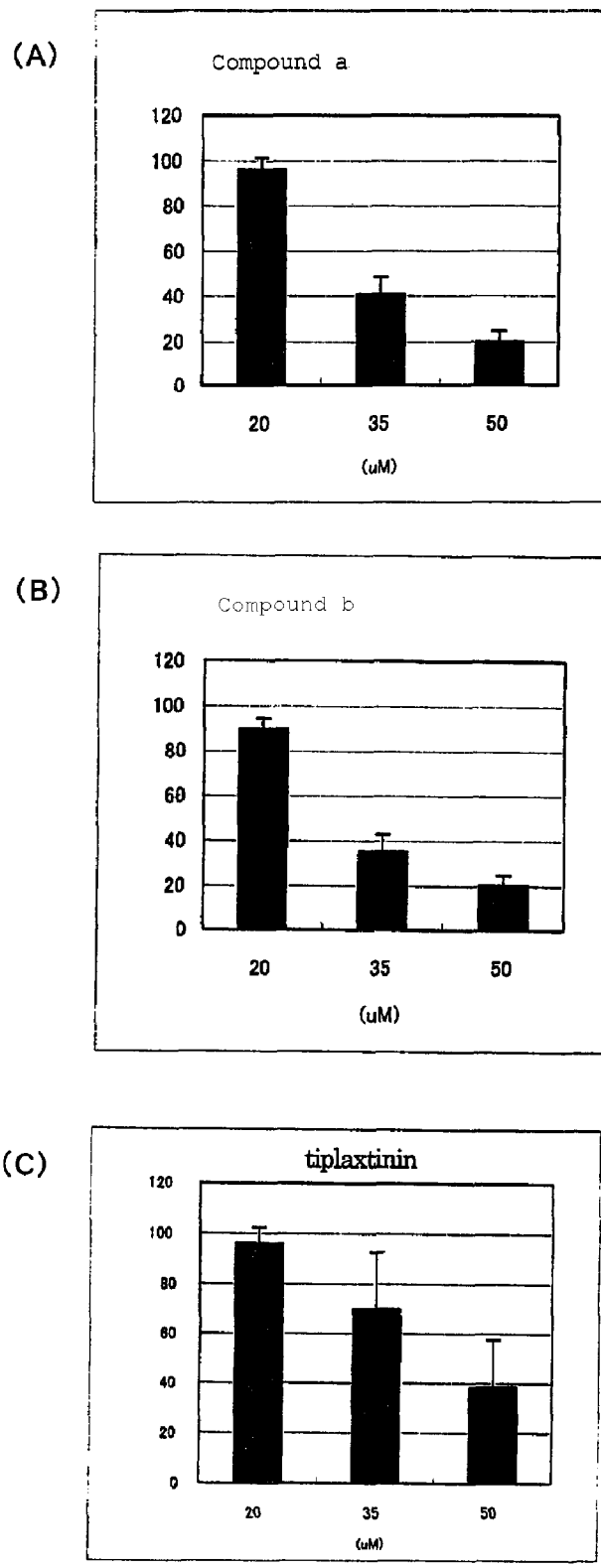

FIG. 4 summarizes the PAI-1 activities (%) of the compounds prepared in Examples 1 to 10.
FIG. 5 summarizes the PAI-1 activities(%) of the compounds prepared in Examples 11 to 20.
FIG. 6 summarizes the PAI-1 activities(%) of the compounds prepared in Examples 21 to 30.
FIG. 7 summarizes the PAI-1 activities(%) of the compounds prepared in Examples 31 to 40.
FIG. 8 summarizes the PAI-1 activities(%) of the compounds prepared in Examples 41 to 50.
FIG. 9 summarizes the PAI-1 activities(%) of the compounds prepared in Examples 51 to 61.
FIG. 10 summarizes the PAI-1 activities(%) of the compounds prepared in Examples 62 to 71.
FIG. 11 summarizes the PAI-1 activities(%) of the compounds prepared in Examples 72 to 81.
FIG. 12 summarizes the PAI-1 activities(%) of the compounds prepared in Examples 82 to 91.
FIG. 13 summarizes the PAI-1 activities(%) of the compounds prepared in Examples 92 to 95.
FIG. 14 shows the PAI-1 inhibitory activity of;
(A) N,N'-bis[3,3'-carboxy-4,4'-phenyl-2,2'-thienyl]hexanedicarboxyamide (compound a),
(B) N,N'-bis[3,3'-carboxy-4,4'-(2,2'-thienyl)-2,2'-thienyl]hexanedicarboxyamide (compound b), and
(C) tiplaxtinin.
The longitudinal axis indicates PAI-1 activity (%) (see Reference Test Example 1 (1)).
FIG. 15 shows the antifibrotic effects of N,N'-bis[3,3'-carboxy-4,4'-(2,2'-thienyl)-2,2'-thienyl]hexanedicarboxyamide (compound b) on bleomycin-induced pulmonary fibrosis, wherein a shows fibrosis scores, and b shows images of histological stains (see Reference Test Example 1 (3)).

BEST MODE FOR CARRYING OUT THE INVENTION

1. Compound of The Invention

The compound of the present invention is an aromatic or heterocyclic carboxylic acid represented by the following general formula (I) (wherein B is a carboxyl group), an ester (wherein B is an alkoxycarbonyl group) thereof, or a bioisoster thereof (wherein B is a biologically equivalent group of the carboxyl group).

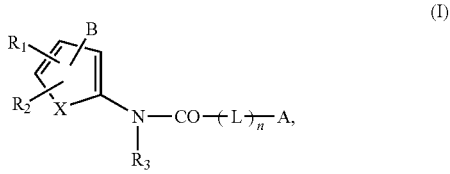

$R_1$ and $R_2$ herein, the same or different, each represent a hydrogen atom, halogen atom, an alkyl, cycloalkyl, cycloalkylalkyl, alkenyl, cycloalkenyl, alkynyl, hydroxyl, alkoxy, cycloalkoxy, alkynyloxy, cycloalkenyloxy, aryloxy, aralkyl, aralkyloxy, heterocyclic ring, heterocyclic-alkyl, or heterocyclic-alkyloxy group; substituted or unsubstituted aryl; or amino, carbamoyl, cyano, carboxy or alkoxycarbonyl that may be substituted or unsubstituted with 1 to 2 substituents. $R_1$ and $R_2$ may adjoin to each other to form a ring.
$R_3$ represents a hydrogen atom; or substituted or unsubstituted alkyl, alkenyl, alkynyl, cycloalkyl, aryl or aralkyl.

X represents an oxygen atom, sulfur atom, a —N(R$_4$)—, —C(R$_5$)═C(R$_6$)—, —C(R$_7$)═N—, or —N═C(R$_8$)— group. Among these groups, R$_4$ is a hydrogen atom, or substituted or unsubstituted alkyl; R$_5$, R$_6$, R$_7$ and R$_8$ each represent a hydrogen atom, halogen atom, or substituted or unsubstituted alkyl or alkoxy.

B represents a carboxy, alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl group.

L represents a substituted or unsubstituted alkylene (some carbon atoms in the alkylene may form a cycloalkyl ring), alkenylene, alkynylene, cycloalkylene, alkyleneoxyalkylene, alkylenethioalkylene, alkylene-SO-alkylene or alkylene-SO$_2$-alkylene; or alkylene-N(R$_9$)-alkylene. R$_9$ is a hydrogen atom, or substituted or unsubstituted alkyl.

n is an integer of 0 or 1.

A represents —COR$_{10}$, —N(R$_{11}$)—COR$_{12}$, —N(R$_{11}$)—SO$_2$—R$_{12}$, —N(R$_{11}$)—CONH—R$_{12}$, or a group represented by the following formula:

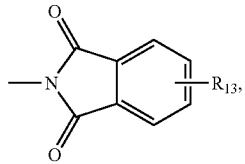

wherein R$_{11}$, R$_{12}$, R$_{13}$ and R$_{10}$ each represent the following groups;

R$_{11}$ is a hydrogen atom or alkyl;

R$_{12}$ is substituted or unsubstituted alkyl, cycloalkyl, aryl, or aralkyl (including diphenylalkyl);

R$_{13}$ is a hydrogen atom, halogen atom, alkyl or alkoxy;

R$_{10}$ is N(R$_{14}$) (R$_{15}$), wherein R$_{14}$ and R$_{15}$, the same or different, each represent a hydrogen atom; substituted or unsubstituted alkyl, alkyenyl, cycloalkenyl, alkynyl, bicycloalkyl, bicycloalkenyl, adamantyl, aryl, heterocyclic ring, aralkyl (including diphenylalky), or heterocyclic-alkyl; or a group represented by the following formula

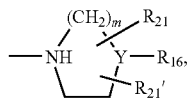

wherein m is an integer of 1 to 4; Y is a nitrogen atom, CH—, C(R$_{16}$')—, C(OH)—, or CH—O—; R$_{16}$ and R$_{16}$', the same or different, each represent a hydrogen atom, or substituted or unsubstituted alkyl, cycloalkyl, alkenyl, cycloalkenyl, alkynyl, bicycloalkyl, bicycloalkenyl, adamantyl, aryl, fluorenyl or aralkyl (including diphenylalkyl); R$_{21}$ and R$_{21}$', the same or different, each represents a hydrogen atom; substituted or unsubstituted alkyl or phenyl.

The designation of each group represented by these characters and specific examples thereof are described below.

Examples of "alkyl", represented by R$_1$ to R$_9$, R$_{11}$ to R$_{16}$, R$_{16}$', R$_{21}$ and R$_{21}$', particularly R$_1$, R$_2$, R$_9$, R$_{14}$, R$_{21}$ and R$_{21}$', in the compound of the present invention include typically C$_{1-12}$, preferably C$_{1-10}$, more preferably C$_{1-8}$, further preferably C$_{1-6}$, and particularly preferably C$_{1-4}$ straight- or branched-chain lower alkyls. These alkyls include groups such as methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, heptyl, 1-methylpentyl, 2-methylpentyl, n-heptyl, isoheptyl, sec-heptyl, tert-heptyl, n-octyl, tert-octyl, 2-methylhexyl, 2-ethylhexyl, etc. Preferable groups are methyl, ethyl, propyl, isopropyl, butyl and isobutyl, more preferable are methyl and ethyl, and particularly preferable is methyl. Among these, "alkyls" represented by R$_3$ to R$_9$, R$_{12}$, R$_{14}$, R$_{15}$, R$_{16}$, R$_{21}$ and R$_{21}$', particularly those represented by R$_9$, R$_{14}$, R$_{21}$ and R$_{21}$' may be substituted or unsubstituted. Examples of substituents include a halogen atom, C$_{1-6}$ lower alkoxy, halogen-substituted C$_{1-6}$ lower alkoxy, hydroxyl, CF$_3$, CF$_3$O, CHF$_2$O, CF$_3$CH$_2$O, cyano, carboxy, alkoxycarbonyl, etc.

Examples of "cycloalkyl", represented by R$_1$ to R$_3$, R$_{12}$, R$_{16}$ and R$_{16}$', in the compound of the present invention include typically C$_{3-7}$, and preferably C$_5$ or C$_6$ cyclic alkyls. These cycloalkyls include groups such as cyclopropyl, cyclobutyl, cyclopentyl, cyclohexyl, cycloheptyl, etc. Among these, "cycloalkyls" represented by R$_3$, R$_{12}$, and R$_{16}$ may have one or more substituents at suitable positions. Examples of substituent include a halogen atom, C$_{1-6}$ lower alkyl, halogen-substituted lower alkyl, C$_{1-6}$ lower alkoxy, halogen-substituted lower alkoxy, hydroxyl, CF$_3$, CF$_3$O, CHF$_2$O, CF$_3$CH$_2$O, cyano, carboxy, and alkoxycarbonyl.

Examples of "cycloalkylalkyl", represented by R$_1$ and R$_2$, in the compound of the present invention include typically C$_{3-7}$, and preferably C$_5$ or C$_6$ cyclic alkyl, having a C$_{1-6}$ lower alkyl substituent. These cycloalkylalkyls include groups such as cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, etc.

Examples of "alkoxy", represented by R$_1$, R$_2$, R$_5$ to R$_8$ and R$_{13}$, particularly by R$_1$ and R$_2$, in the compound of the present invention include hydroxyls substituted with the above-mentioned C$_{1-12}$, preferably C$_{1-10}$, more preferably C$_{1-8}$, further preferably C$_{1-6}$, and particularly preferably C$_{1-4}$ alkyls. Examples of such an alkoxy include groups such as methoxy, ethoxy, 1-propoxy, 2-propoxy, 1-buthoxy, 2-buthoxy, 2-methyl-1-propoxy, 2-methyl-2-propoxy, 1-pentyloxy, 2-pentyloxy, 3-pentyloxy, 2-methyl-2-butoxy, 3-methyl-2-butoxy, 1-hexyloxy, 2-hexyloxy, 3-hexyloxy, 2-methyl-1-pentyloxy, 3-methyl-1-pentyloxy, 2-ethyl-1-butoxy, 2,2-dimethyl-1-butoxy, 2,3-dimethyl-1-butoxy, etc. Preferable among these are methoxy, ethoxy, 1-propoxy, and 2-propoxy, with methoxy being more preferable. Of these, "alkoxys" represented by R$_5$ to R$_8$ may be substituted or unsubstituted, and examples of substituent include a halogen atom, C$_{1-6}$ lower alkyl, halogen-substituted lower alkyl, C$_{1-6}$ lower alkoxy, halogen-substituted lower alkoxy, hydroxyl, CF$_3$, CF$_3$O, CHF$_2$O, CF$_3$CH$_2$O, cyano, carboxy, alkoxycarbonyl, etc.

Examples of "cycloalkoxy", represented by R$_1$ and R$_2$, in the compound of the present invention include C$_{2-8}$, and preferably C$_{4-5}$, cyclic alkoxy. Such cycloalkoxys include groups such as cyclopropyloxy, cyclobutyloxy, cyclopentyloxy, cyclohexyloxy, cycloheptyloxy, etc.

Examples of "alkenyl", represented by R$_1$ to R$_3$ and R$_{14}$ to R$_{16}$ and R$_{16}$', in the compound of the present invention include C$_{2-6}$ straight- or branched-chain alkenyls having 1 to 3 double bonds. Examples of such alkenyl include vinyl, 1-propenyl, 1-methyl-1-propenyl, 2-methyl-1-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-ynyl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl. Of these, the "alkenyl" represented by $R_3$, $R_{14}$ to $R_{16}$ and $R_{16}'$ may be substituted or unsubstituted, and examples of substituent include a halogen atom, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, and alkoxycarbonyl.

Examples of "alkenyloxy", represented by $R_1$ and $R_2$, in the compound of the present invention include hydroxyls substituted with $C_{2-6}$ straight- or branched-chain alkenyls having 1 to 3 double bonds described earlier. Specific examples of such alkenyloxy include vinyloxy, 1-propenyloxy, 1-methyl-1-propenyloxy, 2-methyl-1-propenyloxy, 2-propenyloxy, 2-butenyloxy, 1-butenyloxy, 3-butenyloxy, 2-pentenyloxy, 1-pentenyloxy, 3-pentenyloxy, 4-pentenyloxy, 1,3-butadienyloxy, 1,3-pentadienyloxy, 2-penten-4-yloxy, 2-hexenyloxy, 1-hexenyloxy, 5-hexenyloxy, 3-hexenyloxy, 4-hexenyloxy, 3,3-dimethyl-1-propenyloxy, 2-ethyl-1-propenyloxy, 1,3,5-hexatrienyloxy, 1,3-hexadienyloxy, and 1,4-hexadienyloxy.

Examples of "cycloalkenyl", represented by $R_1$ and $R_2$ and $R_{14}$ to $R_{16}$ and $R_{16}'$, used in the compound of the present invention include $C_{2-6}$ cyclic alkenyls having 1 to 3 double bonds. Of these, "cycloalkenyl", represented by $R_{14}$ to $R_{16}$ and $R_{16}'$, may have one or more substituents at suitable positions. Examples of such a substituent include a halogen atom, $C_{1-6}$ lower alkyl, halogen-substituted lower alkyl, C16 lower alkoxy, halogen-substituted lower alkoxy, hydroxyl, $CF_3$, $CF_3O$, $CHF_2O$, $CF_3CH_2O$, cyano, carboxy, and alkoxycarbonyl.

Examples of "cycloalkenyloxy", represented by $R_1$ and $R_2$, in the compound of the present invention include $C_{2-6}$ cyclic alkenyloxys having 1 to 3 double bonds described earlier.

Examples of "alkynyl", represented by $R_1$ to $R_3$, and $R_{14}$ to $R_{16}$ and $R_{16}'$, in the compound of the present invention include $C_{2-6}$ straight- or branched-chain alkynyls having a triple bond. Specific examples of such alkynyl include ethynyl, 2-propynyl, 2-butynyl, 3-butynyl, 1-methyl-2-propynyl, 2-pentynyl, 2-hexynyl, etc. Of these, "alkynyl" represented by $R_3$ and $R_{14}$ to $R_{16}$ may be substituted or unsubstituted, and examples of a substituent include a halogen atom, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, and alkoxycarbonyl.

Examples of "aryl", represented by $R_1$ to $R_3$, $R_{12}$, $R_{14}$ to $R_{16}$ and $R_{16}'$, particularly by $R_1$, $R_2$, $R_{12}$, $R_{14}$ to $R_{16}$ and $R_{16}'$, in the compound of the present invention preferably include $C_{6-14}$ aromatic hydrocarbon groups. Examples of such an aryl include groups such as phenyl, naphthyl, anthryl, phenanthryl, acenaphthylenyl, etc. Phenyl and naphthyl are preferable, with phenyl being more preferable. Of these, "aryls" represented by $R_1$, $R_2$, $R_{12}$, $R_{14}$ to $R_{16}$ and $R_{16}'$ may be substituted or unsubstituted.

Examples of a substituent with which aryl, represented by $R_1$ and $R_2$, is substituted include a halogen atom, $C_{1-6}$ lower alkyl (preferably $C_{1-4}$ alkyl), halogen-substituted lower alkyl, $C_{1-6}$ lower alkoxy (preferably $C_{1-4}$ alkoxy), halogen-substituted lower alkoxy, hydroxyl, $CF_3$, $CF_3O$, $CHF_2O$, $CF_3CH_2O$, cyano, carboxy, alkoxycarbonyl, and amino that may be substituted with 1 to 2 substituents. Examples of a substituent substituted with a hydrogen atom of amino group include $C_{1-6}$, and preferably $C_{1-2}$ alkyl. Such an amino group may have alkyl groups substituted for two hydrogen atoms, that may form a ring with an oxygen or nitrogen atom. Morpholino or (substituted) piperazino is given as an example of such a group. Preferable are a halogen atom, $C_{1-4}$ alkoxy, cyano, and amino that may be substituted with 1 to 2 substituents (particularly preferable is an amino group wherein two hydrogen atoms are substituted with $C_{1-2}$ alkyl groups, which form a ring with an oxygen atom).

Examples of a substituent with which aryl represented by $R_{12}$, $R_{14}$ to $R_{16}$ and $R_{16}'$ is substituted include a halogen atom, a $C_{1-6}$ alkyl (preferably $C_{1-4}$ alky), halogen-substituted lower alkyl, $C_{1-6}$ alkoxy (preferably $C_{1-4}$ alkoxy), halogen-substituted lower alkoxy, hydroxyl, $CF_3$, $CF_3O$, $CHF_2O$, $CF_3CH_2O$, cyano, carboxy, alkoxycarbonyl, phenyl, and benzoyl group. Preferably are a halogen atom, $C_{1-4}$ alkyl, carboxy, $CF_3$, phenyl, and benzoyl. The phenyl groups with which aryl represented by $R_{15}$ is substituted are those with no substituents.

Examples of "aryloxy", represented by $R_1$ and $R_2$, in the compound of the present invention include hydroxyls substituted with $C_{6-14}$ aromatic hydrocarbon groups. Examples of such aryloxys include groups such as phenyloxy, naphthyloxy, anthryloxy, phenanthryloxy, acenaphthylenyloxy, etc.

Examples of "aralkyl", represented by $R_1$ to $R_3$, $R_{12}$, $R_{14}$ to $R_{16}$ and $R_{16}'$, and particularly $R_1$ and $R_2$, $R_{14}$ to $R_{16}$ and $R_{16}'$ in the compound of the present invention is aralkyl substituted with one or more above-mentioned aryls such phenyl, naphthyl, etc. Examples of these aralkyls include benzyl (phenylmethyl); monophenylalkyl groups such as 1-phenylethyl, 2-phenylethyl, 3-phenylpropyl, 4-phenylbutyl, etc.; diphenylakyl groups such as diphenylmethyl, diphenylethyl, etc.; and mononaphthyl alkyl groups such as 1-naphthyl methyl, 1-naphthyl ethyl, 2-naphtyl methyl, 2-naphthyl ethyl, etc. Of these, "aralkyls" represented by $R_3$, $R_{12}$, $R_{14}$ to $R_{16}$ and $R_{16}'$, particularly by $R_{14}$ to $R_{16}$ and $R_{16}'$, may be substituted. Examples of a substituent include a halogen atom, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, and alkoxycarbonyl. Such substituted aralkyls include, for example, α-hydroxybenzyl, fluorobenzyl, trifluoromethyl benzyl, 1-hydroxy-3-phenylpropyl, 1-hydroxy-1-phenyl ethyl, bis(4-fluorophenyl)methyl, etc.

Examples of "aralkyloxy", represented by $R_1$ and $R_2$, in the compound of the present invention include hydroxyls substituted with any of the aralkyls described above. An preferable example of such aralkyloxy is benzyloxy.

Examples of "halogen atom", represented by $R_1$, $R_2$, $R_5$ to $R_8$, and $R_{13}$, in the compound of the present invention include a fluorine atom, chlorine atom, bromine atom, and iodine atom. Preferable are a fluorine atom and chlorine atom.

"Alkylene" in an "alkylene group", "cycloalkylene group", "alkyleneoxyalkylene group", "alkylenethioalkylene group", "alkylene-SO-alkylene group", "alkylene-$SO_2$-alkylene group" and "alkylene-N($R_9$)-alkylene group" represented by L in formula (I) includes typically $C_{1-12}$, preferably $C_{1-10}$, more preferably $C_{1-8}$, further preferably $C_{1-6}$, and particularly preferably $C_{1-4}$ straight- or branched-chain alkylenes. Examples of such an alkylene include groups such as methylene, ethylene, propylene, trimethylene, 1-ethyl-1,2-ethylene, 1-propyl-1,2-ethylene, 1-isopropyl-1,2-ethylene, 1-butyl-1,2-ethylene, 1,2-dimethyl-1,2-ethylene, tetramethylene, pentamethylene, hexamethylene, heptamethylene, and octamethylene.

Specific examples of "alkylene group" include groups such as methylene, ethylene, propylene (trimethylene), tetramethylene, pentamethylene, and hexamethylene, with trimethylene and tetramethylene being preferable. These alkylene groups encompass those wherein some of the carbon atoms combine to form a cycloalkyl ring as shown in Example 93. Examples of such cycloalkyl ring include a cyclopropyl ring, cyclobutyl ring, cyclopentyl ring, and cyclohexyl ring.

Examples of "cycloalkylene group" preferably include groups such as cyclopropylene, cyclobutylene, cyclopentylene, cyclohexylene, cyclooctylene, etc.; examples of a preferable "alkyleneoxyalkylene group" include groups such as methyleneoxymethylene, ethyleneoxymethylene, methyleneoxyethylene, ethyleneoxyethylene, etc.; examples of a preferable "alkylenethioalkylene group" include methylenethiomethylene, ethylenethiomethylene, methylenethioethylene, and ethylenethioethylene; examples of a preferable "alkylene-SO-alkylene group" include methylene-SO-methylene, ethylene-SO-methylene, methylene-SO-ethylene, and ethylene-SO-ethylene; examples of a preferable "alkylene-$SO_2$-alkylene group" include methylene-$SO_2$-methylene, ethylene-$SO_2$-methylene, methylene-$SO_2$-ethylene, and ethylene-$SO_2$-ethylene. Further, an example of "alkylene-N($R_9$)-alkylene group" is lower alkylene-lower alkylamino-lower alkylene. The lower alkylene used herein includes preferably $C_{1-6}$ alkylene, and preferably methylene, ethylene, propylene, and trimethylene; the lower alkylamino includes $C_{1-6}$ alkylamino, and preferably methylamino, ethylamino, propylamino, isopropylamino, and butylamino. Preferable are methylene-methylamino-methylene, ethylene-methylamino-methylene, methylene-methylamino-ethylene, and ethylene-methylamino-ethylene.

"Alkenylene group", represented by L in formula (I), includes $C_{2-6}$ straight- or branched-chain alkenylene having 1 to 3 double bonds. Examples of such an alkenylene group include groups such as vinylene, 1-methylvinylene, propenylene, 1-butenylene, 2-butenylene, 1-pentenylene, 2-pentenylene, etc.

"Alkynylene group", represented by L in formula (I), includes $C_{2-6}$ straight- or branched-chain alkynylene having a single triple bond. Examples of such an alkynylene group include groups such as ethynylene, propynylene, 1-methylpropynylene, 1-butynylene, 2-butynelene, 1-methylbutynelene, 2-methylbutynylene, 1-pentynylene, and 2-pentynylene.

The "alkylene group", "cycloalkylene group", "alkyleneoxyalkylene group", "alkylenethioalkylene group", "alkylene-SO-alkylene group", "alkylene-$SO_2$-alkylene group", "alkylene-N($R_9$)-alkylene group", "alkenylene group" and "alkynylene group" may be substituted. Examples of a substituent include a halogen atom, $C_{1-4}$ lower alkyl, halogenated lower alkyl, $C_{1-4}$ lower alkoxy, halogenated lower alkoxy, hydroxyl, $CF_3$, $CF_3O$, $CHF_2O$, $CF_3CH_2O$, cyano, carboxy, alkoxycarbonyl, amino, acylamino, benzyloxycarbonylamino (Cbz-NH—), alkoxycarbonylamino (e.g., t-butoxycarbonylamino (tBoc-NH—), methoxycarbonylamino, ethoxycarbonylamino, propoxycarbonylamino, isopropoxycarbonylamino, butoxypropoxycarbonylamino, etc.), acyl, etc.

Examples of "heterocyclic group", represented by $R_1$, $R_2$ $R_{14}$ and $R_{15}$, in the compound of the present invention include 4- to 10-membered saturated and unsaturated heterocyclic groups including 1 to 3 identical or different heteroatoms selected from the group consisting of nitrogen atoms, oxygen atoms and sulfur atoms. Specific examples include unsaturated heterocyclic groups such as pyrrolyl, furyl, thiophenyl, thienyl, pyrazolyl, imidazolyl, oxazolyl, isoxazolyl, thiazolyl, isothiazolyl, oxadiazolyl, thiadiazolyl, triazolyl, tetrazolyl, pyranyl, pyridyl, pyridazinyl, pyrimidinyl, pyrazinyl, azepinyl, azocinyl, etc.; partially or wholly reduced groups of the above unsaturated heterocyclic such as azetidinyl, pyrrolidinyl, pyrrolinyl, imidazolidinyl, imidazolinyl, pyrazolidinyl, pirazolinyl, piperidyl, piperazinyl, morpholinyl, thiomorpholinyl, perhydroazepinyl, perhydroazocinyl, 1,4,5,6-tetrahydropyrimidinyl, 1,2,3,6-tetrahydropyridyl, etc.; condensed groups between the above unsaturated heterocyclic ring or condensed groups between a benzene ring and the above unsaturated heterocyclic rings such as indolyl, indolinyl, benzofuranyl, benzothienyl, benzimidazolyl, benzisooxazolyl, benzisoxazolyl, benzothiazolyl, benzisothiazolyl, benzthiophenyl, quinolyl, isoquinolyl, quinazolinyl, quinoxalinyl, benzoxadiazolyl, benzothiadiazolyl, pyrrolopyrrolyl, pyrrolooxazolyl, pyrrolothiazolyl, pyrrolopyridyl, furopyrrolyl, furopyridyl, thienopyrrolyl, thienopyridyl, imidazopyrrolyl, imidazoimidazolyl, imidazooxazolyl, imidazothiazolyl, imidazoisothiazolyl, imidazopyridyl, imidazopyridazinyl, imidazopyrimidinyl, imidazopyrazinyl, oxazooxazolyl, oxazoisoxazolyl, oxazothiazolyl, oxazoisothiazolyl, oxazopyridyl, thiazoxazolyl, thiaozoisoxazolyl, thiazothiazolyl, thiazoisothiazolyl, thiazopyridyl, etc. Preferable examples are azetidinyl, pyrrolidinyl, piperidinyl, morpholinyl, piperazinyl, homopiperazinyl, tetrahydrofuryl, tetrahydrothienyl, tetrahydropyranyl, pyrrolyl, furyl, thienyl, oxazolyl, isoxazolyl, thiazolyl, isothiazolyl, pyrazolyl, pyridyl, pyrimidinyl, indolyl, isoindolyl, benzofuranyl, benzoxazolyl, benzothiazolyl, benzothiophenyl, quinolyl, and benzisoisoxaril.

These heterocyclic rings may have 1 to 3 substituents at suitable positions, and examples of substituent include a halogen atom, C14 lower alkyl, halogenated lower alkyl, $C_{1-4}$ lower alkoxy, halogenated lower alkoxy, hydroxyl, $CF_3$, $CF_3O$, $CHF_2O$, $CF_3CH_2O$, aryl (preferably phenyl), halogenated aryl, cyano, carboxy, alkoxycarbonyl, etc.

Preferable heterocyclic rings in $R_1$ and $R_2$ are pyrazolyl (e.g., pirazol-4-yl), pyridyl (e.g., pyridin-3-yl, pyridin-4-yl), 2-methylpyrazolyl, quinolyl (quinolin-3-yl), thiazolyl (e.g., thiazol-5-yl), 2,4-dimethylthiazolyl (e.g., 2,4-dimethylthiazol-5-yl), and benzothiophenyl (e.g., benzothiophen-2-yl). Further, preferable heterocyclic rings in $R_{14}$ and $R_{15}$ are thiophenyl (preferably thienyl); or thiophenyl (preferably thienyl) substituted with $C_{1-4}$ alkyl, carboxy, alkoxycarbonyl (e.g., t-butoxycarbonyl) or aryl (preferably phenyl).

Examples of "heterocyclic-alkyl group", represented by $R_1$, $R_2$, $R_{14}$ and $R_{15}$ in the compound of the present invention include those wherein a hydrogen atom in the above heterocyclic rings is substituted with alkyl, and examples of "heterocyclic-alkoxy group", represented by $R_1$ and $R_2$, include those wherein a hydrogen atom in the above heterocyclic rings is substituted with alkoxy. "Alkyl group" and "alkoxy group" used herein are those described earlier.

Examples of "alkoxycarbonyl group", represented by $R_1$, $R_2$ and B in the formula (I), include, for example, t-butoxycarbonyl, methoxycarbonyl, ethoxycarbonyl, propoxycarbonyl, isopropoxy carbonyl, butoxypropoxy carbonyl, etc.

A specific example of "fluorenyl group" represented by $R_{16}$ and $R_{16}'$ is a 9H-fluoren-9-yl group as shown in Example 36.

Examples of "bicycloalkyl group" represented by $R_{14}$ to $R_{16}$ and $R_{16}'$ in the compound of the present invention include typically $C_{5-30}$ substituted or unsubstituted bicycloalkyl, i.e., a monovalent group wherein a hydrogen atom is removed from $C_{5-30}$ bicycloalkane. Examples include bicycle[1,2,2] heptan-2-yl, bicycle[2,2,2]octan-3-yl, etc. Further, examples of "bicycloalkenyl group" represented by $R_{14}$ to $R_{16}$ and $R_{16}$, include typically $C_{3-30}$ substituted or unsubstituted bicycloalkenyl, i.e., a monovalent group wherein a hydrogen atom is removed from $C_{3-30}$ bicycloalkane having a single double bond. Examples include bicyclo[2,2,1]hept-2-en-1-yl, bicyclo[2,2,2]oct-2-en-4-yl, etc.

The aromatic or heterocyclic carboxylic acids of the present invention (wherein substituent B is a carboxy group, hereinafter referred to the same), esters thereof (wherein substituent B is an alkoxycarbonyl group, hereinafter referred to the same), or bioisosters thereof (wherein substituent B is other than a carboxy group, hereinafter referred to the same), represented by the formula (I) preferably encompass thiophen-3-carboxylic acid, an ester or a bioisoster thereof represented by the following formula (II), and benzoic acid, an ester thereof or a bioisoster thereof represented by another following formula (III)

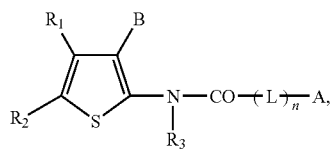

(II)

wherein $R_1$, $R_2$, $R_3$, L, B, n and A are defined as above

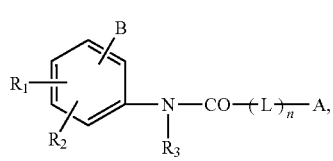

(III)

wherein $R_1$, $R_2$, $R_3$, L, B, n and A are defined as above.

Thiophen-3-carboxylic acid, an ester and a bioisoster thereof (II) herein each refer to a compound having a structure wherein a hydrogen atom at the third position of thiophene is substituted with a carboxy group or an alkoxycarbonyl group represented by B, or substituted with a bioisoster group thereof. Benzoic acid, an ester or a bioisoster thereof (III) refers to a compound having a structure wherein a hydrogen atom (at the ortho, meta, or para position) of benzene is substituted with a carboxy group represented by substituent B, or substituted with a bioisoster group thereof.

(1-1) Thiophen-3-Carboxylic Acid, Ester or Bioisoster Thereof (II)

The above thiophen-3-carboxylic acid, an ester or a bioisoster thereof (II) preferably include;

(II-1) thiophen-3-carboxylic acid, an ester or a bioisoster thereof, represented in the above formula (II), wherein $R_3$ is a hydrogen atom, n is 1, and L is substituted or unsubstituted alkylene, or (II-2) thiophen-3-carboxylic acid, an ester or a bioisoster thereof, represented in the above formula (III), wherein $R_3$ is a hydrogen atom, n is 1, and L is substituted or unsubstituted alkyleneoxyalkylene.

(i) Thiophen-3-Carboxylic Acid, Ester or Bioisoster Thereof (II-1)

Preferable examples of thiophen-3-carboxylic acid, an ester or a bioisoster thereof (II-1) are compounds represented by the following formula, wherein L is a butylene group.

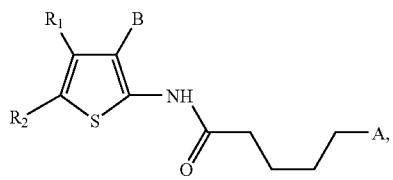

wherein B is carboxy, alkoxycarbonyl, or a bioisoster of carboxylic acid, i.e., 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl.

The groups represented by $R_1$ and $R_2$ in the compound (II-1) herein are defined as above, but preferably, the same or different, a hydrogen atom, lower alkyl, substituted or unsubstituted aryl, and substituted or unsubstituted heterocyclic rings. Examples of lower alkyl include preferably $C_{1-4}$ alkyl, more preferably methyl and ethyl; examples of aryl preferably include phenyl; and examples of heterocyclic ring include preferably pyridyl, more preferably pyridin-3-yl and pyridin-4-yl. Preferable $R_1$ and $R_2$ are, the same or different, each represent a hydrogen atom or phenyl.

A is also defined as above, but is preferably —$COR_{10}$, —$N(R_{11})$—$COR_{12}$, or a group represented by the following formula

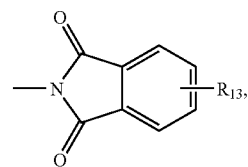

wherein $R_{10}$ to $R_{13}$ are defined as above.

$R_{10}$ of the group —$COR_{10}$ herein is defined as above, but is preferably —$N(R_{14})$ ($R_{15}$), and a group represented by the following formula:

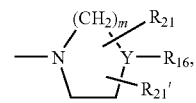

wherein $R_{14}$ to $R_{16}$, m, $R_{21}$ and $R_{21}'$ are defined as above.

Preferable examples of the group represented by the above formula are those wherein m is 2; Y is CH or a nitrogen atom; $R_{16}$ is substituted or unsubstituted alkyl, aryl (preferably phenyl) or aralkyl; and $R_{21}$ and $R_{21}'$ is each a hydrogen atom or substituted or unsubstituted alkyl. Aryl herein is preferably phenyl; aralkyl is preferably diphenylalkyl, and more preferably diphenylmethyl; aralkyl is preferably methyl. Further, examples of a substituent of alkyl, aryl or aralkyl herein include a halogen atom, alkyl, alkoxy, hydroxyl, carboxy or a salt thereof, and alkoxycarbonyl, with halogen atom being preferable.

Preferable examples of —$N(R_{14})$ ($R_{15}$) include groups wherein $R_{14}$ is a hydrogen atom and $R_{15}$ is substituted or unsubstituted aryl (preferably phenyl). Examples of substituent herein include a halogen atom, $CF_3$, benzoyl, alkyl, alkoxy, hydroxyl, carboxy, alkoxycarbonyl, unsaturated phenyl or a salt thereof, with a halogen atom being preferable.

Preferable examples of —$N(R_{11})$—$COR_{12}$ are groups wherein $R_{11}$ is a hydrogen atom and $R_{12}$ is a substituted or unsubstituted aryl (preferably phenyl). Examples of a substituent herein include a halogen atom, alkyl, alkoxy, hydroxyl, carboxy, alkoxycarbonyl or a salt thereof, and with carboxy being preferable.

Further, preferable examples of the group represented by the following formula are those wherein $R_{13}$ is a hydrogen atom.

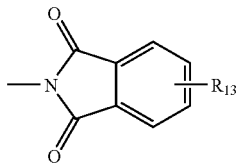

Specific examples of thiophen-3-carboxylic acid, an ester or a bioisoster thereof (II-1) represented by the above formula include the following compounds:
2-(6-oxo-6-(4-phenylpiperidin-1-yl)hexanamido)-4-phenylthiophen-3-carboxylic acid (Example 5),
2-(6-(4-chlorophenylamino)-6-oxo-hexanamido)-4-phenylthiophen-3-carboxylic acid (Example 6),
2-(5-(1,3-dioxoisoindolin-2-yl)pentanamido)-4-phenylthiophen-3-carboxylic acid (Example 16), and
2-(5-(2-carboxybenzamido)pentanamido)-4-phenylthiophen-3-carbon (deesterified moiety of the compound prepared in Example 17).

(ii) Thiophen-3-Carboxylic Acid, Ester or Bioisoster Thereof (II-2)

Preferable examples of thiophen-3-carboxylic acid, an ester or a bioisoster thereof (II-2) include compounds represented by the following formula, wherein L is a methyleneoxymethylene group

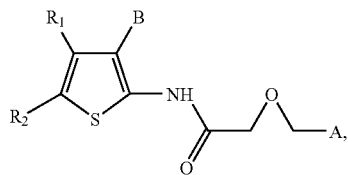

wherein B is carboxy, alkoxycarbonyl, or a bioisoster of carboxy, i.e., alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl.

The groups represented by $R_1$ and $R_2$ in the compound (II-2)(preferably those represented by the above formula) herein are defined as above, but each preferably represent, the same or different, a hydrogen atom, alkyl, substituted or unsubstituted aryl, and a substituted or unsubstituted heterocyclic ring. Examples of alkyl include preferably $C_{1-4}$ alkyl, and more preferably methyl and ethyl; examples of aryl preferably include phenyl; examples of heterocyclic ring include preferably pyridyl, and more preferably pyridin-3-yl and pyridin-4-yl; and thiazolyl, and more preferably thiazol-5-yl. Examples of a substituent of aryl and heterocyclic ring herein include a halogen atom, alkyl, alkoxy, hydroxyl, carboxy, alkoxycarbonyl or a salt thereof, with alkyl being preferable.

A is also defined as above, but is preferably a group represented by —$COR_{10}$.

$R_{10}$ of the group —$COR_{10}$ herein is defined as above, but is preferably —$N(R_{14})(R_{15})$, and a group represented by the following formula:

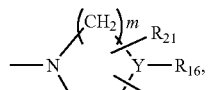

wherein $R_{14}$ to $R_{16}$, m, $R_{21}$ and $R_{21}'$ are defined as above

Preferable examples of the group represented by the above formula include those wherein m is 2; Y is a nitrogen atom; $R_{16}$ is substituted or unsubstituted aryl or aralkyl; and $R_2$, and $R_{21}'$ each represent a hydrogen atom or substituted or unsubstituted alkyl. An example of aryl is preferably phenyl; and examples of aralkyl are preferably diphenylalkyl, and more preferably diphenylmethyl. Examples of a substituent herein include a halogen atom, alkyl, alkoxy, hydroxyl, carboxy, alkoxycarbonyl or a salt thereof.

Preferable —$N(R_{14})(R_{15})$ are groups wherein $R_{14}$ is a hydrogen atom, and $R_{15}$ is substituted or unsubstituted thienyl or aralkyl. Examples of a substituent herein include a halogen atom, alkyl, alkoxy, aryl (preferably phenyl), hydroxyl, carboxy, alkoxycarbonyl or a salt thereof.

Specific examples of thiophen-3-carboxylic acids, esters or bioisosters thereof (II-2) represented by the above formula include the following compounds:
2,2'-(oxybis((1-oxo-2,1-ethanediyl)imino))bis(5-methyl-4-phenylthiophen-3-carboxylic acid) (Example 7),
2,2'-(oxybis((1-oxo-2,1-ethanediyl)imino))bis(5-phenylthiophen-3-carboxylic acid) (Example 8),
2,2'-(oxybis((1-oxo-2,1-ethanediyl)imino))bis-(4-phenylthiophen-3-carboxylic acid) (Example 9),
2-(2-(2-(3-(tert-butoxycarbonyl)-5-methyl-4-phenylthiophen-2-ylamino)-2-oxoethoxy)acetamido)-5-methyl-4-phenylthiophen-3-carboxylic acid (Example 10),
2-(2-(2-(4-benzhydryl piperazin-1-yl)-2-oxoethoxy)acetamido)-5-methyl-4-(pyridin-4-yl)thiophen-3-carboxylic acid (Example 13),
2-(2-(2-(4-benzhydryl piperazin-1-yl)-2-oxoethoxy)acetamido)-5-methyl-4-(pyridin-3-yl)thiophen-3-carboxylic acid (Example 14),
2-(2-(2-(4-benzhydryl piperazin-1-yl)-2-oxoethoxy)acetamido)-5-methyl-4-phenylthiophen-3-carboxylic acid (desalted moiety of the compound prepared in Example 15),
2-(2-(2-(4-benzhydrylpiperazin-1-yl)-2-oxoethoxy)acetamido)-5-(2,4-dimethylthiazol-5-yl)benzoic acid (desalted moiety of the compound prepared in Example 81),
2-(2-(2-(4-benzhydrylamino)-2-oxoethoxy)acetamido)-5-methyl-4-phenylthiophen-3-carboxylic acid (Example 82), and
2-(2-(4-benzhydrylpiperazin-1-yl)-2-oxoethoxy)-N-(5-methyl-4-phenyl-3-(1H-tetrazol-5-yl)thiophen-2-yl)acetamido (Example 90).

Thiophen-3-carboxylic acids of the present invention desirably do not include thiophen-3-carboxylic acids disclosed in the specification filed as PCT/JP2007/050666. The disclosed thiophen-3-carboxylic acids are the compounds (1') represented by the following general formula:

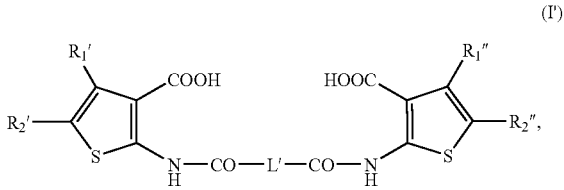

wherein $R_1'$ and $R_1''$, the same or different, each represent a hydrogen atom, substituted or unsubstituted phenyl or thienyl, or $C_{1-6}$ straight- or branched-chain alkyl; $R_2'$ and $R_2''$, the same or different, each represent a hydrogen atom, substituted or unsubstituted phenyl, or $C_{1-6}$ straight- or branched-chain alkyl, or halogen atom. $R_1'$ and $R_2'$, and $R_1''$ and $R_2''$, may join together to form a 5- to 6-membered ring, respectively. L' represents $C_{1-7}$ straight- or branched-chain alkylene, alkenylene, or alkynylene, or $C_{3-8}$ cycloalkylene.

Examples of $C_{1-6}$ straight- or branched-chain alkyl include groups such as methyl, ethyl, n-propyl, isopropyl, n-butyl, isobutyl, sec-butyl, ter-butyl, pentyl, isopentyl, neopentyl, ter-pentyl, hexyl, isohexyl, neohexyl, and ter-hexyl.

In the above formula (I'), $R_1'$ and $R_2'$, and $R_{11}''$ and $R_2''$, together with the carbon to which they bound, may form a 5- or 6-membered ring, respectively. Examples of such a 5- or 6-membered ring are cyclohexane, cyclohexene, 1,3-cyclohexadiene, cyclopentane, cyclopentene, and benzene.

Examples of a substituent of phenyl or thienyl include carboxy, amino and heterocyclic groups, and halogen atom.

L' is $C_{1-7}$ straight- or branched-chain alkylene, alkenylene, or alkynylene; $C_{3-8}$ cycloalkylene. Preferable are $C_{2-5}$ straight- or branched-chain alkylene, $C_6$ cycloalkyelene (cyclohexanediyl), and vinylene. Specific examples of $C_{2-5}$ straight- or branched-chain alkylene include groups such as ethylene, propylene, butylene, pentylene, and —$CH_2C(CH_3)_2CH_2$—. Preferable are butylene, —$CH_2C(CH_3)_2CH_2$—, and cyclohexanediyl.

Thiophen-3-carboxylic acids that are excluded from thiophen-3-carboxylic acids, esters or bioisosters thereof (II) of the present invention are the following specific compounds.

(a) 2-[3-(3'-carboxy-4'-phenylthiophen-2'-ylcarbamoyl)-pentanoylamino]-4-phenylthiophen-3-carboxylic acid, (b) 2-[5-(3'-carboxy-4'-(2-thienyl)thiophen-2'-ylcarbamoyl)-pentanoylamino]-4-(2-thienyl)thiophen-3-carboxylic acid, (c) 2-[3-(3'-carboxy-4',5',6',7'-tetrahydro-benzo[b]thiophen-2'-ylcarbamoyl)-pentanoylamino]-4,5,6,7-tetrahydro-benz[b]thiophen-3-carboxylic acid, (d) 2-[5-(3'-carboxy-4'-isobutylthiophen-2'-ylcarbamoyl)-pentanoylamino]-4-isobutylthiophen-3-carboxylic acid, (e) 2-[3-(3'-carboxy-4',5',6',7'-tetrahydro[b]thiophen-2'-ylcarbamoyl)-propanoylamino]-4,5,6,7-tetrahydro-benzo[b]thiophen-3-carboxylic acid, (h) 2-[4-(3'-carboxy-4'-(2-thienyl)thiophen-2'-ylcarbamoyl)-3,3-dimethylbutyrylamino]-4-(2-thienyl)thiophen-3-carboxylic acid, (j) 2-[4-(3'-carboxy-4',5',6',7'-tetrahydro-benzo[b]thiophen-2-ylcarbamoyl)-3,3-dimethyl]-butyrylamino)-4,5,6,7-tetrahydro-benzo[b]thiophen-3-carboxylic acid (k) 2-[5-(3'-carboxy-4'-phenylthiophen-2'-ylcarbamoyl)-(3,3-dimethyl))butylamino]-4-phenyl-thiophen-3-carboxylic acid (o) 2-[5-(3'-carboxy-4'-(p-chlorophenyl)thiophen-2'-ylcarbamoyl)-pentanoylamino]-4-(p-chlorophenyl)thiophen-3-carboxylic acid (p) 2-[4-(3'-carboxy-4'-isobutylthiophen-2'-ylcarbamoyl)-butyrylamino]-4-isobutylthiophen-3-carboxylic acid (q) 2-[4-(3'-carboxy-4'-isobutylthiophen-2'-ylcarbamoyl)-3,3-dimethylbutyrylamino-dimethylbutyrylamino]-4-isobutylthiophen-3-carboxylic acid (r) 2-[6-(3'-carboxyl-4'-phenylthiophen-2'-ylcarbamoyl)-hexanoylamino]-4-phenylthiophen-3-carboxylic acid (s) 2-[5-(3'-carboxy-5'-methyl-4'-phenylthiophen-2'-ylcarbamoyl)-pentanoylamino]-5-methyl-4-phenylthiophen-3-carboxylic acid (t) 2-[5-(3'-carboxy-5'-phenylthiophen-2'-ylcarbamoyl)-pentanoylamino]-5-phenylthiophen-3-carboxylic acid (u) 2-[5-(3'-carboxy-5'-chlorothiophen-2'-ylcarbamoyl)-pentanoylamino]-5-chlorothiophen-3-carboxylic acid (v) 2-[4-(3'-carboxy-4'-phenylthiophen-2'-ylcarbamoyl)-cyclohexylcarbonylamino]-4-phenylthiophen-3-carboxylic acid (w) 2-[5-(3'-carboxy-5'-isopropyl-4'-methylthiophen-2'-ylcarbamoyl)-pentanoylamino]-4-isobutylthiophen-3-carboxylic acid (x) 2-[3-(3'-carboxy-4'-isobutylthiophen-2'-ylcarbamoyl)-propanoylamino]-4-isobutylthiophen-3-carboxylic acid (y) 2-[5-(3'-carboxy-4'-isopropylthiophen-2'-ylcarbamoyl)-pentanoylamino]-4-isopropyl-o-phen-3-carboxylic acid (z) 2-[5-(3'-carboxy-5'-methylthiophen-2'-ylcarbamoyl)-pentanoylamino]-5-methylthiophen-3-carboxylic acid (zz) 2-[5-(3'-tert-butoxycarbonyl-5'-methylthiophen-2'-ylcarbamoyl)-pentanoylamino]-5-methylthiophen-3-carboxylic acid.

1-2. Benzoic Acid, Ester or Bioisoster Thereof (III)

The above-mentioned benzoic acids, esters and bioisosters thereof (III) preferably include:

(III-1) A benzoic acid, an ester or a bioisoster thereof represented by the above formula (III), wherein $R_3$ is a hydrogen atom, n is 1, and L is substituted or unsubstituted alkylene (some carbon atoms within alkylene may form cycloalkyl), (III-2) a benzoic acid, an ester or a bioisoster thereof represented by the above formula (III), wherein $R_3$ is a hydrogen atom, n is 1, and L is substituted or unsubstituted alkyleneoxyalkylene;

(III-3) A benzoic acid, an ester or a bioisoster thereof represented by the above formula (III), wherein $R_3$ is a hydrogen atom, n is 1, and L is substituted or unsubstituted alkylene-N($R_9$)-alkylene;

(III-4) A benzoic acid, an ester or a bioisoster thereof represented by the above formula (III), wherein $R_3$ is a hydrogen atom, n is 1, and L is substituted or unsubstituted alkylenethioalkylene, alkylene-SO-alkylene or alkylene-$SO_2$-alkylene;

(III-5) A benzoic acid, an ester or a bioisoster thereof represented by the above formula (III), wherein $R_3$ is a hydrogen atom, n is 1, and L is substituted or unsubstituted cycloalkylene; and (III-6) A benzoic acid, an ester or a bioisoster thereof represented by the above formula (III), wherein $R_3$ is a hydrogen atom, and n is 0.

(i) Benzoic Acid, Ester or Bioisoster Thereof (III-1)

Benzoic acid, an ester or a bioisoster thereof (III-1) is preferably a compound represented by the formula below:

(III-1-1) A compound (III-1), wherein L is butylene;

(III-1-2) A compound (III-1), wherein L is substituted propylene; or (III-1-3) A compound (III-1), wherein L is alkylene and some carbon atoms within alkylene form a cycloalkyl ring.

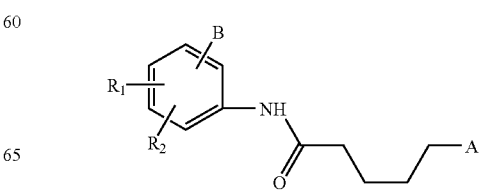

(III-1-1)

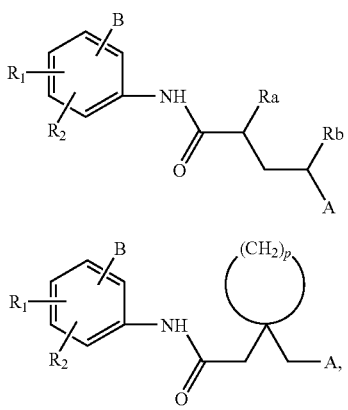

wherein B is carboxy or a bioisoster thereof, i.e., alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl. Wherein $R_1$, $R_2$ and A are defined as above. Ra and Rb are, the same or different, each represent a hydrogen atom or a substituent; and p is an integer of 2 to 5.

B, $R_1$ and $R_2$ may be located at any of the ortho, meta or para positions of a benzene ring to which an imino group is bound. The above compounds (III-1) to (III-3) preferably have B at the ortho position, and $R_1$ and $R_2$ each at the meta position and para position of the above benzene ring.

$R_1$ and $R_2$ herein are defined as above, but are preferably, the same or different, a hydrogen atom, halogen atom, alkyl, substituted or unsubstituted aryl, and substituted or unsubstituted heterocyclic ring. Examples of a halogen atom include preferably a chloride atom or fluoride atom, and more preferably a chloride atom; examples of alkyl include preferably $C_{1-4}$ alkyl, more preferably methyl and ethyl; examples of an aryl include preferably phenyl; and examples of a heterocyclic ring include preferably pyridyl, and more preferably pyridin-3-yl and pyridin-4-yl. Preferable are hydrogen and halogen atom.

A is also defined as above, but, is preferably a group represented by —$COR_{10}$, —$N(R_{11})$—$CONH$—$R_{12}$, or —$N(R_{11})$—$SO_2$—$R_{12}$.

$R_{10}$ of the group represented by —$COR_{10}$ herein is defined as above, but, is preferably a group represented by —$N(R_{14})$ ($R_{15}$) and a group represented by the following formula.

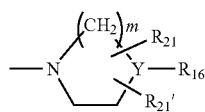

wherein $R_{14}$ to $R_{16}$, m, $R_{21}$ and $R_{21}'$ are defined as above.

Preferable examples of the group represented by the above formula include those wherein m is 2: Y is a nitrogen atom; $R_{16}$ is substituted or unsubstituted aryl or aralkyl; and $R_{21}$ and $R_{21}'$ each represent a hydrogen atom or substituted or unsubstituted alkyl, with a hydrogen atom being preferable. An example of aryl is preferably phenyl; and examples of aralkyl are preferably diphenylalkyl, and more preferably diphenylmethyl. Examples of a substituent herein include a halogen atom, alkyl, alkoxy, hydroxyl, carboxy or a salt or ester thereof, and alkoxycarbonyl, with halogen being preferable.

Examples of —$N(R_{14})$ ($R_{15}$) preferably include a group wherein $R_{14}$ is a hydrogen atom or alkyl; and $R_{15}$ is a substituted or unsubstituted thienyl or aryl (preferably phenyl).

Substituents of aryl herein include, for example, a halogen atom, $CF_3$, benzoyl, alkyl, alkoxy, hydroxyl, carboxy, alkoxycarbonyl, unsubstituted phenyl, or a salt thereof, and with a halogen atom being preferable. Further, substituents of thienyl herein include, for example, aryl, halogen atom, alkyl, alkoxy, hydroxyl, carboxy, alkoxycarbonyl, and a salt thereof. Preferable among these are unsubstituted aryl (particularly phenyl), carboxy, alkoxycarbonyl, and alkyl (particularly isopropyl), or a salt thereof.

Preferable —$N(R_{11})$—$CONH$—$R_{12}$ and —$N(R_{11})$—$SO_2$—$R_{12}$ include groups wherein $R_{11}$ is a hydrogen atom and $R_{12}$ is substituted or unsubstituted aryl, preferably phenyl. Examples of a substituent herein include a halogen atom, alkyl, alkoxy, hydroxyl, carboxy or a salt thereof, and alkoxycarbonyl, with a halogen atom being preferable.

In the benzoic acid, an ester or a bioisoster thereof (III-1-1), A is preferably a group represented by —$COR_{10}$, —$N(R_{11})$—$CONH$—$R_{12}$, or —$N(R_{11})$—$SO_2$—$R_{12}$. —$COR_{10}$ herein is defined as above, but preferably is a group wherein $R_{10}$ is —$N(R_{14})$ ($R_{15}$). $R_{14}$ herein is preferably a hydrogen atom; $R_{15}$ is preferably substituted or unsubstituted aryl or preferably phenyl, or substituted or unsubstituted heterocyclic ring or preferably thienyl. The substituents are as described above.

In the benzoic acid, an ester or a bioisoster thereof (III-1-2), A is preferably a group represented by —$COR_{10}$, and more preferably is a group wherein $R_{10}$ is —$N(R_{14})$ ($R_{15}$), or —$COR_{10}$ having a group represented by the following formula:

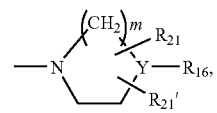

m, Y, $R_{16}$, $R_{21}$ and $R_{21}'$ are defined as above, but preferably m is 2; Y is a nitrogen atom; and $R_{16}$ is substituted or unsubstituted aryl, preferably phenyl, or substituted or unsubstituted aralkyl, preferably diphenylalkyl; $R_{21}$ and $R_{21}'$ each represent a hydrogen atom. A preferable example of a substituent herein is a halogen atom.

A preferable group represented by —$N(R_{14})$ ($R_{15}$) is a group wherein $R_{14}$ is a hydrogen atom or alkyl: and $R_{15}$ is substituted or unsubstituted aryl or preferably phenyl. Substituents of aryl herein include, for example, a halogen atom, $CF_3$, benzoyl, alkyl, alkoxy, hydroxyl, carboxy, alkoxycarbonyl, unsubstituted phenyl, and a salt thereof, with halogen atom being preferable.

In the benzoic acid, an ester or a bioisoster thereof (III-1-2), a substituent Ra or Rb of propylene is, the same or different, each a hydrogen atom, or amino group or amino group protected with a protecting group. A wide variety of protecting groups known as amino-protecting group can be used herein. Examples include a benzyloxycarbonyl group (Cbz group), tert-butyloxycarbonyl (tBoc group), fluorenylmethoxycarbonyl (Fmoc group), alkoxycarbonyl (e.g., groups such as methoxycarbonyl, ethoxycarbonyl, propoxycarbonyl, isopropoxycarbonyl, butoxycarbonyl), and acyl group.

In the benzoic acid, an ester or a bioisoster thereof (III-1-3), A is preferably a group represented by —$COR_{10}$, and more preferably is —$COR_{10}$ wherein $R_{10}$ is a group represented by the following formula:

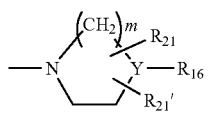

m, Y, $R_{16}$, $R_{21}$ and $R_{21}'$ are defined as above, but preferably m is 2; Y is a nitrogen atom; and $R_{16}$ is substituted or unsubstituted aryl or preferably phenyl, or substituted or unsubstituted aralkyl, preferably diphenylalkyl; $R_{21}$ and $R_{21}'$ are each a hydrogen atom. A preferable example of a substituent herein is a halogen atom.

Further, in the benzoic acid, an ester or a bioisoster thereof (III-1-3), examples of a cycloalkyl ring include a cyclopropane ring (in the formula (III-1-3), p is 2), cyclobutane ring (in the formula (III-1-3), p is 3), cyclopentene ring (in the formula (III-1-3), p is 4) and cyclohexane ring (in the formula (III-1-3), p is 5), with a cyclohexane ring being preferable.

B, $R_1$ and $R_2$ can be located at any of the ortho, meta, and para positions within the benzene ring.

Specific examples of benzoic acids, esters or bioisosters thereof (III-1) of the present invention represented by the above formula include the following compounds:

(III-1-1) Benzoic Acid, Ester or Bioisoster Thereof
2-(6-(3-(tert-butoxycarbonyl)-4-phenylthiophen-2-ylamino)-6-oxo-hexanamido)benzoic acid (desalted moiety of the compound prepared in Example 1),
2-(6-(3-(tert-butoxycarbonyl)-4-phenylthiophen-2-ylamino)-6-oxo-hexanamido)-5-chlorobenzoic acid (desalted moiety of the compound prepared in Example 2),
2-(6-oxo-6-(4-phenylthiophen-2-ylamino)hexanamido)benzoic acid (Example 3),
2-(6-(2-carboxy-4-chlorophenylamino)-6-oxo-hexanamido)-4-phenylthiophen-3-carboxylic acid (Example 4),
2-(6-(3-(tert-butoxycarbonyl)-4-isopropylthiophen-2-ylamino)-6-oxo-hexanamido)benzoic acid (desalted moiety of the compound prepared in Example 11),
2-(6-(4-isopropylthiophen-2-ylamino)-6-oxo-hexanamido) benzoic acid (Example 12),
5-chloro-2-(6-(4-chlorophenylamino)-6-oxo-hexanamido) benzoic acid (Example 27),
5-chloro-2-(5-(3-(4-chlorophenylureido)pentanamido)benzoic acid (Example 60), and
5-chloro-2-(5-(4-chlorophenylsulfonamido)pentanamido) benzoic acid (Example 61).

(III-1-2) Benzoic Acid, Ester or Bioisoster Thereof
2-(2-(benzyloxycarbonylamino)-5-(4-chlorophenylamino)-5-oxopentanamido)-5-chlorobenzoic acid (Example 18),
2-(2-(benzyloxycarbonylamino)-5-((4-chlorophenyl)(methyl)amino)-5-oxopentanamido)-5-chlorobenzoic acid (Example 19),
2-(2-(benzyloxycarbonylamino)-5-oxo-5-(4-phenylpiperazin-1-yl)pentanamido)-5-chlorobenzoic acid (Example 20),
2-(5-(4-benzhydryl piperazin-1-yl)-2-(benzyloxycarbonylamino)-5-oxopentanamido)-5-chlorobenzoic acid (desalted moiety of the compound prepared in Example 21),
2-(5-(4-benzhydryl piperazin-1-yl)-4-(benzyloxycarbonylamino)-5-oxopentanamido)-5-chlorobenzoic acid (Example 22),
2-(5-(4-benzhydryl piperazin-1-yl)-2-(tert-butoxycarbonylamino)-5-oxopentanamido)-5-chlorobenzoic acid (Example 23),
2-(2-amino-5-(4-benzhydryl piperazin-1-yl)-5-oxopentanamido)-5-chlorobenzoic acid (Example 24), and
2-(5-(4-benzhydrylpiperazin-1-yl)-5-oxopentanamido)-5-chlorobenzoic acid (Example 80).

(III-1-3) Benzoic acid, Ester or Bioisoster Thereof
2-(2-(1-(2-(4-benzhydrylpiperazin-1-yl)-2-oxoethyl)cyclohexyl)acetamido)-5-chlorobenzoic acid (desalted moiety of the compound prepared in Example 93)

(ii) Benzoic Acid, Ester or Bioisoster Thereof (III-2)
Preferable benzoic acids, esters or bioisosters thereof (III-2) are the compounds represented by the following formula wherein $R_3$ is a hydrogen atom and L is methyleneoxymethylene in the formula (III),

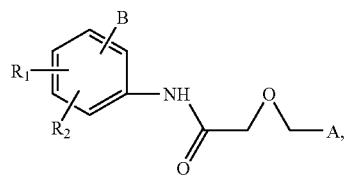

wherein B is carboxy, alkoxycarbonyl, or a bioisoster of carboxy, i.e., 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl. $R_1$, $R_2$ and A are defined as above.

B, $R_1$ and $R_2$ may be located at any of the ortho, meta or para positions of a benzene ring to which an imino group is bound. It is preferable, but not limited, that B be located at the ortho position, and $R_1$ and $R_2$ at the meta position and para position respectively, within the above benzene ring.

A preferable example of such a compound is a compound wherein A is —$COR_{10}$, and more preferable are the following compounds:
(III-2-1) a compound wherein $R_{10}$ of —$COR_{10}$ is —$N(R_{14})(R_{15})$, and
(III-2-2) a compound wherein $R_{10}$ of —$COR_{10}$ is a group represented by the following formula:

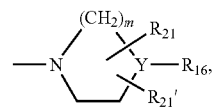

wherein Y, $R_{16}$, m, $R_{21}$ and $R_{21}'$ are defined as above.

A preferable group represented by —$N(R_{14})(R_{15})$ is a group wherein $R_{14}$ is a hydrogen atom or aryl (preferably phenyl); and $R_{15}$ is substituted or unsubstituted aryl, aralkyl, thienyl or adamantyl. Aryl herein is preferably phenyl, and aralkyl herein is preferably diphenylalkyl (more preferably diphenylmethyl), and mononaphthylalkyl (more preferably mononaphthylmethyl). Examples of a substituent of aryl or aralkyl include a halogen atom, $CF_3$, benzoyl, alkyl, alkoxy, hydroxyl, carboxy, alkoxycarbonyl, unsubstituted phenyl, and a salt thereof. More preferable examples of a substituent of aryl include a halogen atom, benzoyl, and carboxy, alkoxycarbonyl, unsubstituted phenyl, and salt thereof. More preferable examples of a substituent of aralkyl include a halogen atom, $CF_3$, carboxy, alkoxycarbonyl, or a salt thereof. Further, examples of a substituent of thienyl include a halogen atom, phenyl, alkyl, alkoxy, hydroxyl, carboxy, alkoxycarbonyl, or a salt thereof. Preferable are a halogen atom, alkyl, phenyl and carboxy, alkoxycarbonyl, or a salt thereof.

In the above formula, Y, m, $R_{16}$ and $R_{21}$ and $R_{21}'$ are defined as above, but preferable are:

(a) a compound wherein m is 2; Y is a nitrogen atom; $R_{16}$ is substituted or unsubstituted aryl, preferably phenyl, substituted or unsubstituted fluorenyl, preferably fluoren-9-yl, or substituted or unsubstituted aralkyl, preferably diphenylmethyl; and $R_{21}$ and $R_{21}'$ are, the same or different, each a hydrogen atom, aralkyl, preferably $C_{1-4}$ alkyl, and more preferably methyl; and examples of a substituent herein include a halogen atom, alkyl, alkoxy, hydroxyl, carboxy, alkoxycarbonyl, and a salt thereof, with halogen being preferable;

(b) is a compound wherein m is 2; Y is CH—O—; $R_{16}$ is substituted or unsubstituted aralkyl or preferably diphenylmethyl; and $R_{21}$ and $R_{21}'$ are each a hydrogen atom; and examples of a substituent herein include a halogen atom, alkyl, alkoxy, hydroxyl, carboxy, alkoxycarbonyl, and a salt thereof, with halogen being preferable; and (c) is a compound wherein m is 2; Y is $C(R_{16}')$—; $R_{16}$ is substituted or unsubstituted aryl or preferably phenyl; and $R_{16}'$ is a substituted or unsubstituted aryl or preferably phenyl; and examples of a substituent herein include a halogen atom, alkyl, alkoxy, hydroxyl, carboxy, alkoxycarbonyl, and a salt thereof, with halogen being preferable.

In the compound of (III-2-1), $R_1$ and $R_2$ are defined as above, but preferably are, the same or different, each a hydrogen atom, halogen atom, substituted or unsubstituted aryl, or a substituted or unsubstituted heterocyclic group. Preferable aryl is phenyl; and preferable heterocyclic groups are pyridyl, are more preferably pyridin-3-yl and pyridin-4-yl. Examples of a substituent herein include halogen, alkyl, alkoxy, cyano, alkyl-substituted amino, morpholino, with morpholin-4-yl being preferable.

In the compound of (III-2-2), $R_1$ and $R_2$ are defined as above, but preferably, the same or different, each present a hydrogen atom, halogen atom, substituted or unsubstituted alkyl, substituted or unsubstituted alkoxy, substituted or unsubstituted aryl or substituted or unsubstituted heterocyclic ring. Examples of alkyl include preferably $C_{1-4}$ alkyl, and more preferably methyl and isobutyl; examples of alkoxy include preferably $C_{1-4}$ alkoxy, and more preferably methoxy and isobutoxy; examples of aryl include preferably phenyl; examples of a heterocyclic ring include preferably pyridyl, and more preferably pyridin-3-yl and pyridine-4-yl; pyrazolyl, and more preferably pirazol-4-yl; quinolyl, and more preferably quinolin-3-yl; and benzothiophenyl, and more preferably benzothiophen-2-yl. Examples of a substituent herein include a halogen atom, alkyl, alkoxy, cyano, alkyl-substituted amino, aryl (preferably phenyl), and morpholino (preferably morpholin-4-yl).

Specific examples of the benzoic acid, an ester or a bioisoster thereof (III-2-1) or (III-2-2) represented by the above formula include the following compounds:

(III-2-1) Carboxylic Acids, Esters or Bioisosters Thereof 2-(2-(2-(4-Chloro-2-(methoxycarbonyl)phenylamino)-2-oxoethoxy)acetamido)-5-methyl-4-phenylthiophen-3-carboxylic acid (Example 33), 2-(2-(2-(3-(tert-butoxycarbonyl)-5-methyl-4-phenylthiophen-2-ylamino)-2-oxoethoxy)acetamido)-5-chlorobenzoic acid (Example 38), 2-(2-(2-(adamantylamino)-2-oxoethoxy)acetamido)-5-chlorobenzoic acid (Example 35), 2-(2-(2-(benzhydrylamino)-2-oxoethoxy)acetamido)-5-chlorobenzoic acid (Example 37), 2-(2-(2-(benzhydrylamino)-2-oxoethoxy)acetamido-5-(pyridine-4-yl)benzoic acid (Example 52), 4-(2-(2-(benzhydrylamino)-2-oxoethoxy)acetamido)-4'-fluorobiphenyl-3-carboxylic acid (Example 66), 5-Chloro-2-(2-(2-oxo-2-(4-phenylbutylamino)ethoxy)acetamido)benzoic acid (Example 70), 2-(2-(2-(bis(4-fluorophenyl)methyl)amino)-2-oxoethoxy)acetamido)-5-chlorobenzoic acid (Example 71), 2-(2-(2-(bis(4-trifluoromethyl)benzyl)amino)-2-oxoethoxy)acetamido)-5-chlorobenzoic acid (Example 72), 2-(2-(2-(bis(4-fluorobenzyl)amino)-2-oxoethoxy)acetamido)-5-chlorobenzoic acid (desalted moiety of the compound prepared in Example 73), 5-Chloro-2-(2-(2-(2,2-diphenylethylamino-2-oxoethoxy)acetamido)benzoic acid (Example 84), 5-Chloro-2-(2-(2-(1-(naphthalene-1-yl)ethylamino)-2-oxoethoxy)acetamido)benzoic acid (Example 68), 5-Cloro-2-(2-(2-(4-chlorophenylamino)-2-oxoethoxy)acetamido)benzoic acid (Example 39), 4-(2-(2-(4-chlorophenylamino)-2-oxoethoxy)acetamido)biphenyl-3-carboxylic acid (Example 58), 2,2'-(oxybis((1-oxo-2,1-ethanediyl)imino))bis(5-phenylbenzen-1-carboxylic acid) (Example 59), 2-(2-(2-(3,5-bis(trifluoromethyl)phenylamino-2-oxoethoxy)acetamido)-5-chlorobenzoic acid (Example 74), 5-Chloro-2-(2-(2-(diphenylamino)-2-oxoethoxy)acetamido)benzoic acid (Example 83), and 2-(2-(2-(2-benzoyl-4-chlorophenylamino)-2-oxoethoxy)acetamido)-5-chlorobenzoic acid (Example 40).

(III-2-2) Carboxylic Acids, Esters or Bioisosters Thereof 2-(2-(2-(4-benzhydryl piperazin-1-yl)-2-oxoethoxy)acetamido)-5-methoxybenzoic acid (Example 28), 5-Chloro-2-(2-(2-(4-(4-chlorophenyl)piperazin-1-yl)-2-oxoethoxy)acetamido)benzoic acid (desalted moiety of the compound prepared in Example 29), 2-(2-(2-(4-benzhydryl piperazin-1-yl)-2-oxoethoxy)acetamido)-5-chlorobenzoic acid (desalted moiety of the compound prepared in Example 30), 2-(2-(2-(4-(bis(4-fluorophenyl)methyl)piperazin-1-yl)-2-oxoethoxy)acetamido)-5-chlorobenzoic acid (Example 34), 2-(2-(2-(4-(9H-fluoren-9-yl)piperazin-1-yl)-2-oxoethoxy)acetamido)-5-chlorobenzoic acid (Example 36), 2-(2-(2-(4-benzhydryl piperazin-1-yl)-2-oxoethoxy)acetamido)-5-fluorobenzoic acid (Example 41), 3-(2-(2-(4-benzhydryl piperazin-1-yl)-2-oxoethoxy)acetamido)benzoic acid (Example 42), 4-(2-(2-(4-benzhydryl piperazin-1-yl)-2-oxoethoxy)acetamido)-3-chlorobenzoic acid (Example 43), 4-(2-(2-(4-benzhydryl piperazin-1-yl)-2-oxoethoxy)acetamido)-4'-fluorobiphenyl-3-carboxylic acid (desalted moiety of the compound prepared in Example 44), 4-(2-(2-(4-benzhydryl piperazin-1-yl)-2-oxoethoxy)acetamido)-2',4'-difluorobiphenyl-3-carboxylic acid (desalted moiety of the compound prepared in Example 45), 4-(2-(2-(4-benzhydryl piperazin-1-yl)-2-oxoethoxy)acetamido)-4'-cyanobiphenyl-3-carboxylic acid (desalted moiety of the compound prepared in Example 46), 4-(2-(2-(4-benzhydryl piperazin-1-yl)-2-oxoethoxy)acetamido)-4'-(dimethylamino)biphenyl-3-carboxylic acid (desalted moiety of the compound prepared in Example 47), 4-(2-(2-(4-benzhydryl piperazin-1-yl)-2-oxoethoxy)acetamido)-4'-methoxybiphenyl-3-carboxylic acid (desalted moiety of the compound prepared in Example 48), 4-(2-(2-(4-benzhydryl piperazin-1-yl)-2-oxoethoxy)acetamido)-4'-morpholinobiphenyl-3-carboxylic acid (desalted moiety of the compound prepared in Example 49), 2-(2-(2-(4-benzhydryl piperazin-1-yl)-2-oxoethoxy)acetamido)-5-(pyridin-4-yl)benzoic acid (desalted moiety of the compound prepared in Example 50), 2-(2-(2-(4-benzhydryl piperazin-1-yl)-2-oxoethoxy)acetamido)-5-bromobenzoic acid (desalted moiety of the compound prepared in Example 51), 2-(2-(2-(4-benzhydryl piperazin-1-yl)-2-oxoethoxy)acetamido)-5-(pyridin-3-yl)benzoic acid (Example 53), 2-(2-(2-(4-benzhydryl piperazin-1-yl)-2-oxoethoxy)acetamido)-5-(pyridin-4-yl)benzoic acid (Example 54), 2-(2-(2-(4-benzhydryl piperazin-1-yl)-2-oxoethoxy)acetamido)-5-(1-methyl-1H-pyrazol-4-yl)benzoic acid (Example 55), 2-(2-(2-(4-benzhydryl piperazin-1-yl)-2-oxoethoxy)acetamido)-5-benzylbenzoic acid (desalted moiety of the compound prepared in Example 56), 4-(2-(2-(4-benzhydryl piperazin-1-yl)-2-oxoethoxy)acetamido)biphenyl-3-carboxylic acid (desalted moiety of the compound prepared in Example 57), 2-(2-(2-(4-benzhydryl piperazin-1-yl)-2-oxoethoxy)acetamido)-5-isobutylbenzoic acid (desalted moiety of the compound prepared in Example 62), 2-(2-(2-(4-benzhydryl piperazin-1-yl)-2-oxoethoxy)acetamido)-5-(1H-pirazol-4-yl)benzoic acid (desalted moiety of the compound prepared in Example 63), 2-(2-(2-(4-benzhydryl piperazin-1-yl)-2-oxoethoxy)acetamido)-5-quinolin-3-yl)benzoic acid (Example 64), 2-(2-(2-(4-benzhydryl piperazin-1-yl)-2-oxoethoxy)acetamido)-5-benzo[b]thiophen-2-yl)benzoic acid (Example 65), 2-(2-(2-(4-benzhydryl piperazin-1-yl)-2-oxoethoxy)acetamido)-4-chlorobenzoic acid (desalted moiety of the compound prepared in Example 75), 2-(2-(2-(4-benzhydryl piperazin-1-yl)-2-oxoethoxy)acetamido)-4-bromobenzoic acid (desalted moiety of the compound prepared in Example 76), 2-(2-(2-(4-benzhydryl piperazin-1-yl)-2-oxoethoxy)acetamido)-4-pyridin-4-yl)benzoic acid (Example 77), 3-(2-(2-(4-benzhydryl piperazin-1-yl)-2-oxoethoxy)acetamido)-4'-fluorobiphenyl-4-carboxylic acid (Example 78), 2-(2-(2-((3S*,5R*)-4-benzhydryl-3,5-dimethylpiperazin-1-yl)-2-oxoethoxy)acetamido)-5-chlorobenzoic acid (Example 85), 2-(2-(2-(4-benzhydryl piperazin-1-yl)-2-oxoethoxy)acetamido)-5-benzyloxy)benzoic acid (desalted moiety of the compound prepared in Example 86), 2-(2-(2-(4-benzhydryl piperazin-1-yl)-2-oxoethoxy)acetamido)-5-isobutoxybenzoic acid (desalted moiety of the compound prepared in Example 87), 2-(2-(4-benzhydryl piperazin-1-yl)-2-oxoethoxy)-N-(4-chloro-2-(1H-tetrazol-5-yl)phenyl)acetamido (Example 88), 2-(2-(2-(4-benzhydryl piperazin-1-yl)-2-oxoethoxy)-N-(4-chloro-2-(5-oxo-4,5-dihydro-1,2,4-oxadiazol-3-yl)phenyl)acetamido (Example 89), 2-(2-(2-(4-benzhydryloxy)piperidin-1-yl)-2-oxoethoxy)acetamido-5-chlorobenzoic acid (desalted moiety of the compound prepared in Example 31), and 5-Chloro-2-(2-(2-(4,4-diphenylpiperidin-1-yl)-2-oxoethoxy)acetamido)benzoic acid (desalted moiety of the compound prepared in Example 32).

(iii) Benzoic Acid, Ester or Bioisoester Thereof (III-3)

The benzoic acids, esters or bioisosters thereof (III-3) are preferably those represented by the following formula, wherein $R_3$ is a hydrogen atom and L is methylene-$N(R_9)$-methylene in the formula (III),

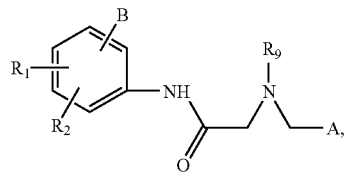

wherein B is carboxy, alkoxycarbonyl, or a bioisoster of carboxy, i.e., 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl; $R_1$, $R_2$, $R_9$ and A are defined as above.

B, $R_1$ and $R_2$ may be located at any of the ortho, meta or para positions of a benzene ring to which an imino group is bound. It is preferable, but not limited, that B be located at the ortho position, and $R_1$ and $R_2$ at the meta position and para position respectively, within the above benzene ring.

$R_1$ and $R_2$ herein are defined as above, but each preferably are, the same or different, a hydrogen atom, halogen atom, alkyl, substituted or unsubstituted aryl, or substituted or unsubstituted heterocyclic ring. Alkyl herein includes, for example, preferably $C_{1-4}$ alkyls, and more preferably methyl and ethyl; aryl preferably includes phenyl; and heterocyclic ring includes preferably pyridyl, and more preferably pyridin-3-yl and pyridin-4-yl; and pyrazolyl, and preferably pyrazol-4-yl. Examples of a substituent herein include a halogen atom, alkyl, alkoxy, cyano, alkyl-substituted amino, aryl (preferably phenyl), and morpholino (preferably morpholin-4-yl). Preferable $R_1$ and $R_2$ are a hydrogen atom and a halogen atom.

Further, A is defined as above, but is preferably —$COR_{10}$. More preferably, $R_{10}$ in —$COR_{10}$ is a —$N(R_{14})(R_{15})$ group, or a group represented by the following group:

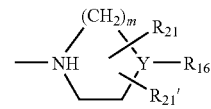

wherein Y, $R_{16}$, m, $R_{21}$ and $R_{21}'$ are defined as above.

Preferable groups represented by —$N(R_{14})(R_{15})$ are those wherein $R_{14}$ is a hydrogen atom; and $R_{15}$ is substituted or unsubstituted aryl or aralkyl. Preferable aryl herein is phenyl, and preferable aralkyl herein is diphenylalkyl (more preferably diphenylmethyl). Examples of an aryl or aralkyl substituent include a halogen atom, $CF_3$, benzoyl, alkyl, alkoxy, hydroxyl, carboxy, alkoxycarbonyl, unsubstituted phenyl, and a salt thereof.

In the above formula, Y, m, $R_{16}$, $R_{21}$ and $R_{21}'$ are defined as above, but preferably m is 2; Y is a nitrogen atom; $R_{16}$ is substituted or unsubstituted aryl or preferably phenyl; or substituted or unsubstituted aralkyl or preferably diphenylmethyl; and $R_{21}$ and $R_{21}'$ are, the same or different, each a hydrogen atom. Examples of a substituent herein include a halogen atom, alkyl, alkoxy, hydroxyl, carboxy, alkoxycarbonyl, and a salt thereof, with a halogen atom being preferable.

$R_9$ is a hydrogen atom, or substituted or unsubstituted alkyl, with alkyl being preferable, and methyl being particularly preferable.

Specific examples of the benzoic acid, an ester or a bioisoster thereof (III-3) represented by the above formula include the following compounds:

5-Chloro-2-(2-((2-(4-chlorophenylamino)-2-oxoethyl)(methyl)amino)acetamido)benzoic acid (Example 25),
2-(2-((2-(4-benzhydryl piperazin-1-yl)-2-oxoethyl)(methyl)amino)acetamido)-5-chlorobenzoic acid (Example 26), and
2-(2-((2-(benzhydrylamino)-2-oxoethyl)(methyl)amino)acetamido)-5-chlorobenzoic acid (Example 91).

(iv) Benzoic Acid, Ester or Bioisoster Thereof (III-4)

Preferable examples of the benzoic acids, esters or bioisosters thereof (III-4) are those wherein $R_3$ is a hydrogen atom and L is methylenethiomethylene, methylene-SO-methylene, or methylene-$SO_2$-methylene in the formula (III), as represented by the following formula

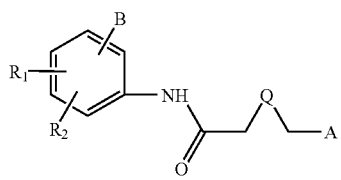

wherein Q is a sulfur atom, sulfinyl, or sulfonyl; B is carboxy, alkoxycarbonyl, or a bioisoster of carboxy, i.e. 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl. $R_1$, $R_2$, and A are defined as above.

B, $R_1$ and $R_2$ may be located at any of the ortho, meta or para positions of a benzene ring to which an imino group is bound. It is preferable, but not limited, that B be located at the ortho position, and $R_1$ and $R_2$ at the meta position and para position respectively, within the above benzene ring.

$R_1$ and $R_2$ herein are defined as above, but each preferably are, the same or different, a hydrogen atom, halogen atom, alkyl, substituted or unsubstituted aryl, or substituted or unsubstituted heterocyclic ring. Alkyl herein includes, for example, preferably $C_{1-4}$ alkyl, and more preferably methyl and ethyl; aryl preferably includes phenyl; and a heterocyclic ring includes preferably pyridyl, and more preferably pyridin-3-yl and pyridin-4-yl; and pyrazolyl, and preferably pyrazol-4-yl. Examples of a substituent herein include a halogen atom, alkyl, alkoxy, cyano, alkyl-substituted amino, phenyl, and morpholino (preferably morpholin-4-yl). Preferable $R_1$ and $R_2$ are a hydrogen and halogen atom.

Further, A is defined as above, but is preferably —$COR_{10}$. More preferably, $R_{10}$ in —$COR_{10}$ is a group —$N(R_{14})(R_{15})$, or a group represented by the following group:

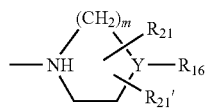

wherein Y, $R_{16}$, m, $R_{21}$ and $R_{21}'$ are defined as above.

Preferable groups represented by —$N(R_{14})(R_{15})$ are those wherein $R_{14}$ is a hydrogen atom; and $R_{15}$ is substituted or unsubstituted aryl or aralkyl. Preferable aryl herein is phenyl, and preferable aralkyl herein is diphenylalkyl (more preferably diphenylmethyl). Examples of an aryl or aralkyl substituent herein include a halogen atom, $CF_3$, benzoyl, alkyl, alkoxy, hydroxyl, carboxy, alkoxycarbonyl, unsubstituted phenyl, and a salt thereof.

In the above formula, Y, m, $R_{16}$, $R_{21}$ and $R_{21}'$ are defined as above, but preferably m is 2; Y is a nitrogen atom; $R_{16}$ is substituted or unsubstituted aryl, and preferably phenyl; or a substituted or unsubstituted aralkyl, and preferably diphenylmethyl; and $R_{21}$ and $R_{21}'$ are, the same or different, each a hydrogen atom. Examples of a substituent herein include a halogen atom, alkyl, alkoxy, hydroxyl, carboxy, alkoxycarbonyl, or a salt thereof, and with a halogen atom being preferable.

A specific benzoic acid, ester or bioisoster thereof (III-4) represented by the above formula is, for example, the following compound:
2-(2-(2-(4-benzhydrylpiperazin-1-yl)-2-oxoethylthio)acetamido)-5-chlorobenzoic acid (Example 92).

(v) Benzoic Acid, Ester or Bioisoster Thereof (III-5)

Preferable examples of the benzoic acids, esters or bioisosters thereof (III-5) are those wherein $R_3$ is a hydrogen atom and L is substituted or unsubstituted cycloalkylene in the formula (III), as represented by the following formula (III-5)

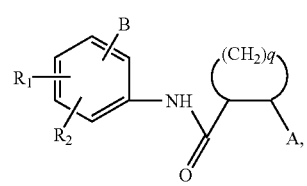

wherein B is carboxy, alkoxycarbonyl, or a bioisoster thereof, i.e., 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl. $R_1$, $R_2$, and A are defined as above. q is an integer of 1 to 4.

B, $R_1$ and $R_2$ may be located at any of the ortho, meta and para positions of a benzene ring to which an imino group is bound. It is preferable, but not limited, that B be located at the ortho position, and $R_1$ and $R_2$ at the meta position and para position respectively, within the above benzene ring.

$R_1$ and $R_2$ herein are defined as above, but are preferably, the same or different, each a hydrogen atom, halogen atom, alkyl, substituted or unsubstituted aryl, or substituted or unsubstituted heterocyclic ring. Alkyl herein includes, for example, preferably $C_{1-4}$ alkyl, and more preferably methyl and ethyl; aryl preferably includes phenyl; and a heterocyclic ring includes preferably pyridyl, and more preferably pyridin-3-yl and pyridin-4-yl, and pyrazolyl, and preferably pyrazol-4-yl. Examples of a substituent herein include a halogen atom, alkyl, alkoxy, cyano, alkyl-substituted amino, aryl (preferably phenyl), and morpholino (preferably morpholin-4-yl). Preferably $R_1$ and $R_2$ are a hydrogen and halogen atom.

Further, A is defined as above, but is preferably —$COR_{10}$. More preferably, $R_{10}$ in —$COR_{10}$ is a —$N(R_{14})(R_{15})$ group, or a group represented by the following group:

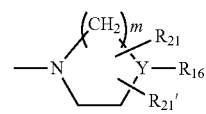

wherein Y, $R_{16}$, m, $R_{21}$ and $R_{21}'$ are defined as above.

Preferable groups represented by —$N(R_{14})(R_{15})$ are those wherein $R_{14}$ is a hydrogen atom; and $R_{15}$ is substituted or unsubstituted aryl or aralkyl. Preferable aryl herein is phenyl, and preferable aralkyl herein is diphenylalkyl (more preferably diphenylmethyl). Examples of an aryl or aralkyl substituent herein include a halogen atom, CF$_3$, benzoyl, alkyl, alkoxy, hydroxyl, carboxy, alkoxycarbonyl, unsubstituted phenyl, or a salt thereof.

In the above formula, Y, m, R$_{16}$, R$_{21}$ and R$_{21}$' are defined as above, but preferably m is 2; Y is a nitrogen atom; R$_{16}$ is substituted or unsubstituted aryl, and preferably phenyl, or substituted or unsubstituted aralkyl, and preferably diphenylmethyl; and R$_{21}$ and R$_{21}$' are, the same or different, each a hydrogen atom. Examples of a substituent herein include a halogen atom, alkyl, alkoxy, hydroxyl, carboxy, alkoxycarbonyl, and a salt thereof, and with a halogen atom being preferable.

Examples of a substituent of cycloalkylene include C$_{1-6}$ alkyl, preferably C$_{1-4}$ alkyl.

Specific benzoic acids, esters or bioisosters thereof (III-5) represented by the above formula, for example, include the following compounds:
2-((1S*,2S*)-2-(4-benzhydrylpyperazine-1-carbonyl)cyclohexanecarboxamido-5-chlorobenzoic acid (desalted moiety of the compound prepared in Example 94), and
2-((1S*,2R*)-2-(4-benzhydrylpyperazine-1-carbonyl)cyclohexanecarboxamido-5-chlorobenzoic acid (desalted moiety of the compound prepared in Example 95)

(vi) Benzenecaraboxylic Acid, Ester or Bioisoster Thereof (III-6)

Preferable examples of benzoic acids, esters or bioisosters thereof (III-6) are those wherein R$_3$ is a hydrogen atom and n is 0 in the formula (III), as represented by the following formula

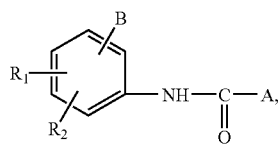

(III-6)

wherein B is carboxy, alkoxycarbonyl, or a bioisoster of carboxy, i.e., 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl. R$_1$, R$_2$, and A are defined as above.

B, R$_1$ and R$_2$ may be located at any of the ortho, meta and para positions of a benzene ring to which an imino group is bound. It is preferable, but not limited, that B be located at the ortho position, and R$_1$ and R$_2$ at the meta position and para position respectively, within the above benzene ring.

R$_1$ and R$_2$ herein are defined as above, but preferably, the same or different, each are a hydrogen atom, halogen atom, alkyl, substituted or unsubstituted aryl, or substituted or unsubstituted heterocyclic ring. Alkyl herein includes, for example, preferably C$_{1-4}$ alkyl, and more preferably methyl and ethyl; aryl preferably includes phenyl; and heterocyclic ring includes preferably pyridyl, and more preferably pyridin-3-yl and pyridin-4-yl; and pyrazolyl, and preferably pyrazol-4-yl. Examples of a substituent herein include a halogen atom, alkyl, alkoxy, cyano, alkyl-substituted amino, aryl (preferably phenyl), and morpholino (preferably morpholin-4-yl). Preferably R$_1$ and R$_2$ are a hydrogen atom and a halogen atom.

Further, A is defined as above, but is preferably —COR$_{10}$. More preferably, R$_{10}$ in —COR$_{10}$ is a —N(R$_{14}$)(R$_{15}$) group, or a group represented by the following group.

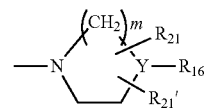

wherein Y, R$_{16}$, m, R$_{21}$ and R$_{21}$' are defined as above.

Preferable groups represented by —N(R$_{14}$)(R$_{15}$) are those wherein R$_{14}$ is a hydrogen atom; and R$_{15}$ is substituted or unsubstituted aryl or aralkyl. Preferable aryl herein is phenyl; and preferable aralkyl herein is diphenylalkyl (more preferably diphenylmethyl). Examples of a aryl or aralkyl substituent herein include a halogen atom, CF$_3$, benzoyl, alkyl, alkoxy, hydroxyl, carboxy, alkoxycarbonyl, unsubstituted phenyl, and a salt thereof.

In the above formula, Y, m, R$_{16}$, R$_{21}$ and R$_{21}$' are defined as above, but preferably m is 2; Y is a nitrogen atom; R$_{16}$ is substituted or unsubstituted aryl, and preferably phenyl, or substituted or unsubstituted aralkyl, and preferably diphenylmethyl; and R$_{21}$ and R$_{21}$' are, the same or different, each a hydrogen atom. Examples of a substituent herein include a halogen atom, alkyl, alkoxy, hydroxyl, carboxy, alkoxycarbonyl, and a salt thereof, with a halogen atom being preferable.

A specific benzoic acid, an ester or a bioisoster thereof (III-6) represented by the above formula is, for example, the following compound:
2-(2-(Benzhydrylamino)-2-oxoacetamido)-5-chlorobenzoic acid (Example 79).

The compound (I) of the present invention may be the abovementioned various carboxylic acids, esters or bioisosters thereof described above in the form of a free radical, but may be in the form of a salt.

Examples of the salt as used herein typically include pharmaceutically acceptable salts, e.g., a salt formed with an inorganic base or organic base, and a salt formed with a basic amino acid, etc. Examples of an inorganic base include alkali metals such as sodium, potassium, etc.; alkaline earth metals such as calcium, magnesium, etc.; aluminium, ammonium, etc. Examples of an organic base include primary amines such as ethanolamine, etc.; secondary amines such as diethylamine, diethanolamine, dicyclohexylamine, N,N'-dibenzylethylenediamine, etc.; tertiary amines such as trimethylamine, triethylamine, pyridine, picoline, triethanolamine, etc. Examples of a basic amino acid include arginine, lysine, ornithine, etc.

Further, examples of an ester residue include straight- or branched-chain C$_{1-6}$ alkyl, C$_{7-19}$ aralkyl, and preferably straight- or branched-chain C$_{1-4}$ alkyl.

Further, when the carboxylic acid represented by the general formula (I), a salt thereof, carboxylate ester thereof, or a bioisoster of the carboxylic acid form a solvate (e.g. solvate with water (hydrate) or alcohol), such a solvate is also encompassed in the present invention. Furthermore, the present invention encompasses all the compounds that are converted to a carboxylic acid or a bioisoster thereof represented by the above general formula (I) and a pharmaceutically acceptable salt when metabolized in vivo (e.g., a so-called prodrug).

(2) Method for Producing the Compound of the Present Invention

Method for producing an aromatic or heterocyclic carboxylic acid, ester or a bioisoster thereof, and a salt thereof of the present invention, represented by the general formula (I) are specifically described below.

However, the present invention is not limited thereto. Further, for the production of the compound, the order of production steps is not limited to those described below, and can suitably be replaced in accordance with the practice of the industry of interest. Furthermore, whenever a reaction functional group is found in any step, the group can be suitably protected and deprotected unless otherwise specified. Reagents in addition to those listed below can be suitably used to promote reaction progress.

Figure 1:
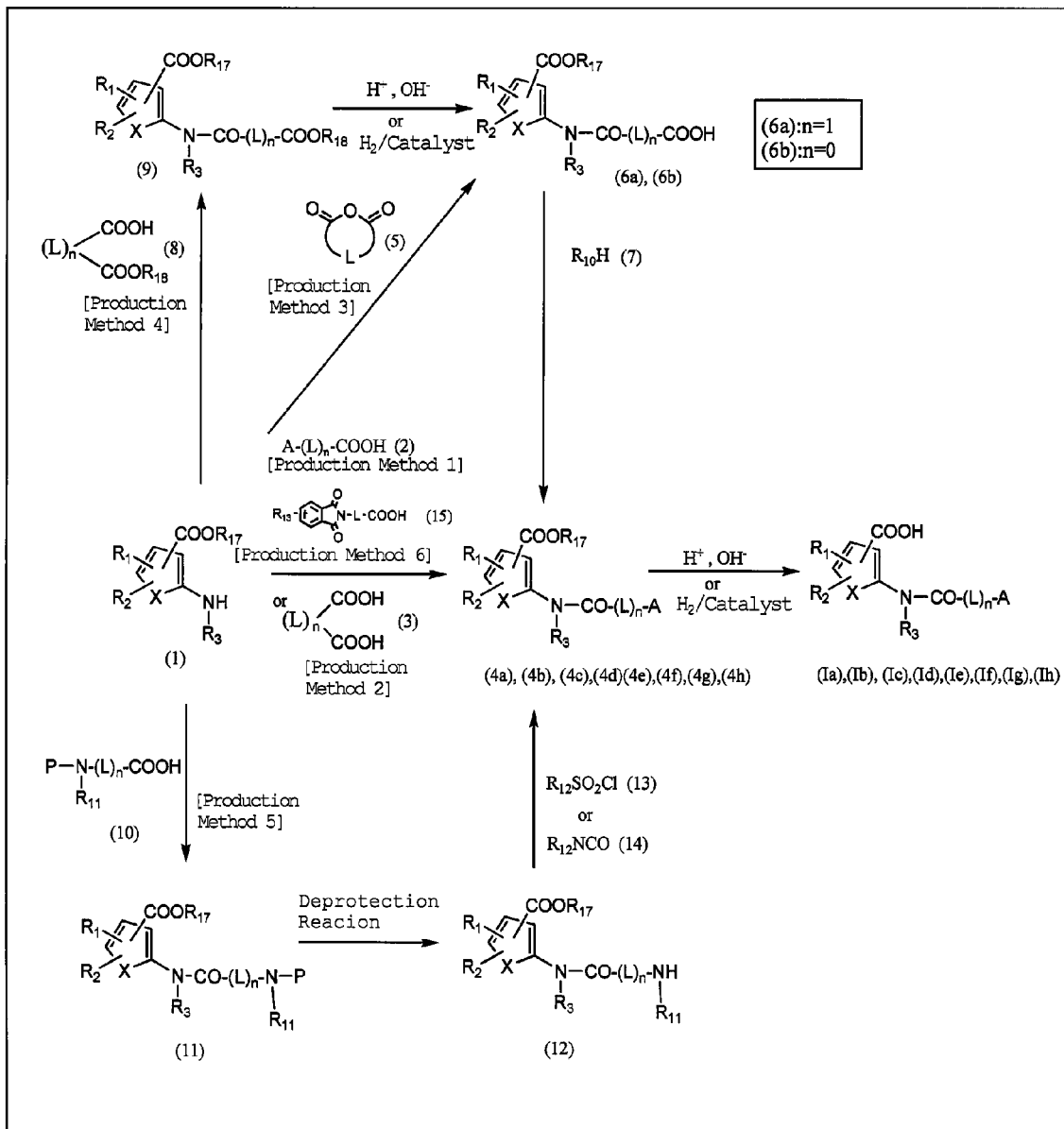
FIG. 1 shows the production methods of the compound (I) of the present invention. In the figure, $R_{17}$ and $R_{18}$ each represent an alkyl, aryl or aralkyl group, and P represents a protective group. Other symbols are defined as those in the specification, except for the cases shown below.
Compound (4b): A=

FIGS. 1, 2 and 3 show the production steps of the compound (I) of the present invention.

In FIG. 1, the alkyl represented by $R_{17}$ and $R_{18}$ is preferably a $C_{1-4}$ straight- or branched chain alkyl with methyl and ethyl being more preferable; the aryl is preferably phenyl; and the aralkyl is preferably diphenylalkyl with diphenylmethyl being more preferable.

(2-1) Production Method 1 (See FIG. 1)

The compound (1) and compound (2) are condensed to produce the compound (4a) equivalent to an ester moiety of the aromatic or heterocyclic carboxylic acid of the present invention.

The condensation reaction may be carried out between the compounds (1) and (2) in the presence of a known condensing agent, or by converting the compound (2) to a reactive derivative before further reacting with the compound (1).

Examples of condensing agents include known agents such as dicyclohexylcarbodiimide (DCC), water-soluble carbodiimide (WSC) [e.g., 1-ethyl-3-(3-dimethyleminopropyl)carbodiimide hydrochloride, etc.], carbonyldiimidazol (CDI), benzotriazol-1-yl-oxytri(pyrrolidino)phosphonium hexafluorophosphate (PyBOP), N-hydroxysuccinimide (HOSu), 1-hydroxybenzotriazole (HOBT), etc.

Further, the reactive derivative of the compound (2) includes, for example, acid chlorides (e.g., chloride, bromide, etc.), active esters (e.g., p-nitrophenyl ester, pentachlorophenyl ester, esters reacted with N-hydroxysuccinimide; esters reacted with 1-hydroxybenzotriazole, etc.), imidazolide, and mixed acid anhydrides (e.g., mixed acid anhydrides formed with methoxy formic acid, ethoxy formic acid, propoxy formic acid, butoxy formic acid, isobutoxy formic acid, tert-butoxy formic acid, phenoxy formic acid, 2,2-dimethylpropionate, methanesulfonic acid, benzenesulfonic acid, toluenesulfonic acid, etc.). These reactive derivatives may be reacted with the compound (1) after being formed or as they are formed within a reaction system, or may be isolated from the reaction system before reacting with the compound (1).

The reaction of the compounds (1) and (2) with the reactive derivative is typically carried out in a solvent and, if necessary, in the presence of a base. An inactive organic solvent is commonly used as a solvent; however, water can sometimes be used as a solvent, or a mixture thereof can also be used. Examples of usable organic solvents include halogenated alkyls (e.g., methylene chloride, chloroform, etc.); aromatic hydrocarbons (e.g., benzene, toluene, xylene, anisole, etc.); ethers (e.g., diethyleter, diisopropyl ether, methyl isobutyl ether, methyl cyclopentyl ether, tetrahydrofuran(THF), dioxane, etc.); esters (e.g., methyl acetate, ethyl acetate, isopropyl acetate, butyl acetate, etc.); ketones (e.g., acetone, methyl ethyl ketone, methyl isobutyl ketone, etc.); acetonitrile, N,N-dimethylformamide (DMF), N,N-dimethylacetamide (DMA), N-methylpiperidone, dimethyl sulfoxide; etc. Usable bases include inorganic bases (e.g., sodium hydrogencarbonate, potassium hydrogencarbonate, sodium carbonate, potassium carbonate, sodium hydroxide, potassium hydroxide, lithium hydroxide, etc.); and organic bases (e.g., pyridine, triethyl amine, N,N-diisopropylethylamine, N-methyl morpholine, N-methylpiperidine, etc.). The reaction temperature varies depending on the condensing agent used, or the kind of reactive derivative of the compound (2); but typically ranges from about −30° C. to about 120° C., and preferably between about −10° C. to about 100° C. The amount of the condensing agent and the base is typically about 1 to about 5 equivalent weights, and preferably about 1 to about 3 equivalent weight, per mol of the compound (2). The amount of the compound (2), when used in the form of a reactive derivative, is about 1 to about 5 equivalent weight, and preferably about 1 to about 2 equivalent weight, per mol of the compound (1).

Removal of Ester Linkage $R_{17}$

The thus prepared ester moiety (4a) can be made into the compound (1a) of the present invention in the form of a free radical carboxylic acid by removing the ester linkage $R_{17}$ therefrom. The conditions to perform such a removal vary depending on the kind of $R_{17}$, but preferably used acids include hydrogen chloride, hydrogen bromide, methanesulfonic acid, benzenesulfonic acid, p-toluenesulfonic acid, trifluoroacetic acid, etc., when $R_{17}$ is a t-butyl group. In this case, the removal reaction is typically carried out in an inactive solvent (e.g., benzene, toluene, ethylether, isopropyl ether, THF, ethyl acetate, dichloromethane, chloroform, etc.) at about 0° C. to about 60° C. The amount of acid used varies depending on the kind thereof, but typically about 1 to about 10 equivalent weight per mol of the compound (4a). Further, when trifluoroacetic acid is used as the acid, it can also be used as a solvent.

When $R_{17}$ is alkyl, aryl or aralkyl, an alkali hydrolysis reaction can be employed. In this case, suitably usable alkalis include lithium hydroxide, sodium hydroxide, potassium hydroxide, barium hydroxide, etc., and suitably usable solvents include methanol, ethanol, dioxane, THF, or mixtures thereof, etc. The amount of alkali used is typically about 1 to about 3 equivalent weight, per mole of the compound (4a), and the reaction temperature ranges from about 0° C. to about 80° C. In an alkali hydrolysis reaction, a salt is first formed from the alkali used. Thus, $R_{17}$ can be isolated as a salt thereof, or can be isolated as a free radical carboxilic acid by neutralizing using a suitable acid (e.g., acetic acid, hydrochloric acid, sulfuric acid, etc.). Alternatively, a free radical carboxylic acid is first isolated, and treated with alkali to convert it to an alkali salt. Further, when the compound (1a) of the present invention contains a basic nitrogen functional group in molecules, $R_{17}$ can be isolated as an acid chloride of the compound (1a) by treating with an equivalent or excessive weight of an acid.

In addition to the above method, when $R_{17}$ is an aralkyl group (e.g., benzyl), the compound (4a) can be converted to a free radical carboxylic acid by being subjected to catalytic reduction by a known method using hydrogen gas in the presence of a catalyst such as palladium carbon, palladium black, etc.

Further, when the compound (4a) is such wherein A is a functional group having an ester linkage, the ester linkage can be removed together with the $R_{17}$ ester linkage, or either one of the ester linkages can be selectively removed by changing the reaction conditions. Alternatively, when the compound (4) is a group wherein A is substituted or unsubstituted 3-carboxy-2-ethynyl, the carboxy group is decarbonized and converted to a hydrogen atom. The decarbonization reaction can be carried out under, for example, the reaction conditions for removing t-butyl, and the reaction can also be performed by further proceeding the reaction after the removal of t-butyl.

(2-2) Production Method 2 (See FIG. 1)

In place of the compound (2) used in the above Production Method 1, the compound (1) is reacted with a dicarboxylic acid (3) or a reactive derivative thereof in the same manner as above to produce a reaction compound of the compound (3)

having a single molecule and the compound (1) having two molecules, i.e., a symmetrical compound (4b) wherein A is represented by the following formula:

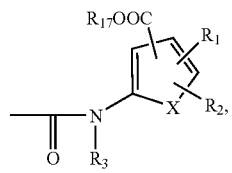

wherein X, $R_1$ to $R_3$, and $R_{17}$ are defined as above.

In this reaction, a preferable reactive derivative of the compound (3) is dichloride, and the amount thereof used is about 0.5 to about 2 equivalent weight, and preferably about 0.5 to about 0.7 equivalent weight, per mol of the compound (1). The ester linkage $R_{17}$ can be removed from the thus obtained ester moiety (4b) in accordance with the method described in the production method 1, thereby being converted to the compound (1b) of the present invention in the form of a free radical carboxylic acid (wherein A is a group represented by the above formula).

(2-3) Production Method 3 (See FIG. 1)

An ester-carboxylic acid (6a) can be easily produced using an intramolecular anhydride in dicarboxylic acid (5) as the reactive derivative of the dicarboxylic acid (3) used in the production method 2.

The reaction between the compounds (1) and (5) is typically carried out in a solvent at about 30° C. to about 100° C., and preferably about 50° C. to about 80° C. The solvent employable is any of those inactive in the reaction, and examples include hydrocarbons (e.g., hexane, heptane, cyclohexane, etc.), halogenated hydrocarbons (e.g., dichloromethane, chloroform, etc.), aromatic hydrocarbons (e.g., benzene, toluene, xylene, anisole, etc.), ethers (e.g., ethyl ether, isopropyl ether, etc.), esters (e.g., methyl acetate, ethyl acetate, butyl acetate, etc.), dioxane, tetrahydrofuran (THF), acetonitrile, pyridine, dimethylformamide (DMF), dimethylacetamide (DMA), etc. The amount of the compound (5) used is about 1 to about 2 equivalent weight, and preferably about 1 to about 1.5 equivalent weight, per mole of the compound (1).

The reaction may be carried out in the presence of a base as necessary, and pyridine, picoline, 4-dimethylaminopyridine, triethylamine, N-methylpiperidine, N-methyl morpholine, etc., can be used in an amount of about 1 to about 3 equivalent weight, and preferably about 1 to about 2 equivalent weight, per mol of the compound (1).

Subsequently, the obtained ester-carboxylic acid (6a) or a reactive derivative thereof is reacted with a compound (7) represented by $R_{10}H$ ($R_{10}$ is defined as above) to synthesize a compound (4c) wherein A is represented by —$COR_{10}$. The $R_{10}H$ (7) used herein is a amine compound, which is reacted with the compound (6a) or a reactive derivative thereof, thereby easily converting the compound (7) to the compound (4c) wherein A is $COR_{10}$. This reaction is carried out in the same manner as in the reaction between the compounds (1) and (2) described in the production method 1, or by a method equivalent thereto.

The thus prepared ester moiety (4c) can be detached from its ester linkage $R_{17}$ in accordance with the method described in production method 1, and hence converted to the compound (1c) of the present invention in the form of a free radical carboxylic acid wherein A is represented by —$COR_{10}$.

(2-4) Production Method 4 (See FIG. 1)

The compound (6a) produced in the above production method 3 can also be produced by reacting the compound (1) and ester-carboxylic acid (8) (n is 1 in the formula) or a reactive derivative thereof, and selectively removing either one of the ester linkages of the diester compound (9) formed. Alternatively, when ester-carboxylic acid (8) wherein n is 0 is used, a compound (6b) wherein n is 0 can be produced. The reaction between the compound (1) and compound (8) can be carried out in the same manner as in the reaction between compound (1) and compound (2) described in the production method 1. $R_{17}$ and $R_{18}$ are preferably determined in combination so that $R_{18}$ is more selectively removed. Examples of such a combination include a) $R_{17}$=t-butyl, benzyl, etc., and $R_{18}$=methyl, ethyl, propyl, or like alkyl; or b) $R_{17}$=methyl, ethyl, propyl, or like alkyl and $R_{18}$=t-butyl, benzyl, etc. The method for selectively removing the $R_{18}$ ester moiety varies depending on the kind, but can be carried out in the same manner as the ester removal method of the compound (4a), or a method equivalent thereto.

The obtained ester-carboxylic acid (6a), (6b) or a reactive derivative thereof is then reacted with the compound (7) in the same manner as in production method 3, whereby a compound (4c) or (4c), wherein A is —$COR_{10}$, is synthesized. Further, the prepared ester moiety (4c) or (4d), detached from its ester linkage $R_{17}$ in the same manner as in production method 3, can be converted to the compound (1c) or (1d) of the present invention in the form of a free radical carboxylic acid (A is —$COR_{10}$ in the formula).

(2-5) Production Method 5 (See FIG. 1)

The compound (1) and the compound (10) are reacted to form a compound (11), from which the protecting group (denoted by P) is eliminated from the amino group to obtain amine (12), with which sulfonyl chloride (13) or isocyanate (14) is reacted to produce either compound (4e) or compound (4f).

The reaction between the compound (1) and compound (10) can be carried out in the same manner as in the reaction between the compound (1) and compound (2) in the production method 1, thereby easily producing the compound (11). The deprotection reaction of the compound (11) varies depending on the kind of protecting group used, but preferable protecting groups are those commonly used in peptide chemistry because the deprotection reaction is easily carried out under known deprotection conditions. Typical examples of amino-protecting group herein include benzyloxycarbonyl and t-butoxycarbonyl.

To the thus obtained compound (12), the sulfonyl chloride moiety (13) is reacted to synthesize the compound (4e) wherein A is a group represented by —N($R_{11}$)—$SO_2$—$R_{12}$, or the isocyanate moiety (14) is reacted to synthesize the compound (4f) wherein A is a group represented by —N($R_{11}$)—CONH—$R_{12}$.

The reaction between the compound (12) and compound (13) is typically carried out in a solvent and, if necessary, in the presence of a base. The solvent used herein is typically an inactive organic solvent, and examples include halogenated alkyls (e.g., methylene chloride, chloroform, etc.), aromatic hydrocarbons (e.g., benzene, toluene, xylene, anisole, etc.), ethers (e.g., diethyl ether, diisopropyl ether, methyl isobutyl ether, methyl cyclopentyl ether, tetrahydrofuran (THF), dioxane, etc.), esters (e.g., methyl acetate, ethyl acetate, isopropyl acetate, butyl acetate, etc.), ketones (e.g., acetone, methyl ethyl ketone, methyl isobutyl ketone, etc.), acetonitrile, N,N-dimethylformamide (DMF), N,N-dimethylacetamide (DMA), N-methyl piperidone, dimethyl sulfoxide, etc. Usable bases are, for example, pyridine, triethylamine, N,N- diisopropylethylamine, N-methylmorpholine, N-methylpyridine, etc. The reaction temperature typically ranges from about −30° C. to about 100° C., and preferably about −10° C. to about 80° C. The amount of condensing agent and base is typically about 1 to about 2 equivalent weight, and preferably about 1 to about 1.5 equivalent weight, per mol of the compound (12).

The reaction between the compound (12) and compound (14) is typically carried out in an inactive organic solvent, such as halogenated alkyls (e.g., methylene chloride, chloroform, etc.), aromatic hydrocarbons (e.g., benzene, toluene, xylene, anisole, etc.), ethers (e.g., diethyl ether, diisopropyl ether, methyl isobutyl ether, methyl cyclopentyl ether, tetrahydrofuran (THF), dioxane, etc.), esters (e.g., methyl acetate, ethyl acetate, isopropyl acetate, butyl acetate, etc.), ketones (e.g., acetone, methyl ethyl ketone, methyl isobutyl ketone, etc.), acetonitrile, N,N-dimethyl formamide (DMF), N,N-dimethylacetamide (DMA), N-methyl piperidone, dimethyl sulfoxide, pyridine, etc. The reaction temperature typically ranges from about −10° C. to about 100° C., and preferably about 0° C. to about 80° C. The amount of the compound (14) used is about 1 to about 2 equivalent weight, and preferably about 1.2 to about 1.5 equivalent weight, per mol of the compound (12).

Subsequently, ester linkages are each removed in the same manner as described in the production method 1 from the thus obtained compound (4e) wherein A is a group represented by —N(R$_{11}$)—SO$_2$—R$_{12}$ or from the compound (4f) wherein A is a group represented by —N(R$_{11}$)—CONH—R$_{12}$, thereby producing a compound (1e) wherein A is —N(R$_{11}$)—SO$_2$—R$_{12}$ or a compound (1f) wherein A is —N(R$_{11}$)—CONH—R$_{12}$, respectively.

(2-6) Production Method 6 (See FIG. 1)

In the production method 1, the compound (1) is reacted with the compound (2) wherein A is represented by the following formula:

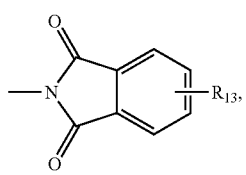

wherein R$_{13}$ is defined as above;
namely, a compound represented by the following formula (15) or a reactive derivative thereof:

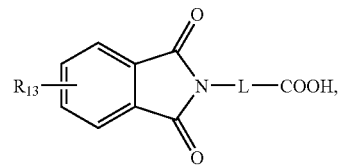

wherein R$_{13}$ and L are defined as above;
to synthesize a compound (4g) represented by the following general formula:

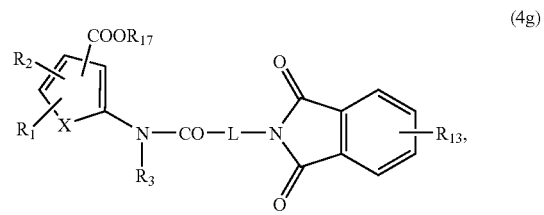

wherein R$_1$, R$_2$, R$_3$, R$_{13}$, R$_{17}$, X and L are defined as above.
Subsequently, the R$_{17}$ ester linkage is selectively removed by a method that does not adversely affect (substitute) phthalyl, i.e., a method that does not employ alkali, thereby synthesizing the compound (Ig) of the present invention represented by the following general formula:

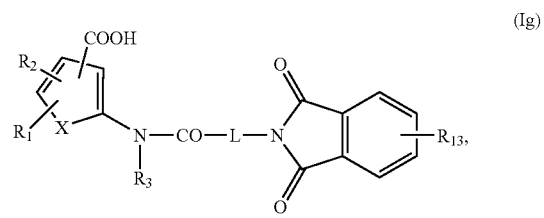

wherein R$_1$, R$_2$, R$_3$, R$_{13}$, X and L are defined as above.
To remove the R$_{17}$ ester linkage without affecting phthalyl in the compound (4g), R$_{17}$ is preferably selected so that it is selectively removed. For example, the compound (4g), prepared using as a starting material a compound (1) wherein R$_{17}$ is t-butyl, can be converted to a free radical carboxylic acid compound (Ig) using an acid in the same manner as in the above. Alternatively, when R$_{17}$ is benzyl, for example, catalytic reduction using Pd catalyst can be employed to selectively detach R$_{17}$ and form the compound (Ig).

(2-7) Production Method 7 (See FIG. 1 and the Following Formula)

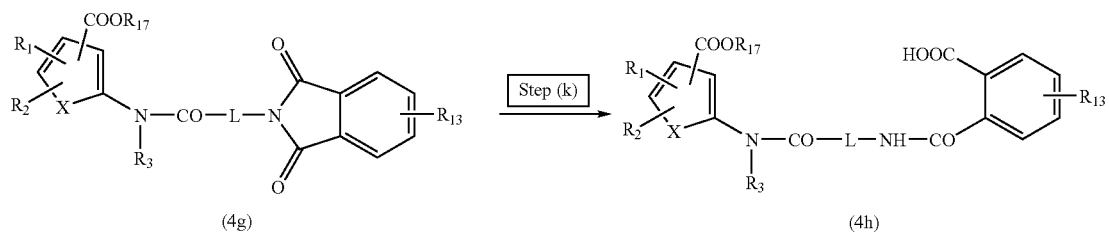

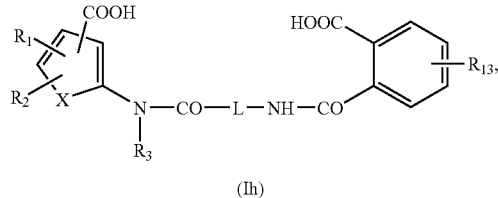

(Ih)

wherein $R_1$, $R_2$, $R_3$, $R_{13}$, $R_{17}$, L and X are defined as above.

As shown above, the compound (4g) obtained in the production process 6 is treated with alkali, and phthalyl is thereby partially hydrolyzed, forming an ester carboxylic acid (4h) (step (k)). Further, the $R_{17}$ ester linkage of the formed ester carboxylic acid (4h) is hydrolyzed (step (x)), forming a compound (Ih).

The compound (Ih) is equivalent to the compound (I), wherein n is 1, A is —N($R_{11}$)—CO$R_{12}$ wherein $R_{11}$ is hydrogen, $R_{12}$ is (substituted) o-carboxyphenyl.

The reaction between the compound (1) and compound (15) or a reactive derivative thereof can be carried out, for example, in the same manner as in the reaction between the compound (1) and compound (2) or a reactive derivative thereof described in the production method 1.

(2-8) Production Method 8 (See the Following Formula)

Among the compounds (4a) to (4h) in FIG. 1, the compound (4') wherein $R_2$ is halogen atom (w) can easily substitute the halogen atom with other functional group, i.e., a functional group $R_2'''$, thus forming a compound (4") wherein $R_2$ is a non-halogen functional group $R_2'''$.

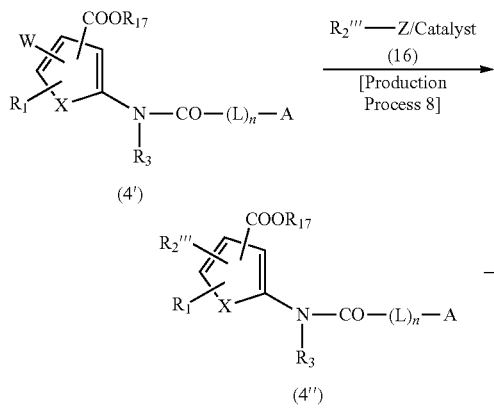

wherein $R_2'''$ represents alkyl, cycloalkyl, alkenyl, cycloalkenyl, alkynyl, alkoxy, cycloalkoxy, alkenyloxy, cycloalkenyloxy, aryl, aryloxy, aralkyl, aralkyloxy, heterocyclic group, heterocyclic-alkyl, heterocyclic-alkyloxy; W is halogen atom; Z is a group represented by —B(OR$_{20}$)OR$_{20}$ wherein $R_{20}$ is hydrogen or alkyl; when $R_{20}$ is alkyl, both alkyls may join to form a ring), or a group represented by —ZnW (wherein W is halogen atom); respectively.

The compound (4') includes each of the compounds (4a') to (4h') wherein $R_2$ is halogen atom in the compounds (4a) to (4h). The compound (4") further includes each of the compounds (4a") to (4h") wherein $R_2$ is a $R_2'''$ group, but not a halogen atom, in the compounds (4a) to (4h).

In the present process, the compound (4') and the compound (16) represented by $R_2'''$—Z are reacted in the presence of a catalyst as necessary. The reaction conditions vary depending on the kind of halogen atom, $R_2'''$, Z, etc.; however, when Z is —B(OR$_{20}$) OR$_{20}$, i.e., the compound (16) which is boric acid or (cyclic) boric acid ester residue is used, preferable examples of the catalyst include palladium catalysts (e.g., tetrakis(triphenylphosphine)palladium(0), bis(dibenzylideneacetone)palladium(0), palladium acetate, etc.); and preferable examples of a halogen represented by W include a chlorine atom, bromine atom, iodine atom, with a bromine and iodine atom being particularly preferable. The reaction is typically carried out in a solvent (e.g., DMF, 1,4-dioxane, toluene, THF, etc.) in the presence of, if necessary, a base (e.g., sodium carbonate, potassium carbonate, potassium phosphate, etc.). The reaction temperature is about 20° C. to about 120° C., and preferably about 30° C. to about 100° C. The amount of the compound (16) used is about 1 to about 5 equivalent weight, and preferably about 1.5 to about 2 equivalents weight, per mol of the compound (4'). The amount of a catalyst used is about 0.05 to about 0.5 equivalent weight, and preferably about 0.1 to about 0.2 equivalent weight, per mol of the compound (4').

Further, when a so-called zinc reagent represented by $R_2'''$—ZnW' is used as the compound (16), palladium catalysts (e.g. tetrakis(triphenylphosphine))palladium(0), bis (dibenzylideneacetone)palladium(0), palladium acetate) are preferably used. The amount of the zinc reagent (16) used is about 1 to about 3 equivalent weight, and preferably about 1.5 to about 2 equivalent weight, per mol of the compound (4').

When the compound (7) represented by $R_{10}$=$R_{14}R_{15}$N (the group may be cyclic amine wherein $R_{14}$ and $R_{15}$ are joined, and a heteroatom such as an oxygen atom may be present within the cycle) is used as the compound (16), palladium catalysts (e.g., tetrakis(triphenylphosphine))palladium(0), bis(dibenzylideneacetone)palladium(0), palladium acetate) are preferably used. The amount of the cyclic amine (16) used is about 1 to about 3 equivalent weight, and preferably about 1.5 to about 2 equivalent weight, per mole of the compound (4').

(2-9) Production Method 9a (See FIG. 2) and Production Method 9b (See FIG. 3)

The reaction between the compound (17) and compound (5) can be carried out in the same manner as in the reaction between the compound (1) and compound (5) described in the production method 3, or by a method equivalent thereto, to produce cyano-carboxylic acid (18) wherein n is 1 in the formula shown in FIG. 2. Cyanocarboxylic acid (18) wherein n is 0 in the formula shown in FIG. 2 can be produced by the method for producing an ester carboxylic acid (6b) (Step (e) and Step (f)) shown in Production Method 4 or by a method equivalent thereto.

The obtained cyano-carboxylic acid (18) or a reactive derivative thereof is then reacted with the compound (7) represented by $R_{10}$H($R_{10}$ is defined as above), thereby synthesizing a nitrile compound (19) represented by A=—CO$R_{10}$. The reaction can be carried out in the same manner as in the reaction between the compounds (1) and (2) described in the production method 1, or by a method equivalent thereto. The thus prepared nitrile compound (19) is reacted to an azide to produce a tetrazole compound (20) (a compound wherein B group is 1H-tetrazole-5-yl), which is a bioisoster of the carboxylic acid compound (1c) or (1d).

The reaction between the compound (19) and an azide (sodium azide, trimethylsilyl azide, etc.) is typically carried out in a solvent (chloroform, toluene, xylene, diethyl ether, THF, dioxane, ethyl acetate, methyl ethyl ketone, acetonitrile, DMF, DMA, DMSO, ethanol, water, or a mixture thereof) preferably in the presence of a tin compound (n-tributyltinchloride, di-n-butyltinoxide, etc.) or Lewis acid (zinc bromide, copper iodide, etc.). The reaction temperature typically ranges from about 20° C. to about 120° C., and preferably about 50° C. to about 100° C. The amount of an azide compound used is typically about 1 to about 10 equivalent weight, and preferably about 1 to about 5 equivalent weight, per mol of the compound (19). The amount of the tin compound used is typically about 0.1 to about 5 equivalent weight, and preferably about 0.1 to about 1.5 equivalent weight, per mol of the compound (19). The amount of the Lewis acid used is typically about 0.1 to about 5 equivalent weight, and preferably about 0.1 to about 1.5 equivalent weight, per mol of the compound (19) (Production Method 9a).

As shown in FIG. 3, a tetrazole compound (26), a bioisoster of the carboxylic acid represented by general formula (Ia), can be produced by condensing the compound (17) and compound (2) to form a nitrile compound (25), which is then reacted with an azide (production method 9b).

(2-10) Production Method 10a (See FIG. 2) and Production Method 10b (See FIG. 3)

The compound (19) produced by the production method 9 described above is reacted with hydroxylamine hydrochloride, and hence converted to an amidoxime compound (21). A 1,2,4-oxadiazol-5-on compound (22), a bioisoster of the carboxylic acid (Ic) or (Id), can be produced from the amidoxime compound (21).

The reaction between the compound (19) and hydroxylamine hydrochloride is typically carried out in a solvent (chloroform, toluene, xylene, diethyl ether, THF, dioxane, ethyl acetate, methyl ethyl ketone, acetonitrile, DMF, DMA, DMSO, ethanol, water, or a mixture thereof) preferably in the presence of a base (pyridine, triethylamine, N,N-diisopropylethylamine, N-methylmorpholine, N-methylpyridine, potassium carbonate, sodium hydroxide, etc.). The reaction temperature typically ranges from about –30° C. to about 120° C., and preferably about 20° C. to about 100° C. The amount of hydroxylamine hydrochloride and base used is typically about 1 to about 2 equivalent weight, and preferably about 1 to about 1.5 equivalent weight, per mol of the compound (19).

For the production of the compound (22), the amidoxime compound (21) is reacted with chlorocarbonic acid monoesters (methyl chlorocarbonate, ethyl chlorocarbonate, isopropyl chlorocarbonate, butyl chlorocarbonate, isobutyl chlorocarbonate, phenyl chlorocarbonate, 2-ethylhexyl chlorocarbonate, etc.) in a solvent (chloroform, toluene, xylene, diethyl ether, THF, dioxane, ethyl acetate, methyl ethyl ketone, acetonitrile, DMF, DMA, DMSO, ethanol, or a mixture thereof) preferably in the presence of a base (triethylamine, N-methylmorpholine, pyridine, DBU, DBN, sodium hydride, etc.), subjected to suitable after treatment, and cyclized with heat. The amidoxime compound (21) is reacted with N,N'-carbonyldiimidazole (CDI) in a solvent (chloroform, toluene, xylene, diethyl ether, THF, dioxane, ethyl acetate, methyl ethyl ketone, acetonitrile, DMF, DMA, DMSO, ethanol, etc.) preferably in the presence of a base (triethylamine, N-methylmorpholine, pyridine, 1,8-diazabicyclo[5.4.0]undeca-7-ene (DBU), 1,5-diazabicyclo[4.3.0]non-5-ene (DBN), sodium hydride, etc.).

The reaction temperature of the compound (21) and chlorocarbonic acid ester typically ranges from about –30° C. to about 100° C., and preferably from about –10° C. to about 50° C. The reaction temperature during the cyclization reaction typically ranges from about 40° C. to about 180° C., and preferably from about 80° C. to about 150° C. The temperature of the reaction between the compound (19) and CDI typically ranges from about 20° C. to about 100° C., and preferably from about 40° C. to about 100° C. The amount of chlorocarbonic acid monoester and base are typically about 1 to about 2 equivalent weight, and preferably about 1 to about 1.5 equivalent weight, per mol of the compound (19).

Thus, the compound (22), a bioisoster of the carboxylic acid (Ic) or (Id), having 4,5-dihydro-5-oxo-4H-1,2,4,-oxadiazol-3-yl group can be produced (production method 10a).

As shown in FIG. 3, the 1,2,4-oxadiazol-5-on compound (28), a bioisoster of the carboxylic acid represented by the general formula (Ia) can be produced by reacting the compound (25) produced by the production method 9b described earlier and hydroxylamine hydrochloride to form an amidoxime compound (27), which is then reacted with an active carbonyl compound (production method 10b).

(2-11) Production Method 11a (See FIG. 2) and Production Method 11b (See FIG. 3)

Further, the amidoxime compound (21) is produced in the same manner as in the production method 10, from which a 1,2,4-oxadiazol-5-thion compound (23), a bioisoster of the carboxylic acid (Ic) or (Id), is produced.

More specifically, the compound (21) is reacted with 1,1'-thiocarbonyldiimidazole (TCDI) in a solvent (chloroform, toluene, xylene, diethyl ether, THF, dioxane, ethyl acetate, methyl ethyl ketone, acetonitrile, DMF, DMA, DMSO, ethanol, or a mixture thereof) preferably in the presence of a base (triethylamine, N-methylmorpholine, pyridine, DBU, DBN, sodium hydride, etc.). Thus, the compound (23), a bioisoster of the carboxylic acid (Ic) or (Id), and having a 4,5-dihydro-5-thioxo-4H-1,2,4-oxadiazol-3-yl group, can be produced. The reaction temperature typically ranges from about –30° C. to about 100° C., and preferably from about –10° C. to about 50° C. The amount of TCDI and base used is typically about 1 to about 10 equivalent weight, and preferably about 1 to about 1.5 equivalent weight, per mol of the compound (21) (production method 11a).

As shown in FIG. 3, the 1,2,4-oxadiazol-5-thion compound (29), a bioisoster of the carboxylic acid represented by the general formula (Ia), can be produced by reacting the compound (27) obtained by the above production method 10b with 1,1'-thiocarbonyldiimidazole (production method 11b).

(2-12) Production Method 12a (See FIG. 2) and Production Method 12b (See FIG. 3)

Further, the amidoxime compound (21) is produced in the same manner as in the production method 10, from which 1,2,4-thiadiazol-5-on compound (24), a bioisoster of the carboxylic acid (Ic) or (Id), can be produced.

More specifically, the compound (21) is reacted with TCDI in a solvent (chloroform, toluene, xylene, diethyl ether, THF, dioxane, ethyl acetate, methyl ethyl ketone, acetonitrile, DMF, DMA, DMSO, methanol, ethanol, or a mixture thereof), subjected to suitable aftertreatment, and further reacted in a solvent in the presence of a boron trifluoride diethyl ether complex or silica gel. Thus, the compound (24), a bioisoster of the carboxylic acid (Ic) or (Id), having a 4,5-dihydro-5-oxo-1,2,4,-thiadiazol-3-yl group, can be produced. The reaction temperature typically ranges from about −30° C. to about 100° C., and preferably from about −10° C. to about 50° C. The amount of TCDI used is typically about 1 to about 3 equivalent weight, and preferably about 1 to about 1.5 equivalent weight, per mol of the compound (22). The amount of boron trifluoride diethyl ether complex used is typically about 1 to about 10 equivalent weight, and preferably about 3 to about 6 equivalent weight, per mol of the compound (21). The amount of silica gel used is typically about 1 to about 50 times the weight, and preferably about 5 to about 20 times the weight, of the weight of the compound (21) (production method 12a).

As shown in FIG. 3, a 1,2,4-thiadiazol-5-on compound (30), a bioisoster of the carboxylic acid represented by the general formula (Ia), can be produced by reacting the compound (27) obtained by the production method 10b described above with 1,1'-thiocarbonyldiimidazole in the absence of a base, and subsequently reacting with an acid (production method 12b).

In the general formula (I), a sulfoxide compound (III-4-2) wherein n is 1 and L is alkylene-SO-alkylene can be produced by oxidizing a compound (III-4-1) wherein n is 1 and L is alkylenethioalkylene.

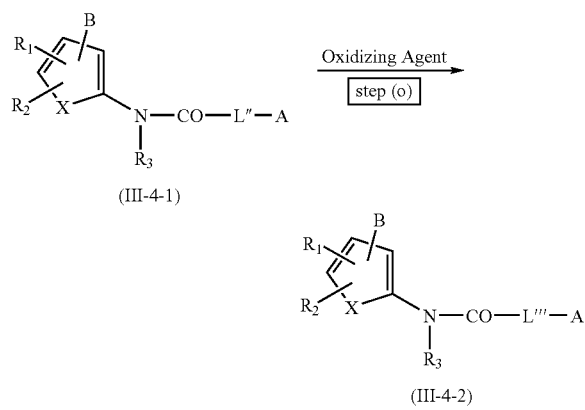

(III-4-1)

(III-4-2)

wherein $R_1$, $R_2$, $R_3$, B and X are defined as above, L" represents alkylenethioalkylene, and L''' represents alkylene-SO-alkylene.

Further, in the general formula (I), a sulfone compound (III-4-3) wherein n is 1 and L is alkylene-$SO_2$-alkylene can be produced by oxidizing the compound (III-4-1) wherein n is 1 and L is alkylenethioalkylene or an oxide thereof (III-4-2).

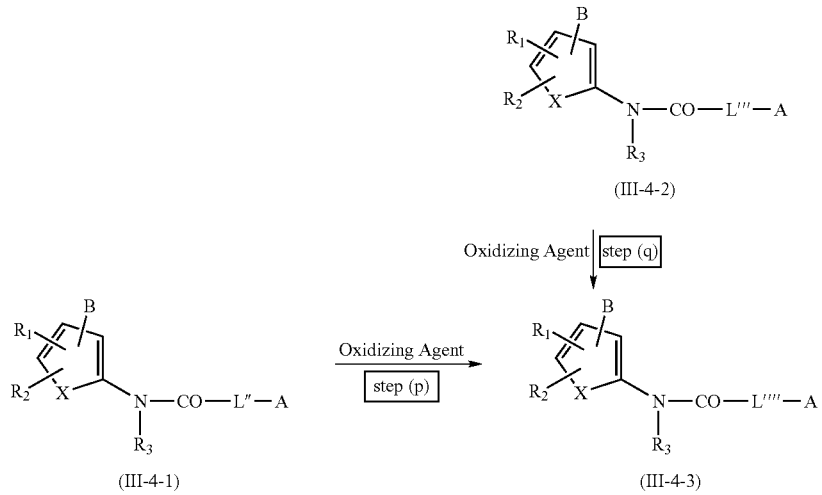

(III-4-2)

(III-4-1)

(III-4-3)

wherein $R_1$, $R_2$, $R_3$, B, X, L" and L''' are defined as above, and L"" represents alkylene-$SO_2$-alkylene.

Examples of the oxidizing agent used herein include hydrogen peroxide, peracetic acid, meta-chloro perbenzoic acid, etc. The amount of an oxidizing agent used is typically about 0.5 to about 2 equivalent weight, and preferably about 0.8 to about 1.2 equivalent weight, per mol of the compound (III-4-1).

Any solvents inactive to the reaction are usable, and examples include hydrocarbons (e.g., hexane, heptane, cyclohexane, etc.), halogenated hydrocarbons (e.g., dichloromethane, chloroform, etc.), aromatic hydrocarbons (e.g., benzene, toluene, xylene, anisole, etc.), ethers (e.g., ethyl ether, isopropyl ether, etc.), esters (e.g., methyl acetate, ethyl acetate, butyl acetate, etc.), ketones (e.g., acetone, methyl ethyl ketone, methyl isobutyl ketone, etc.), dioxane, tetrahydrofuran (THF), dimethyl formamide (DMF), dimethylacetamide (DMA), acetate, ethanol, water, or mixtures thereof, etc. The reaction temperature typically ranges from about −30° C. to about 80° C., and preferably about −20° C. to about 40° C.

Furthermore, an optically-active sulfoxide compound (III-4-2) can also be produced by the use of a resolving agent, or by a reaction in which one of the enantiomers is preferentially obtained by the combination of an oxidizing agent, a transitional metal such as titanium, and an asymmetric ligand. Examples of the transition metal include ortho-tetraisopropyl titanate, etc.; examples of an asymmetric ligand include diethyl ester tartrate, etc.; and examples of a resolving agent include 10-camphorsulfonic acid, 1-phenylethylamine, etc. Any reaction solvents inactive to the reaction are usable, and examples include hydrocarbons (e.g., hexane, heptane, cyclohexane, etc.), halogenated hydrocarbons (e.g., dichloromethane, chloroform, etc.), aromatic hydrocarbons (e.g., benzene, toluene, xylene, anisole, etc.), ethers (e.g., ethyl ether, isopropyl ether, etc.), esters (e.g., methyl acetate, ethyl acetate, butyl acetate, etc.), ketones (e.g., acetone, methyl ethyl ketone, methyl isobutyl ketone, etc.), dioxane, tetrahydrofuran (THF), dimethyl formamide (DMF), dimethylacetamide (DMA), acetate, ethanol, water, or mixtures thereof, etc.

The reaction temperature typically ranges from about −40° C. to about 80° C., and preferably from about −20° C. to about 40° C. The amount of oxidizing agent used is typically about 0.5 to about 2 equivalent weight, and preferably about 0.8 to about 1.2 equivalent weight, per mol of the compound (III-4-1). The amount of transitional metal and asymmetric ligand used is about 0.1 to about 3 equivalent weight, and preferably about 0.5 to about 2 equivalent weight, per mol of the compound (III-4-1). The amount of resolving agent used is about 0.5 to about 2 equivalents weight, and preferably about 0.8 to about 1.2 equivalent weight, per mol of the sulfoxide compound (III-4-2).

Examples of the oxidizing agent used to produce the sulfone compound (IIII-4-3) include hydrogen peroxide, peracetic acid, meta-chloro perbenzoic acid, etc.; any solvents inactive to the reaction are usable, and examples include hydrocarbons (e.g., hexane, heptane, cyclohexane, etc.), halogenated hydrocarbons (e.g., dichloromethane, chloroform, etc.), aromatic hydrocarbons (e.g., benzene, toluene, xylene, anisole, etc.), ethers (e.g., ethyl ether, isopropyl ether, etc.), esters (e.g., methyl acetate, ethyl acetate, butyl acetate, etc.), ketones (e.g., acetone, methyl ethyl ketone, methyl isobutyl ketone, etc.), dioxane, tetrahydrofuran (THF), dimethyl formamide (DMF), dimethylacetamide (DMA), acetate, ethanol, water, or mixtures thereof, etc. The reaction temperature typically ranges from about 0° C. to about 100° C., and preferably from about 20° C. to about 50° C. The amount of oxidizing agent used is typically about 2 to about 20 equivalent weight, and preferably about 3 to about 10 equivalent weight, per mol of the compound (III-4-1), and about 1 to about 10 equivalent weight, and preferably about 2 to about 5 equivalent weight, per mol of the sulfoxide compound (III-4-2).

Alternatively, in place of the compound (III-4-1), a synthesis intermediate (2), (3), (4a), (4b), (4c), (4e), (4f), (4g), (4h), (4'), (4''), (5), (6a) (8), (9), (15), (18), (19), or (25) is oxidized as a substrate, and a condensation reaction may follow. The oxidization reaction in this reaction can be carried out in the same manner as in the above, and the sulfoxide compound (III-4-2) or sulfone compound (III-4-3), the corresponding target compound, can also be obtained.

(3) PAI-1 Inhibitor

The present invention provides the use of the compound (I) described earlier as a PAI-1 inhibitor. Namely, the present invention provides a PAI-1 inhibitor containing the compound (I) described earlier as an active component. In other words, the PAI-1 inhibitor of the present invention contains the compound (I) described earlier as an active component.

The PAI-1 inhibitory action of the compound (I) can be evaluated with an in vitro assay system. An example of such an in vitro assay system is that in which PAI-1 activity to tissue plasminogen activator (t-PA) in the presence of the compound (I) are measured. The PAI-1 activity can be measured based on the formation of a reaction product formed by the action of t-PA to a substrate as an indicator. For example, Test Example to be described later demonstrates an in vitro assay system by which PAI-1 activity is measured based on an amount of p-nitroanilide (reaction product) formed by the action of t-PA on a chromogenic substrate (S-2288) as an indicator. The smaller the amount of the reaction product produced, the higher the PAI-1 inhibitory activity is assessed.

Alternatively, the PAI-1 inhibitory action of the compound (I) can be evaluated based on the formation of a complex between PAI-1 and t-PA (PAI-1/t-PA complex) measured by, for example, a western blotting method in the presence of the compound (I). The smaller the amount of the PAI-1/t-PA complex formed (PAI-1/t-PA complex formation inhibition), the higher the PAI-1 inhibitory activity is assessed.

The compounds (I) have inhibitory action on PAI-1 activity. Of these, preferable compounds are those in Examples 2, 7, 8, 10, 13 to 15, 18, 20 to 23, 30 to 38, 44 to 57 and 59; more preferable are those in Examples 7, 8, 10, 13 to 15, 21 to 23, 31 to 34, 38, 44 to 56 and 59; and particularly preferable are those in Examples 15, 23, 31 to 33, 44 to 47, 52, 54, 56 and 59. These compounds have outstanding PAI-inhibitory action as revealed in Text Example to be described later. This action enables plasmin to better degrade fibrin and fibrinogen, to promote the fibrinolytic system of the living body, and to improve an impaired fibrinolytic system of a living body.

Further, it has been revealed that PAI-1 is one of the factors that causes tissue fibril formation. According to the compound (I), tissue fibril formation and the diseases associated therewith can be prevented or ameliorated by virtue of the inhibitory action rendered by the compound on PAI-1 activity.

The PAI-1 inhibitor of the present invention contains such a compound (I) as an active component. Such a PAI-1 inhibitor may consist of 100% of the compound (I), or may contain an effective amount of the compound (I) so that PAI-1 inhibitory action is exhibited. The compound (I) content is not limited, but typically ranges from 0.1 to 99 wt. %, and preferably from 1 to 80 wt. %, in the PAI-1 inhibitor.

(4) Pharmaceutical Composition

The present invention provides a pharmaceutical composition containing the PAI-1 inhibitor described above as an active component. In other words, the pharmaceutical composition of the present invention contains the above-mentioned compound (I) as a active component. The pharmaceutical composition of the present invention has PAI-1 inhibitory action due to an effective amount of the compound (I) contained therein. As a result, the composition enhances the degradation of fibrin and fibrinogen by plasmin, and has a promoting action on the fibrinolytic system and also has an improvement action on a deteriorated fibrinolytic system of a living body.

For these actions, the pharmaceutical composition of the present invention can be used as a fibrinolytic-system-promoting drug. More specifically, the pharmaceutical composition of the present invention is useful as a preventive or treatment agent for the thrombotic diseases and pathologies with which PAI-1 activity is involved, or for the diseases and pathologies caused by decreased fibrinolytic system. Examples of such diseases or pathologies include thromboses in an artery, thromboses in a vein, deep-vein thrombosis (DVT) occurring during surgery, disseminated intravascular coagulation syndrome (DIC), angiopathy, neuropathy, retinopathy or nephropathy as a diabetic complication, or restenosis occurring after percutaneous transluminal coronary angioplasty (PTCA), or like other diseases associated with thrombogenesis. The thrombus in a artery herein refers to thrombosis in the brain, such as cerebral thrombosis, cerebral embolism, transient ischemic attack; thrombosis in the heart, such as angina pectoris, myocardial infarction; thrombosis in a lower extremity, such as lower extremity acute arterial thrombosis; and thrombosis in the upper intestinal tract, such as upper intestinal tract arterial thrombosis. Thrombus in a vein herein refers to thrombosis in the extremities, such as deep-vein thrombosis; or thrombosis occurring when a blood clot travels to the lungs, such as pulmonary embolism.

The pharmaceutical composition of the present invention has PAI-1 inhibitory action due to an effective amount of the compound (I) contained therein. As a result, the composition has a preventive or ameliorating action on tissue and organ fibril formation. For this action, the pharmaceutical composition of the present invention is useful as a preventive or treatment agent for the diseases and pathologies related to tissue or organ fibril formation associated with PAI-1 activity. Examples of such diseases and pathologies include fibrous tissues involved in pulmonary fibrosis, myocardial infarction; fibrous tissues involved in nephropathy, etc.

The pharmaceutical composition of the present invention is typically prepared by adding a pharmaceutically acceptable carrier or an additive in addition to the compound (I) in an effective amount to promote (or improve) the fibrinolytic system or for anti-fibril formation. The compound (I) content in the pharmaceutical composition is suitably determined in accordance with the kind of disease and pathology and administration form, but is typically 0.001 to 50 wt. %, and particularly 0.01 to 10 wt. % of the total weight (100 wt. %), of the pharmaceutical composition when formulated for systemic administration.

Examples of administration routes for the pharmaceutical composition of the present invention include oral administration as well as parenteral administration such as intravenous administration, intramuscular administration, subcutaneous administration, membrane administration, transdermal administration, rectal administration, etc. Oral administration and intravenous administration are preferable, with oral administration being more preferable. The pharmaceutical composition of the present invention can be prepared in various formulations (dosage forms) in accordance with such an administration route. Formulations (dosage forms) used in the present invention are described below, but are not limited thereto. Any formulation commonly used in the pharmaceutical industry can be employed.

Dosage form examples for oral administration include powders, granules, capsules, pills, tablets, elixirs, suspensions, emulsions and syrups, from which a suitable formulation can be selected. Further, these formulations can be modified to be slowly released, stable, easily disintegrated, hardly disintegrated, enteric-coated, easily absorbed, etc.

Dosage form examples for intravenous administration, intramuscular administration, or subcutaneous administration include injection or drip infusion (including dried products prepared before use), etc., from which a suitable formulation can be selected.

Dosage form examples for membrane administration, transdermal administration, or rectal administration include chewable tablets, sublingual tablets, buccal tablets, lozenges, ointments, patches, liquids, etc., from which a suitable formulation can be selected in accordance with an application site. Further, these formulations can also be modified to be slowly released, stable, easily disintegrated, hardly disintegrated, easily absorbed, etc.

The pharmaceutical composition of the present invention can contain a pharmaceutically acceptable carrier and additive in accordance with the dosage form (oral administration or various parenteral administrations). Examples of pharmaceutically acceptable carriers and additives include solvents, excipients, coating agents, bases, binders, lubricants, disintegrating agents, solubilizers suspending agents, viscosity imparting agents, emulsifiers, stabilizers, buffers, isotonizing agent, pain-relieving agent, preservatives, flavor agents, fragrances, and coloring agents. Specific examples of a pharmaceutically acceptable carrier and additive are given below, but are not limited thereto.

Examples of a solubilizer include purified water, sterilized purified water, injection water, physiological saline, peanut oil, ethanol, glycerol, etc. Examples of an excipient include starches (e.g., potato starch, wheat starch, corn starch), lactose, glucose, saccharose, crystalline cellulose, calcium sulfate, calcium carbonate, sodium hydrogencarbonate, sodium chloride, talc, titanium oxide, trehalose, xylitol, etc.

Examples of binders includes starches and derivatives thereof, cellulose and derivatives thereof (e.g., methylcellulose, ethylcellulose, hydroxypropyl cellulose, carboxymethyl cellulose), gelatins, sodium alginate, traganth, gum arabic, or like natural polymer compounds; polyvinylpyrrolidone, polyvinylalcohols, or like synthesized polymer compounds; dextrin, hydroxypropyl starch, etc.

Examples of lubricants include light anhydrous silicic acid, stearic acid and salts thereof (e.g., stearic acid magnesium), talc, waxes, wheat starch, macrogols, hydrogen-added vegetable oils, sucrose fatty-acid ester, polyethylene glycol, silicone oil, etc.

Examples of disintegrating agents include starches and derivatives thereof, agar, gelatin powders, sodium hydrogencarbonate, calcium carbonate, celluloses and derivatives thereof, hydroxypropyl starch, carboxymethyl cellulose and salts as well as crosslinked moieties thereof, low-substituted hydroxypropyl cellulose, etc.

Examples of solubilizers include cyclodextrin, ethanol, propylene glycol, polyethylene glycol, etc. Examples of suspending agents include sodium carboxymethylcellulose, polyvinyl pyrrolidone, gum arabic, traganth, sodium alginate, aluminium monostearate, citric acid, various surfactants, etc.

Examples of viscosity imparting agents include sodium carboxymethylcellulose, polyvinyl pyrrolidone, methylcellulose, hydroxypropyl methylcellulose, polyvinyl alcohol, traganth, gum arabic, sodium alginate, etc.

Examples of emulsifiers include gum arabic, cholesterol, traganth, methylcellulose, lecithin, various surfactants (e.g., Polyoxyl 40 Stearate, sorbitan sesquioleate, polysorbate 80, sodium lauryl sulfate), etc.

Examples of stabilizers include tocopherol, chelating agents (e.g., EDTA, thioglycolic acid), inactive gases (e.g., nitrogen, carbon dioxide), reductants (e.g., sodium hydrogensulfite, sodium thiosulfate, ascorbic acid, rongalite), etc.

Examples of buffers include dibasic sodium phosphate, sodium acetate, sodium citrate, boric acid, etc.

Examples of isotonizing agents include sodium chloride, glucose, etc. Examples of pain-relieving agents include local anesthetics (procaine hydrochloride, lidocaine), benzyl alcohol, glucose, sorbitol, amino acids, etc.

Examples of flavor agents include saccharose, saccharine, glycyrrhiza extract, sorbitol, xylitol, glycerol, etc. Examples of fragrances include orange peel tincture, rose oils, etc. Examples of coloring agents include water-soluble food dyes, lake dyes, etc.

Examples of preservatives include benzoic acids and salts thereof, peroxybenzoic acid esters, chlorobutanol, inverted soaps, benzyl alcohol, phenyl, thimerosal, dehydroacetic acid, boric acid, etc.

Examples of coating agents include saccharose, hydroxypropyl cellulose (HPC), shellac, gelatins, glycerol, sorbitol, hydroxypropyl methylcellulose (HPMC), ethylcellulose, polyvinylpyrrolidone (PVP), hydroxypropyl methylcellulose phthalate (HPMCP), cellulose acetate phthalate (CAP), methyl methacrylate-methacrylic acid copolymer and polymers described above, etc.

Examples of bases include vaselines, liquid paraffins, carnauba wax, beef tallow, hydrogenated oils, paraffins, bee wax, vegetable oils, macro goals, macrogol fatty-acid ester, stearic acid, sodium carboxymethylcellulose, bentonite, cacao butter, Witepsol, gelatins, stearyl alcohol, hydrous lanolin, cetanol, light liquid paraffins, hydrophilic vaselines, simple ointments, white ointments, hydrophilic ointments, macrogol ointments, hard fats, o/w emulsion bases, w/o emulsion bases, etc.

Known drug delivery systems (DDS) can be applied for the dosage forms given above. The term DDS formulation as used in the present specification refers to slow-released formulations, locally-applied formulations (lozenges, buccal tablets, sublingual tablets, etc.), drug control-released formulations, enteric coated formulations and gastric soluble formulations, etc., that are all prepared in the best form considering administration route, bioavailability, side effects, etc.

When the pharmaceutical composition of the present invention is used as a preventive drug or treatment drug for pathologies related to a compromised fibrinolytic system (thrombogenesis), the dosage for oral administration ranges preferably from 0.03 to 300 mg/kg of body weight, and more preferably from 0.1 to 50 mg/kg of body weight, on the compound (I) basis. The dosage for intravenous administration is selected from a range so that an effective concentration of the compound (I) in blood is preferably from 0.2 to 50 µg/mL, and more preferably from 0.5 to 20 µg/mL.

Further, when the pharmaceutical composition of the present invention is used as a preventive drug or a treatment drug for pathologies related to tissue fibril formation, the dosage for oral administration ranges preferably from 0.03 to 300 mg/kg of body weight, and more preferably from 0.1 to 50 mg/kg of body weight, on the compound (I) basis. When intravenously administered, the dosage of the composition is selected from a range so that an effective concentration of the compound (I) in blood is preferably from 0.2 to 50 µg/mL, and more preferably from 0.5 to 20 µg/mL. The dosages above are variable depending on age, sex, physique, etc., of a patient.

EXAMPLES

The present invention will be described in more detail below with reference to Examples and Experimental Examples. However, the present invention is not limited to such Examples. In these Examples, nuclear magnetic resonance spectra ($^1$H-NMR) were measured using a Varian Gemini 200. Chemical shift is shown as a δ value (ppm) using tetramethylsilane (TMS) as an internal standard. Each column chromatography elution was completed under observation using TLC (Thin Layer Chromatography). For TLC observation, silica gel 60F$_{254}$ produced by Merck Co. was used as the TLC plate. Silica gel 60 (70 to 230 meshes) produced by Merck Co. was used as the silica gel for each column.

The chemical names used in the Examples are given as the Japanese translation of the chemical names used by Chem-Draw Ultra Version 10.0 from CambridgeSoft Corporation.

Example 1

Production of Sodium 2-(6-(3-(tert-Butoxycarbonyl)-4-phenylthiophen-2-ylamino)-6-oxohexanamido)benzoate The titled compound was prepared according to Steps (i) to (v) below.

(i) tert-Butyl 2-amino-4-phenylthiophene-3-carboxylate 10.6 g (88.2 mmol) of acetophenone, 20 g (141.6 mmol) of tert-butyl cyanoacetate, 5.3 g (88.2 mmol) of acetic acid and 6.2 g (70.8 mmol) of morpholine were heated to reflux in 50 ml of toluene for 12.5 hours while removing water. After cooling, the reaction mixture was washed using water. The resulting organic layer was dried over anhydrous sodium sulfate, and subsequently the solvent was distilled off under reduced pressure. 100 ml of DMF, 2.8 g (88.2 mmol) of sulfur and 7.7 g (88.2 mmol) of morpholine were added to the residue obtained, and the mixture was stirred overnight. After adding ethyl acetate, the reaction mixture was washed with water. The resultant organic layer was dried over anhydrous sodium sulfate. Subsequently, the solvent was distilled off under reduced pressure. The crude product obtained was separated and purified by silica gel column chromatography, and was subsequently recrystallized with hexane to give 14.7 g of tert-butyl 2-amino-4-phenylthiophene 3-carboxylate (yield: 61%).

$^1$H-NMR (CDCl$_3$) δ: 1.19 (9H, s), 6.01 (2H, bs), 6.03 (1H, s), 7.23-7.36 (5H, m).

(ii) tert-Butyl 2-(6-methoxy-6-oxohexanamido)-4-phenylthiophene-3-carboxylate

A mixture of 15.8 g (88.2 mmol) of methyl adipoyl chloride and 24.3 g (88.2 mmol)(theoretical value) of tert-butyl 2-amino-4-phenylthiophene-3-carboxylate (crude product) obtained using the same method as in Example 1-(i) was stirred in a DMA solution at room temperature for 1 hour. The reaction mixture was poured into ice water, and sodium hydrogen carbonate was then added to alkalize. The precipitate was filtered off, washed with water and hexane, and dried to give 30.3 g of tert-butyl 2-(6-methoxy-6-oxohexanamido)-4-phenylthiophene-3-carboxylate (yield: 82%).

$^1$H-NMR (CDCl$_3$) δ: 1.19 (9H, s), 1.64-1.92 (4H, m), 2.39 (2H, t, J=7.1 Hz), 2.55 (2H, t, J=7.1 Hz), 3.68 (3H, s), 6.55 (1H, d, J=0.7 Hz), 7.21-7.39 (5H, m), 11.3 (1H, s).

(iii) 6-(3-(tert-Butoxycarbonyl)-4-phenylthiophen-2-ylamino)-6-oxohexanoic Acid 29.0 g (69.4 mmol) of tert-butyl 2-(6-methoxy-6-oxohexanamido)-4-phenylthiophene-3-carboxylate was dissolved in 100 ml of THF. Subsequently, 104 ml of a 1N aqueous sodium hydroxide solution was added, and the mixture stirred at 50 to 60° C. for 2.5 hours. After concentrating the reaction mixture, the resulting aqueous solution was washed with ethyl acetate. 1N hydrochloric acid was added to weakly acidify the aqueous solution, which was then extracted with ethyl acetate. The organic layer obtained was dried over anhydrous sodium sulfate, and the solvent was distilled off under reduced pressure. The resulting crude product was recrystallized with ethyl acetate-hexane to give 20.2 g of 6-(3-(tert-butoxycarbonyl)-4-phenylthiophen-2-ylamino)-6-oxohexanoic acid (yield 72%).

$^1$H-NMR (CDCl$_3$) δ: 1.19 (9H, s), 1.66-1.94 (4H, m), 2.43 (2H, t, J=7.1 Hz), 2.56 (2H, t, J=7.1 Hz), 6.55 (1H, s), 7.19-7.40 (5H, m), 11.3 (1H, s).

(iv) tert-Butyl 2-(6-(2-(methoxycarbonyl)phenylamino)-6-oxohexanamido)-4-phenylthiophene-3-carboxylate After adding 1.0 g (2.48 mmol) of the 6-(3-(tert-butoxycarbonyl)-4-phenylthiophen-2-ylamino)-6-oxohexanoic acid to THF, 376 mg (3.72 mmol) of triethylamine and 473 mg (3.47 mmol) of isobutyl chloroformate were added and stirred for 1 hour at 0° C. 450 mg (2.97 mmol) of methyl anthranilate was then added and stirred for 1 hour. After adding ethyl acetate, the mixture was washed with a saturated sodium chloride solution, and then dried over anhydrous sodium sulfate. The solvent was distilled off under reduced pressure. The crude product obtained was separated and purified by silica gel column chromatography to give 730 mg of tert-butyl 2-(6-(2-(methoxycarbonyl)phenylamino)-6-oxohexanamido)-4-phenylthiophene-3-carboxylate (yield 55%).

$^1$H-NMR (CDCl$_3$) δ: 1.19 (9H, s), 1.80-1.94 (4H, m), 2.43-2.66 (4H, m), 3.93 (3H, s), 6.54 (1H, s), 7.03-7.13 (1H, m), 7.20-7.40 (5H, m), 7.49-7.58 (1H, m), 8.00-8.06 (1H, m), 8.69-8.76 (1H, m), 11.1 (1H, s), 11.3 (1H, s).

(v) Sodium 2-(6-(3-(tert-butoxycarbonyl)-4-phenylthiophen-2-ylamino)-6-oxohexanamido)benzoate 730 mg (1.36 mmol) of the tert-butyl 2-(6-(2-(methoxycarbonyl)phenylamino)-6-oxohexanamido)-4-phenylthiophene-3-carboxylate was dissolved in THF, 2 ml of a 1N aqueous sodium hydroxide solution was then added and stirred at 50 to 60° C. for 6 hours. Subsequently, the reaction mixture was distilled off under reduced pressure to give the residue. THF and ethyl acetate were then added to the resulting residue, and the mixture was filtered. After vacuum concentration of the filtrate, IPE was added, and the resulting residue was collected by filtration to obtain the titled sodium 2-(6-(3-(tert-butoxycarbonyl)-4-phenylthiophen-2-ylamino)-6-oxohexanamido)benzoate (yield 33%).

$^1$H-NMR (DMSO-d$_6$) δ: 1.17 (9H, s), 1.53-1.80 (4H, m), 2.25-2.40 (2H, m), 2.55-2.67 (2H, m), 6.84 (1H, s), 6.86-6.96 (1H, m), 7.17-7.43 (6H, m), 7.94-8.00 (1H, m), 8.42-8.50 (1H, m), 11.0 (1H, s), 14.3 (1H, s).

Example 2

Production of sodium 2-(6-(3-(tert-butoxycarbonyl)-4-phenylthiophen-2-ylamino)-6-oxohexanamido)-5-chlorobenzoate The above titled compound was prepared according to Steps (i) and (ii) described below.

(i) tert-Butyl 2-(6-(4-chloro-2-(methoxycarbonyl)phenylamino)-6-oxohexanamido)-4-phenylthiophene-3-carboxylate Using the same method as in Example 1-(iv), methyl 2-amino-5-chlorobenzoate was reacted with the 6-(3-(tert-butoxycarbonyl)-4-phenylthiophen-2-ylamino)-6-oxohexanoic acid obtained in Example 1-(iii) to give tert-butyl 2-(6-(4-chloro-2-(methoxycarbonyl)phenylamino)-6-oxohexanamido)-4-phenylthiophene-3-carboxylate (yield 46%).

$^1$H-NMR (CDCl$_3$) δ: 1.19 (9H, s), 1.81-1.93 (4H, m), 2.46-2.64 (4H, m), 3.94 (3H, s), 6.54 (1H, d, J=0.9 Hz), 7.20-7.39 (5H, m), 7.48 (1H, dd, J=9.2, 2.6 Hz), 7.99 (1H, d, J=2.6 Hz), 8.72 (1H, d, J=9.2 Hz), 11.0 (1H, s), 11.3 (1H, s).

(ii) Sodium 2-(6-(3-(tert-butoxycarbonyl)-4-phenylthiophen-2-ylamino)-6-oxohexanamido)-5-chlorobenzoate Using the same method as in Example 1-(v), the titled sodium 2-(6-(3-(tert-butoxycarbonyl)-4-phenylthiophen-2-ylamino)-6-oxohexanamido)-5-chlorobenzoate (yield 77%) was obtained using the tert-butyl 2-(6-(4-chloro-2-(methoxycarbonyl)phenylamino)-6-oxohexanamido)-4-phenylthiophene-3-carboxylate.

$^1$H-NMR (DMSO-d$_6$) δ: 1.17 (9H, s), 1.60-1.75 (4H, m), 2.25-2.40 (2H, m), 2.51-2.64 (2H, m), 6.83 (1H, s), 7.20-7.44 (6H, m), 7.92 (1H, d, J=2.7 Hz), 8.49 (1H, d, J=8.8 Hz), 11.0 (1H, s), 14.3 (1H, s).

Example 3

Production of 2-(6-oxo-6-(4-phenylthiophen-2-ylamino)hexanamido)benzoic acid

The sodium 2-(6-(3-(tert-butoxycarbonyl)-4-phenylthiophen-2-ylamino)-6-oxohexanamido)benzoate of Example 1-(v) was neutralized with hydrochloric acid, and 950 mg (1.82 mmol) of the resulting 2-(6-(3-(tert-butoxycarbonyl)-4-phenylthiophen-2-ylamino)-6-oxohexanamido)benzoic acid and 5 ml of TFA were stirred in 4 ml of methylene chloride as a solvent at 40° C. for 11 hours. After concentration, the reaction mixture was separated and purified by silica gel column chromatography to give the titled 2-(6-oxo-6-(4-phenylthiophen-2-ylamino)hexanamido)benzoic acid (yield 18%).

$^1$H-NMR (DMSO-d$_6$) δ: 1.52-1.80 (4H, m), 2.28-2.48 (4H, m), 6.88-7.50 (7H, m), 7.56-7.68 (2H, m), 7.90-8.12 (1H, m), 8.40-8.58 (1H, m), 11.5 (1H, s), 13.4 (1H, s).

Example 4

Production of 2-(6-(2-carboxy-4-chlorophenylamino)-6-oxohexanamido)-4-phenylthiophen-3-carboxylic acid The sodium 2-(6-(3-(tert-butoxycarbonyl)-4-phenylthiophen-2-ylamino)-6-oxohexanamido)-5-chlorobenzoate of Example 2-(ii) was neutralized with hydrochloric acid. 390 mg (0.70 mmol) of the resulting 2-(6-(3-(tert-butoxycarbonyl)-4-phenylthiophen-2-ylamino)-6-oxohexanamido)-5-chlorobenzoic acid and 2 ml of TFA were stirred in 4 ml of methylene chloride as a solvent at 0° C. for 4 hours, and the mixture was then stirred at room temperature for 2 hours. After concentrating the reaction mixture, hexane was added. The precipitate was collected by filtration, washed with IPE, and dried to give the titled 2-(6-(2-carboxy-4-chlorophenylamino)-6-oxohexanamido)-4-phenylthiophen-3-carboxylic acid (yield 95%).

$^1$H-NMR (DMSO-d$_6$) δ: 1.60-1.80 (4H, m), 2.40-2.70 (4H, m), 6.84 (1H, s), 7.20-7.46 (5H, m), 7.65 (1H, dd, J=9.0, 2.7 Hz), 7.90 (1H, d, J=2.7 Hz), 8.50 (1H, d, J=9.0 Hz), 11.0 (1H, s), 11.3 (1H, s).

Example 5

Production of 2-(6-oxo-6-(4-phenylpiperidin-1-yl)hexanamido)-4-phenylthiophen-3-carboxylic acid The above titled compound was prepared according to Steps (i) and (ii) described below.

(i) tert-Butyl 2-(6-oxo-6-(4-phenylpiperidin-1-yl)hexanamido)-4-phenylthiophen-3-carboxylate After adding 1.0 g (2.48 mmol) of the 6-(3-(tert-butoxycarbonyl)-4-phenylthiophen-2-ylamino)-6-oxohexanoic acid obtained in Example 1-(iii) to THF, 376 mg (3.71 mmol) of triethylamine and 474 mg (3.50 mmol) of isobutyl chloroformate were added at 0° C., and the mixture was stirred for 1 hour at 0° C. Subsequently, 480 mg (2.97 mmol) of 4-phenyl piperidine was added and stirred at room temperature for 1 hour. Ethyl acetate was added to the reaction mixture, washed with a saturated sodium hydrogen carbonate and a saturated sodium chloride solution, and then dried over anhydrous sodium sulfate. The solvent was distilled off under reduced pressure. The crude product obtained was separated and purified by silica gel column chromatography to give 850 mg of tert-butyl 2-(6-Oxo-6-(4-phenylpiperidin-1-yl)hexanamido)-4-phenylthiophen-3-carboxylate (yield 63%).

$^1$H-NMR (CDCl$_3$) δ: 1.19 (9H, s), 1.48-2.00 (8H, m), 2.36-2.83 (6H, m), 3.03-3.23 (1H, m), 3.92-4.06 (1H, m), 4.72-4.86 (1H, m), 6.54 (1H, d, J=0.7 Hz), 7.13-7.40 (10H, m), 11.3 (1H, s).

(ii) 2-(6-Oxo-6-(4-phenylpiperidin-1-yl)hexanamido)-4-phenylthiophen-3-carboxylic acid 850 mg (1.56 mmol) of the tert-butyl 2-(6-oxo-6-(4-phenylpiperidin-1-yl)hexanamido)-4-phenylthiophen-3-carboxylate and 2 ml of TFA were stirred in 5 ml of methylene chloride as a solvent at room temperature for 9 hours. After concentrating the reaction mixture, the precipitate obtained by the addition of IPE was collected by filtration, washed with ethyl acetate and dried, thus giving the titled 2-(6-oxo-6-(4-phenylpiperidin-1-yl)hexanamido)-4-phenylthiophen-3-carboxylic acid (yield 92%).

$^1$H-NMR (DMSO-d$_6$) δ: 1.10-1.90 (8H, m), 2.10-2.85 (6H, m), 3.00-3.10 (1H, m), 3.90-4.10 (1H, m), 4.24-4.44 (1H, m), 6.84 (1H, s), 7.10-7.50 (10H, m), 11.2 (1H, s).

Example 6

Production of 2-(6-(4-chlorophenylamino)-6-oxohexanamido)-4-phenylthiophen-3-carboxylic acid The above titled compound was prepared according to Steps (i) and (ii) described below.

(i) tert-Butyl 2-(6-(4-chlorophenylamino)-6-oxohexanamido)-4-phenylthiophen-3-carboxylate Using the same method as in Example 5-(i), 4-chloroaniline was reacted with the 6-(3-(tert-butoxycarbonyl)-4-phenylthiophen-2-ylamino)-6-oxohexanoic acid obtained in Example 1-(iii) to give tert-butyl 2-(6-(4-chlorophenylamino)-6-oxohexanamido)-4-phenylthiophen-3-carboxylate (yield 93%).

$^1$H-NMR (CDCl$_3$) δ: 1.19 (9H, s), 1.78-1.94 (4H, m), 2.44-2.61 (4H, m), 6.57 (1H, s), 7.22-7.34 (5H, m), 7.53-7.58 (2H, m), 7.78 (1H, s), 11.4 (1H, s).

(ii) 2-(6-(4-Chlorophenylamino)-6-oxohexanamido)-4-phenylthiophen-3-carboxylic acid Using the same method as in Example 5-(ii), the titled 2-(6-(4-chlorophenylamino)-6-oxohexanamido)-4-phenylthiophen-3-carboxylic acid (yield 33%) was obtained using tert-butyl 2-(6-(4-chlorophenylamino)-6-oxohexanamido)-4-phenylthiophen-3-carboxylate.

$^1$H-NMR (DMSO-d$_6$) δ: 1.52-1.72 (4H, m), 2.23-2.42 (2H, m), 2.51-2.65 (2H, m), 6.84 (1H, s), 7.23-7.40 (7H, m), 7.58-7.67 (2H, m), 10.0 (1H, s), 11.3 (1H, s), 13.0 (1H, bs).

Example 7

Production of 2,2'-(oxybis((1-oxo-2,1-ethanediyl)imino))bis(5-methyl-4-phenylthiophen-3-carboxylic acid)

The above titled compound was prepared according to Steps (i) to (iii) described below.

(i) tert-Butyl 2-amino-5-methyl-4-phenylthiophene-3-carboxylate 5.0 g (37.3 mmol) of propiophenone, 8.4 g (59.6 mmol) of tert-butyl cyanoacetate, 2.2 g (37.3 mmol) of acetic acid and 2.6 g (29.8 mmol) of morpholine were heated to reflux while removing water in 50 ml of toluene for 10.5 hours. After cooling, the reaction mixture was washed with water. After drying the resulting organic layer over anhydrous sodium sulfate, the solvent was distilled off under reduced pressure. 50 ml of DMF, 1.2 g (37.3 mmol) of sulfur and 3.3 g (37.3 mmol) of morpholine were added to the resultant residue, and the mixture was stirred overnight. Subsequently, ethyl acetate was added to the reaction mixture, and washed with water. The resultant organic layer was dried over anhydrous sodium sulfate, and the solvent was then distilled off under reduced pressure. The crude product obtained was separated and purified by silica gel column chromatography to obtain 3.5 g of tert-butyl 2-amino-5-methyl-4-phenylthiophene-3-carboxylate (yield 33%).

$^1$H-NMR (CDCl$_3$) δ: 1.10 (9H, s), 2.02 (3H, s), 5.89 (2H, bs), 7.09-7.38 (5H, m).

(ii) 2,2'-(Oxybis((1-oxo-2,1-ethanediyl)imino))bis(tert-butyl 5-methyl-4-phenylthiophene-3-carboxylate)

A mixture of 295 mg (1.73 mmol) of diglycolyl chloride and 1.0 g (3.46 mmol) of tert-butyl 2-amino-5-methyl-4-phenylthiophene-3-carboxylate was stirred in 10 ml of DMA at room temperature for 12 hours. The reaction mixture was poured into ice water, and sodium hydrogen carbonate was then added to alkalize. The precipitate was filtered off. The filtrate was dried, and separated and purified by silica gel column chromatography to give 0.94 g of 2,2'-(oxybis((1-oxo-2,1-ethanediyl)imino))bis(tert-butyl 5-methyl-4-phenylthiophene-3-carboxylate) (yield 80%).

$^1$H-NMR (CDCl$_3$) δ: 1.04 (18H, s), 2.12 (6H, s), 4.43 (4H, s), 7.06-7.40 (10H, m), 12.1 (2H, s).

(iii) 2,2'-(Oxybis((1-oxo-2,1-ethanediyl)imino))bis(5-methyl-4-phenylthiophen-3-carboxylic acid)

0.94 g (1.4 mmol) of 2,2'-(oxybis((1-oxo-2,1-ethanediyl)imino))bis(tert-butyl 5-methyl-4-phenylthiophene-3-carboxylate) and 2 ml of TFA was stirred in 5 ml of methylene chloride while being cooled with ice for 8 hours. After concentrating the reaction mixture, hexane was added to separate the precipitate by filtration. The precipitate was washed with ethyl acetate, and dried to give the titled 2,2'-(oxybis((1-oxo-2,1-ethanediyl)imino))bis(5-methyl-4-phenylthiophen-3-carboxylic acid) (yield 96%).

$^1$H-NMR (DMSO-d$_6$) δ: 2.09 (6H, s), 4.49 (4H, s), 7.08-7.46 (10H, m), 12.0 (2H, s).

Example 8

Production of 2,2'-(oxybis((1-oxo-2,1-ethanediyl)imino))bis(5-phenylthiophen-3-carboxylic acid)

The above titled compound was prepared according to Steps (i) to (iii) described below.

(i) tert-Butyl 2-amino-5-phenylthiophene-3-carboxylate

Using the same method as in Example 7-(i), tert-butyl 2-amino-5-phenylthiophene-3-carboxylate (yield 11%) was obtained using phenylacetaldehyde.

$^1$H-NMR (CDCl$_3$) δ: 1.57 (9H, s), 5.95 (2H, bs), 7.10-7.48 (6H, m).

(ii) 2,2'-(Oxybis((1-oxo-2,1-ethanediyl)imino))bis(tert-butyl 5-phenylthiophene-3-carboxylate)

Using the same method as in Example 7-(ii), 2,2'-(oxybis((1-oxo-2,1-ethanediyl)imino))bis(tert-butyl 5-phenylthiophene-3-carboxylate) was obtained using tert-butyl 2-amino-5-phenylthiophene-3-carboxylate (yield 65%).

$^1$H-NMR (CDCl$_3$) δ: 1.49 (18H, s), 4.46 (4H, s), 7.22-7.44 (8H, m), 7.55-7.69 (4H, m), 11.9 (2H, s).

(iii) 2,2'-(Oxybis((1-oxo-2,1-ethanediyl)imino))bis(5-phenylthiophen-3-carboxylic acid)

Using the same method as in Example 7-(iii), the titled 2,2'-(oxybis((1-oxo-2,1-ethanediyl)imino))bis(5-phenylthiophen-3-carboxylic acid) (yield 50%) was obtained using 2,2'-(oxybis((1-oxo-2,1-ethanediyl)imino))bis(tert-butyl 5-phenylthiophene-3-carboxylate.

$^1$H-NMR (DMSO-d$_6$) δ: 4.55 (4H, s), 7.24-7.75 (12H, m), 11.8 (2H, s), 13.4 (2H, bs).

Example 9

Production of 2,2'-(oxybis((1-oxo-2,1-ethanediyl)imino))bis(4-phenylthiophen-3-carboxylic acid)

The above titled compound was prepared according to Steps (i) and (ii) described below.

(i) 2,2'-(Oxybis((1-oxo-2,1-ethanediyl)imino))bis(tert-butyl 4-phenylthiophene-3-carboxylate)

Using the same method as in Example 7-(ii), 2,2'-(oxybis((1-oxo-2,1-ethanediyl)imino))bis(tert-butyl 4-phenylthiophene-3-carboxylate) (yield 70%) was obtained using the tert-butyl 2-amino-4-phenylthiophene-3-carboxylate of Example 1-(i).

$^1$H-NMR (CDCl$_3$) δ: 1.11 (18H, s), 4.46 (4H, s), 6.60 (2H, d, J=0.7 Hz), 7.18-7.39 (10H, m), 12.2 (2H, s).

(ii) 2,2'-(Oxybis((1-oxo-2,1-ethanediyl)imino))bis(4-phenylthiophen-3-carboxylic acid)

Using the same method as in Example 7-(iii), the titled 2,2'-(oxybis((1-oxo-2,1-ethanediyl)imino))bis(4-phenylthiophen-3-carboxylic acid) (yield 95%) was obtained using 2,2'-(oxybis((1-oxo-2,1-ethanediyl)imino))bis(tert-buty 4-phenylthiophene-3-carboxylate).

$^1$H-NMR (DMSO-d$_6$) δ: 4.52 (4H, s), 6.92 (2H, s), 7.10-7.58 (10H, m), 12.0 (2H, s), 13.1 (2H, bs).

Example 10

Production of 2-(2-(2-(3-(tert-butoxycarbonyl)-5-methyl-4-phenylthiophen-2-ylamino)-2-oxoethoxy)acetamido)-5-methyl-4-phenylthiophen-3-carboxylic acid Using the same method as in Example 7-(iii), 1.5 g (2.22 mmol) of 2,2'-(oxybis((1-oxo-2,1-ethanediyl)imino))bis(tert-butyl 5-methyl-4-phenylthiophene-3-carboxylate of Example 7-(ii) and 3 ml of TFA were reacted in 30 ml of methylene chloride at room temperature. Subsequently, the reactant was concentrated. The crude product obtained was separated and purified by silica gel column chromatography to obtain the titled 2-(2-(2-(3-(tert-butoxycarbonyl)-5-methyl-4-phenylthiophen-2-ylamino)-2-oxoethoxy)acetamido)-5-methyl-4-phenylthiophen-3-carboxylic acid (yield 19%).

$^1$H-NMR (DMSO-d$_6$) δ: 0.98 (9H, s), 2.07 (3H, s), 2.09 (3H, s), 4.49 (4H, s), 7.07-7.45 (10H, m), 11.7 (1H, s), 12.1 (1H, s).

Example 11

Production of sodium 2-(6-(3-(tert-butoxycarbonyl)-4-isopropylthiophen-2-ylamino)-6-oxohexanamido)benzoate The above titled compound was prepared according to Steps (i) to (v) described below.

(i) tert-Butyl 2-amino-4-isopropylthiophene-3-carboxylate

A mixture of 15.2 g (176 mmol) of 3-methyl-2-butanone, 24.9 g (176 mmol) of tert-butyl cyanoacetate, 5.7 g (176 mmol) of sulfur and 15.4 g (176 mmol) of morpholine were added to 75 ml of DMF, and stirred under the argon atmosphere at room temperature for 15 hours. Subsequently, the reaction mixture was then stirred at 70 to 80° C. for 8 hours. The reaction mixture was poured into a sodium chloride solution, and was extracted with ethyl acetate. Subsequently, the resulting organic layer was washed with water, and the solvent was distilled off under reduced pressure. The obtained crude product was separated and purified by silica gel column chromatography to give 18.3 g of tert-butyl 2-amino-4-isopropylthiophene-3-carboxylate (yield 43%).

$^1$H-NMR (CDCl$_3$) δ: 1.18 (6H, d, J=6.8 Hz), 1.57 (9H, s), 3.39 (1H, septet, J=6.8 Hz), 5.87 (1H, d, J=1.0 Hz), 6.02 (2H, bs).

(ii) tert-Butyl 4-isopropyl-2-(6-methoxy-6-oxohexanamido)thiophene-3-carboxylate A mixture of 3.4 ml (22 mmol) of methyl adipoyl chloride and 4.8 g (20 mmol) of the tert-butyl 2-amino-4-isopropylthiophene-3-carboxylate was stirred in DMA at room temperature for 1 hour. The reaction mixture was poured into ice water, then alkalized with sodium hydrogen carbonate, and then extracted with ethyl acetate. The resultant organic layer was washed with a saturated sodium chloride solution and water, dried over anhydrous sodium sulfate, and concentrated. Hexane was added to the resultant residue. The precipitate was filtered off, washed with hexane, and dried to give 7.11 g of tert-butyl 4-isopropyl-2-(6-methoxy-6-oxohexanamido)thiophene-3-carboxylate (yield 92%).

$^1$H-NMR (CDCl$_3$) δ: 1.21 (6H, d, J=6.8 Hz), 1.61 (9H, s), 1.63-1.87 (4H, m), 2.30-2.42 (2H, m), 2.42-2.53 (2H, m), 3.47 (1H, septet, J=6.8 Hz), 3.67 (3H, s), 6.42 (1H, d, J=0.9 Hz), 11.5 (1H, s).

(iii) 6-(3-(tert-Butoxycarbonyl)-4-isopropylthiophen-2-ylamino)-6-oxohexanoic acid 3.83 g (10 mmol) of the tert-butyl 4-isopropyl-2-(6-methoxy-6-oxohexanamido)thiophene-3-carboxylate was dissolved into 30 ml of THF. Subsequently, 12 ml of a 1N aqueous sodium hydroxide solution was added, and the mixture was stirred at 50 to 60° C. for 40 minutes. After concentrating the reaction mixture, 1N hydrochloric acid was added to the resulting aqueous solution, which was then extracted with ethyl acetate. The organic layer obtained was dried over anhydrous sodium sulfate, and then concentrated to give 2.34 g of 6-(3-(tert-butoxycarbonyl)-4-isopropylthiophen-2-ylamino)-6-oxohexanoic acid (yield 63%).

$^1$H-NMR (CDCl$_3$) δ: 1.21 (6H, d, J=6.8 Hz), 1.61 (9H, s), 1.63-1.94 (4H, m), 2.36-2.58 (4H, m), 3.46 (1H, septet, J=6.8 Hz), 6.42 (1H, s), 11.5 (1H, s).

(iv) tert-Butyl 4-isopropyl-2-(6-(2-(methoxycarbonyl)phenylamino)-6-oxohexanamido)thiophene-3-carboxylate After adding 739 mg (2.0 mmol) of the 6-(3-(tert-butoxycarbonyl)-4-isopropylthiophen-2-ylamino)-6-oxohexanoic acid to THF, 0.31 ml (2.2 mmol) of triethylamine and 0.17 ml (2.2 mmol) of methane sulfonyl chloride were added at 0° C., and the mixture was stirred for 1 hour at 0° C. Subsequently, 0.29 ml (2.2 mmol) of methyl anthranilate was added and stirred for 1 hour, and then heated to reflux for 5 hours. Ethyl acetate was added to the reaction mixture, washed with a saturated sodium chloride solution, and then dried over anhydrous sodium sulfate. The solvent was distilled off under reduced pressure. The crude product obtained was separated and purified by silica gel column chromatography to give 767 mg of tert-butyl 4-isopropyl-2-(6-(2-(methoxycarbonyl)phenylamino)-6-oxohexanamido)thiophene-3-carboxylate (yield 76%).

$^1$H-NMR (CDCl$_3$) δ: 1.21 (6H, d, J=6.6 Hz), 1.60 (9H, s), 1.80-1.93 (4H, m), 2.47-2.60 (4H, m), 3.46 (1H, septet, J=6.6 Hz), 3.92 (3H, s), 6.41 (1H, s), 7.03-7.11 (1H, m), 7.49-7.58 (1H, m), 7.98-8.06 (1H, m), 8.68-8.74 (1H, m), 11.1 (1H, s), 11.6 (1H, s).

(v) Sodium 2-(6-(3-(tert-butoxycarbonyl)-4-isopropylthiophen-2-ylamino)-6-oxohexanamido)benzoate 767 mg (1.5 mmol) of tert-butyl 4-isopropyl-2-(6-(2-(methoxycarbonyl)phenylamino)-6-oxohexanamido)thiophene-3-carboxylate was dissolved into 5 ml of THF. Subsequently, 1.8 ml of a 1N aqueous sodium hydroxide solution was added, and the mixture was heated to reflux for 3 hours. After cooling, 1N hydrochloric acid was subsequently added to neutralize, and the mixture was then extracted with ethyl acetate. The organic layer obtained was then washed with a saturated sodium chloride solution, dried over anhydrous sodium sulfate, and concentrated to give 2-(6-(3-(tert-butoxycarbonyl)-4-isopropylthiophen-2-ylamino)-6-oxohexanamido)benzoic acid (yield 89%). Among these, 250 mg (0.51 mmol) was dissolved into THF, and a 1N aqueous sodium hydroxide solution was added to alkalize. The resulting solution was concentrated. The precipitated solid was filtered off, washed with water and ethyl acetate, and was then dried to give the titled sodium 2-(6-(3-(tert-butoxycarbonyl)-4-isopropylthiophen-2-ylamino)-6-oxohexanamido)benzoate (yield 62%).

$^1$H-NMR (DMSO-d$_6$) δ: 1.17 (6H, d, J=6.8 Hz), 1.56 (9H, s), 1.60-1.74 (4H, m), 2.23-2.39 (2H, m), 2.46-2.63 (2H, m), 3.43 (1H, septet, J=6.8 Hz), 6.65 (1H, s), 6.86-6.99 (1H, m), 7.14-7.30 (1H, m), 7.93-8.02 (1H, m), 8.40-8.50 (1H, m), 11.1 (1H, s).

Example 12

Production of 2-(6-(4-isopropylthiophen-2-ylamino)-6-oxohexanamido)benzoic acid 430 mg (0.88 mmol) of the 2-(6-(3-(tert-butoxycarbonyl)-4-isopropylthiophen-2-ylamino)-6-oxohexanamido)benzoic acid obtained in Example 11-(v) and 5 ml of TFA were stirred in 2 ml of methylene chloride at 40° C. for 13 hours, and the mixture was then stirred at room temperature overnight. After concentration, the reaction mixture was separated and purified by silica gel column chromatography to give the titled 2-(6-(4-isopropylthiophen-2-ylamino)-6-oxohexanamido)benzoic acid (yield 49%).

$^1$H-NMR (DMSO-d$_6$) δ: 1.15 (6H, d, J=6.8 Hz), 1.40-1.80 (4H, m), 2.10-2.50 (4H, m), 2.80 (1H, septet, J=6.8 Hz), 6.49 (1H, s), 6.59 (1H, s), 6.90-7.10 (1H, m), 7.20-7.40 (1H, m), 7.80-8.30 (1H, m), 8.40-8.60 (1H, m), 11.1 (1H, s), 13.2 (1H, bs).

Example 13

Production of 2-(2-(2-(4-benzhydrylpiperazin-1-yl)-2-oxoethoxy)acetamido)-5-methyl-4-(pyridin-4-yl)thiophen-3-carboxylic acid The above titled compound was prepared according to Steps (i) to (iv) described below.

(i) tert-Butyl 2-amino-5-methyl-4-(pyridin-4-yl)thiophene-3-carboxylate 5 g (37.0 mmol) of 4-propionyl pyridine, 8.4 g (59.3 mmol) of tert-butyl cyanoacetate, 2.2 g (37.2 mmol) of acetic acid and 2.6 g (29.6 mmol) of morpholine were heated to reflux while removing water in 50 ml of toluene for 5.5 hours. After cooling, the reaction mixture was washed with water. After drying the resulting organic layer over anhydrous sodium sulfate, the solvent was distilled off under reduced pressure. 20 ml of DMF, 1.2 g (37.0 mmol) of sulfur and 3.2 g (37.0 mmol) of morpholine were added to the obtained residue, and the mixture was stirred at room temperature for 5.5 hours. Water was added to the reaction mixture, and the precipitate was separated by filtration. The separated precipitate was suspended in THF-ethyl acetate, then filtered and concentrated to give 4.3 g of tert-butyl 2-amino-5-methyl-4-(pyridin-4-yl)thiophene-3-carboxylate (yield 40%).

$^1$H-NMR (CDCl$_3$) δ: 1.13 (9H, s), 2.02 (3H, s), 6.02 (2H, bs), 7.11 (2H, dd, J=4.4, 1.6 Hz), 8.58 (2H, dd, J=4.4, 1.6 Hz).

(ii) 2-(2-(3-(tert-Butoxycarbonyl)-5-methyl-4-(pyridin-4-yl)thiophen-2-ylamino)-2-oxoethoxy)acetic acid A mixture of 3.0 g (10.3 mmol) of the tert-butyl 2-amino-5-methyl-4-(pyridin-4-yl)thiophene-3-carboxylate and 1.56 g (13.4 mmol) of diglycolic acid anhydride was heated to reflux in THF for 2 hours. The reaction mixture was filtered at room temperature, thus giving 3.6 g of 2-(2-(3-(tert-butoxycarbonyl)-5-methyl-4-(pyridin-4-yl)thiophen-2-ylamino)-2-oxoethoxy)acetic acid (yield 86%).

$^1$H-NMR (DMSO-d$_6$) δ: 1.12 (9H, s), 2.11 (3H, s), 4.28 (2H, s), 4.34 (2H, s), 7.23 (2H, dd, J=4.4, 1.6 Hz), 8.59 (2H, dd, J=4.4, 1.6 Hz), 11.6 (1H, s).

(iii) tert-Butyl 2-(2-(2-(4-benzhydrylpiperazin-1-yl)-2-oxoethoxy)acetamido)-5-methyl-4-(pyridin-4-yl)thiophen-3-carboxylate After adding 2.0 g (4.9 mmol) of the 2-(2-(3-(tert-butoxycarbonyl)-5-methyl-4-(pyridin-4-yl)thiophen-2-ylamino)-2-oxoethoxy)acetic acid to THF, 647 mg (6.4 mmol) of triethylamine and 806 mg (5.9 mmol) of isobutyl chloroformate were added at 0° C., and the mixture was stirred for 1 hour. Subsequently, 1.37 g (5.41 mmol) of 1-benzhydrylpiperazine was added, and the mixture was stirred at room temperature for 2.5 hours. Ethyl acetate was added to reaction mixture, which was washed with a saturated sodium chloride solution, and then dried over anhydrous sodium sulfate. The solvent was distilled off under reduced pressure. The crude product obtained was separated and purified by silica gel column chromatography to give 1.7 g of tert-butyl 2-(2-(2-(4-benzhydrylpiperazin-1-yl)-2-oxoethoxy)acetamido)-5-methyl-4-(pyridin-4-yl)thiophen-3-carboxylate (yield 56%).

$^1$H-NMR (CDCl$_3$) δ: 1.10 (9H, s), 2.12 (3H, s), 2.34-2.46 (4H, m), 3.48-3.70 (4H, m), 4.23 (1H, s), 4.30 (2H, s), 4.34 (2H, s), 7.10 (2H, dd, J=4.4, 1.6 Hz), 7.12-7.43 (10H, m), 8.61 (2H, dd, J=4.4, 1.6 Hz), 11.9 (1H, s).

(iv) 2-(2-(2-(4-Benzhydrylpiperazin-1-yl)-2-oxoethoxy)acetamido)-5-methyl-4-(pyridin-4-yl)thiophen-3-carboxylic acid 1.71 g (2.78 mmol) of the tert-butyl 2-(2-(2-(4-benzhydrylpiperazin-1-yl)-2-oxoethoxy)acetamido)-5-methyl-4-(pyridin-4-yl)thiophen-3-carboxylate and 4 ml of TFA were stirred in 10 ml of methylene chloride at room temperature for 2 hours. After concentration, the reaction mixture was separated and purified by silica gel column chromatography. To the resultant solid, water and 1N hydrochloric acid were added and heated to dissolve, and a 1N aqueous sodium hydroxide solution was then added at room temperature to neutralize. The precipitate obtained was separated by filtration, washed with IPE, and then dried to give the titled 2-(2-(2-(4-benzhydrylpiperazin-1-yl)-2-oxoethoxy)acetamido)-5-methyl-4-(pyridin-4-yl)thiophen-3-carboxylic acid (yield 37%).

$^1$H-NMR (DMSO-d$_6$) δ: 2.11 (3H, s), 2.20-2.40 (4H, m), 3.27-3.55 (4H, m), 4.24 (2H, s), 4.32 (1H, s), 4.36 (2H, s), 7.10-7.50 (12H, m), 8.50-8.58 (2H, m), 12.1 (1H, bs).

Example 14

2-(2-(2-(4-Benzhydrylpiperazin-1-yl)-2-oxoethoxy)acetamido)-5-methyl-4-(pyridin-3-yl)thiophene-3-carboxylic acid The above titled compound was prepared according to Steps (i) to (iv) described below.

(i) tert-Butyl 2-amino-5-methyl-4-(pyridin-3-yl)thiophene-3-carboxylate

Using the same method as in Example 13-(i), tert-butyl 2-amino-5-methyl-4-(pyridin-3-yl)thiophene-3-carboxylate was obtained using 3-propionyl pyridine (yield 26%).

$^1$H-NMR (CDCl$_3$) δ: 1.13 (9H, s), 2.02 (3H, s), 6.08 (2H, bs), 7.25-7.33 (1H, m), 7.44-7.53 (1H, m), 8.41-8.45 (1H, m), 8.49-8.55 (1H, m).

(ii) 2-(2-(3-(tert-Butoxycarbonyl)-5-methyl-4-(pyridin-3-yl)thiophen-2-ylamino)-2-oxoethoxy)acetic acid Using the same method as in Example 13-(ii), 2-(2-(3-(tert-butoxycarbonyl)-5-methyl-4-(pyridin-3-yl)thiophen-2-ylamino)-2-oxoethoxy)acetic acid was obtained using the tert-butyl 2-amino-5-methyl-4-(pyridin-3-yl)thiophene-3-carboxylate (yield 90%).

$^1$H-NMR (DMSO-d$_6$) δ: 1.11 (9H, s), 2.10 (3H, s), 4.28 (2H, s), 4.34 (2H, s), 7.39-7.49 (1H, m), 7.59-7.68 (1H, m), 8.36-8.40 (1H, m), 8.51-8.56 (1H, m), 11.6 (1H, s), 12.9 (1H, bs).

(iii) tert-Butyl 2-(2-(2-(4-benzhydrylpiperazin-1-yl)-2-oxoethoxy)acetamido)-5-methyl-4-(pyridin-3-yl)thiophene-3-carboxylate Using the same method as in Example 13-(iii), tert-butyl 2-(2-(2-(4-benzhydrylpiperazin-1-yl)-2-oxoethoxy)acetamido)-5-methyl-4-(pyridin-3-yl)thiophene-3-carboxylate was obtained using the 2-(2-(3-(tert-butoxycarbonyl)-5-methyl-4-(pyridin-3-yl)thiophen-2-ylamino)-2-oxoethoxy)acetic acid (yield 42%).

$^1$H-NMR (CDCl$_3$) δ: 1.09 (9H, s), 2.13 (3H, s), 2.33-2.47 (4H, m), 3.48-3.70 (4H, m), 4.23 (1H, s), 4.30 (2H, s), 4.34 (2H, s), 7.21-7.55 (12H, m), 8.42 (1H, dd, J=2.2, 0.7 Hz), 8.55 (1H, dd, J=4.9, 1.7 Hz), 11.9 (1H, s).

(iv) 2-(2-(2-(4-Benzhydrylpiperazin-1-yl)-2-oxoethoxy)acetamido)-5-methyl-4-(pyridin-3-yl)thiophene-3-carboxylic acid Using the same method as in Example 13-(iv), the titled 2-(2-(2-(4-benzhydrylpiperazin-1-yl)-2-oxoethoxy)acetamido)-5-methyl-4-(pyridin-3-yl)thiophene-3-carboxylic acid was obtained using tert-butyl 2-(2-(2-(4-benzhydrylpiperazin-1-yl)-2-oxoethoxy)acetamido)-5-methyl-4-(pyridin-3-yl)thiophene-3-carboxylate (yield 23%).

$^1$H-NMR (DMSO-d$_6$) δ: 2.14 (3H, s), 2.30-2.80 (4H, m), 3.30-3.70 (4H, m), 4.27 (2H, s), 4.41 (2H, s), 4.50 (1H, bs), 7.20-7.65 (11H, m), 7.84-7.94 (1H, m), 8.54-8.66 (2H, m), 11.9 (1H, s).

Example 15

Production of sodium 2-(2-(2-(4-benzhydrylpiperazin-1-yl)-2-oxoethoxy)acetamido)-5-methyl-4-phenylthiophene-3-carboxylate The above titled compound was prepared according to Steps (i) to (iii) described below.

(i) 2-(2-(3-(tert-Butoxycarbonyl)-5-methyl-4-phenylthiophen-2-ylamino)-2-oxoethoxy)acetic acid Using the same method as in Example 13-(ii), 2-(2-(3-(tert-butoxycarbonyl)-5-methyl-4-phenylthiophen-2-ylamino)-2-oxoethoxy)acetic acid was obtained using the tert-butyl 2-amino-5-methyl-4-phenylthiophene-3-carboxylate of Example 7-(i) (yield 96%).

¹H-NMR (DMSO-d₆) δ: 1.10 (9H, s), 2.09 (3H, s), 4.28 (2H, s), 4.33 (2H, s), 7.10-7.20 (2H, m), 7.31-7.45 (3H, m), 11.6 (1H, s), 12.9 (1H, bs).

(ii) tert-Buty 2-(2-(2-(4-benzhydrylpiperazin-1-yl)-2-oxoethoxy)acetamido)-5-methyl-4-phenylthiophene-3-carboxylate Using the same method as in Example 13-(iii), tert-butyl 2-(2-(2-(4-benzhydrylpiperazin-1-yl)-2-oxoethoxy)acetamido)-5-methyl-4-phenylthiophene-3-carboxylate was obtained using 2-(2-(3-(tert-butoxycarbonyl)-5-methyl-4-phenylthiophen-2-ylamino)-2-oxoethoxy)acetic acid (yield 74%).
¹H-NMR (CDCl₃) δ: 1.06 (9H, s), 2.12 (3H, s), 2.32-2.46 (4H, m), 3.49-3.71 (4H, m), 4.22 (1H, s), 4.29 (2H, s), 4.34 (2H, s), 7.06-7.43 (15H, m), 11.9 (1H, s).

(iii) Sodium 2-(2-(2-(4-benzhydrylpiperazin-1-yl)-2-oxoethoxy)acetamido)-5-methyl-4-phenylthiophene-3-carboxylate Using the same reaction conditions as in Example 13-(iv), 2-(2-(2-(4-benzhydrylpiperazin-1-yl)-2-oxoethoxy)acetamido)-5-methyl-4-phenylthiophen-3-carboxylic acid was obtained using tert-butyl 2-(2-(2-(4-benzhydrylpiperazin-1-yl)-2-oxoethoxy)acetamido)-5-methyl-4-phenylthiophene-3-carboxylate, and was dissolved into ethyl acetate. A 1N aqueous sodium hydroxide solution was added to the solution, and the resultant precipitate was filtered and dried to obtain the titled sodium 2-(2-(2-(4-benzhydrylpiperazin-1-yl)-2-oxoethoxy)acetamido)-5-methyl-4-phenylthiophene-3-carboxylate (yield 45%).
¹H-NMR (DMSO-d₆) δ: 2.05 (3H, s), 2.20-2.35 (4H, m), 3.25-3.55 (4H, m), 4.14 (2H, s), 4.29 (2H, s), 4.33 (1H, s), 7.06-7.48 (15H, m), 14.3 (1H, s).

Example 16

Production of 2-(5-(1,3-dioxoisoindolin-2-yl)pentanamido)-4-phenylthiophen-3-carboxylic acid The above titled compound was prepared according to Steps (i) to (iii) described below.

(i) 5-(1,3-Dioxoisoindolin-2-yl)pentanoic Acid

A mixture of 5 g (42.7 mmol) of 5-aminopentanoic acid, 10.3 g (46.9 mmol) of N-carbethoxyphthalimide and 6.1 g (59.8 mmol) of triethylamine was heated to reflux in 100 ml of THF for 16 hours. After cooling, the solvent was distilled off under reduced pressure. The resulting residue was diluted with ethyl acetate, and extracted with a 10% aqueous sodium hydrogen carbonate solution. 1N hydrochloric acid was added to acidify the aqueous layer obtained. The precipitate was separate by filtration, washed with water, and dried to give 9.3 g of 5-(1,3-dioxoisoindolin-2-yl)pentanoic acid (yield 88%).
¹H-NMR (CDCl₃) δ: 1.60-1.86 (4H, m), 2.41 (2H, t, J=7.1 Hz), 3.72 (2H, t, J=6.7 Hz), 7.66-7.77 (2H, m), 7.79-7.90 (2H, m), 10.4 (1H, bs).

(ii) tert-Butyl 2-(5-(1,3-dioxoisoindolin-2-yl)pentanamido)-4-phenylthiophene-3-carboxylate 3 ml of thionyl chloride was added to 3.0 g (12.1 mmol) of a 5-(1,3-dioxoisoindolin-2-yl)pentanoic acid-containing toluene solution. The mixture was stirred at 60° C. for 2 hours, and was concentrated. After adding 20 ml of DMA to the resultant residue, 3.0 g (11.0 mmol) of tert-butyl 2-amino-4-phenylthiophene-3-carboxylate was added, and the mixture was stirred at room temperature for 0.5 hours. The reaction mixture was poured into ice water, and then alkalized with sodium hydrogen carbonate. The precipitate was filtered off, washed with water, and dried to quantitatively give tert-butyl 2-(5-(1,3-dioxoisoindolin-2-yl)pentanamido)-4-phenylthiophene-3-carboxylate.
¹H-NMR (CDCl₃) δ: 1.18 (9H, s), 1.75-1.85 (4H, m), 2.52-2.63 (2H, m), 3.69-3.83 (2H, m), 6.54 (1H, d, J=0.9 Hz), 7.20-7.39 (5H, m), 7.65-7.75 (2H, m), 7.80-7.89 (2H, m), 11.3 (1H, s).

(iii) 2-(5-(1,3-Dioxoisoindolin-2-yl)pentanamido)-4-phenylthiophen-3-carboxylic acid 0.51 g (1.0 mmol) of the tert-butyl 2-(5-(1,3-dioxoisoindolin-2-yl)pentanamido)-4-phenylthiophene-3-carboxylate and 1 ml of TFA was stirred in 5 ml of methylene chloride as a solvent at room temperature for 2 hours. After concentrating the reaction mixture, the residue was separated by filtration, and crystallized using hexane-IPE. Subsequently, the crystal was filtered and dried to quantitatively give the titled 2-(5-(1,3-dioxoisoindolin-2-yl)pentanamido)-4-phenylthiophen-3-carboxylic acid.
¹H-NMR (DMSO-d₆) δ: 1.50-1.80 (4H, m), 2.50-2.70 (2H, m), 3.50-3.70 (2H, m), 6.84 (1H, s), 7.20-7.50 (5H, m), 7.75-7.95 (4H, m), 11.2 (1H, s).

Example 17

Production of 2-(5-(3-(tert-butoxycarbonyl)-4-phenylthiophen-2-ylamino)-5-oxopentylcarbamoyl)benzoic acid 1.0 g (1.98 mmol) of the tert-butyl 2-(5-(1,3-dioxoisoindolin-2-yl)pentanamido)-4-phenylthiophene-3-carboxylate obtained in Example 16-(ii) was dissolved into 10 ml of THF. Subsequently, 3 ml of a 1N aqueous sodium hydroxide solution was added, and the mixture was stirred at room temperature for 4 hours. The reaction mixture was distilled off under reduced pressure, and 1N hydrochloric acid was added to neutralize the resultant residue. The obtained precipitate was separated, washed with water and IPE, and dried to give the titled 2-(5-(3-(tert-butoxycarbonyl)-4-phenylthiophen-2-ylamino)-5-oxopentylcarbamoyl)benzoic acid (yield 77%).
¹H-NMR (CDCl₃) δ: 1.18 (9H, s), 1.60-2.00 (4H, m), 2.50-2.66 (2H, m), 3.40-3.60 (2H, m), 6.54 (1H, s), 6.82 (1H, t, J=5.5 Hz), 7.16-7.56 (8H, m), 7.96-8.08 (1H, m), 11.3 (1H, s).

Example 18

Production of 2-(2-(benzyloxycarbonylamino)-5-(4-chlorophenylamino)-5-oxopentanamido)-5-chlorobenzoic acid The above titled compound was prepared according to Steps (i) to (iv) described below.

(i) Methyl 2-(2-(benzyloxycarbonylamino)-5-tert-butoxy-5-oxopentanamido)-5-chlorobenzoate After adding 5.0 g (14.8 mmol) of DL-Z-Glu(Ot-Bu)OH to acetonitrile, 3.66 g (4.46 mmol) of N-methyl imidazole and 3.39 g (17.8 mmol) of p-toluene sulfonyl chloride were added and stirred for 1 hour at 0° C.

Subsequently, 2.62 g (14.1 mmol) of methyl 2-amino-5-chlorobenzoate was added and stirred at room temperature overnight. After concentration, the reaction mixture was diluted with ethyl acetate, and washed with water. After drying the resulting organic layer over anhydrous sodium sulfate, the solvent was distilled off under reduced pressure. The crude product obtained was separated and purified by silica gel column chromatography, thus giving 7.36 g of methyl 2-(2-(benzyloxycarbonylamino)-5-tert-butoxy-5-oxopentanamido)-5-chlorobenzoate (yield 99%).

Also, condensation was performed in the presence of benzotriazol-1-yl-oxytripyrrolidinophosphonium hexafluorophosphate (PyBOP) and N-ethyldiisopropylamine to give methyl 2-(2-(benzyloxycarbonylamino)-5-tert-butoxy-5-oxopentanamido)-5-chlorobenzoate.

$^1$H-NMR (CDCl$_3$) δ: 1.42 (9H, s), 1.91-2.65 (4H, m), 3.89 (3H, s), 4.29-4.48 (1H, m), 5.13 (1H, d, J=12.8 Hz), 5.19 (1H, d, J=12.8 Hz), 5.82 (1H, d, J=7.1 Hz), 7.11-7.43 (5H, m), 7.48 (1H, dd, J=9.2, 2.6 Hz), 7.99 (1H, d, J=2.6 Hz), 8.68 (1H, d, J=9.2 Hz), 11.5 (1H, s).

(ii) 4-(Benzyloxycarbonylamino)-5-(4-chloro-2-(methoxycarbonyl)phenylamino)-5-oxopentanoic acid 1.42 g (2.81 mmol) of the methyl 2-(2-(benzyloxycarbonylamino)-5-tert-butoxy-5-oxopentanamido)-5-chlorobenzoate and 5 ml of TFA were stirred in 20 ml of methylene chloride while being cooled with ice for 4 hours. After concentration, the reaction mixture was crystallized with mixture solution of ethyl acetate-hexane. The crystal was filtered, and dried to give 4-(benzyloxycarbonylamino)-5-(4-chloro-2-(methoxycarbonyl)phenylamino)-5-oxopentanoic acid (yield 93%).

$^1$H-NMR (DMSO-d$_6$) δ: 1.69-1.96 (1H, m), 1.96-2.23 (1H, m), 2.29-2.45 (2H, m), 3.86 (3H, s), 4.00-4.22 (1H, m), 5.03 (1H, d, J=12.4 Hz), 5.15 (1H, d, J=12.4 Hz), 7.06-7.52 (5H, m), 7.71 (1H, dd, J=9.0, 2.6 Hz), 7.93 (1H, d, J=2.6 Hz), 8.27 (1H, d, J=6.8 Hz), 8.49 (1H, d, J=9.0 Hz), 11.2 (1H, s), 12.2 (1H, bs).

(iii) Methyl 2-(2-(benzyloxycarbonylamino)-5-(4-chlorophenylamino)-5-oxopentanamido)-5-chlorobenzoate After adding 1.0 g (2.23 mmol) of the 4-(benzyloxycarbonylamino)-5-(4-chloro-2-(methoxycarbonyl)phenylamino)-5-oxopentanoic acid to THF, 271 mg (2.67 mmol) of triethylamine and 281 mg (2.45 mmol) of methane sulfonyl chloride was added at 0° C., and the mixture was stirred for 1 hour at 0° C. Subsequently, 284 mg (2.23 mmol) of 4-chloroaniline was added, and the mixture was stirred at room temperature for 2 hours. Ethyl acetate was added to the reaction mixture, which was washed with a saturated sodium chloride solution and saturated sodium hydrogen carbonate, and then dried over anhydrous sodium sulfate. The solvent was distilled off under reduced pressure. The crude product obtained was separated and purified by silica gel column chromatography to give 440 mg of methyl 2-(2-(benzyloxycarbonylamino)-5-(4-chlorophenylamino)-5-oxopentanamido)-5-chlorobenzoate (yield 35%).

$^1$H-NMR (DMSO-d$_6$) δ: 1.80-2.08 (1H, m), 2.08-2.36 (1H, m), 2.40-2.57 (2H, m), 3.85 (3H, s), 4.06-4.23 (1H, m), 5.01 (1H, d, J=12.4 Hz), 5.16 (1H, d, J=12.4 Hz), 7.03-7.66 (9H, m), 7.71 (1H, dd, J=9.0, 2.6 Hz), 7.93 (1H, d, J=2.6 Hz), 8.06 (1H, d, J=7.5 Hz), 8.51 (1H, d, J=9.0 Hz), 10.1 (1H, s), 11.2 (1H, s).

(iv) 2-(2-(Benzyloxycarbonylamino)-5-(4-chlorophenylamino)-5-oxopentanamido)-5-chlorobenzoic acid 440 mg (0.79 mmol) of the methyl 2-(2-(benzyloxycarbonylamino)-5-(4-chlorophenylamino)-5-oxopentanamido)-5-chlorobenzoate was dissolved into 10 ml of THF. Subsequently, 1.2 ml of a 1N aqueous sodium hydroxide solution was added, and the mixture was stirred at room temperature for 2 hours. After concentrating the reaction mixture, water and 1N hydrochloric acid were added to acidify the resultant residue, and the mixture was then concentrated. After separating and purifying the residue obtained by silica gel column chromatography, and crystallized with ethyl acetate. The crystals were separated by filtration and dried to give the titled 2-(2-(benzyloxycarbonylamino)-5-(4-chlorophenylamino)-5-oxopentanamido)-5-chlorobenzoic acid (yield 64%).

$^1$H-NMR (DMSO-d$_6$) δ: 1.80-2.30 (2H, m), 2.40-2.45 (2H, m), 4.00-4.28 (1H, m), 5.01 (1H, d, J=12.7 Hz), 5.11 (1H, d, J=12.7 Hz), 7.04-7.65 (9H, m), 7.47 (1H, dd, J=9.0, 2.7 Hz), 7.90 (1H, d, J=7.1 Hz), 8.01 (1H, d, J=2.7 Hz), 8.57 (1H, d, J=9.0 Hz), 10.1 (1H, s), 13.3 (1H, s).

Example 19

Production of 2-(2-(benzyloxycarbonylamino)-5-((4-chlorophenyl)(methyl)amino)-5-oxopentanamido)-5-chlorobenzoic acid The above titled compound was prepared according to Steps (i) and (ii) described below.

(i) Methyl 2-(2-(benzyloxycarbonylamino)-5-((4-chlorophenyl)(methyl)amino)-5-oxopentanamido)-5-chlorobenzoate Using the same method as in Example 18-(iii), 4-chloro-N-methylaniline was reacted with the 4-(benzyloxycarbonylamino)-5-(4-chloro-2-(methoxycarbonyl)phenylamino)-5-oxopentanoic acid of Example 18-(ii) to obtain methyl 2-(2-(benzyloxycarbonylamino)-5-((4-chlorophenyl)(methyl)amino)-5-oxopentanamido)-5-chlorobenzoate (yield 50%).

$^1$H-NMR (DMSO-d$_6$) δ: 1.60-2.35 (4H, m), 3.14 (3H, s), 3.84 (3H, s), 3.91-4.12 (1H, m), 5.02 (1H, d, J=12.3 Hz), 5.10 (1H, d, J=12.3 Hz), 7.06-7.29 (9H, m), 7.70 (1H, dd, J=9.2, 2.6 Hz), 7.86-8.00 (2H, m), 8.44 (1H, d, J=9.2 Hz), 11.1 (1H, s).

(ii) 2-(2-(Benzyloxycarbonylamino)-5-((4-chlorophenyl)(methyl)amino)-5-oxopentanamido)-5-chlorobenzoic acid Using the same method as in Example 18-(iv), the titled 2-(2-(benzyloxycarbonylamino)-5-((4-chlorophenyl)(methyl)amino)-5-oxopentanamido)-5-chlorobenzoic acid was obtained using the methyl 2-(2-(benzyloxycarbonylamino)-5-((4-chlorophenyl)(methyl)amino)-5-oxopentanamido)-5-chlorobenzoate (yield 91%).

$^1$H-NMR (DMSO-d$_6$) δ: 1.64-2.35 (4H, m), 3.13 (3H, s), 3.90-4.10 (1H, m), 4.97 (1H, d, J=12.7 Hz), 5.08 (1H, d, J=12.7 Hz), 7.10-7.50 (10H, m), 7.69 (1H, d, J=7.3 Hz), 7.96 (1H, d, J=2.7 Hz), 8.47 (1H, d, J=8.8 Hz), 13.8 (1H, s).

Example 20

Production of 2-(2-(benzyloxycarbonylamino)-5-oxo-5-(4-phenylpiperazin-1-yl)pentanamido)-5-chlorobenzoic acid The above titled compound was prepared according to Steps (i) and (ii) described below.

(i) Methyl 2-(2-(benzyloxycarbonylamino)-5-oxo-5-(4-phenylpiperazin-1-yl)pentanamido)-5-chlorobenzoate Using the same method as in Example 18-(iii), 1-phenyl piperazine was reacted with the 4-(benzyloxycarbonylamino)-5-(4-chloro-2-(methoxycarbonyl)phenylamino)-5-oxopentanoic acid of Example 18-(ii) to give methyl 2-(2-(benzyloxycarbonylamino)-5-oxo-5-(4-phenylpiperazin-1-yl)pentanamido)-5-chlorobenzoate (yield 52%).

$^1$H-NMR (CDCl$_3$) δ: 2.12-2.72 (4H, m), 3.00-3.18 (4H, m), 3.49-3.63 (2H, m), 3.69-3.80 (2H, m), 3.87 (3H, s), 4.29-4.49 (1H, m), 5.11 (1H, d, J=12.6 Hz), 5.19 (1H, d, J=12.6 Hz), 6.47 (1H, d, J=6.6), 6.83-7.00 (3H, m), 7.12-7.43 (7H, m), 7.48 (1H, dd, J=9.2, 2.6 Hz), 7.99 (1H, d, J=2.6 Hz), 8.70 (1H, d, J=9.2 Hz), 11.6 (1H, s).

(ii) 2-(2-(Benzyloxycarbonylamino)-5-oxo-5-(4-phenylpiperazin-1-yl)pentanamido)-5-chlorobenzoic acid Using the same method as in Example 18-(iv), the titled 2-(2-(benzyloxycarbonylamino)-5-oxo-5-(4-phenylpiperazin-1-yl)pentanamido)-5-chlorobenzoic acid was obtained using methyl 2-(2-(benzyloxycarbonylamino)-5-oxo-5-(4-phenylpiperazin-1-yl)pentanamido)-5-chlorobenzoate (yield 87%).

$^1$H-NMR (DMSO-d$_6$) δ: 1.70-2.30 (2H, m), 2.33-2.60 (4H, m), 2.90-3.20 (4H, m), 3.40-3.70 (4H, m), 4.03-4.20 (1H, m), 4.99 (1H, d, J=12.7 Hz), 5.13 (1H, d, J=12.7 Hz), 6.70-7.50 (9H, m), 7.61 (1H, dd, J=9.0, 2.7 Hz), 7.96 (1H, d, J=2.7 Hz), 7.98 (1H, d, J=7.1 Hz), 8.60 (1H, d, J=9.0 Hz), 12.3 (1H, s).

Example 21

Production of sodium 2-(5-(4-benzhydrylpiperazin-1-yl)-2-(benzyloxycarbonylamino)-5-oxopentanamido)-5-chlorobenzoate The above titled compound was prepared according to Steps (i) and (ii) described below.

(i) Methyl 2-(5-(4-benzhydrylpiperazin-1-yl)-2-(benzyloxycarbonylamino)-5-oxopentanamido)-5-chlorobenzoate Using the same method as in Example 18-(iii), 1-benzhydrylpiperazine was reacted with the 4-(benzyloxycarbonylamino)-5-(4-chloro-2-(methoxycarbonyl)phenylamino)-5-oxopentanoic acid of Example 18-(ii) to obtain methyl 2-(5-(4-benzhydrylpiperazin-1-yl)-2-(benzyloxycarbonylamino)-5-oxopentanamido)-5-chlorobenzoate (yield 47%).

$^1$H-NMR (CDCl$_3$) δ: 2.06-2.60 (8H, m), 3.31-3.45 (2H, m), 3.52-3.65 (2H, m), 3.86 (3H, s), 4.17 (1H, s), 4.22-4.43 (1H, m), 5.11 (1H, d, J=13.0 Hz), 5.19 (1H, d, J=13.0 Hz), 6.56 (1H, d, J=8.0 Hz), 7.10-7.51 (15H, m), 7.48 (1H, dd, J=9.0, 2.6 Hz), 8.00 (1H, d, J=2.6 Hz), 8.69 (1H, d, J=9.0 Hz), 11.5 (1H, s).

(ii) Sodium 2-(5-(4-benzhydrylpiperazin-1-yl)-2-(benzyloxycarbonylamino)-5-oxopentanamido)-5-chlorobenzoate After the completion of the reaction under the same reaction conditions as in Example 18-(iv), the solvent was distilled off under reduced pressure. The resultant precipitate was separated by filtration, and washed with water to give the titled sodium 2-(5-(4-benzhydrylpiperazin-1-yl)-2-(benzyloxycarbonylamino)-5-oxopentanamido)-5-chlorobenzoate (yield 91%).

$^1$H-NMR (DMSO-d$_6$) δ: 1.70-2.44 (8H, m), 3.20-3.40 (4H, m), 3.92-4.12 (1H, m), 4.28 (1H, s), 4.98 (1H, d, J=12.8 Hz), 5.08 (1H, d, J=12.8 Hz), 7.00-7.50 (16H, m), 7.73 (1H, d, J=7.6 Hz), 7.95 (1H, d, J=2.9 Hz), 8.49 (1H, d, J=8.8 Hz), 14.4 (1H, s).

Example 22

Production of 2-(5-(4-benzhydrylpiperazin-1-yl)-4-(benzyloxycarbonylamino)-5-oxopentanamido)-5-chlorobenzoic acid The above titled compound was prepared according to Steps (i) to (iii) described below.

(i) 2-(Benzyloxycarbonylamino)-5-(4-chloro-2-(methoxycarbonyl)phenylamino)-5-oxopentanoic acid A mixture of 2.0 g (7.1 mmol) of DL-Cbz-Glu-OH and 1.47 g (7.1 mmol) of DCC was stirred in ethyl acetate at room temperature overnight. After filtering the reaction mixture and concentrating the filtrate, 1.3 g (7.1 mmol) of methyl 2-amino-5-chlorobenzoate and 10 ml of DMSO were added, and the mixture was heated at 100° C. for 24 hours. The reaction mixture was diluted with ethyl acetate, washed with water, and then dried over anhydrous sodium sulfate. After the organic solvent was distilled off under reduced pressure, the reaction mixture was separated and purified by silica gel column chromatography to give 850 mg of 2-(benzyloxycarbonylamino)-5-(4-chloro-2-(methoxycarbonyl)phenylamino)-5-oxopentanoic acid (yield 27%).

$^1$H-NMR (CD$_3$OD) δ: 1.85-2.70 (4H, m), 3.92 (3H, s), 4.15-4.35 (1H, m), 5.05 (2H, s), 7.20-7.40 (5H, m), 7.51 (1H, dd, J=9.0, 2.4 Hz), 7.94 (1H, d, J=2.4 Hz), 8.48 (1H, d, 9.0 Hz).

(ii) Methyl 2-(5-(4-benzhydrylpiperazin-1-yl)-4-(benzyloxycarbonylamino)-5-oxopentanamido)-5-chlorobenzoate After adding 770 mg (1.72 mmol) of the 2-(benzyloxycarbonylamino)-5-(4-chloro-2-(methoxycarbonyl)phenylamino)-5-oxopentanoic acid to THF, 208 mg (2.06 mmol) of triethylamine and 216 mg (1.89 mmol) of methane sulfonyl chloride were added at 0° C., and the mixture was stirred for 3 hours at 0° C. Subsequently, 433 mg (1.72 mmol) of 1-benzhydrylpiperazine was added and stirred at room temperature for 3 hours. Ethyl acetate was added to the reaction mixture, which was washed with a saturated sodium chloride solution and saturated sodium hydrogen carbonate, and then dried over anhydrous sodium sulfate. The solvent was distilled off under reduced pressure. The crude product obtained was separated and purified by silica gel column chromatography to give 450 mg of methyl 2-(5-(4-benzhydrylpiperazin-1-yl)-4-(benzyloxycarbonylamino)-5-oxopentanamido)-5-chlorobenzoate (yield 38%).

$^1$H-NMR (CDCl$_3$) δ: 1.62-1.89 (1H, m), 2.05-2.30 (1H, m), 2.30-2.63 (6H, m), 3.48-3.80 (4H, m), 3.91 (3H, s), 4.22 (1H, s), 4.70-4.80 (1H, m), 5.05 (2H, s), 5.85 (1H, d, J=7.9 Hz), 7.02-7.46 (16H, m), 7.98 (1H, d, J=2.6 Hz), 8.64 (1H, d, J=9.0 Hz), 10.2 (1H, s).

(iii) 2-(5-(4-Benzhydrylpiperazin-1-yl)-4-(benzyloxycarbonylamino)-5-oxopentanamido)-5-chlorobenzoic acid 410 mg (0.60 mmol) of the methyl 2-(5-(4-benzhydrylpiperazin-1-yl)-4-(benzyloxycarbonylamino)-5-oxopentanamido)-5-chlorobenzoate was dissolved into 5 ml of THF. Subsequently, 0.9 ml of a 1N aqueous sodium hydroxide solution was added, and the mixture was stirred at room temperature for 3.5 hours. After concentrating the reaction mixture, water and 1N hydrochloric acid were added to acidify the resultant residue. The precipitate obtained was separated by filtration, washed with IPE, and then dried to give the titled 2-(5-(4-benzhydrylpiperazin-1-yl)-4-(benzyloxycarbonylamino)-5-oxopentanamido)-5-chlorobenzoic acid (yield 92%).

$^1$H-NMR (DMSO-d$_6$) δ: 1.60-2.10 (2H, m), 2.30-2.70 (6H, m), 3.20-4.00 (4H, m), 4.35-4.80 (2H, m), 4.96 (1H, d, J=11.4 Hz), 5.03 (1H, d, J=11.4 Hz), 7.10-7.70 (16H, m), 7.64 (1H, dd, J=9.0, 2.7 Hz), 7.92 (1H, d, J=2.7 Hz), 8.46 (1H, d, J=9.0 Hz), 11.0 (1H, s).

Example 23

Production of 2-(5-(4-benzhydrylpiperazin-1-yl)-2-(tert-butoxycarbonylamino)-5-oxopentanamido)-5-chlorobenzoic acid The above titled compound was prepared according to Steps (i) to (iv) described below.

(i) Methyl 2-(5-(benzyloxy)-2-(tert-butoxycarbonylamino)-5-oxopentanamido)-5-chlorobenzoate After adding 4.0 g (11.9 mmol) of DL-Boc-Glu(OBzl)-OH to acetonitrile, 2.9 g (35.6 mmol) of N-methyl imidazole and 2.7 g (14.2 mmol) of p-toluene sulfonyl chloride were added and stirring for 1 hour at 0° C. Subsequently, 2.2 g (11.9 mmol) of methyl 2-amino-5-chlorobenzoate was added, and the mixture was stirred at room temperature overnight. After concentration, the reaction mixture was diluted with ethyl acetate, and washed with water. After drying the resulting organic layer over anhydrous sodium sulfate, the solvent was distilled off under reduced pressure. The crude product obtained was separated and purified by silica gel column chromatography to give 2.5 g of methyl 2-(5-(benzyloxy)-2-(tert-butoxycarbonylamino)-5-oxopentanamido)-5-chlorobenzoate (yield 41%).

$^1$H-NMR (CDCl$_3$) δ: 1.46 (9H, s), 1.95-2.15 (1H, m), 2.23-2.43 (1H, m), 2.49-2.62 (2H, m), 3.92 (3H, s), 4.26-4.45 (1H, m), 5.13 (2H, s), 5.35 (1H, d, J=8.2 Hz), 7.29-7.42 (5H, m), 7.49 (1H, dd, J=9.2, 2.6 Hz), 8.00 (1H, d, J=2.6 Hz), 8.69 (1H, d, J=9.2 Hz), 11.5 (1H, s).

(ii) 4-(tert-Butoxycarbonylamino)-5-(4-chloro-2-(methoxycarbonyl)phenylamino)-5-oxopentanoic Acid 2.46 g (4.87 mmol) of the methyl 2-(5-(benzyloxy)-2-(tert-butoxycarbonylamino)-5-oxopentanamido)-5-chlorobenzoate was dissolved into ethyl acetate, 150 mg of 5% Pd/C was added under a hydrogen atmosphere, and the mixture was stirred overnight. THF was added to the resultant solution. The solution was then filtered and concentrated to quantitatively give 4-(tert-butoxycarbonylamino)-5-(4-chloro-2-(methoxycarbonyl)phenylamino)-5-oxopentanoic acid.

$^1$H-NMR (DMSO-d$_6$) δ: 1.42 (9H, s), 1.60-2.20 (2H, m), 2.34 (2H, t, J=9.0 Hz), 3.89 (3H, s), 3.94-4.11 (1H, m), 7.61 (1H, d, J=7.0 Hz), 7.73 (1H, dd, J=9.2, 2.6 Hz), 7.93 (1H, d, J=2.6 Hz), 8.54 (1H, d, J=9.2 Hz), 11.2 (1H, s), 12.2 (1H, s).

(iii) Methyl 2-(5-(4-benzhydrylpiperazin-1-yl)-2-(tert-butoxycarbonylamino)-5-oxopentanamido)-5-chlorobenzoate After adding 2.0 g (4.87 mmol) of 4-(tert-butoxycarbonylamino)-5-(4-chloro-2-(methoxycarbonyl)phenylamino)-5-oxopentanoic acid to THF, 591 mg (5.84 mmol) of triethylamine and 614 mg (5.35 mmol) of methane sulfonyl chloride were added at 0° C., and the mixture was stirred for 1.5 hours at 0° C. Subsequently, 1.23 g (4.87 mmol) of 1-benzhydrylpiperazine was added, and stirred at room temperature for 4 hours. Ethyl acetate was added to the reaction mixture, which was washed with a saturated sodium chloride solution and a saturated sodium hydrogen carbonate, and then dried over anhydrous sodium sulfate. The solvent was distilled off under reduced pressure. The crude product obtained was separated and purified by silica gel column chromatography to give 760 mg of methyl 2-(5-(4-benzhydrylpiperazin-1-yl)-2-(tert-butoxycarbonylamino)-5-oxopentanamido)-5-chlorobenzoate (yield 24%).

$^1$H-NMR (CDCl$_3$) d: 1.47 (9H, s), 2.06-2.60 (8H, m), 3.37-3.50 (2H, m), 3.55-3.66 (2H, m), 3.91 (3H, s), 4.19 (1H, s), 4.20-4.37 (1H, m), 5.97 (1H, d, J=5.7 Hz), 7.11-7.46 (10H, m), 7.48 (1H, dd, J=9.2, 2.6 Hz), 8.00 (1H, d, J=2.6 Hz), 8.71 (1H, d, J=2.6 Hz), 11.5 (1H, s).

(iv) 2-(5-(4-Benzhydrylpiperazin-1-yl)-2-(tert-butoxycarbonylamino)-5-oxopentanamido)-5-chlorobenzoic acid 760 mg (1.17 mmol) of the methyl 2-(5-(4-benzhydrylpiperazin-1-yl)-2-(tert-butoxycarbonylamino)-5-oxopentanamido)-5-chlorobenzoate was dissolved into 5 ml of THF. Subsequently, 1.8 ml of a 1N aqueous sodium hydroxide solution was added, and the mixture was stirred at room temperature for 3 hours. 1N hydrochloric acid was added to acidify, and the reaction mixture was concentrated. The resulting residue was separated by filtration and washed with water, and was then dried to give the titled 2-(5-(4-benzhydrylpiperazin-1-yl)-2-(tert-butoxycarbonylamino)-5-oxopentanamido)-5-chlorobenzoic acid (yield 95%).

$^1$H-NMR (DMSO-d$_6$) δ: 1.37 (9H, s), 1.60-2.50 (8H, m), 3.28-3.52 (4H, m), 3.80-4.04 (1H, m), 4.27 (1H, s), 7.00-7.60 (11H, m), 7.54 (1H, dd, J=9.0, 2.9 Hz), 7.97 (1H, d, J=2.9 Hz), 8.60 (1H, d, J=9.0 Hz), 12.7 (1H, s).

Example 24

Production of 2-(2-amino-5-(4-benzhydrylpiperazin-1-yl)-5-oxopentanamido)-5-chlorobenzoic acid 400 mg (0.63 mmol) of the 2-(5-(4-benzhydrylpiperazin-1-yl)-2-(tert-butoxycarbonylamino)-5-oxopentanamido)-5-chlorobenzoic acid obtained in Example 23-(iv) and 1 ml of TFA were stirred in 2 ml of methylene chloride while being cooled with ice for 1.5 hours. Subsequently, the mixture was stirred at room temperature for 1.5 hours. After concentrating the reaction mixture, the precipitate obtained by the addition of IPE-hexane was separated by filtration. After dissolving the resulting crystal in a 1N aqueous sodium hydroxide solution, the solution was neutralized with 1N hydrochloric acid. The resultant precipitate was filtered and dried to give the titled 2-(2-amino-5-(4-benzhydrylpiperazin-1-yl)-5-oxopentanamido)-5-chlorobenzoic acid (yield 71%).

$^1$H-NMR (DMSO-$d_6$) δ: 1.84-2.30 (6H, m), 2.30-2.50 (2H, m), 3.10-3.60 (4H, m), 3.96-4.09 (1H, m), 4.14 (1H, s), 7.12-7.43, (11H, m), 7.96 (1H, d, J=2.7 Hz), 8.36 (1H, d, J=8.8 Hz), 7.90-8.80 (2H, m), 14.5 (1H, s).

Example 25

Production of 5-chloro-2-(2-((2-(4-chlorophenylamino)-2-oxoethyl)(methyl)amino)acetamido)benzoic acid The above titled compound was prepared according to Steps (i) to (iii) described below.

(i) 2-((2-(4-Chloro-2-(methoxycarbonyl)phenylamino)-2-oxoethyl)(methyl)amino)acetic acid A mixture of 3.17 g (21.6 mmol) of N-methyliminodiacetic acid and 16 ml of acetic anhydride was heated to reflux for 0.5 hours. After concentrating the solution obtained, 4.0 g (21.6 mmol) of methyl 2-amino-5-chlorobenzoate and 20 ml of THF were added, and the mixture was heated to reflux for 1.5 hours. After filtration of the reaction mixture, the filtrate was concentrated. The crude product obtained was separated and purified by silica gel column chromatography to give 5.0 g of 2-((2-(4-chloro-2-(methoxycarbonyl)phenylamino)-2-oxoethyl)(methyl)amino)acetic acid (yield 73%).

$^1$H-NMR (DMSO-$d_6$) δ: 2.46 (3H, s), 3.38 (2H, s), 3.46 (2H, s), 3.89 (3H, s), 7.68 (1H, dd, J=9.0, 2.4 Hz), 7.91 (1H, d, J=2.4 Hz), 8.64 (1H, d, J=9.0 Hz), 11.6 (1H, s).

(ii) Methyl 5-chloro-2-(2-((2-(4-chlorophenylamino)-2-oxoethyl)(methyl)amino)acetamido)benzoate After adding 1.0 g (3.18 mmol) of 2-((2-(4-chloro-2-(methoxycarbonyl)phenylamino)-2-oxoethyl)(methyl)amino)acetic acid to THF, 386 mg (3.82 mmol) of triethylamine and 400 mg (3.50 mmol) of methane sulfonyl chloride were added at 0° C., and the mixture was stirred for 1 hour at 0° C. Subsequently, 405 mg (3.18 mmol) of 4-chloroaniline was added, and the mixture was stirred at room temperature overnight. Ethyl acetate was added to the reaction mixture, which was washed with a saturated sodium chloride solution, and was then dried over anhydrous sodium sulfate. The solvent was distilled off under reduced pressure. The crude product obtained was separated and purified by silica gel column chromatography to give 491 mg of methyl 5-chloro-2-(2-((2-(4-chlorophenylamin)-2-oxoethyl)(methyl)amino)acetamido)benzoate (yield 36%).

$^1$H-NMR (CDCl$_3$) δ: 2.48 (3H, s), 3.39 (4H, s), 3.88 (3H, s), 7.14-7.36 (2H, m), 7.55 (1H, dd, J=9.2, 2.6 Hz), 7.65-7.72 (2H, m), 8.05 (1H, d, J=2.6 Hz), 8.81 (1H, d, J=9.2 Hz), 9.29 (1H, s), 12.0 (1H, s).

(iii) 5-Chloro-2-(2-((2-(4-chlorophenylamino)-2-oxoethyl)(methyl)amino)acetamido)benzoic acid 491 mg (1.16 mmol) of methyl 5-chloro-2-(2-((2-(4-chlorophenylamino)-2-oxoethyl)(methyl)amino)acetamido)benzoate was dissolved into 5 ml of THF, subsequently, 1.7 ml of a 1N aqueous sodium hydroxide solution was added, and stirred at 40° C. for 0.5 hours. 1N hydrochloric acid was added to the reaction mixture. After neutralization, the mixture was concentrated, and the aqueous solution obtained was extracted with ethyl acetate. After drying the resultant organic layer over anhydrous sodium sulfate, the solvent was distilled off under reduced pressure, IPE was added to the residue and the precipitate was separated and dried to give the titled 5-chloro-2-(2-((2-(4-chlorophenylamino)-2-oxoethyl)(methyl)amino)acetamido)benzoic acid (yield 90%).

$^1$H-NMR (DMSO-$d_6$) δ: 2.35 (3H, s), 3.33 (2H, 5), 3.38 (2H, s), 7.24-7.38 (2H, m), 7.48 (1H, dd, J=9.0, 2.7 Hz), 7.98 (1H, d, J=2.7 Hz), 8.00-8.14 (2H, m), 8.61 (1H, d, J=9.0 Hz), 10.3 (1H, s), 13.7 (1H, s).

Example 26

Production of 2-(2-((2-(4-benzhydrylpiperazin-1-yl)-2-oxoethyl)(methyl)amino)acetamido)-5-chlorobenzoic acid The above titled compound was prepared according to Steps (i) and (ii) described below.

(i) Methyl 2-(2-((2-(4-benzhydrylpiperazin-1-yl)-2-oxoethyl)(methyl)amino)acetamido)-5-chlorobenzoate Using the same method as in Example 25-(ii), 1-benzhydrylpiperazine was reacted with the 2-((2-(4-chloro-2-(methoxycarbonyl)phenylamino)-2-oxoethyl)(methyl)amino)acetic acid obtained in Example 25-(i) to give methyl 2-(2-((2-(4-benzhydrylpiperazin-1-yl)-2-oxoethyl)(methyl)amino)acetamido)-5-chlorobenzoate was obtained using (yield 44%).

$^1$H-NMR (CDCl$_3$) δ: 2.29-2.43 (4H, m), 2.48 (3H, s), 3.35 (2H, s), 3.44 (2H, s), 3.54-3.66 (4H, m), 3.71 (3H, s), 4.15 (1H, s), 7.10-7.40 (10H, m), 7.50 (1H, dd, J=9.2, 2.6 Hz), 7.99 (1H, d, J=2.6 Hz), 8.78 (1H, d, J=9.2 Hz), 11.8 (1H, s).

(ii) 2-(2-((2-(4-Benzhydrylpiperazin-1-yl)-2-oxoethyl)(methyl)amino)acetamido)-5-chlorobenzoic acid Using the same method as in Example 25-(iii), the titled 2-(2-((2-(4-benzhydrylpiperazin-1-yl)-2-oxoethyl)(methyl)amino)acetamido)-5-chlorobenzoic acid was obtained using methyl 2-(2-((2-(4-benzhydrylpiperazin-1-yl)-2-oxoethyl)(methyl)amino)acetamido)-5-chlorobenzoate (yield 70%).

$^1$H-NMR (DMSO-$d_6$) δ: 2.18-2.32 (4H, m), 2.42 (3H, s), 3.34 (2H, s), 3.49 (2H, s), 3.35-3.60 (4H, m), 4.25 (1H, s), 7.10-7.45 (10H, m), 7.66 (1H, dd, J=9.0, 2.6 Hz), 7.94 (1H, d, J=2.6 Hz), 8.64 (1H, d, J=9.0 Hz), 12.1 (1H, s).

Example 27

Production of 5-chloro-2-(6-(4-chlorophenylamino)-6-oxohexanamido)benzoic acid

The above titled compound was prepared according to Steps (i) to (iv) described below.

(i) Methyl 6-(4-chlorophenylamino)-6-oxohexanoate

A mixture of 7.4 ml (48 mmol) of methyl adipoyl chloride and 6.7 g (53 mmol) of 4-chloroaniline was stirred in DMA at room temperature overnight. The reaction mixture was (ii) 6-(4-Chlorophenylamino)-6-oxohexanoic acid 11.0 g (44.5 mmol) of the methyl 6-(4-chlorophenylamino)-6-oxohexanoate was dissolved into 445 ml of THF. Subsequently, 61 ml of a 1N aqueous sodium hydroxide solution was added, and the mixture was stirred at 60° C. for 2 hours. After concentration of the reaction mixture, 1N hydrochloric acid was added and stirred in the aqueous solution obtained. The resulting precipitate was filtered off, washed with ethyl acetate, water and IPE, and dried to give 10.3 g of 6-(4-chlorophenylamino)-6-oxohexanoic acid (yield 91%).

$^1$H-NMR (DMSO-d$_6$) δ: 1.50-1.67 (4H, m), 2.21-2.35 (4H, m), 7.30-7.38 (2H, m), 7.59-7.66 (2H, m), 10.0 (1H, s), 12.0 (1H, bs).

(iii) Methyl 5-chloro-2-(6-(4-chlorophenylamino)-6-oxohexanamido)benzoate 2.2 ml of thionyl chloride was added to 770 mg (3 mmol) of 6-(4-chlorophenylamino)-6-oxohexanoic acid, and the mixture was stirred at room temperature for 1 hour. The solvent was distilled off under reduced pressure to give an acid chloride. A mixture of the acid chloride obtained and 610 mg (3.3 mmol) of 2-amino 5-chloromethyl benzoate was stirred in DMA at room temperature overnight. The reaction mixture was poured into ice water, sodium hydrogen carbonate was added to alkalize, and was extracted with ethyl acetate. The organic layer was dried over anhydrous sodium sulfate, and the solvent was distilled off under reduced pressure. After adding IPE to the residue obtained, the precipitate was separated and dried to give 610 mg of methyl 5-chloro-2-(6-(4-chlorophenylamino)-6-oxohexanamido)benzoate (yield 48%).

$^1$H-NMR (CDCl$_3$) δ: 1.80-1.87 (4H, m), 2.39-2.56 (4H, m), 3.93 (3H, s), 7.23-7.30 (2H, m), 7.47-7.54 (3H, m), 7.69 (1H, s), 8.00 (1H, d, J=2.7 Hz), 8.70 (1H, d, J=9.2 Hz), 11.0 (1H, s).

(iv) 5-Chloro-2-(6-(4-chlorophenylamino)-6-oxohexanamido)benzoic acid 570 mg (1.3 mmol) of methyl 5-chloro-2-(6-(4-chlorophenylamino)-6-oxohexanamido)benzoate was dissolved into 13 ml of THF. Subsequently, 2 ml of a 1N aqueous sodium hydroxide solution was added, and the mixture was stirred at 60° C. for 3 hours. The reaction mixture was concentrated, and water and 1N hydrochloric acid were added to acidify the resulting aqueous solution. The precipitate was then separated, washed with water, IPE and ethyl acetate, and dried to give the titled 5-chloro-2-(6-(4-chlorophenylamino)-6-oxohexanamido)benzoic acid (yield 92%).

$^1$H-NMR (DMSO-d$_6$) δ: 1.53-1.72 (4H, m), 2.27-2.38 (4H, m), 7.27-7.40 (2H, m), 7.53-7.67 (2H, m), 7.60 (1H, dd, J=9.0, 2.7 Hz), 7.91, (1H, d, J=2.7 Hz), 8.50 (1H, d, J=9.0 Hz), 10.1 (1H, s), 11.5 (1H, s).

Example 28

Production of 2-(2-(2-(4-benzhydrylpiperazin-1-yl)-2-oxoethoxy)acetamido)-5-methoxybenzoic acid The above titled compound was prepared according to Steps (i) to (iii) described below.

(i) 2-(2-(2-(Ethoxycarbonyl)-4-methoxyphenylamino)-2-oxoethoxy)acetic acid

A mixture of 400 mg (2.0 mmol) of ethyl 2-amino-5-methoxybenzoate (Japanese Unexamined Patent Application Publication No. 9-208543) and 238 mg (2.0 mmol) of diglycolic acid anhydride was heated to reflux in THF for 2.5 hours. The solvent was distilled off under reduced pressure, to precipitate the crystal. A mixed solution of ethyl acetate and hexane was added and stirred in the precipitated crystal. Subsequently, the crystal was separated by filtration and dried to give 504 mg of 2-(2-(2-(ethoxycarbonyl)-4-methoxyphenylamino)-2-oxoethoxy)acetic acid (yield 79%).

$^1$H-NMR (DMSO-d$_6$) δ: 1.33 (3H, t, J=7.1 Hz), 3.79 (3H, s), 4.17 (2H, s), 4.25 (2H, s), 4.34 (2H, q, J=7.1 Hz), 7.26 (1H, dd, J=9.3, 3.2 Hz), 7.45 (1H, d, J=3.2 Hz), 8.46 (1H, d, J=9.3 Hz), 11.1 (1H, s), 12.8 (1H, bs).

(ii) Ethyl 2-(2-(2-(4-benzhydrylpiperazin-1-yl)-2-oxoethoxy)acetamido)-5-methoxybenzoate 490 mg (1.6 mmol) of 2-(2-(2-(ethoxycarbonyl)-4-methoxyphenylamino)-2-oxoethoxy)acetic acid was suspended in 10 ml of THF, a catalytic quantity of DMF was then added while being cooled with ice, subsequently 240 mg (1.9 mmol) of oxalyl chloride was added, and the mixture was stirred for 1 hour. After concentrating the reaction mixture, a mixture of the acid chloride obtained and 437 mg (1.7 mmol) of 1-benzhydrylpiperazine was stirred in DMA at room temperature for 1.5 hours. The reaction mixture was poured into ice water, then sodium hydrogen carbonate was added to alkalize, and the resultant was extracted with ethyl acetate. The organic layer obtained was dried over anhydrous sodium sulfate, and the solvent was distilled off under reduced pressure. The resulting crude product was separated and purified by silica gel column chromatography to give 490 mg of ethyl 2-(2-(2-(4-benzhydrylpiperazin-1-yl)-2-oxoethoxy)acetamido)-5-methoxybenzoate (yield 57%).

$^1$H-NMR (CDCl$_3$) δ: 1.34 (3H, t, J=7.2 Hz), 2.32-2.46 (4H, m), 3.49-3.70 (4H, m), 3.83 (3H, s), 4.20 (2H, s), 4.21 (1H, s), 4.25 (2H, q, J=7.2 Hz), 4.34 (2H, s), 7.07-7.44 (11H, m), 7.63 (1H, d, J=3.1 Hz), 8.67 (1H, d, J=9.3 Hz), 11.5 (1H, s).

(iii) 2-(2-(2-(4-Benzhydrylpiperazin-1-yl)-2-oxoethoxy)acetamido)-5-methoxybenzoic acid 490 mg (0.90 mmol) of the ethyl 2-(2-(2-(4-benzhydrylpiperazin-1-yl)-2-oxoethoxy)acetamido)-5-methoxybenzoate was dissolved in 5 ml of THF. Subsequently, 1.4 ml of a 1N aqueous sodium hydroxide solution was added and stirred at 60° C. for 3 hours. After concentration of the reaction mixture, water and 1N hydrochloric acid were added to neutralize the resultant aqueous solution, and the mixture was extracted with ethyl acetate. The organic layer obtained was dried over anhydrous sodium sulfate, and the solvent was then distilled off under reduced pressure. The crude product obtained was separated and purified by silica gel column chromatography to give the titled 2-(2-(2-(4-benzhydrylpiperazin-1-yl)-2-oxoethoxy)acetamido)-5-methoxybenzoic acid (yield 46%).

$^1$H-NMR (DMSO-d$_6$) δ: 2.21-2.33 (4H, m), 3.31-3.53 (4H, m), 3.76 (3H, s), 4.08 (2H, s), 4.29 (1H, s), 4.33 (2H, s), 7.08-7.47 (11H, m), 7.50 (1H, d, J=3.2 Hz), 8.53 (1H, d, J=9.0 Hz), 12.1 (1H, s).

Example 29

Production of sodium 5-chloro-2-(2-(2-(4-(4-chlorophenyl)piperazin-1-yl)-2-oxoethoxy)acetamido)benzoate The above titled compound was prepared according to Steps (i) to (iii) described below.

(i) 2-(2-(4-Chloro-2-(methoxycarbonyl)phenylamino)-2-oxoethoxy)acetic acid 10 g (53.9 mmol) of methyl 2-amino-5-chlorobenzoate and 6.88 g (59.3 mmol) of diglycolic acid anhydride were heated to reflux in 135 ml of THF for 3 hours. After cooling, the reaction mixture was concentrated. The residue was separated by filtration, washed with IPE, and dried to give 15.7 g of 2-(2-(4-chloro-2-(methoxycarbonyl)phenylamino)-2-oxoethoxy)acetic acid (yield 97%).

$^1$H-NMR (DMSO-d$_6$) δ: 3.90 (3H, s), 4.22 (2H, s), 4.28 (2H, s), 7.71 (1H, dd, J=9.0, 2.7 Hz), 7.93 (1H, d, J=2.7 Hz), 8.62 (1H, d, J=8.8 Hz), 11.4 (1H, s) 12.9 (1H, bs).

(ii) Methyl 5-chloro-2-(2-(2-(4-(4-chlorophenyl)piperazin-1-yl)-2-oxoethoxy)acetamido)benzoate 0.81 g (2.7 mmol) of 2-(2-(4-chloro-2-(methoxycarbonyl)phenylamino)-2-oxoethoxy)acetic acid, 16 mg (0.22 mmol) of DMF and 0.28 ml (3.24 mmol) of oxalyl chloride were stirred in 9 ml of THF at 0° C. for 30 minutes. After completion of the reaction, the solvent was distilled off under reduced pressure and the residue was dried. To this residue, 0.76 g (3.24 mmol) of (4-chlorophenyl)piperazine hydrochloride and 0.56 ml (4.05 mmol) of triethylamine (added only when the amine component to be condensed is hydrochloride) were stirred in 9 ml of DMA at room temperature overnight. After completion of the reaction, an aqueous sodium hydrogen carbonate solution was added; the mixture was extracted with additional ethyl acetate, and washed with a saturated sodium chloride solution. After drying the resultant organic layer over anhydrous sodium sulfate, the solvent was distilled off under reduced pressure. The crude product obtained was separated and purified by silica gel column chromatography to give 1.12 g of methyl 5-chloro-2-(2-(2-(4-(4-chlorophenyl)piperazin-1-yl)-2-oxoethoxy)acetamido)benzoate (yield 86%).

$^1$H-NMR (CDCl$_3$) δ: 3.14-3.19 (4H, m), 3.67-3.82 (4H, m), 3.91 (3H, s), 4.25 (2H, s), 4.43 (2H, s), 6.81-6.87 (2H, m), 7.19-7.27 (2H, m), 7.51 (1H, dd, J=9.0, 2.7 Hz), 8.01 (1H, d, J=2.7 Hz), 8.76 (1H, d, J=9.0 Hz), 11.7 (1H, s).

(iii) Sodium 5-chloro-2-(2-(2-(4-(4-chlorophenyl)piperazine-1-yl)-2-oxoethoxy)acetamido)benzoate 1.12 g (2.33 mmol) of methyl 5-chloro-2-(2-(2-(4-(4-chlorophenyl)piperazin-1-yl)-2-oxoethoxy)acetamido)benzoate was dissolved in 23 ml of THF. Subsequently, a 1N aqueous sodium hydroxide solution was added and stirred at 60° C. for 1 hour. After cooling, the THF was distilled off under reduced pressure, and water was added to the residue to wash it. The resultant residue was washed again with IPE to give the titled sodium 5-chloro-2-(2-(2-(4-(4-chlorophenyl)piperazine-1-yl)-2-oxoethoxy)acetamido)benzoate (yield 93%).

$^1$H-NMR (DMSO-d$_6$) δ: 3.03-3.21 (4H, m), 3.40-3.61 (4H, m), 4.12 (2H, s), 4.40 (2H, s), 6.94 (2H, d, J=9.1 Hz), 7.23 (2H, d, J=9.1 Hz), 7.39 (1H, dd, J=8.8, 2.7 Hz), 7.96 (1H, d, J=2.7 Hz), 8.57 (1H, d, J=8.8 Hz), 13.9 (1H, s). 4.4 (1H, s).

Example 30

Preparation of sodium 2-(2-(2-(4-benzhydrylpiperazin-1-yl)-2-oxoethoxy)acetamido)-5-chlorobenzoate The titled compound was prepared according to Steps (i) and (ii) described below.

(i) Methyl 2-(2-(2-(4-benzhydrylpiperazin-1-yl)-2-oxoethoxy)acetamido)-5-chlorobenzoate Using the same method as in Example 29-(ii), 2-(2-(4-chloro-2-(methoxycarbonyl)phenylamino)-2-oxoethoxy)acetic acid obtained in Example 29-(i) was reacted with 1-benzhydrylpiperazine to give methyl 2-(2-(2-(4-benzhydrylpiperazin-1-yl)-2-oxoethoxy)acetamido)-5-chlorobenzoate (yield: 78%).

$^1$H-NMR (CDCl$_3$) δ: 2.40-2.50 (4H, m), 3.50-3.66 (4H, m), 3.81 (3H, s), 4.21 (2H, s), 4.21 (1H, s), 4.34 (2H, s), 7.14-7.41 (10H, m), 7.49 (1H, dd, J=9.0, 2.7 Hz), 7.99 (1H, d, J=2.7 Hz), 8.75 (1H, d, J=9.0 Hz), 11.7 (1H, s).

(ii) Sodium 2-(2-(2-(4-benzhydrylpiperazin-1-yl)-2-oxoethoxy)acetamido)-5-chlorobenzoate Using the same method as in Example 29-(iii), the titled sodium 2-(2-(2-(4-benzhydrylpiperazin-1-yl)-2-oxoethoxy)acetamido)-5-chlorobenzoate (yield: 79%) was obtained using methyl 2-(2-(2-(4-benzhydrylpiperazin-1-yl)-2-oxoethoxy)acetamido)-5-chlorobenzoate.

$^1$H-NMR (DMSO-d$_6$): 2.28-2.48 (4H, m), 3.34-3.44 (4H, m), 4.06 (2H, s), 4.29 (2H, s), 4.32 (1H, s), 7.14-7.45 (11H, m), 7.93 (1H, d, J=2.7 Hz), 8.52 (1H, d, J=8.8 Hz), 14.4 (1H, s).

Example 31

Preparation of sodium 2-(2-(2-(4-benzhydryloxy)piperidin-1-yl)-2-oxoethoxy)acetamido-5-chlorobenzoate The titled compound was prepared according to Steps (i) and (ii) described below.

(i) Methyl 2-(2-(2-(4-benzhydryloxy)piperidin-1-yl)-2-oxoethoxy)acetamido-5-chlorobenzoate Using the same method as in Example 29-(ii), 2-(2-(4-chloro-2-(methoxycarbonyl)phenylamino)-2-oxoethoxy)acetic acid obtained in Example 29-(i) was reacted with (4-benzhydryloxy)piperidine (Chem. Pharm. Bull. 51(2) 122-133 (2003)) to give methyl 2-(2-(2-(4-benzhydryloxy)piperidin-1-yl)-2-oxoethoxy)acetamido-5-chlorobenzoate (yield: 21%).

$^1$H-NMR (CDCl$_3$): 1.60-1.95 (4H, m), 3.20-3.95 (5H, m), 3.88 (3H, s), 4.22 (2H, s), 4.37 (2H, s), 5.51 (1H, s), 7.17-7.40

(10H, s), 7.49 (1H, dd, J=9.0, 2.6 Hz), 8.00 (1H, d, J=2.6 Hz), 8.75 (1H, d, J=9.0 Hz), 11.7 (1H, s).

(ii) Sodium 2-(2-(2-(4-benzhydryloxy)piperidin-1-yl)-2-oxoethoxy)acetamido-5-chlorobenzoate Using the same method as in Example 29-(iii), the titled sodium 2-(2-(2-(4-benzhydryloxy)piperidin-1-yl)-2-oxoethoxy)acetamido-5-chlorobenzoate (yield: 71%) was obtained using methyl 2-(2-(2-(4-benzhydryloxy)piperidin-1-yl)-2-oxoethoxy)acetamido-5-chlorobenzoate.

$^1$H-NMR (DMSO-d$_6$) δ: 1.40-2.00 (4H, m), 3.00-3.90 (5H, m), 4.08 (2H, s), 4.32 (2H, s), 5.66 (1H, s), 7.12-7.42 (11H, m), 7.96 (1H, d, J=2.7 Hz), 8.55 (1H, d, J=8.8 Hz), 14.3 (1H, s).

Example 32

Preparation of sodium 5-chloro-2-(2-(2-(4,4-diphenylpiperidin-1-yl)-2-oxoethoxy)acetamido)benzoate The titled compound was prepared according to Steps (i) and (ii) described below.

(i): Methyl 5-chloro-2-(2-(2-(4,4-diphenylpiperidin-1-yl)-2-oxoethoxy)acetamido)benzoate Using the same method as in Example 29-(ii), 2-(2-(4-chloro-2-(methoxycarbonyl)phenylamino)-2-oxoethoxy) acetic acid obtained in Example 29-(i) was reacted with 4,4-diphenylpiperidine hydrochloride to give methyl 5-chloro-2-(2-(2-(4,4-diphenylpiperidin-1-yl)-2-oxoethoxy)acetamido) benzoate (yield: 49%).

$^1$H-NMR (CDCl$_3$) δ: 2.40-2.52 (4H, m), 3.46-3.77 (4H, m), 3.81 (3H, s), 4.23 (2H, s), 4.38 (2H, s), 7.10-7.37 (10H, m), 7.49 (1H, dd, J=9.2, 2.6 Hz), 8.00 (1H, d, J=2.6 Hz), 8.75 (1H, d, J=9.2 Hz), 11.7 (1H, s).

(ii) Sodium 5-chloro-2-(2-(2-(4,4-diphenylpiperidin-1-yl)-2-oxoethoxy)acetamido)benzoate Using the same method as in Example 29-(iii), the titled sodium 5-chloro-2-(2-(2-(4,4-diphenylpiperidin-1-yl)-2-oxoethoxy)acetamido)benzoate (yield: 88%) was obtained using methyl 5-chloro-2-(2-(2-(4,4-diphenylpiperidin-1-yl)-2-oxoethoxy)acetamido)benzoate.

$^1$H-NMR (DMSO-d$_6$) δ: 2.16-2.50 (4H, m), 3.30-3.52 (4H, m), 4.08 (2H, s), 4.35 (2H, s), 7.00-7.40 (11H, m), 7.96 (1H, d, J=2.7 Hz), 8.54 (1H, d, J=8.8 Hz), 14.3 (1H, s).

Example 33

Preparation of 2-(2-(2-(4-chloro-2-(methoxycarbonyl)phenylamino)-2-oxoethoxy)acetamido)-5-methyl-4-phenylthiophene-3-carboxylic acid The titled compound was prepared according to Steps (i) and (ii) described below.

(i) tert-Butyl 2-(2-(2-(4-chloro-2-(methoxycarbonyl) phenylamino)-2-oxoethoxy)acetamido)-5-methyl-4-phenylthiophene-3-carboxylate 0.81 g (2.7 mmol) of 2-(2-(4-chloro-2-(methoxycarbonyl) phenylamino)-2-oxoethoxy)acetic acid obtained in Example 29-(i), 16 mg (0.22 mmol) of DMF, and 0.28 ml (3.24 mmol) of oxalyl chloride were stirred in 9 ml of THF at 0° C. for 30 minutes. After completion of the reaction, the solvent was distilled off under reduced pressure and dried. 0.94 g (3.24 mmol) of tert-butyl 2-amino-5-methyl-4-phenylthiophene 3-carboxylate was added to this residue and stirred in 9 ml of DMA at room temperature overnight. After completion of the reaction, the reaction mixture was poured into ice water. Subsequently, sodium hydrogen carbonate was added, and the precipitated solid was filtered off and dried to give 1.60 g of tert-butyl 2-(2-(2-(4-chloro-2-(methoxycarbonyl)phenylamino)-2-oxoethoxy)acetamido)-5-methyl-4-phenylthiophene-3-carboxylate.

$^1$H-NMR (CDCl$_3$) δ: 0.99 (9H, s), 2.13 (3H, s), 3.85 (3H, s), 4.34 (2H, s), 4.44 (2H, s), 7.09-7.39 (5H, m), 7.51 (1H, dd, J=9.2, 2.6 Hz), 8.00 (1H, d, J=2.6 Hz), 8.75 (1H, d, J=9.2 Hz), 11.9 (1H, s), 12.0 (1H, s).

(ii) 2-(2-(2-(4-Chloro-2-(methoxycarbonyl)phenylamino)-2-oxoethoxy)acetamido)-5-methyl-4-phenylthiophene 3-carboxylic acid 0.85 g (1.48 mmol) of tert-butyl 2-(2-(2-(4-chloro-2-(methoxycarbonyl)phenylamino)-2-oxoethoxy)acetamido)-5-methyl-4-phenylthiophene-3-carboxylate and 1.1 ml of TFA were stirred in 15 ml of methylene chloride at room temperature overnight. After concentrating the reaction mixture, the residue was collected by filtration, washed with ethyl acetate-IPE and dried to give the titled 2-(2-(2-(4-chloro-2-(methoxycarbonyl)phenylamino)-2-oxoethoxy)acetamido)-5-methyl-4-phenylthiophene-3-carboxylic acid (yield: 68%).

$^1$H-NMR (DMSO-d$_6$) δ: 2.99 (3H, s), 3.77 (3H, s), 4.37 (2H, s), 4.49 (2H, s), 7.14-7.40 (5H, m), 7.73 (1H, dd, J=7.8, 2.4 Hz), 7.94 (1H, d, J=2.4 Hz), 8.59 (1H, d, J=7.8 Hz), 11.5 (1H, s), 11.9 (1H, s), 12.6 (1H, bs).

Example 34

Preparation of 2-(2-(2-(4-(bis(4-fluorophenyl)methyl)piperazin-1-yl)-2-oxoethoxy)acetamido)-5-chlorobenzoic acid The titled compound was prepared according to Steps (i) and (ii) described below.

(i) Methyl 2-(2-(2-(4-(bis(4-fluorophenyl)methyl) piperazin-1-yl)-2-oxoethoxy)acetamido)-5-chlorobenzoate 0.81 g (2.7 mmol) of 2-(2-(4-chloro-2-(methoxycarbonyl) phenylamino)-2-oxoethoxy)acetic acid obtained in Example 29-(i), 16 mg (0.22 mmol) of DMF, and 0.28 ml (3.24 mmol) of oxalyl chloride were stirred in 9 ml of THF at 0° C. for 30 minutes. After completion of the reaction, the solvent was distilled off under reduced pressure and dried. 0.93 g (3.24 mmol) of 1-bis(4-fluorophenyl)methyl)piperazine was added to this residue, and the mixture was stirred in 9 ml of DMA at room temperature overnight. After completion of the reaction, an aqueous sodium hydrogen carbonate solution was added, and extracted with ethyl acetate, and the extract was washed with a saturated sodium chloride solution. After the obtained organic layer was dried over anhydrous sodium sulfate, the solvent was distilled off under reduced pressure. The obtained crude product was separated and purified by silica gel column chromatography to give 1.50 g of methyl 2-(2-(2-(4-(bis(4-fluorophenyl)methyl)piperazin-1-yl)-2-oxoethoxy)acetamido)-5-chlorobenzoate (yield: 97%).

$^1$H-NMR (CDCl$_3$) δ: 2.35-2.40 (4H, m), 3.50-3.66 (4H, m), 3.83 (3H, s), 4.22 (2H, s), 4.22 (1H, s), 4.35 (2H, s), 6.93-7.02 (4H, m), 7.26-7.36 (4H, m), 7.51 (1H, dd, J=9.1, 2.6 Hz), 8.00 (1H, d, J=2.6 Hz), 8.75 (1H, d, J=9.1 Hz), 11.7 (1H, s).

(ii) 2-(2-(2-(4-(bis(4-fluorophenyl)methyl)piperazin-1-yl)-2-oxoethoxy)acetamido)-5-chlorobenzoic acid 1.47 g (2.56 mmol) of methyl 2-(2-(2-(4-(bis(4-fluorophenyl)methyl)piperazin-1-yl)-2-oxoethoxy)acetamido)-5-chlorobenzoate was dissolved in 26 ml of THF. Subsequently, a 1N aqueous sodium hydroxide solution was then added, and the mixture was stirred at 60° C. for 1 hour. After cooling, THF was distilled off under reduced pressure. Water was added to the residue and the mixture was neutralized with 1N hydrochloric acid. The obtained residue was washed with IPE to give the titled 2-(2-(2-(4-(bis(4-fluorophenyl)methyl)piperazin-1-yl)-2-oxoethoxy)acetamido)-5-chlorobenzoate (yield: 93%).

$^1$H-NMR (DMSO-$d_6$) δ: 2.20-2.38 (4H, m), 3.35-3.57 (4H, m), 4.13 (2H, s), 4.35 (2H, s), 4.40 (1H, s), 7.08-7.46 (8H, m), 7.65 (1H, dd, J=9.0, 2.4 Hz), 7.95 (1H, d, J=2.4 Hz), 8.67 (1H, d, J=9.0 Hz), 12.1 (1H, s).

Example 35

Preparation of 2-(2-(2-(1-adamantylamino)-2-oxoethoxy)acetamido)-5-chlorobenzoate The titled compound was prepared according to Steps (i) and (ii) described below.

(i) Methyl 2-(2-(2-(1-adamantylamino)-2-oxoethoxy)acetamido)-5-chlorobenzoate

Using the same method as in Example 34-(i), 2-(2-(4-chloro-2-(methoxycarbonyl)phenylamino)-2-oxoethoxy) acetic acid obtained in Example 29-(i) was reacted with 1-adamantylamine to give methyl 2-(2-(2-(1-adamantylamino)-2-oxoethoxy)acetamido)-5-chlorobenzoate (yield: 55%).

$^1$H-NMR (CDCl$_3$) δ: 1.60-1.70 (6H, m), 2.02-2.13 (9H, m), 3.98 (3H, s), 4.02 (2H, s), 4.05 (2H, s), 6.51 (1H, s), 7.53 (1H, dd, J=9.0, 2.6 Hz), 8.05 (1H, d, J=2.6 Hz), 8.77 (1H, d, J=9.0 Hz), 11.8 (1H, s).

(ii) 2-(2-(2-(1-Adamantylamino)-2-oxoethoxy)acetamido)-5-chlorobenzoate

Using the same method as in Example 34-(ii), the titled 2-(2-(2-(1-adamantylamino)-2-oxoethoxy)acetamido)-5-chlorobenzoate was obtained using methyl 2-(2-(2-(1-adamantylamino)-2-oxoethoxy)acetamido)-5-chlorobenzoic acid (yield: 65%).

$^1$H-NMR (DMSO-$d_6$) δ: 1.56-1.70 (6H, m), 1.90-2.13 (9H, m), 3.98 (2H, s), 4.17 (2H, s), 7.03 (1H, s), 7.69 (1H, dd, J=9.0, 2.4 Hz), 7.98 (1H, d, J=2.4 Hz), 8.66 (1H, d, J=9.0 Hz), 11.9 (1H, s), 13.8 (1H, bs).

Example 36

Preparation of 2-(2-(2-(4-(9H-fluoren-9-yl)piperazin-1-yl)-2-oxoethoxy)acetamido)-5-chlorobenzoic acid The titled compound was prepared according to Steps (i) and (ii) described below.

(i) Methyl 2-(2-(2-(4-(9H-fluoren-9-yl)piperazin-1-yl)-2-oxoethoxy)acetamido)-5-chlorobenzoate Using the same method as in Example 34-(i), 2-(2-(4-chloro-2-(methoxycarbonyl)phenylamino)-2-oxoethoxy) acetic acid obtained in Example 29-(i) was reacted with 1-(9H-Fluoren-9-yl)piperazine (Example 36-(iii)) to give methyl 2-(2-(2-(4-(9H-fluoren-9-yl)piperazin-1-yl)-2-oxoethoxy)acetamido)-5-chlorobenzoate (yield: 95%).

$^1$H-NMR (CDCl$_3$) δ: 2.45-2.47 (4H, m), 2.75-2.80 (2H, m), 3.41-3.43 (2H, m), 3.62-3.67 (2H, m), 3.80 (3H, s), 4.19 (2H, s), 4.31 (2H, s), 4.85 (1H, s), 7.21-7.68 (9H, m), 7.98 (1H, d, J=2.6 Hz), 8.73 (1H, d, J=9.1 Hz), 11.6 (1H, s).

(ii) 2-(2-(2-(4-(9H-fluoren-9-yl)piperazin-1-yl)-2-oxoethoxy)acetamido)-5-chlorobenzoic acid Using the same method as in Example 34-(ii), the titled 2-(2-(2-(4-(9H-fluoren-9-yl)piperazin-1-yl)-2-oxoethoxy)acetamido)-5-chlorobenzoate (yield: 96%) was obtained using methyl 2-(2-(2-(4-(9H-fluoren-9-yl)piperazin-1-yl)-2-oxoethoxy)acetamido)-5-chlorobenzoate.

$^1$H-NMR (DMSO-$d_6$) δ: 2.42-2.53 (2H, m), 3.24-3.57 (4H, m), 4.11 (2H, s), 4.34 (2H, s), 4.97 (1H, s), 7.25-7.80 (8H, m), 7.67 (1H, dd, J=9.1, 2.6 Hz), 7.94 (1H, d, J=2.6 Hz), 8.66 (1H, d, J=9.1 Hz), 11.9 (1H, s).

(iii) Synthesis of 1-(9H-fluoren-9-yl)piperazine 14.7 g (60 mmol) of 9-bromofluorene, 6.85 g (60 mmol) of 1-formylpiperazine, and 8.29 g (60 mmol) of potassium carbonate were stirred in 70 ml of DMF at room temperature for 4 hours. After completion of the reaction, water was added and the mixture was extracted with ethyl acetate. After the obtained organic layer was dried over anhydrous sodium sulfate, the solvent was distilled off under reduced pressure. IPE was added to crystallize the obtained crude product, thus giving 10.8 g of 4-(9H-fluoren-9-yl)piperazin-1-carboxaldehyde (yield: 65%).

$^1$H-NMR (CDCl$_3$) δ: 2.54 (2H, t, J=5.1 Hz), 2.69 (2H, t, J=5.1 Hz), 3.30 (2H, t, J=5.1 Hz), 3.54 (2H, t, J=5.1 Hz), 4.86 (1H, s), 7.25-7.42 (4H, m), 7.57-7.70 (4H, m), 7.97 (1H, s).

Further, 5.01 g (18 mmol) of 4-(9H-fluoren-9-yl)piperazine-1-carboxaldehyde, and 6 ml of 6N hydrochloric acid were stirred in 24 ml of 1,4-dioxane at 80° C. for 6 hours. The reaction mixture was concentrated and then neutralized with aqueous ammonia. Water was added and the mixture was extracted with ethyl acetate. After the obtained organic layer was dried over anhydrous sodium sulfate, the solvent was distilled off under reduced pressure. Ethyl acetate-IPE was added to crystallize the obtained crude product, thus giving 1-(9H-fluoren-9-yl)piperazine (yield: 42%).

$^1$H-NMR (CDCl$_3$) δ: 1.53 (1H, bs), 2.58-2.62 (4H, m), 2.81-2.86 (4H, m), 4.80 (1H, s), 7.23-7.40 (4H, m), 7.63-7.70 (4H, m).

Example 37

Preparation of 2-(2-(2-(benzhydrylamino)-2-oxoethoxy)acetamido)-5-chlorobenzoate The titled compound was prepared according to Steps (i) and (ii) described below.

(i): Methyl 2-(2-(2-(benzhydrylamino)-2-oxoethoxy)acetamido)-5-chlorobenzoate

Using the same method as in Example 34-(i), 2-(2-(4-chloro-2-(methoxycarbonyl)phenylamino)-2-oxoethoxy)

acetic acid obtained in Example 29-(i) was reacted with diphenylmethylamine to give methyl 2-(2-(2-(benzhydrylamino)-2-oxoethoxy)acetamido)-5-chlorobenzoate (yield: 66%).

$^1$H-NMR (CDCl$_3$) δ: 3.32 (3H, s), 4.21 (2H, s), 4.25 (2H, s), 6.48 (1H, d, J=9.2 Hz), 7.25-7.36 (10H, m), 7.52 (1H, dd, J=9.0, 2.6 Hz), 7.90 (1H, d, J=9.2 Hz), 7.98 (1H, d, J=2.6 Hz), 8.76 (1H, d, J=9.0 Hz), 11.9 (1H, s).

(ii): 2-(2-(2-(Benzhydrylamino)-2-oxoethoxy)acetamido)-5-chlorobenzoate

Using the same method as in Example 34-(ii), the titled 2-(2-(2-(benzhydrylamino)-2-oxoethoxy)acetamido)-5-chlorobenzoate was obtained using methyl 2-(2-(2-(benzhydrylamino)-2-oxoethoxy)acetamido)-5-chlorobenzoate (yield: 92%).

$^1$H-NMR (DMSO-d$_6$) δ: 4.23 (2H, s), 4.25 (2H, s), 6.20 (1H, d, J=8.5 Hz), 7.22-7.35 (10H, m), 7.67 (1H, dd, J=9.0, 2.6 Hz), 7.96 (1H, d, J=2.6 Hz), 8.66 (1H, d, J=9.0 Hz), 8.81 (1H, d, J=8.5 Hz), 12.0 (1H, s).

Example 38

Preparation of 2-(2-(2-(3-(tert-butoxycarbonyl)-5-methyl-4-phenylthiophen-2-ylamino)-2-oxoethoxy)acetamido)-5-chlorobenzoic acid Using the same method as in Example 34-(ii), the titled 2-(2-(2-(3-(tert-carbobutoxy)-5-methyl-4-phenylthiophen-2-ylamino)-2-oxoethoxy)acetamido)-5-chlorobenzoic acid (yield: 56%) was obtained using tert-butyl 2-(2-(2-(4-chloro-2-(methoxycarbonyl)phenylamino)-2-oxoethoxy)acetamido)-5-methyl-4-phenylthiophen-3-carboxylate obtained in Example 33-(i).

$^1$H-NMR (DMSO-d$_6$) δ: 0.93 (9H, s), 2.09 (3H, s), 4.35 (2H, s), 4.47 (2H, s), 7.12-7.42 (5H, m), 7.62 (1H, dd, J=9.0, 2.4 Hz), 7.94 (1H, d, J=2.4 Hz), 8.64 (1H, d, J=9.0 Hz), 11.7 (1H, s), 12.5 (1H, s).

Example 39

Preparation of 5-chloro-2-(2-(2-(4-chlorophenylamino)-2-oxoethoxy)acetamido)benzoic acid The titled compound was prepared according to Steps (i) and (ii) described below.

(i): Methyl 5-chloro-2-(2-(2-(4-chlorophenylamino)-2-oxoethoxy)acetamido)benzoate Using the same method as in Example 34-(i), 2-(2-(4-chloro-2-(methoxycarbonyl)phenylamino)-2-oxoethoxy) acetic acid obtained in Example 29-(i) was reacted with 4-chloroaniline to give methyl 5-chloro-2-(2-(2-(4-chlorophenylamino)-2-oxoethoxy)acetamido)benzoate (yield: 51%).

$^1$H-NMR (CDCl$_3$) δ: 3.85 (3H, s), 4.26 (2H, s), 4.27 (2H, s), 7.26-7.35 (2H, m), 7.55 (1H, dd, J=9.2, 2.6 Hz), 7.65-7.75 (2H, m), 8.05 (1H, d, J=2.6 Hz), 8.78 (1H, d, J=9.2 Hz), 8.83 (1H, s), 11.9 (1H, s).

(ii) 5-Chloro-2-(2-(2-(4-chlorophenylamino)-2-oxoethoxy)acetamido)benzoic acid

Using the same method as in Example 34-(ii), the titled 5-chloro-2-(2-(2-(4-chlorophenylamino)-2-oxoethoxy)acetamido)benzoic acid (yield: 93%) was obtained using methyl 5-chloro-2-(2-(2-(4-chlorophenylamino)-2-oxoethoxy)acetamido)benzoate.

$^1$H-NMR (DMSO-d$_6$) δ: 4.28 (2H, s), 4.31 (2H, s), 7.32-7.43 (2H, m), 7.68-7.78 (2H, m), 7.70 (1H, dd, J=9.0, 2.7 Hz), 7.98 (1H, d, J=2.7 Hz), 8.69 (1H, d, J=9.0 Hz), 9.88 (1H, s), 11.9 (1H, s).

Example 40

Preparation of 2-(2-(2-(2-benzoyl-4-chlorophenylamino)-2-oxoethoxy)acetamido)-5-chlorobenzoic acid The titled compound was prepared according to Steps (i) and (ii) described below.

(i): Methyl 2-(2-(2-(2-benzoyl-4-chlorophenylamino)-2-oxoethoxy)acetamido)-5-chlorobenzoate Using the same method as in Example 34-(i), 2-(2-(4-chloro-2-(methoxycarbonyl)phenylamino)-2-oxoethoxy) acetic acid obtained in Example 29-(i) was reacted with 2-benzoyl-4-chloroaniline to give methyl 2-(2-(2-(2-benzoyl-4-chlorophenylamino)-2-oxoethoxy)acetamido)-5-chlorobenzoate (yield: 87%).

$^1$H-NMR (CDCl$_3$) δ: 3.62 (3H, s), 4.28 (2H, s), 4.29 (2H, s), 7.40-7.70 (8H, m), 7.92 (1H, d, J=2.6 Hz), 8.53-8.62 (1H, m), 8.72 (1H, d, J=9.0 Hz), 11.1 (1H, s), 11.8 (1H, s).

(ii) 2-(2-(2-(2-Benzoyl-4-chlorophenylamino)-2-oxoethoxy)acetamido)-5-chlorobenzoic acid Using the same method as in Example 34-(ii), the titled 2-(2-(2-(2-benzoyl-4-chlorophenylamino)-2-oxoethoxy)acetamido)-5-chlorobenzoic acid was obtained using methyl 2-(2-(2-(2-benzoyl-4-chlorophenylamino)-2-oxoethoxy)acetamido)-5-chlorobenzoate (yield: 60%).

$^1$H-NMR (DMSO-d$_6$) δ: 4.09 (2H, s), 4.11 (2H, s), 7.40-7.70 (7H, m), 7.69 (1H, dd, J=9.0, 2.7 Hz), 7.88 (1H, d, J=2.7 Hz), 8.01 (1H, d, J=8.8 Hz), 8.61 (1H, d, J=9.0 Hz), 10.5 (1H, s), 12.3 (1H, s).

Example 41

Preparation of 2-(2-(2-(4-benzhydrylpiperazin-1-yl)-2-oxoethoxy)acetamido)-5-fluorobenzoic acid The titled compound was prepared according to Steps (i) to (iii) described below.

(i) 2-(2-(4-Fluoro-2-(methoxycarbonyl)phenylamino)-2-oxoethoxy)acetic acid 5.0 g (29.6 mmol) of methyl 2-amino-5-fluorobenzoate and 3.78 g (32.6 mmol) of diglycolic anhydride were heated in 74 ml of THF under reflux for 4 hours. After cooling, the reaction mixture was concentrated. The residue was collected by filtration, washed with IPE, and dried to give 7.77 g of 2-(2-(4-fluoro-2-(methoxycarbonyl)phenylamino)-2-oxoethoxy)acetic acid (yield: 92%).

$^1$H-NMR (DMSO-d$_6$) δ: 3.89 (3H, s), 4.20 (2H, s), 4.27 (2H, s), 7.55 (1H, dddd, J=14.6, 5.1, 3.1, 1.4 Hz), 7.73 (1H, dd, J=9.3, 3.1 Hz), 8.60 (1H, dddd, J=14.6, 9.3, 5.1, 3.1 Hz), 11.3 (1H, s).

(ii) Methyl 2-(2-(2-(4-benzhydrylpiperazin-1-yl)-2-oxoethoxy)acetamido)-5-fluorobenzoate 0.77 g (2.7 mmol) of 2-(2-(4-fluoro-2-(methoxycarbonyl)phenylamino)-2-oxoethoxy)acetic acid, 16 mg (0.22 mmol) of DMF, 0.28 ml (3.24 mmol) of oxalyl chloride were stirred in 9 ml THF at 0° C. for 30 minutes. After completion of the reaction, the solvent was distilled off under reduced pressure and dried. After adding 0.82 g (3.24 mmol) of 1-benzhydrylpiperazine and 0.56 ml (4.05 mmol) of triethylamine (added only when the amine component to be condensed is hydrochloride) to this residue, the mixture was stirred in 9 ml of DMA at room temperature overnight. After completion of the reaction, an aqueous sodium hydrogen carbonate solution was added, and the mixture was extracted with ethyl acetate. The extract was washed with a saturated sodium chloride solution. After the obtained organic layer was dried over anhydrous sodium sulfate, the solvent was distilled off under reduced pressure. The obtained crude product was separated and purified by silica gel column chromatography to give 1.26 g of methyl 2-(2-(2-(4-benzhydrylpiperazin-1-yl)-2-oxoethoxy)acetamido)-5-fluorobenzoate (yield: 90%).

$^1$H-NMR (CDCl$_3$) δ: 2.28-2.42 (4H, m), 3.51-3.66 (4H, m), 3.79 (3H, s), 4.22 (2H, s), 4.22 (1H, s), 4.35 (2H, s), 7.15-7.42 (11H, m), 7.70 (1H, dd, J=9.2, 3.3 Hz), 8.76 (1H, dd, J=9.2, 5.2 Hz), 11.6 (1H, s).

(iii) 2-(2-(2-(4-Benzhydrylpiperazin-1-yl)-2-oxoethoxy)acetamido)-5-fluorobenzoic acid 1.25 g (2.41 mmol) of methyl 2-(2-(2-(4-benzhydrylpiperazin-1-yl)-2-oxoethoxy)acetamido)-5-fluorobenzoate was dissolved in 24 ml of THF. Subsequently, a 1N aqueous sodium hydroxide solution was added the mixture was stirred at 60° C. for 1 hour. After cooling, THF was distilled off under reduced pressure, water was added to the residue and the mixture was neutralized with 1N hydrochloric acid. The obtained residue was washed with IPE to give the titled 2-(2-(2-(4-benzhydrylpiperazin-1-yl)-2-oxoethoxy)acetamido)-5-fluorobenzoic acid (yield: 93%).

$^1$H-NMR (DMSO-d$_6$) δ: 2.35-2.59 (4H, m), 3.49-3.60 (4H, m), 4.14 (2H, s), 4.37 (2H, s), 4.53 (1H, s), 7.19-7.60 (11H, m), 7.73 (1H, dd, J=9.3, 2.9 Hz), 8.68 (1H, dd, J=9.3, 5.1 Hz), 11.7 (1H, s).

Example 42

Preparation of 3-(2-(2-(4-benzhydrylpiperazin-1-yl)-2-oxoethoxy)acetamido)benzoic acid The titled compound was prepared according to Steps (i) to (iii) described below.

(i) 2-(2-(3-(Methoxycarbonyl)phenylamino)-2-oxoethoxy)acetic acid

Using the same method as in Example 41 (i), 2-(2-(3-(methoxycarbonyl)phenylamino)-2-oxoethoxy)acetic acid (yield: 98%) was obtained using methyl 3-aminobenzoate.

$^1$H-NMR (DMSO-d$_6$) δ: 3.86 (3H, s), 4.21 (2H, s), 4.23 (2H, s), 7.48 (1H, t, J=6.8 Hz), 7.66 (1H, d, J=6.8 Hz), 7.96 (1H, d, J=6.8 Hz), 8.34 (1H, s), 10.1 (1H, s), 12.9 (1H, bs).

(ii) Methyl 3-(2-(2-(4-benzhydrylpiperazin-1-yl)-2-oxoethoxy)acetamido)benzoate Using the same method as in Example 41 (ii), methyl 3-(2-(2-(4-benzhydrylpiperazin-1-yl)-2-oxoethoxy)acetamido)benzoate (yield: 60%) was obtained using 2-(2-(3-(methoxycarbonyl)phenylamino)-2-oxoethoxy)acetic acid.

$^1$H-NMR (CDCl$_3$) δ: 2.38-2.44 (4H, m), 3.32-3.38 (2H, m), 3.69-3.72 (2H, m), 3.91 (3H, s), 4.20 (2H, s), 4.26 (1H, s), 4.34 (2H, s), 7.17-7.43 (10H, m), 7.54-8.27 (4H, m), 10.2 (1H, s).

(iii) 3-(2-(2-(4-Benzhydrylpiperazin-1-yl)-2-oxoethoxy)acetamido)benzoic acid Using the same method as in Example 41-(iii), the titled 3-(2-(2-(4-benzhydrylpiperazin-1-yl)-2-oxoethoxy)acetamido)benzoic acid (yield: 27%) was obtained using methyl 3-(2-(2-(4-benzhydrylpiperazin-1-yl)-2-oxoethoxy)acetamido)benzoate.

$^1$H-NMR (DMSO-d$_6$) δ: 2.29-2.38 (4H, m), 3.38-3.53 (4H, m), 4.15 (2H, s), 4.32 (1H, s), 4.38 (2H, s), 7.15-7.47 (11H, m), 7.62-7.66 (1H, m), 7.80-7.85 (1H, m), 8.26-8.28 (1H, m), 10.6 (1H, s).

Example 43

Preparation of 4-(2-(2-(4-benzhydrylpiperazin-1-yl)-2-oxoethoxy)acetamido)-3-chlorobenzoic acid The titled compound was prepared according to Steps (i) to (iii) described below.

(i) 2-(2-(2-Chloro-4-(methoxycarbonyl)phenylamino)-2-oxoethoxy)acetic acid

Using the same method as in Example 41 (i), 2-(2-(2-chloro-4-(methoxycarbonyl)phenylamino)-2-oxoethoxy) acetic acid (yield: 89%) was obtained using 4-amino-3-chlorobenzoate methyl.

$^1$H-NMR (DMSO-d$_6$) δ: 3.86 (3H, s), 4.30 (4H, s), 7.90-8.38 (3H, m), 9.61 (1H, s), 12.9 (1H, bs).

(ii) Methyl 4-(2-(2-(4-benzhydrylpiperazin-1-yl)-2-oxoethoxy)acetamido)-3-chlorobenzoate Using the same method as in Example 41 (ii), methyl 4-(2-(2-(4-benzhydrylpiperazin-1-yl)-2-oxoethoxy)acetamido)-3-chlorobenzoate (yield: 46%) was obtained using 2-(2-(2-chloro-4-(methoxycarbonyl)phenylamino)-2-oxoethoxy)acetic acid.

$^1$H-NMR (CDCl$_3$) δ: 2.38-2.43 (4H, m), 3.36-3.66 (4H, m), 3.91 (3H, s), 4.23 (2H, s), 4.25 (1H, s), 4.33 (2H, s), 7.19-7.42 (10H, m), 7.91-8.08 (2H, m), 8.55 (1H, d, J=8.6 Hz), 9.51 (1H, s).

(iii) 4-(2-(2-(4-Benzhydrylpiperazin-1-yl)-2-oxoethoxy)acetamido)-3-chlorobenzoic acid Using the same method as in Example 41-(iii), the titled 4-(2-(2-(4-benzhydrylpiperazin-1-yl)-2-oxoethoxy)acetamido)-3-chlorobenzoic acid (yield: 10%) was obtained using methyl 4-(2-(2-(4-benzhydrylpiperazin-1-yl)-2-oxoethoxy) acetamido)-3-chlorobenzoate.

$^1$H-NMR (DMSO-d$_6$) δ: 2.23-2.40 (4H, m), 3.28-3.51 (4H, m), 4.20 (2H, s), 4.33 (1H, s), 4.42 (2H, s), 7.15-7.45 (10H, m), 7.88-7.98 (2H, m), 8.32 (1H, d, J=8.3 Hz), 9.97 (1H, s), 13.2 (1H, bs).

Example 44

Preparation of sodium 4-(2-(2-(4-benzhydrylpiperazin-1-yl)-2-oxoethoxy)acetamido)-4'-fluorobiphenyl-3-carboxylate The titled compound was prepared according to Steps (i) to (iv) described below.

(i) 2-(2-(4-Bromo-2-(methoxycarbonyl)phenylamino)-2-oxoethoxy)acetic acid 11.5 g (50.0 mmol) of methyl 2-amino-5-bromobenzoate, and 6.38 g (55.0 mmol) of diglycolic anhydride were heated in 125 ml of THF under reflux for 3 hours. After cooling, the reaction mixture was concentrated. The residue was collected by filtration, washed with IPE, and dried to give 15.9 g of 2-(2-(4-bromo-2-(methoxycarbonyl)phenylamino)-2-oxoethoxy)acetic acid (yield: 92%).

$^1$H-NMR (DMSO-$d_6$) δ: 3.89 (3H, s), 4.20 (2H, s), 4.26 (2H, s), 7.85 (1H, dd, J=9.0, 3.0 Hz), 8.08 (1H, d, J=3.0 Hz), 8.57 (1H, d, J=9.0 Hz), 11.4 (1H, s), 12.9 (1H, bs).

(ii) Methyl 2-(2-(2-(4-benzhydrylpiperazin-1-yl)-2-oxoethoxy)acetamido)-5-bromobenzoate 3.01 g (8.7 mmol) of 2-(2-(4-bromo-2-(methoxycarbonyl)phenylamino)-2-oxoethoxy)acetic acid, 51 mg (0.70 mmol) of DMF, and 0.89 ml (10.4 mmol) of oxalyl chloride were stirred in 29 ml of THF at 0° C. for 30 minutes. After completion of the reaction, the solvent was distilled off under reduced pressure and dried. 2.62 g (10.4 mmol) of 1-benzhydrylpiperazine was added to this residue and the mixture was stirred in 29 ml of DMA at room temperature overnight. After completion of the reaction, an aqueous sodium hydrogen carbonate solution was added, and the mixture was extracted with ethyl acetate. The extract was washed with a saturated sodium chloride solution. After the obtained organic layer was dried over anhydrous sodium sulfate, the solvent was distilled off under reduced pressure. The obtained crude product was separated and purified by silica gel column chromatography to give 4.60 g of methyl 2-(2-(2-(4-benzhydrylpiperazin-1-yl)-2-oxoethoxy)acetamido)-5-bromobenzoate (yield: 91%).

$^1$H-NMR (CDCl$_3$) δ: 2.31-2.48 (4H, m), 3.50-3.66 (4H, m), 3.81 (3H, s), 4.21 (2H, s), 4.22 (1H, s), 4.34 (2H, s), 7.14-7.41 (10H, m), 7.64 (1H, dd, J=9.2, 2.6 Hz), 8.15 (1H, d, J=2.6 Hz), 8.68 (1H, d, J=9.2 Hz), 11.6 (1H, s).

(iii) Methyl 4-(2-(2-(4-benzhydrylpiperazin-1-yl)-2-oxoethoxy)acetamido)-4'-fluorobiphenyl-3-carboxylate 1.16 g (2.0 mmol) of methyl 2-(2-(2-(4-benzhydrylpiperazin-1-yl)-2-oxoethoxy)acetamido)-5-bromobenzoate, 0.67 g (3.0 mmol) of 4-(4,4,5,5-tetramethyl-1,3,2-dioxaborolan-2-yl)fluorobenzene, 0.23 g (0.2 mmol) of tetrakis(triphenylphosphine)palladium (0), and 0.98 g (3.0 mmol) of cesium carbonate were heated in 20 ml of THF under reflux for 15 hours. After completion of the reaction, THF was distilled off under reduced pressure. Ethyl acetate was added, and the solid was separated by filtration. The organic layer was washed with a saturated sodium chloride solution and dried over anhydrous sodium sulfate, and the solvent was then distilled off under reduced pressure. The obtained crude product was separated and purified by silica gel column chromatography to give 1.04 g of methyl 4-(2-(2-(4-benzhydrylpiperazin-1-yl)-2-oxoethoxy)acetamido)-4'-fluorobiphenyl-3-carboxylate (yield: 87%).

$^1$H-NMR (CDCl$_3$) δ: 2.38-2.42 (4H, m), 3.53-3.67 (4H, m), 3.83 (3H, s), 4.22 (1H, s), 4.24 (2H, s), 4.37 (2H, s), 7.10-7.58 (14H, m), 7.73 (1H, dd, J=8.7, 2.4 Hz), 8.21 (1H, d, J=2.4 Hz), 8.82 (1H, d, J=8.7 Hz), 11.7 (1H, s).

(iv) Sodium 4-(2-(2-(4-benzhydrylpiperazin-1-yl)-2-oxoethoxy)acetamido)-4'-fluorobiphenyl-3-carboxylate 1.01 g (1.70 mmol) of methyl 4-(2-(2-(4-benzhydrylpiperazin-1-yl)-2-oxoethoxy)acetamido)-4'-fluorobiphenyl-3-carboxylate was dissolved in 17 ml of THF, and a 1N aqueous sodium hydroxide solution was then added and the mixture was stirred at 60° C. for 1 hour. After cooling, THF was distilled off under reduced pressure, and the residue was washed with water. The obtained residue was washed with IPE to give the titled sodium 4-(2-(2-(4-benzhydrylpiperazin-1-yl)-2-oxoethoxy)acetamido)-4'-fluorobiphenyl-3-carboxylate (yield: 54%).

$^1$H-NMR (DMSO-$d_6$) δ: 2.29-2.39 (4H, m), 3.31-3.59 (4H, m), 4.09 (2H, s), 4.32 (2H, s), 4.32 (1H, s), 7.14-7.69 (15H, m), 8.27 (1H, d, J=2.2 Hz), 8.58 (1H, d, J=8.5 Hz), 14.5 (1H, s).

Example 45

Preparation of sodium 4-(2-(2-(4-benzhydrylpiperazin-1-yl)-2-oxoethoxy)acetamido)-2',4'-difluorobiphenyl-3-carboxylate The titled compound was prepared according to Steps (i) and (ii) described below.

(i) Methyl 4-(2-(2-(4-benzhydrylpiperazin-1-yl)-2-oxoethoxy)acetamido)-2',4'-difluorobiphenyl-3-carboxylate Methyl 2-(2-(2-(4-benzhydrylpiperazin-1-yl)-2-oxoethoxy)acetamido)-5-bromobenzoate obtained in Example 44-(ii) was reacted with 2-(4,4,5,5-tetramethyl-1,3,2-dioxaborolan-2-yl)-1,5-difluorobenzene in the same manner as in Example 44-(iii) to give methyl 4-(2-(2-(4-benzhydrylpiperazin-1-yl)-2-oxoethoxy)acetamido)-2',4'-difluorobiphenyl-3-carboxylate (yield: 95%).

$^1$H-NMR (DMSO-$d_6$) δ: 2.31-2.45 (4H, m), 3.53-3.65 (4H, m), 3.82 (3H, s), 4.22 (1H, s), 4.24 (2H, s), 4.37 (2H, s), 6.87-7.02 (2H, m), 7.15-7.46 (11H, m), 7.66-7.72 (1H, m), 8.17-8.19 (1H, m), 8.83 (1H, d, J=8.8 Hz), 11.8 (1H, s).

(ii) Sodium 4-(2-(2-(4-benzhydrylpiperazin-1-yl)-2-oxoethoxy)acetamido)-2',4'-difluorobiphenyl-3-carboxylate Using the same method as in Example 44-(iv), the titled sodium 4-(2-(2-(4-benzhydrylpiperazin-1-yl)-2-oxoethoxy)acetamido)-2',4'-difluorobiphenyl-3-carboxylate (yield: 73%) was obtained using methyl 4-(2-(2-(4-benzhydrylpiperazin-1-yl)-2-oxoethoxy)acetamido)-2',4'-difluorobiphenyl-3-carboxylate.

$^1$H-NMR (DMSO-$d_6$) δ: 2.19-2.38 (4H, m), 3.38-3.51 (4H, m), 4.10 (2H, s), 4.30 (1H, s), 4.32 (2H, s), 7.14-7.62 (14H, m), 8.18 (1H, s), 8.63 (1H, d, J=8.5 Hz), 13.9 (1H, s).

Example 46

Preparation of sodium 4-(2-(2-(4-benzhydrylpiperazin-1-yl)-2-oxoethoxy)acetamido)-4'-cyanobiphenyl-3-carboxylate The titled compound was prepared according to Steps (i) and (ii) described below.

(i) Methyl 4-(2-(2-(4-benzhydrylpiperazin-1-yl)-2-oxoethoxy)acetamido)-4'-cyanobiphenyl-3-carboxylate Using the same method as in Example 44-(iii), methyl 2-(2-(2-(4-benzhydrylpiperazin-1-yl)-2-oxoethoxy)acetamido)-5-bromobenzoate obtained in Example 44-(ii) was reacted with 4-(4,4,5,5-tetramethyl-1,3,2-dioxaborolan-2-yl)benzonitrile to give methyl 4-(2-(2-(4-benzhydrylpiperazin-1-yl)-2-oxoethoxy)acetamido)-4'-cyanobiphenyl-3-carboxylate (yield: 84%).
$^1$H-NMR (CDCl$_3$) δ: 2.38-2.43 (4H, m), 3.51-3.65 (4H, m), 3.86 (3H, s), 4.23 (1H, s), 4.25 (2H, s), 4.38 (2H, s), 7.15-7.42 (10H, m), 7.67-7.74 (4H, m), 7.78 (1H, dd, J=8.8, 2.4 Hz), 8.28 (1H, d, J=2.4 Hz), 8.89 (1H, d, J=8.8 Hz), 11.8 (1H, s).

(ii) Sodium 4-(2-(2-(4-benzhydrylpiperazin-1-yl)-2-oxoethoxy)acetamido)-4'-cyanobiphenyl-3-carboxylate Using the same method as in Example 44-(iv), the titled sodium 4-(2-(2-(4-benzhydrylpiperazin-1-yl)-2-oxoethoxy)acetamido)-4'-cyanobiphenyl-3-carboxylate (yield: 82%) was obtained using methyl 4-(2-(2-(4-benzhydrylpiperazin-1-yl)-2-oxoethoxy)acetamido)-4'-cyanobiphenyl-3-carboxylate.
$^1$H-NMR DMSO-d$_6$ δ: 2.18-2.38 (4H, m), 3.30-3.48 (4H, m), 4.11 (2H, s), 4.29 (1H, s), 4.35 (2H, s), 7.13-7.42 (10H, m), 7.85-7.94 (5H, m), 8.37 (1H, d, J=2.4 Hz), 8.72 (1H, d, J=8.5 Hz), 13.2 (1H, s).

Example 47

Preparation of sodium 4-(2-(2-(4-benzhydrylpiperazin-1-yl)-2-oxoethoxy)acetamido)-4'-(dimethylamino)biphenyl-3-carboxylate The titled compound was prepared according to Steps (i) and (ii) described below.

(i) Methyl 4-(2-(2-(4-benzhydrylpiperazin-1-yl)-2-oxoethoxy)acetamido)-4'-(dimethylamino) biphenyl-3-carboxylate Using the same method as in Example 44-(iii), methyl 2-(2-(2-(4-benzhydrylpiperazin-1-yl)-2-oxoethoxy)acetamido)-5-bromobenzoate obtained in Example 44-(ii) was reacted with N,N-dimethyl[4-(4,4,5,5-tetramethyl-1,3,2-dioxaborolan-2-yl)phenyl]amine to quantitatively obtain methyl 4-(2-(2-(4-benzhydrylpiperazin-1-yl)-2-oxoethoxy)acetamido)-4'-(dimethylamino)biphenyl-3-carboxylate.
$^1$H-NMR (CDCl$_3$) δ: 2.31-2.48 (4H, m), 3.03 (6H, s), 3.53-3.67 (4H, m), 3.81 (3H, s), 4.21 (1H, s), 4.23 (2H, s), 4.36 (2H, s), 6.82-6.84 (2H, m), 7.14-7.51 (12H, m), 7.75 (1H, dd, J=8.8, 2.2 Hz), 8.22 (1H, d, J=2.2 Hz), 8.77 (1H, d, J=8.8 Hz), 11.7 (1H, s).

(ii) Sodium 4-(2-(2-(4-benzhydrylpiperazin-1-yl)-2-oxoethoxy)acetamido)-4'-(dimethylamino)biphenyl-3-carboxylate Using the same method as in Example 44-(iv), the titled sodium 4-(2-(2-(4-benzhydrylpiperazin-1-yl)-2-oxoethoxy)acetamido)-4'-(dimethylamino)biphenyl-3-carboxylate (yield: 79%) was obtained using methyl 4-(2-(2-(4-benzhydrylpiperazin-1-yl)-2-oxoethoxy)acetamido)-4'-(dimethylamino)biphenyl-3-carboxylate.
$^1$H-NMR (DMSO-d$_6$) δ: 2.20-2.38 (4H, m), 2.92 (6H, s), 3.23-3.51 (4H, m), 4.06 (2H, s), 4.30 (2H, s), 4.30 (1H, s), 6.79 (2H, d, J=8.8 Hz), 7.14-7.53 (13H, m), 8.22 (1H, d, J=2.2 Hz), 8.51 (1H, d, J=8.5 Hz), 14.4 (1H, s).

Example 48

Preparation of sodium 4-(2-(2-(4-benzhydrylpiperazin-1-yl)-2-oxoethoxy)acetamido)-4'-methoxybiphenyl-3-carboxylate The titled compound was prepared according to Steps (i) and (ii) described below.

(i) Methyl 4-(2-(2-(4-benzhydrylpiperazin-1-yl)-2-oxoethoxy)acetamido)-4'-methoxy biphenyl-3-carboxylate Using the same method as in Example 44-(iii), 2-(2-(2-(4-benzhydrylpiperazin-1-yl)-2-oxoethoxy)acetamido)-5-bromobenzoate obtained in Example 44-(ii) was reacted with p-methoxyphenylboronic acid (using an aqueous sodium carbonate solution as a base and toluene/methanol as a solvent) to give methyl 4-(2-(2-(4-benzhydrylpiperazin-1-yl)-2-oxoethoxy)acetamido)-4'-methoxybiphenyl-3-carboxylate (yield: 89%).
$^1$H-NMR (CDCl$_3$) δ: 2.38-2.44 (4H, m), 3.57-3.87 (4H, m), 3.82 (3H, s), 3.86 (3H, s), 4.22 (1H, s), 4.23 (2H, s), 4.36 (2H, s), 6.96-7.01 (2H, m), 7.14-7.55 (12H, m), 7.75 (1H, dd, J=8.6, 2.2 Hz), 8.22 (1H, d, J=2.2 Hz), 8.79 (1H, d, J=8.6 Hz), 11.7 (1H, s).

(ii) Sodium 4-(2-(2-(4-benzhydrylpiperazin-1-yl)-2-oxoethoxy)acetamido)-4'-methoxybiphenyl-3-carboxylate Using the same method as in Example 44-(iv), the titled sodium 4-(2-(2-(4-benzhydrylpiperazin-1-yl)-2-oxoethoxy)acetamido)-4'-methoxybiphenyl-3-carboxylate (yield: 50%) was obtained using methyl 4-(2-(2-(4-benzhydrylpiperazin-1-yl)-2-oxoethoxy)acetamido)-4'-methoxybiphenyl-3-carboxylate.
$^1$H-NMR (DMSO-d$_6$) δ: 2.21-2.35 (4H, m), 3.32-3.56 (4H, m), 3.79 (3H, s), 4.11 (2H, s), 4.29 (1H, s), 4.34 (2H, s), 7.02 (2H, d, J=8.8 Hz), 7.13-7.41 (10H, m), 7.60 (2H, d, J=8.8 Hz), 7.71 (1H, dd, J=8.5, 2.2 Hz), 8.24 (1H, d, J=2.2 Hz), 8.64 (1H, d, J=8.5 Hz), 13.1 (1H, s).

Example 49

Preparation of sodium 4-(2-(2-(4-benzhydrylpiperazin-1-yl)-2-oxoethoxy)acetamido)-4'-morpholinobiphenyl-3-carboxylate The titled compound was prepared according to Steps (i) and (ii) described below.

(i) Methyl 4-(2-(2-(4-benzhydrylpiperazin-1-yl)-2-oxoethoxy)acetamido)-4'-morpholinobiphenyl-3-carboxylate Using the same method as in Example 44-(iii), methyl 2-(2-(2-(4-benzhydrylpiperazin-1-yl)-2-oxoethoxy)acetamido)-5-bromobenzoate obtained in Example 44-(ii) was reacted with 4-[4-(4,4,5,5-tetramethyl-1,3,2-dioxaborolan-2-yl)phenyl]morpholine to give methyl 4-(2-(2-(4-benzhydrylpiperazin-1-yl)-2-oxoethoxy)acetamido)-4'-morpholinobiphenyl-3-carboxylate (yield: 81%).

$^1$H-NMR (CDCl$_3$) δ: 2.38-2.43 (4H, m), 3.18-3.24 (4H, m), 3.57-3.66 (4H, m), 3.82 (3H, s), 3.86-3.91 (4H, m), 4.22 (1H, s), 4.23 (2H, s), 4.36 (2H, s), 6.96-7.01 (2H, m), 7.14-7.55 (12H, m), 7.75 (1H, dd, J=8.8, 2.2 Hz), 8.22 (1H, d, J=2.2 Hz), 8.79 (1H, d, J=8.8 Hz), 11.7 (1H, s).

(ii) Sodium 4-(2-(2-(4-benzhydrylpiperazin-1-yl)-2-oxoethoxy)acetamido)-4'-morpholinobiphenyl-3-carboxylate Using the same method as in Example 44-(iv), the titled sodium 4-(2-(2-(4-benzhydrylpiperazin-1-yl)-2-oxoethoxy)acetamido)-4'-morpholinobiphenyl-3-carboxylate (yield: 60%) was obtained using methyl 4-(2-(2-(4-benzhydrylpiperazin-1-yl)-2-oxoethoxy)acetamido)-4'-morpholinobiphenyl-3-carboxylate.

$^1$H-NMR (DMSO-d$_6$) δ: 2.19-2.35 (4H, m), 3.09-3.22 (4H, m), 3.38-3.51 (4H, m), 3.68-3.82 (4H, m), 4.10 (2H, s), 4.30 (1H, s), 4.33 (2H, s), 7.02 (2H, d, J=8.8 Hz), 7.14-7.43 (10H, m), 7.54 (2H, d, J=8.8 Hz), 7.68 (1H, dd, J=8.6, 2.2 Hz), 8.23 (1H, d, J=2.2 Hz), 8.61 (1H, d, J=8.6 Hz), 13.2 (1H, s).

Example 50

Preparation of sodium 2-(2-(2-(4-benzhydrylpiperazin-1-yl)-2-oxoethoxy)acetamido)-5-(pyridin-4-yl)benzoate The titled compound was prepared according to Steps (i) and (ii) described below.

(i) Methyl 2-(2-(2-(4-benzhydrylpiperazin-1-yl)-2-oxoethoxy)acetamido)-5-(pyridin-4-yl)benzoate Using the same method as in Example 44-(iii), methyl 2-(2-(2-(4-benzhydrylpiperazin-1-yl)-2-oxoethoxy)acetamido)-5-bromobenzoate obtained in Example 44-(ii) was reacted with 4-(4,4,5,5-tetramethyl-1,3,2-dioxaborolan-2-yl)pyridine to give methyl 2-(2-(2-(4-benzhydrylpiperazin-1-yl)-2-oxoethoxy)acetamido)-5-(pyridin-4-yl)benzoate (yield: 88%).

$^1$H-NMR (CDCl$_3$) δ: 2.39-2.42 (4H, m), 3.55-3.87 (4H, m), 3.87 (3H, s), 4.23 (1H, s), 4.26 (2H, s), 4.38 (2H, s), 7.19-7.54 (12H, m), 7.85 (1H, dd, J=8.8, 1.7 Hz), 8.67 (1H, d, J=1.7 Hz), 8.69-8.76 (2H, m), 8.91 (1H, d, J=8.8 Hz), 11.8 (1H, s).

(ii) Sodium 2-(2-(2-(4-benzhydrylpiperazin-1-yl)-2-oxoethoxy)acetamido)-5-(pyridin-4-yl)benzoate Using the same method as in Example 44-(iv), the titled sodium 2-(2-(2-(4-benzhydrylpiperazin-1-yl)-2-oxoethoxy)acetamido)-5-(pyridin-4-yl)benzoate (yield: 67%) was obtained using methyl 2-(2-(2-(4-benzhydrylpiperazin-1-yl)-2-oxoethoxy)acetamido)-5-(pyridin-4-yl)benzoate.

$^1$H-NMR (DMSO-d$_6$) δ: 2.19-2.38 (4H, m), 3.28-3.58 (4H, m), 4.11 (2H, s), 4.30 (1H, s), 4.33 (2H, s), 7.14-7.43 (10H, m), 7.67 (2H, d, J=6.2 Hz), 7.81 (1H, dd, J=8.6, 2.5 Hz), 8.43 (1H, d, J=2.5 Hz), 8.60 (2H, d, J=6.2 Hz), 8.66 (1H, d, J=8.6 Hz), 14.3 (1H, s).

Example 51

Preparation of sodium 2-(2-(2-(4-benzhydrylpiperazin-1-yl)-2-oxoethoxy)acetamido)-5-bromobenzoate Using the same method as in Example 44-(iv), the titled sodium 2-(2-(2-(4-benzhydrylpiperazin-1-yl)-2-oxoethoxy)acetamido)-5-bromobenzoate (yield: 79%) was obtained using methyl 2-(2-(2-(4-benzhydrylpiperazin-1-yl)-2-oxoethoxy)acetamido)-5-bromobenzoate obtained in Example 44-(ii).

$^1$H-NMR (DMSO-d$_6$) δ: 2.20-2.39 (4H, m), 3.30-3.59 (4H, m), 4.08 (2H, s), 4.30 (1H, s), 4.30 (2H, s), 7.14-7.44 (10H, m), 7.53 (1H, dd, J=9.0, 2.7 Hz), 8.09 (1H, d, J=2.7 Hz), 8.51 (1H, d, J=9.0 Hz), 13.7 (1H, s).

Example 52

Preparation of 2-(2-(2-benzhydrylamino)-2-oxoethoxy)acetamido-5-(pyridin-4-yl)benzoic acid The titled compound was prepared according to Steps (i) to (iii) described below.

(i) Methyl 2-(2-(2-benzhydrylamino)-2-oxoethoxy)acetamido-5-bromobenzoate 2.18 g (6.3 mmol) of 2-(2-(4-bromo-2-(methoxycarbonyl)phenylamino)-2-oxoethoxy)acetic acid obtained in Example 44-(i), 37 mg (0.51 mmol) of DMF, and 0.65 ml (7.56 mmol) of oxalyl chloride were stirred in 19 ml THF at 0° C. for 30 minutes. After completion of the reaction, the solvent was distilled off under reduced pressure and dried. 1.09 ml (6.3 mmol) of diphenylmethylamine was added to this residue, and the mixture was stirred in 19 ml of DMA at room temperature overnight. After completion of the reaction, an aqueous sodium hydrogen carbonate solution was added, and the mixture was extracted with ethyl acetate. The extract was washed with a saturated sodium chloride solution, and the obtained organic layer was dried over anhydrous sodium sulfate. The solvent was then distilled off under reduced pressure. The obtained crude product was separated and purified by silica gel column chromatography to give 2.55 g of methyl 2-(2-(2-benzhydrylamino)-2-oxoethoxy)acetamido-5-bromobenzoate (yield: 79%).

$^1$H-NMR (CDCl$_3$) δ: 3.33 (3H, s), 4.20 (2H, s), 4.24 (2H, s), 6.48 (1H, d, J=9.1 Hz), 7.21-7.35 (10H, m), 7.65 (1H, dd, J=9.0, 2.4 Hz), 7.88 (1H, d, J=9.1 Hz), 8.13 (1H, d, J=2.4 Hz), 8.69 (1H, d, J=9.0 Hz), 11.9 (1H, s).

(ii) Methyl 2-(2-(2-benzhydrylamino)-2-oxoethoxy)acetamido-5-(pyridin-4-yl)benzoate 1.02 g (2.0 mmol) of methyl 2-(2-(2-benzhydrylamino)-2-oxoethoxy)acetamido-5-bromobenzoate, 0.62 g (3.0 mmol) of 4-(4,4,5,5-tetramethyl-1,3,2-dioxaborolan-2-yl)pyridine, 0.23 g (0.2 mmol) of tetrakis(triphenylphosphine)palladium (0), 0.98 g (3.0 mmol) of cesium carbonate were heated in 20 ml of THF under reflux for 15 hours. After completion of the reaction, THF was distilled off under reduced pressure. After ethyl acetate was added and the solid was separated by filtration, the organic layer was washed with a saturated sodium chloride solution, and dried over anhydrous sodium sulfate. The solvent was then distilled off under reduced pressure. The obtained crude product was separated and purified by silica gel column chromatography to give 0.64 g of methyl 2-(2-(2-benzhydrylamino)-2-oxoethoxy)acetamido-5-(pyridin-4-yl)benzoate (yield: 63%).

$^1$H-NMR (CDCl$_3$) δ: 3.38 (3H, s), 4.24 (2H, s), 4.27 (2H, s), 6.50 (1H, d, J=9.1 Hz), 7.23-7.52 (12H, m), 7.83-7.94 (2H, m), 8.32 (1H, d, J=2.4 Hz), 8.66-8.69 (2H, m), 8.92 (1H, d, J=8.6 Hz), 12.0 (1H, s).

(iii) 2-(2-(2-Benzhydrylamino)-2-oxoethoxy)acetamido-5-(pyridin-4-yl)benzoic acid 0.63 g (1.24 mmol) of methyl 2-(2-(2-benzhydrylamino)-2-oxoethoxy)acetamido-5-(pyridin-4-yl)benzoate was dissolved in 12 ml of THF. Subsequently, a 1N aqueous sodium hydroxide solution was added, and the mixture was stirred at 60° C. for 1 hour. After cooling, THF was distilled off under reduced pressure. Water was added to the residue and the mixture was neutralized with 1N hydrochloric acid. The obtained residue was washed with IPE to give the titled 2-(2-(2-benzhydrylamino)-2-oxoethoxy)acetamido-5-(pyridin-4-yl)benzoic acid (yield: 68%).

$^1$H-NMR (DMSO-d$_6$) δ: 4.26 (4H, s), 6.20 (1H, d, J=8.7 Hz), 7.23-7.35 (10H, m), 7.74 (2H, d, J=5.6 Hz), 8.09 (1H, dd, J=8.5, 2.4 Hz), 8.40 (1H, d, J=2.4 Hz), 8.64 (2H, d, J=5.6 Hz), 8.76-8.80 (2H, m), 12.1 (1H, s).

Example 53

Preparation of 2-(2-(2-(4-benzhydrylpiperazin-1-yl)-2-oxoethoxy)acetamido)-5-(pyridin-3-yl)benzoic acid The titled compound was prepared according to Steps (i) and (ii) described below.

(i) Methyl 2-(2-(2-(4-benzhydrylpiperazin-1-yl)-2-oxoethoxy)acetamido)-5-(pyridin-3-yl)benzoate Using the same method as in Example 52-(ii), methyl 2-(2-(2-(4-benzhydrylpiperazin-1-yl)-2-oxoethoxy)acetamido)-5-bromobenzoate obtained in Example 44-(ii) was reacted with 3-pyridineboronic acid act (using an aqueous sodium carbonate solution as a base and toluene/methanol as a solvent) to give methyl 2-(2-(2-(4-benzhydrylpiperazin-1-yl)-2-oxoethoxy)acetamido)-5-(pyridin-3-yl)benzoate (yield: 80%).

$^1$H-NMR (CDCl$_3$) δ: 2.38-2.43 (4H, m), 3.53-3.67 (4H, m), 3.85 (3H, s), 4.25 (1H, s), 4.29 (2H, s), 4.38 (2H, s), 7.15-7.42 (11H, m), 7.78 (1H, dd, J=8.6, 2.4 Hz), 7.86-7.91 (1H, m), 8.27 (1H, d, J=2.4 Hz), 8.61 (1H, dd, J=5.0, 1.7 Hz), 8.85-8.91 (2H, m), 11.8 (1H, s).

(ii) 2-(2-(2-(4-Benzhydrylpiperazin-1-yl)-2-oxoethoxy)acetamido)-5-(pyridin-3-yl)benzoic acid Using the same method as in Example 52-(iii), the titled 2-(2-(2-(4-benzhydrylpiperazin-1-yl)-2-oxoethoxy)acetamido)-5-(pyridin-3-yl)benzoic acid (yield: 66%) was obtained using methyl 2-(2-(2-(4-benzhydrylpiperazin-1-yl)-2-oxoethoxy)acetamido)-5-(pyridin-3-yl)benzoic acid.

$^1$H-NMR (DMSO-d$_6$) δ: 2.28-2.40 (4H, m), 3.38-3.59 (4H, m), 4.17 (2H, s), 4.34 (1H, s), 4.38 (2H, s), 7.15-7.54 (11H, m), 8.00-8.13 (2H, m), 8.30 (1H, d, J=2.4 Hz), 8.59 (1H, d, J=4.9 Hz), 8.79 (1H, d, J=8.8 Hz), 8.92 (1H, d, J=2.4 Hz), 11.9 (1H, s).

Example 54

Preparation of 2-(2-(2-(4-benzhydrylpiperazin-1-yl)-2-oxoethoxy)acetamido)-5-(pyridin-4-yl)benzoic acid Using the same method as in Example 52-(iii), the titled 2-(2-(2-(4-benzhydrylpiperazin-1-yl)-2-oxoethoxy)acetamido)-5-(pyridin-4-yl)benzoic acid (yield: 68%) was obtained using methyl 2-(2-(2-(4-benzhydrylpiperazin-1-yl)-2-oxoethoxy)acetamido)-5-(pyridin-4-yl)benzoate obtained in Example 50-(i).

$^1$H-NMR (DMSO-d$_6$) δ: 2.26-2.42 (4H, m), 3.25-3.60 (4H, m), 4.17 (2H, s), 4.38 (1H, s), 4.38 (2H, s), 7.16-7.79 (12H, m), 8.11 (1H, dd, J=8.8, 2.2 Hz), 8.39 (1H, d, J=2.2 Hz), 8.65-8.83 (3H, m), 12.0 (1H, s).

Example 55

Preparation of 2-(2-(2-(4-benzhydrylpiperazin-1-yl)-2-oxoethoxy)acetamido)-5-(1-methyl-1H-pyrazol-4-yl)benzoic acid The titled compound was prepared according to Steps (i) and (ii) described below.

(i) Methyl 2-(2-(2-(4-benzhydrylpiperazin-1-yl)-2-oxoethoxy)acetamido)-5-(1-methyl-1H-pyrazole 4-yl)benzoate Using the same method as in Example 52-(ii), methyl 2-(2-(2-(4-benzhydrylpiperazin-1-yl)-2-oxoethoxy)acetamido)-5-bromobenzoate obtained in Example 44-(ii) was reacted with 1-methyl-4-(4,4,5,5-tetramethyl-1,3,2-dioxaborolan-2-yl)-1H-pyrazole to quantitatively obtain methyl 2-(2-(2-(4-benzhydrylpiperazin-1-yl)-2-oxoethoxy)acetamido)-5-(1-methyl-1H-pyrazol-4-yl)benzoate.

$^1$H-NMR (CDCl$_3$) δ: 2.37-2.55 (4H, m), 3.55-3.64 (4H, m), 3.82 (3H, s), 3.95 (3H, s), 4.22 (1H, s), 4.22 (2H, s), 4.35 (2H, s), 7.18-7.41 (10H, m), 7.64 (1H, dd, J=8.7, 2.4 Hz), 7.65 (1H, s), 7.76 (1H, s), 8.11 (1H, d, J=2.4 Hz), 8.75 (1H, d, J=8.7 Hz), 11.6 (1H, s).

(ii) 2-(2-(2-(4-Benzhydrylpiperazin-1-yl)-2-oxoethoxy)acetamido)-5-(1-methyl-1H-pyrazol-4-yl)benzoic acid Using the same method as in Example 52-(iii), the titled 2-(2-(2-(4-benzhydrylpiperazin-1-yl)-2-oxoethoxy)acetamido)-5-(1-methyl-1H-pyrazol-4-yl)benzoic acid (yield: 71%) was obtained using methyl 2-(2-(2-(4-benzhydrylpiperazin-1-yl)-2-oxoethoxy)acetamido)-5-(1-methyl-1H-pyrazol-4-yl)benzoate.

$^1$H-NMR (DMSO-d$_6$) δ: 2.20-2.38 (4H, m), 3.25-3.60 (4H, m), 3.86 (3H, s), 4.12 (2H, s), 4.31 (1H, s), 4.35 (2H, s), 7.15-7.43 (10H, m), 7.78-7.86 (2H, m), 8.12-8.18 (2H, m), 8.62 (1H, d, J=8.6 Hz), 11.8 (1H, s).

Example 56

Preparation of sodium 2-(2-(2-(4-benzhydrylpiperazin-1-yl)-2-oxoethoxy)acetamido)-5-benzylbenzoate The titled compound was prepared according to Steps (i) and (ii) described below.

(i) Methyl 2-(2-(2-(4-benzhydrylpiperazin-1-yl)-2-oxoethoxy)acetamido)-5-benzylbenzoate 1.16 g (2.0 mmol) of methyl 2-(2-(2-(4-benzhydrylpiperazin-1-yl)-2-oxoethoxy)acetamido)-5-bromobenzoate obtained in Example 44-(ii), 6.0 ml (3.0 mmol) of a THF solution of 0.5M benzylzinc bromide, and 0.23 g (0.2 mmol) of tetrakis(triphenylphosphine)palladium (0) were heated in 20 ml of THF under reflux for 2 hours. After completion of the reaction, THF was distilled off under reduced pressure. Ethyl acetate was added, and washed with an ammonium chloride aqueous solution and a saturated sodium chloride solution, and dried over anhydrous sodium sulfate. The solvent was then distilled off under reduced pressure. The obtained crude product was separated and purified by silica gel column chromatography to give 0.55 g of methyl 2-(2-(2-(4-benzhydrylpiperazin-1-yl)-2-oxoethoxy)acetamido)-5-benzylbenzoate (yield: 47%).
$^1$H-NMR (CDCl$_3$) δ: 2.34-2.52 (4H, m), 3.55-3.73 (4H, m), 3.76 (3H, s), 3.96 (2H, s), 4.20 (2H, s), 4.21 (1H, s), 4.33 (2H, s), 7.12-7.40 (16H, m), 7.86 (1H, d, J=2.2 Hz), 8.65 (1H, d, J=8.6 Hz), 11.6 (1H, s).

(ii) Sodium 2-(2-(2-(4-benzhydrylpiperazin-1-yl)-2-oxoethoxy)acetamido)-5-benzylbenzoate 0.55 g (0.93 mmol) of methyl 2-(2-(2-(4-benzhydrylpiperazin-1-yl)-2-oxoethoxy)acetamido)-5-benzylbenzoate was dissolved in 9 ml of THF. Subsequently, a 1N aqueous sodium hydroxide solution was added, and the mixture was stirred at 60° C. for 2 hour. After cooling, THF was distilled off under reduced pressure, the residue was washed with water. The obtained residue was washed with IPE to give the titled sodium 2-(2-(2-(4-benzhydrylpiperazin-1-yl)-2-oxoethoxy)acetamido)-5-benzylbenzoate (yield: 54%).
$^1$H-NMR (DMSO-d$_6$) δ: 2.18-2.36 (4H, m), 3.21-3.53 (4H, m), 3.90 (2H, s), 4.07 (2H, s), 4.26 (1H, s), 4.32 (2H, s), 7.14-7.41 (16H, m), 7.86 (1H, d, J=2.2 Hz), 8.49 (1H, d, J=8.3 Hz), 13.0 (1H, s).

Example 57

Preparation of sodium 4-(2-(2-(4-benzhydrylpiperazin-1-yl)-2-oxoethoxy)acetamido)biphenyl-3-carboxylate The titled compound was prepared according to Steps (i) to (iii) described below.

(i) 2-(2-(3-(Methoxycarbonyl)biphenyl-4-ylamino)-2-oxoethoxy)acetic acid 1.48 g (6.5 mmol) of methyl 4-aminobiphenyl-3-carboxylate (J. Med. Chem., 45, 4443 to 4459 (2002)) and 0.84 g (7.2 mmol) of diglycolic anhydride were heated in 16 ml of THF under reflux for 3 hours. After cooling, the reaction mixture was concentrated. The residue was collected by filtration, washed with IPE, and dried to give 1.99 g of 2-(2-(3-(methoxycarbonyl) biphenyl-4-ylamino)-2-oxoethoxy)acetic acid (yield: 89%).
$^1$H-NMR (DMSO-d$_6$) δ: 3.93 (3H, s), 4.23 (2H, s), 4.29 (2H, s), 7.35-7.71 (5H, m), 7.98 (1H, dd, J=8.8, 2.4 Hz), 8.24 (1H, d, J=2.4 Hz), 8.71 (1H, d, J=8.8 Hz), 11.5 (1H, s), 12.9 (1H, bs).

(ii) Methyl 4-(2-(2-(4-benzhydrylpiperazin-1-yl)-2-oxoethoxy)acetamido)biphenyl-3-carboxylate 0.93 g (2.7 mmol) of 2-(2-(3-(methoxycarbonyl)biphenyl-4-ylamino)-2-oxoethoxy)acetic acid, 16 mg (0.22 mmol) of DMF, and 0.28 ml (3.24 mmol) of oxalyl chloride were stirred in 9 ml THF at 0° C. for 30 minutes. After completion of the reaction, the solvent was distilled off under reduced pressure and dried. 0.76 g (3.0 mmol) of 1-benzhydrylpiperazine was added to this residue and stirred in 9 ml of DMA at room temperature overnight. After completion of the reaction, an aqueous sodium hydrogen carbonate solution was added, and the mixture was extracted with ethyl acetate, the extract was washed with a saturated sodium chloride solution. After the obtained organic layer was dried over anhydrous sodium sulfate, the solvent was then distilled off under reduced pressure. The obtained crude product was separated and purified by silica gel column chromatography to give 0.95 g of methyl 4-(2-(2-(4-benzhydrylpiperazin-1-yl)-2-oxoethoxy)acetamido)biphenyl-3-carboxylate (yield: 61%).
$^1$H-NMR (CDCl$_3$) δ: 2.38-2.44 (4H, m), 3.54-3.64 (4H, m), 3.83 (3H, s), 4.22 (1H, s), 4.24 (2H, s), 4.37 (2H, s), 7.14-7.62 (15H, m), 7.79 (1H, dd, J=8.7, 2.2 Hz), 8.27 (1H, d, J=2.2 Hz), 8.83 (1H, d, J=8.7 Hz), 11.7 (1H, s).

(iii) Sodium 4-(2-(2-(4-benzhydrylpiperazin-1-yl)-2-oxoethoxy)acetamido)biphenyl-3-carboxylate 0.94 g (1.60 mmol) of methyl 4-(2-(2-(4-benzhydrylpiperazin-1-yl)-2-oxoethoxy)acetamido)biphenyl-3-carboxylate was dissolved in 16 ml of THF. Subsequently, a 1N aqueous sodium hydroxide solution was added, and the mixture was stirred at 60° C. for 1 hour. After cooling, THF was distilled off under reduced pressure, and water was added to wash the residue. The obtained residue was washed with IPE to give the titled sodium 4-(2-(2-(4-benzhydrylpiperazin-1-yl)-2-oxoethoxy)acetamido)biphenyl-3-carboxylate (yield: 88%).
$^1$H-NMR (DMSO-d$_6$) δ: 2.23-2.40 (4H, m), 3.30-3.58 (4H, m), 4.14 (2H, s), 4.28 (1H, s), 4.36 (2H, s), 7.13-7.66 (15H, m), 7.85 (1H, dd, J=8.5, 2.2 Hz), 8.30 (1H, d, J=2.2 Hz), 8.72 (1H, d, J=8.5 Hz), 12.6 (1H, s).

Example 58

Preparation of 4-(2-(2-(4-chlorophenylamino)-2-oxoethoxy)acetamido)biphenyl-3-carboxylic acid The titled compound was prepared according to Steps (i) and (ii) described below.

(i) Methyl 4-(2-(2-(4-chlorophenylamino)-2-oxoethoxy)acetamido)biphenyl-3-carboxylate Using the same method as in Example 57-(ii), 2-(2-(3-(methoxycarbonyl)biphenyl-4-ylamino)-2-oxoethoxy)acetic acid obtained in Example 57-(i) was reacted with 4-chloroaniline to give methyl 4-(2-(2-(4-chlorophenylamino)-2-oxoethoxy)acetamido)biphenyl-3-carboxylate (yield: 41%).

$^1$H-NMR (CDCl$_3$) δ: 3.83 (3H, s), 4.30 (4H, s), 7.26-7.70 (9H, m), 7.84 (1H, dd, J=8.7, 2.2 Hz), 8.32 (1H, d, J=2.2 Hz), 8.86 (1H, d, J=8.7 Hz), 8.92 (1H, s), 11.9 (1H, s).

(ii) 4-(2-(2-(4-chlorophenylamino)-2-oxoethoxy)acetamido)biphenyl-3-carboxylic acid After methyl 4-(2-(2-(4-chlorophenylamino)-2-oxoethoxy)acetamido)biphenyl-3-carboxylate was reacted under the same conditions as in Example 57-(iii), THF was distilled off under reduced pressure. Water was added to the residue, and the mixture was neutralized with 1N hydrochloric acid to give the titled 4-(2-(2-(4-chlorophenylamino)-2-oxoethoxy)acetamido)biphenyl-3-carboxylic acid (yield: 67%).

$^1$H-NMR (DMSO-d$_6$) δ: 4.30 (2H, s), 4.33 (2H, s), 7.30-7.55 (5H, m), 7.64-7.80 (4H, m), 7.96 (1H, dd, J=8.8, 2.4 Hz), 8.28 (1H, d, J=2.4 Hz), 8.76 (1H, d, J=8.8 Hz), 9.91 (1H, s), 12.0 (1H, s).

Example 59

Preparation of 2,2'-(oxybis((1-oxo-2,1-ethanediyl)imino))bis(5-phenylbenzene-1-carboxylic acid)

The titled compound was prepared according to Steps (i) and (ii) described below.

(i) Methyl 2,2'-(oxybis((1-oxo-2,1-ethanediyl)imino))bis(5-phenylbenzene-1-carboxylate)

1.50 g (6.6 mmol) of methyl 4-aminobiphenyl-3-carboxylate, and 0.36 ml (3.0 mmol) of diglycolyl chloride were stirred in 22 ml of DMA at room temperature overnight. After completion of the reaction, an aqueous sodium hydrogen carbonate solution was added, and the precipitated solid was filtered off. The obtained residue was washed with IPE to give 1.59 g of methyl 2,2'-(oxybis((1-oxo-2,1-ethanediyl)imino))bis(5-phenylbenzene-1-carboxylate) (yield: 96%).

$^1$H-NMR (CDCl$_3$) δ: 3.80 (6H, s), 4.40 (4H, s), 7.33-7.63 (10H, m), 7.82 (2H, dd, J=8.8, 2.2 Hz), 8.29 (2H, d, J=2.2 Hz), 8.85 (2H, d, J=8.8 Hz), 11.9 (2H, s).

(ii) 2,2'-(oxybis((1-oxo-2,1-ethanediyl)imino))bis(5-phenylbenzene-1-carboxylic acid)

0.99 g (1.8 mmol) of methyl 2,2'-(oxybis((1-oxo-2,1-ethanediyl)imino))bis(5-phenylbenzene-1-carboxylate) was dissolved in 18 ml of THF. Subsequently, a 1N aqueous sodium hydroxide solution was added, and the mixture was stirred at 60° C. for 3 hour. After cooling, THF was distilled off under reduced pressure. Water was added to wash the residue. The obtained residue was washed with IPE to give the titled 2,2'-(oxybis((1-oxo-2,1-ethanediyl)imino))bis(5-phenylbenzene-1-carboxylic acid) (yield: 86%).

$^1$H-NMR (DMSO-d$_6$) δ: 4.36 (4H, s), 7.30-7.73 (10H, m), 7.86 (2H, dd, J=8.8, 2.4 Hz), 8.25 (2H, d, J=2.4 Hz), 8.71 (2H, d, J=8.8 Hz), 12.6 (2H, s).

Example 60

Preparation of 5-chloro-2-(5-(3-(4-chlorophenyl)ureido)pentanamido)benzoic acid

The titled compound was prepared according to Steps (i) to (iv) described below.

(i) Methyl 2-(5-(tert-butoxycarbonylamino)pentanamido)-5-chlorobenzoate 0.45 g (2.4 mmol) of methyl 2-amino-5-chlorobenzoate was dissolved in 8 ml of acetonitrile. Subsequently, 0.57 ml (7.2 mmol) of N-methylimidazole and 0.55 g (2.9 mmol) of p-toluenesulfonic acid chloride were added, and the mixture was stirred at 0° C. for 30 minutes. Then, 0.52 g (2.4 mmol) of 5-(tert-butoxycarbonylamino)pentanoic acid was added, and the mixture was stirred at room temperature overnight. After completion of the reaction, an aqueous sodium hydrogen carbonate solution was added, and the mixture was extracted with ethyl acetate. The extract was washed with a saturated sodium chloride solution. After the obtained organic layer was dried over anhydrous sodium sulfate, the solvent was distilled off under reduced pressure. The obtained crude product was separated and purified by silica gel column chromatography to give 0.77 g of methyl 2-(5-(tert-butoxycarbonylamino)pentanamido)-5-chlorobenzoate (yield: 83%).

$^1$H-NMR (CDCl$_3$) δ: 1.44 (9H, s), 1.53-1.85 (4H, m), 2.47 (2H, t, J=5.5 Hz), 3.17 (2H, q, J=6.4 Hz), 3.94 (3H, s), 4.63 (1H, bs), 7.48 (1H, dd, J=9.1, 2.5 Hz), 7.99 (1H, d, J=2.5 Hz), 8.71 (1H, d, J=9.1 Hz), 11.0 (1H, s).

(ii) Methyl 2-(5-aminopentanamido)-5-chlorobenzoate trifluoroacetic acid Salt 3.11 g (8.1 mmol) of methyl 2-(5-(tert-butoxycarbonylamino)pentanamido)-5-chlorobenzoate and 8 ml of trifluoroacetic acid were stirred in 41 ml of methylene chloride at room temperature for 1 hour. After completion of the reaction, the solvent was distilled off under reduced pressure. Ethyl acetate was added, and washed with an aqueous sodium hydrogen carbonate solution and a saturated sodium chloride solution. After the obtained organic layer was dried over anhydrous sodium sulfate, the solvent was distilled off under reduced pressure to give 2.61 g of methyl 2-(5-aminopentanamido)-5-chlorobenzoate trifluoroacetic acid salt (yield: 81%).

$^1$H-NMR (CDCl$_3$) δ: 1.72-1.75 (4H, m), 2.37-2.49 (2H, m), 2.89-2.96 (2H, m), 3.91 (3H, s), 6.38 (2H, bs), 7.43 (1H, dd, J=9.0, 2.4 Hz), 7.93 (1H, d, J=2.4 Hz), 8.57 (1H, d, J=9.0 Hz), 11.0 (1H, s).

(iii) Methyl 5-chloro-2-(5-(3-(4-chlorophenyl)ureido)pentanamido)benzoate 0.88 g (2.2 mmol) of methyl 2-(5-aminopentanamido)-5-chlorobenzoate trifluoroacetic acid salt, 0.37 g (2.4 mmol) of 4-chlorophenyl isocyanate, and 0.46 ml (3.3 mmol) of triethylamine were stirred in 7 ml of methylene chloride at room temperature for 2 hours. After completion of the reaction, the solvent was distilled off under reduced pressure. Ethyl acetate was added, and the mixture was washed with a saturated sodium chloride solution. After the obtained organic layer was dried over anhydrous sodium sulfate, the solvent was distilled off under reduced pressure to give 0.76 g of methyl 5-chloro-2-(5-(3-(4-chlorophenyl)ureido)pentanamido)benzoate (yield: 79%).

$^1$H-NMR (DMSO-d$_6$) δ: 1.44-1.67 (4H, m), 2.41 (2H, t, J=7.1 Hz), 3.10 (2H, q, J=5.9 Hz), 3.84 (3H, s), 6.24 (1H, t, J=5.9 Hz), 7.22-7.46 (4H, m), 7.66 (1H, dd, J=9.0, 2.6 Hz), 7.84 (1H, d, J=2.6 Hz), 8.20 (1H, d, J=9.0 Hz), 8.62 (1H, s), 10.5 (1H, s).

(iv) 5-Chloro-2-(5-(3-(4-chlorophenyl) ureido)pentanamido)benzoic acid 0.44 g (1.0 mmol) of methyl 5-chloro-2-(5-(3-(4-chlorophenyl)ureido)pentanamido)benzoate was dissolved in 10 ml of THF. Subsequently, a 1N aqueous sodium hydroxide solution was added and the mixture was stirred at 60° C. for 1 hour. After cooling, THF was distilled off under reduced pressure. Water was added to the residue, and the mixture was neutralized with 1N hydrochloric acid. The obtained residue was washed with IPE to give the titled 5-chloro-2-(5-(3-(4-chlorophenyl)ureido)pentanamido)benzoic acid (yield: 75%).
$^1$H-NMR (DMSO-d$_6$) δ: 1.45-1.69 (4H, m), 2.40-2.52 (2H, m), 3.06-3.16 (2H, m), 6.22 (1H, t, J=5.6 Hz), 7.22-7.45 (4H, m), 7.65 (1H, dd, J=9.0, 2.7 Hz), 7.91 (1H, d, J=2.7 Hz), 8.50 (1H, d, J=9.0 Hz), 8.59 (1H, s), 11.0 (1H, s).

Example 61

Preparation of 5-chloro-2-(5-(4-chlorophenylsulfonamido)pentanamido)benzoic acid The titled compound was prepared according to Steps (i) and (ii) described below.

(i) Methyl 5-chloro-2-(5-(4-chlorophenylsulfonamido)pentanamido)benzoate

Using the same method as in Example 60-(iii), methyl 2-(5-aminopentanamido)-5-chlorobenzoate trifluoroacetic acid salt obtained in Example 60-(ii) was reacted with p-chlorobenzenesulfonic acid chloride to give methyl 5-chloro-2-(5-(4-chlorophenylsulfonamido)pentanamido)benzoate (yield: 90%).
$^1$H-NMR (CDCl$_3$) δ: 1.54-1.78 (4H, m), 2.42 (2H, t, J=6.9 Hz), 2.99 (2H, q, J=6.2 Hz), 3.95 (3H, s), 4.96 (1H, t, J=6.2 Hz), 7.42-7.52 (3H, m), 7.76-7.83 (2H, m), 7.99 (1H, d, J=2.6 Hz), 8.65 (1H, d, J=9.2 Hz), 11.0 (1H, s).

(ii) 5-Chloro-2-(5-(4-chlorophenylsulfonamido)pentanamido)benzoic acid

Using the same method as in Example 60-(iv), the titled 5-chloro-2-(5-(4-chlorophenylsulfonamido)pentanamido) benzoic acid (yield: 31%) was obtained using methyl 5-chloro-2-(5-(4-chlorophenyl sulfonamido)pentanamido) benzoate.
$^1$H-NMR (DMSO-d$_6$) δ: 1.38-1.62 (4H, m), 2.31-2.38 (2H, m), 2.73-2.82 (2H, m), 7.62-7.82 (6H, m), 7.91 (1H, d, J=2.7 Hz), 8.48 (1H, d, J=9.0 Hz), 11.0 (1H, s).

Example 62

Preparation of sodium 2-(2-(2-(4-benzhydrylpiperazin-1-yl)-2-oxoethoxy)acetamido)-5-isobutylbenzoate The titled compound was prepared according to Steps (i) and (ii) described below.

(i) Methyl 2-(2-(2-(4-benzhydrylpiperazin-1-yl)-2-oxoethoxy)acetamido)-5-isobutylbenzoate 1.16 g (2.0 mmol) of methyl 2-(2-(2-(4-benzhydrylpiperazin-1-yl)-2-oxoethoxy)acetamido)-5-bromobenzoate obtained in Example 44-(ii), 16 ml (8.0 mmol) of a THF solution of 0.5M isobutylzinc bromide, 0.23 g (0.2 mmol) of tetrakis(triphenylphosphine)palladium (0) were heated in 10 ml of THF under reflux for 2 hours. After completion of the reaction, THF was distilled off under reduced pressure, and ethyl acetate was added. After the mixture was washed with an ammonium chloride aqueous solution and a saturated sodium chloride solution and dried over anhydrous sodium sulfate, the solvent was distilled off under reduced pressure. The obtained crude product was separated and purified by silica gel column chromatography to give 0.32 g of methyl 2-(2-(2-(4-benzhydrylpiperazin-1-yl)-2-oxoethoxy)acetamido)-5-isobutylbenzoate (yield: 25.0%).
$^1$H-NMR (CDCl$_3$) δ: 0.89 (3H, s), 0.92 (3H, s), 1.74-1.98 (1H, m), 2.34-2.41 (4H, m), 2.46 (2H, d, J=7.1 Hz), 3.53-3.67 (4H, m), 3.78 (3H, s), 4.21 (2H, s), 4.22 (1H, s), 4.35 (2H, s), 7.14-7.23 (11H, m), 7.79 (1H, d, J=2.2 Hz), 8.64 (1H, d, J=8.6 Hz), 11.6 (1H, s).

(ii) Sodium 2-(2-(2-(4-benzhydrylpiperazin-1-yl)-2-oxoethoxy)acetamido)-5-isobutylbenzoate 0.32 g (0.54 mmol) of methyl 2-(2-(2-(4-benzhydrylpiperazin-1-yl)-2-oxoethoxy)acetamido)-5-isobutylbenzoate was dissolved in 9.3 ml of THF. Subsequently, a 1N aqueous sodium hydroxide solution was added and the mixture was stirred at 50° C. for 2 hours. After cooling, THF was distilled off under reduced pressure. The residue was washed with water. The obtained residue was washed with IPE to give the titled sodium 2-(2-(2-(4-benzhydrylpiperazin-1-yl)-2-oxoethoxy)acetamido)-5-isobutylbenzoate (yield: 80.0%).
$^1$H-NMR (DMSO-d$_6$) δ: 0.83 (3H, s), 0.86 (3H, s), 1.71-1.86 (1H, m), 2.18-2.38 (4H, m), 2.39 (2H, d, J=6.8 Hz), 3.21-3.63 (4H, m), 4.06 (2H, s), 4.27 (1H, s), 4.34 (2H, s), 7.16-7.42 (11H, m), 7.79 (1H, d, J=1.9 Hz), 8.45 (1H, d, J=8.5 Hz), 13.6 (1H, s).

Example 63

Preparation of sodium 2-(2-(2-(4-benzhydrylpiperazin-1-yl)-2-oxoethoxy)acetamido)-5-(1H-pyrazol-4-yl)benzoate The titled compound was prepared according to Steps (i) to (iii) described below.

(i) Tert-butyl 4-(4-(2-(2-(4-benzhydrylpiperazin-1-yl)-2-oxoethoxy)acetamido)-3-(methoxycarbonyl)phenyl)-1H-pyrazole-1-carboxylate 1.16 g (2.0 mmol) of methyl 2-(2-(2-(4-benzhydrylpiperazin-1-yl)-2-oxoethoxy)acetamido)-5-bromobenzoate obtained in Example 44-(ii), 0.88 g (3.0 mmol) of tert-butyl 4-(4,4,5,5-tetramethyl-1,3,2-dioxaborolan-2-yl)-1H-pyrazol-1-carboxylate, 0.23 g (0.2 mmol) of tetrakis(triphenylphosphine)palladium (0), and 0.98 g (3.0 mmol) of cesium carbonate were heated in 20 ml of THF under reflux for 23 hours. After completion of the reaction, THF was distilled off under reduced pressure. After ethyl acetate was added and the solid was separated by filtration, the organic layer was washed with a saturated sodium chloride solution, and dried over anhydrous sodium sulfate. The solvent was then distilled off under reduced pressure. The obtained crude product was separated and purified by silica gel column chromatography to give 0.79 g of tert-butyl 4-(4-(2-(2-(4-benzhydrylpiperazin-1-yl)-2-oxoethoxy)acetamido)-3-(methoxycarbonyl)phenyl)-1H-pyrazol-1-carboxylate (yield: 59.2%).

¹H-NMR (CDCl₃) δ: 1.69 (9H, s), 2.38-2.42 (4H, m), 3.55-3.64 (4H, m), 3.85 (3H, s), 4.10 (1H, s), 4.14 (2H, s), 4.36 (2H, s), 7.18-7.42 (10H, m), 7.71 (1H, dd, J=8.8, 2.2 Hz), 8.00 (1H, s), 8.17 (1H, d, J=2.2 Hz), 8.32 (1H, s), 8.80 (1H, d, J=8.8 Hz), 11.7 (1H, s).

(ii) Methyl 2-(2-(2-(4-benzhydrylpiperazin-1-yl)-2-oxoethoxy)acetamido)-5-(1H-pyrazol-4-yl)benzoate 1.10 g of tert-butyl 4-(4-(2-(2-(4-benzhydrylpiperazin-1-yl)-2-oxoethoxy)acetamido)-3-(methoxycarbonyl)phenyl)-1H-pyrazol-1-carboxylate and 1.3 ml of trifluoroacetic acid were stirred in 8.3 ml of methylene chloride for 3 hours. After completion of the reaction, methylene chloride was distilled off under reduced pressure. The residue was formed into a powder using ethyl acetate/n-hexane to give methyl 2-(2-(2-(4-benzhydrylpiperazin-1-yl)-2-oxoethoxy)acetamido)-5-(1H-pyrazol-4-yl)benzoate (yield: 84.5%).
¹H-NMR (CDCl₃) δ: 3.20-3.41 (4H, m), 3.87 (3H, s), 4.00-4.19 (4H, m), 4.22 (2H, s), 4.46 (2H, s), 4.90 (1H, s), 7.38-7.98 (14H, m), 8.67 (1H, d, J=8.8 Hz), 11.1 (1H, br), 11.5 (1H, s).

(iii) Sodium 2-(2-(2-(4-benzhydrylpiperazin-1-yl)-2-oxoethoxy)acetamido)-5-(1H-pyrazol-4-yl)benzoate 1.10 g (1.38 mmol) of methyl 2-(2-(2-(4-benzhydrylpiperazin-1-yl)-2-oxoethoxy)acetamido)-5-(1H-pyrazol-4-yl)benzoate was dissolved in 14 ml of THF. Subsequently, a 1N aqueous sodium hydroxide solution was added, and the mixture was stirred at 50° C. for 1 hour. After cooling, THF was distilled off under reduced pressure, and water was added to wash the residue. The obtained residue was washed with IPE to give the titled sodium 2-(2-(2-(4-benzhydrylpiperazin-1-yl)-2-oxoethoxy)acetamido)-5-(1H-pyrazol-4-yl)benzoate (yield: 39.0%).
¹H-NMR (DMSO-d₆) δ: 2.18-2.38 (4H, m), 3.21-3.58 (4H, m), 4.10 (2H, s), 4.27 (1H, s), 4.35 (2H, s), 7.13-7.45 (10H, m), 7.73 (1H, dd, J=8.8, 2.2 Hz), 8.04 (2H, s), 8.19 (1H, d, J=2.2 Hz), 8.59 (1H, d, J=8.8 Hz), 12.7 (1H, s).

Example 64

Preparation of 2-(2-(2-(4-benzhydrylpiperazin-1-yl)-2-oxoethoxy)acetamido)-5-(quinolin-3-yl)benzoic acid The titled compound was prepared according to Steps (i) and (ii) described below.

(i) Methyl 2-(2-(2-(4-benzhydrylpiperazin-1-yl)-2-oxoethoxy)acetamido)-5-(quinolin-3-yl)benzoate 4.81 g (8.29 mmol) of methyl 2-(2-(2-(4-benzhydrylpiperazin-1-yl)-2-oxoethoxy)acetamido)-5-bromobenzoate obtained in Example 44-(ii), 2.0 g (11.6 mmol) of 3-quinolineboronic acid, 0.29 g (0.25 mmol) of tetrakis(triphenylphosphine)palladium (0), and 11.6 ml (11.6 mmol) of a 2N aqueous sodium carbonate solution were heated in 7 ml of methanol and 28 ml of toluene for 7 hours. After completion of the reaction, the solvent was distilled off under reduced pressure. After ethyl acetate was added and the solid was separated by filtration, the organic layer was washed with a saturated sodium chloride solution, and dried over anhydrous sodium sulfate. The solvent was then distilled off under reduced pressure. The obtained crude product was separated and purified by silica gel column chromatography to give 4.59 g of methyl 2-(2-(2-(4-benzhydrylpiperazin-1-yl)-2-oxoethoxy)acetamido)-5-(quinolin-3-yl)benzoate (yield: 88.1%).
¹H-NMR (CDCl₃) δ: 2.37-2.45 (4H, m), 3.50-3.68 (4H, m), 3.88 (3H, s), 4.23 (1H, s), 4.27 (2H, s), 4.39 (2H, s), 7.18-7.43 (10H, m), 7.53-8.24 (5H, m), 8.31 (1H, d, J=2.0 Hz), 8.40 (1H, d, J=2.4 Hz), 8.95 (1H, d, J=8.8 Hz), 9.18 (1H, d, J=2.4 Hz), 11.8 (1H, s).

(ii) 2-(2-(2-(4-Benzhydrylpiperazin-1-yl)-2-oxoethoxy)acetamido)-5-(quinolin-3-yl)benzoic acid 2.0 g (3.18 mmol) of methyl 2-(2-(2-(4-benzhydrylpiperazin-1-yl)-2-oxoethoxy)acetamido)-5-(quinolin-3-yl)benzoate was dissolved in 20 ml of THF. Subsequently, a 1N aqueous sodium hydroxide solution was added, and the mixture was stirred at 50° C. for 1 hour. After cooling, THF was distilled off under reduced pressure, and the residue was neutralized with a 1N aqueous HCl solution, and washed with water. The obtained residue was washed with IPE to give the titled 2-(2-(2-(4-benzhydrylpiperazin-1-yl)-2-oxoethoxy)acetamido)-5-(quinolin-3-yl)benzoic acid (yield: 70.3%).
¹H-NMR (DMSO-d₆) δ: 2.19-2.38 (4H, m), 3.28-3.57 (4H, m), 4.19 (2H, s), 4.32 (1H, s), 4.40 (2H, s), 7.18-7.42 (10H, m), 7.60-8.21 (5H, m), 8.48 (1H, d, J=2.3 Hz), 8.70 (1H, d, J=2.2 Hz), 8.85 (1H, d, J=8.8 Hz), 9.28 (1H, d, J=2.2 Hz), 12.0 (1H, s).

Example 65

Preparation of 2-(2-(2-(4-benzhydrylpiperazin-1-yl)-2-oxoethoxy)acetamido)-5-(benzo[b]thiophen-2-yl)benzoic acid The titled compound was prepared according to Steps (i) and (ii) described below.

(i) Methyl 2-(2-(2-(4-benzhydrylpiperazin-1-yl)-2-oxoethoxy)acetamido)-5-(benzo[b]thiophen-2-yl)benzoate Using the same method as in Example 64 (i), methyl 2-(2-(2-(4-benzhydrylpiperazin-1-yl)-2-oxoethoxy)acetamido)-5-bromobenzoate obtained in Example 44-(ii) was reacted with (benzo[b]thiophen-2-yl)boronic acid to quantitatively obtain methyl 2-(2-(2-(4-benzhydrylpiperazin-1-yl)-2-oxoethoxy)acetamido)-5-(benzo[b]thiophen-2-yl)benzoate.
¹H-NMR (CDCl₃) δ: 2.37-2.42 (4H, m), 3.48-3.69 (4H, m), 3.85 (3H, s), 4.22 (1H, s), 4.24 (2H, s), 4.37 (2H, s), 7.18-7.41 (12H, m), 7.55 (1H, s), 7.75-7.83 (2H, m), 7.88 (1H, dd, J=8.8, 2.3 Hz), 8.35 (1H, d, J=2.3 Hz), 8.84 (1H, d, J=8.8 Hz), 11.8 (1H, s).

(ii) 2-(2-(2-(4-Benzhydrylpiperazin-1-yl)-2-oxoethoxy)acetamido)-5-(benzo[b]thiophen-2-yl)benzoic acid Using the same method as in Example 64 (ii), the titled 2-(2-(2-(4-benzhydrylpiperazin-1-yl)-2-oxoethoxy)acetamido)-5-(benzo[b]thiophen-2-yl)benzoic acid (yield: 80.3%) was obtained using methyl 2-(2-(2-(4-benzhydrylpiperazin-1-yl)-2-oxoethoxy)acetamido)-5-(benzo[b]thiophen-2-yl)benzoic acid.
¹H-NMR (DMSO-d₆) δ: 2.21-2.39 (4H, m), 3.37-3.54 (4H, m), 4.17 (2H, s), 4.31 (1H, s), 4.37 (2H, s), 7.15-7.43 (12H, m), 7.80-8.19 (3H, m), 7.90 (1H, s), 8.34 (1H, d, J=2.5 Hz), 8.77 (1H, d, J=8.8 Hz), 12.0 (1H, s).

Example 66

Preparation of 4-(2-(2-(benzhydrylamino)-2-oxoethoxy)acetamido)-4'-fluorobiphenyl-3-carboxylic acid The titled compound was prepared according to Steps (i) and (ii) described below.

(i) Methyl 4-(2-(2-(benzhydrylamino)-2-oxoethoxy)acetamido)-4'-fluorobiphenyl-3-carboxylate 1.02 g (2.0 mmol) of methyl 2-(2-(2-benzhydrylamino)-2-oxoethoxy)acetamido-5-bromobenzoate obtained in Example 52-(i), 0.67 g (3.0 mmol) of 4-(4,4,5,5-tetramethyl-1,3,2-dioxaborolan-2-yl)fluorobenzene, 0.23 g (0.2 mmol) of tetrakis(triphenylphosphine) palladium (0), and 0.98 g (3.0 mmol) of cesium carbonate were heated in 20 ml of THF under reflux for 18 hours. After completion of the reaction, THF was distilled off under reduced pressure. After ethyl acetate was added and the solid was separated by filtration, the organic layer was washed with a saturated sodium chloride solution, and dried over anhydrous sodium sulfate. The solvent was then distilled off under reduced pressure. The obtained crude product was separated and purified by silica gel column chromatography to give 0.79 g of methyl 4-(2-(2-(benzhydrylamino)-2-oxoethoxy)acetamido)-4'-fluorobiphenyl-3-carboxylic acid (yield: 75.0%).

$^1$H-NMR (CDCl$_3$) δ: 3.35 (3H, s), 4.24 (2H, s), 4.27 (2H, s), 6.50 (1H, d, J=9.0 Hz), 7.02-7.58 (14H, m), 7.76 (1H, dd, J=8.8, 2.4 Hz), 7.96 (1H, d, J=9.0 Hz), 8.19 (1H, d, J=2.4 Hz), 8.84 (1H, d, J=8.8 Hz), 12.0 (1H, s).

(ii) 4-(2-(2-(Benzhydrylamino)-2-oxoethoxy)acetamido)-4'-fluorobiphenyl-3-carboxylic acid 0.78 g (1.48 mmol) of methyl 4-(2-(2-(benzhydrylamino)-2-oxoethoxy)acetamido)-4'-fluorobiphenyl-3-carboxylate was dissolved in 15 ml of THF. Subsequently, a 1N aqueous sodium hydroxide solution was added and the mixture was stirred at 50° C. for 1 hour. After cooling, THF was distilled off under reduced pressure, and the residue was neutralized with 1N aqueous HCl solution, and washed with water. The obtained residue was washed with IPE to give the titled 4-(2-(2-(benzhydrylamino)-2-oxoethoxy)acetamido)-4'-fluorophenyl-3-carboxylic acid (yield: 97.6%).

$^1$H-NMR (DMSO-d$_6$) δ: 4.24 (2H, s), 4.26 (2H, s), 6.20 (1H, d, J=8.6 Hz), 7.19-7.40 (12H, m), 7.43-7.79 (2H, m), 7.93 (1H, dd, J=8.8, 2.2 Hz), 8.24 (1H, d, J=2.2 Hz), 8.76 (1H, d, J=8.8 Hz), 8.80 (1H, d, J=8.6 Hz), 12.0 (1H, s), 13.8 (1H, br).

Example 67

Preparation of 5-chloro-2-(2-(2-(2,6-diisopropylphenylamino)-2-oxoethoxy)acetamido)benzoic acid The titled compound was prepared according to Steps (i) and (ii) described below.

(i) Methyl 5-chloro-2-(2-(2-(2,6-diisopropylphenylamino)-2-oxoethoxy)acetamido)benzoate 1.5 g (5.0 mmol) of 2-(2-(4-chloro-2-(methoxycarbonyl)phenylamino)-2-oxoethoxy)acetic acid obtained in Example 29-(i), 0.94 ml (5.0 mmol) of 2,6-diisopropylaniline, 1.15 g (6.0 mmol) of 1-ethyl-3-(3-dimethylaminopropyl)carbodiimide hydrochloride, and 0.81 g (6.0 mmol) of 1-hydroxybenzotriazole were stirred in 11 ml of DMA for 2 hours. After completion of the reaction, the reaction solution was poured into an aqueous sodium hydrogen carbonate solution. The solid was separated by filtration and washed with city water to give 1.15 g of methyl 5-chloro-2-(2-(2-(2,6-diisopropylphenylamino)-2-oxoethoxy)acetamido)benzoate (yield: 50.0%).

$^1$H-NMR (CDCl$_3$) δ: 1.18 (6H, s), 1.21 (6H, s), 3.07-3.21 (2H, m), 3.35 (3H, s), 4.31 (2H, s), 4.36 (2H, s), 7.18-7.38 (3H, m), 7.54 (1H, dd, J=9.1, 2.6 Hz), 7.98 (1H, d, J=2.6 Hz), 8.73 (1H, s), 8.78 (1H, d, J=9.1 Hz), 12.0 (1H, s).

(ii) 5-Chloro-2-(2-(2-(2,6-diisopropylphenylamino)-2-oxoethoxy)acetamido)benzoic acid 1.15 g (2.49 mmol) of methyl 5-chloro-2-(2-(2-(2,6-diisopropylphenylamino)-2-oxoethoxy)acetamido)benzoate was dissolved in 12 ml of THF. Subsequently, a 1N aqueous sodium hydroxide solution was added, and the mixture was stirred at 50° C. for 1 hour. After cooling, THF was distilled off under reduced pressure, and the residue was neutralized with a 1N aqueous HCl solution, and washed with water. The obtained residue was washed with IPE to give the titled 5-chloro-2-(2-(2-(2,6-diisopropylphenylamino)-2-oxoethoxy)acetamido)benzoic acid (yield: 69.4%).

$^1$H-NMR (DMSO-d$_6$) δ: 1.11 (6H, s), 1.14 (6H, s), 2.99-3.18 (2H, m), 4.31 (2H, s), 4.35 (2H, s), 7.16-7.38 (3H, m), 7.69 (1H, dd, J=9.0, 2.4 Hz), 7.96 (1H, d, J=2.4 Hz), 8.66 (1H, d, J=9.0 Hz), 9.27 (1H, s), 11.9 (1H, s).

Example 68

Preparation of 5-chloro-2-(2-(2-(1-(naphthalen-1-yl)ethylamino)-2-oxoethoxy)acetamido)benzoic acid The titled compound was prepared according to Steps (i) and (ii) described below.

(i) Methyl 5-chloro-2-(2-(2-(1-(naphthalen-1-yl)ethylamino)-2-oxoethoxy)acetamido)benzoate Using the same method as in Example 67-(i), 2-(2-(4-chloro-2-(methoxycarbonyl)phenylamino)-2-oxoethoxy)acetic acid obtained in Example 29-(i) was reacted with 1-(1-naphthyl)ethylamine to give methyl 5-chloro-2-(2-(2-(1-(naphthalen-1-yl)ethylamino)-2-oxoethoxy)acetamido)benzoate (yield: 90.3%).

$^1$H-NMR (CDCl$_3$) δ: 1.76 (3H, d, J=6.9 Hz), 3.73 (3H, s), 4.11-4.19 (4H, m), 6.04-6.18 (1H, m), 7.39-7.63 (6H, m), 7.71-7.84 (2H, m), 7.99 (1H, d, J=2.6 Hz), 8.15 (1H, d, J=8.2 Hz), 8.73 (1H, d, J=9.0 Hz), 11.7 (1H, s).

(ii) 5-Chloro-2-(2-(2-(1-(naphthalen-1-yl)ethylamino)-2-oxoethoxy)acetamido)benzoic acid Using the same method as in Example 67-(ii), the titled 5-chloro-2-(2-(2-(1-(naphthalen-1-yl)ethylamino)-2-oxoethoxy)acetamido)benzoic acid (yield: 93.4%) was obtained using methyl 5-chloro-2-(2-(2-(1-(naphthalen-1-yl)ethylamino)-2-oxoethoxy)acetamido)benzoic acid.

$^1$H-NMR (DMSO-d$_6$) δ: 1.58 (3H, d, J=7.0 Hz), 4.15 (2H, s), 4.20 (2H, s), 5.78-5.86 (1H, m), 7.43-8.01 (8H, m), 8.15 (1H, d, J=7.3 Hz), 8.36 (1H, d, J=8.0 Hz), 8.65 (1H, d, J=9.0 Hz), 11.9 (1H, s).

Example 69

Preparation of 5-chloro-2-(2-(2-(5-isopropyl-2-methylphenylamino)-2-oxoethoxy)acetamido)benzoic acid The titled compound was prepared according to Steps (i) and (ii) described below.

(i) Methyl 5-chloro-2-(2-(2-(5-isopropyl-2-methylphenylamino)-2-oxoethoxy)acetamido)benzoate Using the same method as in Example 67-(i), 2-(2-(4-chloro-2-(methoxycarbonyl)phenylamino)-2-oxoethoxy) acetic acid obtained in Example 29-(i) was reacted with 2-methyl-5-isopropylaniline to give methyl 5-chloro-2-(2-(2-(5-isopropyl-2-methylphenylamino)-2-oxoethoxy)acetamido) benzoate (yield: 89.0%).

$^1$H-NMR (CDCl$_3$) δ: 1.23 (6H, d, J=7.0 Hz), 2.27 (3H, s), 2.76-2.94 (1H, m), 3.59 (3H, s), 4.26 (2H, s), 4.29 (2H, s), 7.02 (1H, dd, J=7.7, 1.6 Hz), 7.15 (1H, d, J=7.7 Hz), 7.48 (1H, d, J=1.6 Hz), 7.53 (1H, dd, J=9.2, 2.4 Hz), 8.00 (1H, d, J=2.4 Hz), 8.67 (1H, s), 8.77 (1H, d, J=9.2 Hz), 12.0 (1H, s).

(ii) 5-Chloro-2-(2-(2-(5-isopropyl-2-methylphenylamino)-2-oxoethoxy)acetamido)benzoic acid Using the same method as in Example 67-(ii), the titled 5-chloro-2-(2-(2-(5-isopropyl-2-methylphenylamino)-2-oxoethoxy)acetamido)benzoic acid (yield: 76.7%) was obtained using methyl 5-chloro-2-(2-(2-(5-isopropyl-2-methylphenylamino)-2-oxoethoxy)acetamido)benzoate.

$^1$H-NMR (DMSO-d$_6$) δ: 1.17 (6H, d, J=6.8 Hz), 2.17 (3H, s), 2.74-2.94 (1H, m), 4.31 (4H, s), 6.98 (1H, dd, J=7.8, 1.6 Hz), 7.13 (1H, d, J=7.8 Hz), 7.34 (1H, s), 7.68 (1H, dd, J=9.0, 2.5 Hz), 7.96 (1H, d, J=2.5 Hz), 8.67 (1H, d, J=9.0 Hz), 9.22 (1H, s), 12.0 (1H, s).

Example 70

Preparation of 5-chloro-2-(2-(2-oxo-2-(4-phenylbutylamino)ethoxy)acetamido)benzoic acid The titled compound was prepared according to Steps (i) and (ii) described below.

(i) Methyl 5-chloro-2-(2-(2-oxo-2-(4-phenylbutylamino)ethoxy)acetamido)benzoate

Using the same method as in Example 67-(i), 2-(2-(4-chloro-2-(methoxycarbonyl)phenylamino)-2-oxoethoxy) acetic acid obtained in Example 29-(i) was reacted with 4-phenylbutylamine to give methyl 5-chloro-2-(2-(2-oxo-2-(4-phenylbutylamino)ethoxy)acetamido)benzoate (yield: 94.8%).

$^1$H-NMR (CDCl$_3$) δ: 1.64-1.73 (4H, m), 2.61-2.68 (2H, m), 3.37-3.49 (2H, m), 3.80 (3H, s), 4.12 (2H, s), 4.16 (2H, s), 7.12-7.30 (6H, m), 7.52 (1H, dd, J=9.1, 2.5 Hz), 8.02 (1H, d, J=2.5 Hz), 8.75 (1H, d, J=9.1 Hz), 11.8 (1H, s).

(ii) 5-chloro-2-(2-(2-oxo-2-(4-phenyl butylamino)ethoxy)acetamido)benzoic acid

Using the same method as in Example 67-(ii), the titled 5-chloro-2-(2-(2-oxo-2-(4-phenylbutylamino)ethoxy)acetamido)benzoic acid (yield: 94.3%) was obtained using methyl 5-chloro-2-(2-(2-oxo-2-(4-phenylbutylamino)ethoxy)acetamido)benzoic acid.

$^1$H-NMR (DMSO-d$_6$) δ: 1.47-1.59 (4H, m), 2.55-2.61 (2H, m), 3.13-3.22 (2H, m), 4.07 (2H, s), 4.18 (2H, s), 7.11-7.29 (5H, m), 7.70 (1H, dd, J=8.8, 2.7 Hz), 7.87 (1H, t, J=5.6 Hz), 7.97 (1H, d, J=2.7 Hz), 8.67 (1H, d, J=8.8 Hz), 11.9 (1H, s).

Example 71

Preparation of 2-(2-(2-(bis(4-fluorophenyl)methyl) amino-2-oxoethoxy)acetamido)-5-chlorobenzoic acid The titled compound was prepared according to Steps (i) and (ii) described below.

(i) Methyl 2-(2-(2-(bis(4-fluorophenyl)methyl) amino-2-oxoethoxy)acetamido)-5-chlorobenzoate Using the same method as in Example 67-(i), 2-(2-(4-chloro-2-(methoxycarbonyl)phenylamino)-2-oxoethoxy) acetic acid obtained in Example 29-(i) was reacted with bis (4-fluorophenyl)methanamine to give methyl 2-(2-(2-(bis(4-fluorophenyl)methyl)amino-2-oxoethoxy)acetamido)-5-chlorobenzoate (yield: 75.0%).

$^1$H-NMR (CDCl$_3$) δ: 3.39 (3H, s), 4.19 (2H, s), 4.21 (2H, s), 6.45 (1H, d, J=8.8 Hz), 6.94-7.38 (7H, m), 7.53 (1H, dd, J=8.9, 2.5 Hz), 7.84 (1H, d, J=8.8 Hz), 7.99 (1H, d, J=2.5 Hz), 8.75 (1H, d, J=8.9 Hz), 11.8 (1H, s).

(ii) 2-(2-(2-(bis(4-fluorophenyl)methyl)amino-2-oxoethoxy)acetamido)-5-chlorobenzoic acid Using the same method as in Example 67-(ii), the titled 2-(2-(2-(bis(4-fluorophenyl)methylamino)-2-oxoethoxy)acetamido)-5-chlorobenzoic acid (yield: 50.8%) was obtained using methyl 2-(2-(2-(bis(4-fluorophenyl)methyl)amino-2-oxoethoxy)acetamido)-5-chlorobenzoate.

$^1$H-NMR (DMSO-d$_6$) δ: 4.22 (2H, s), 4.23 (2H, s), 6.22 (1H, d, J=8.6 Hz), 7.14-7.41 (7H, m), 7.69 (1H, dd, J=9.0, 2.7 Hz), 7.97 (1H, d, J=2.7 Hz), 8.67 (1H, d, J=9.0 Hz), 8.79 (1H, d, J=8.6 Hz), 11.8 (1H, s).

Example 72

Preparation of 2-(2-(2-(bis(4-(trifluoromethyl)benzyl)amino)-2-oxoethoxy)acetamido)-5-chlorobenzoic acid The titled compound was prepared according to Steps (i) and (ii) described below.

(i) Methyl 2-(2-(2-(bis(4-(trifluoromethyl)benzyl) amino)-2-oxoethoxy)acetamido)-5-chlorobenzoate Using the same method as in Example 67-(i), 2-(2-(4-chloro-2-(methoxycarbonyl)phenylamino)-2-oxoethoxy) acetic acid obtained in Example 29-(i) was reacted with bis (4-(trifluoromethyl)benzyl)amine to give methyl 2-(2-(2-(bis (4-(trifluoromethyl)benzyl)amino)-2-oxoethoxy) acetamido)-5-chlorobenzoate (yield: 44.1%).

$^1$H-NMR (CDCl$_3$): 3.86 (3H, s), 4.29 (2H, s), 4.48 (2H, s), 4.59 (2H, s), 4.67 (2H, s), 7.26-7.37 (4H, m), 7.50 (1H, dd, J=9.1, 2.6 Hz), 7.54-7.63 (4H, m), 8.00 (1H, d, J=2.6 Hz), 8.72 (1H, d, J=9.1 Hz), 11.7 (1H, s).

(ii) 2-(2-(2-(Bis(4-(trifluoromethyl)benzyl)amino)-2-oxoethoxy)acetamido)-5-chlorobenzoic acid Using the same method as in Example 67-(ii), the titled 2-(2-(2-(bis(4-(trifluoromethyl)benzyl)amino)-2-oxoethoxy)acetamido)-5-chlorobenzoic acid (yield: 59.0%) was obtained using methyl 2-(2-(2-(bis(4-(trifluoromethyl)benzyl)amino)-2-oxoethoxy)acetamido)-5-chlorobenzoate.

$^1$H-NMR (DMSO-d$_6$) δ: 4.20 (2H, s), 4.53 (2H, s), 4.59 (2H, s), 4.63 (2H, s), 7.42-7.67 (9H, m), 7.94 (1H, d, J=2.6 Hz), 8.63 (1H, d, J=9.0 Hz), 12.3 (1H, s).

Example 73

Preparation of sodium 2-(2-(2-(bis(4-fluorobenzyl)amino)-2-oxoethoxy)acetamido)-5-chlorobenzoate The titled compound was prepared according to Steps (i) and (ii) described below.

(i) Methyl 2-(2-(2-(bis(4-fluorobenzyl)amino)-2-oxoethoxy)acetamido)-5-chlorobenzoate Using the same method as in Example 67-(i), 2-(2-(4-chloro-2-(methoxycarbonyl)phenylamino)-2-oxoethoxy)acetic acid obtained in Example 29-(i) was reacted with N,N-bis(4-fluorobenzyl)amine to give methyl 2-(2-(2-(bis(4-fluorobenzyl)amino)-2-oxoethoxy)acetamido)-5-chlorobenzoate (yield: 25.9%).

$^1$H-NMR (CDCl$_3$): 3.88 (3H, s), 4.29 (2H, s), 4.43 (2H, s), 4.46 (2H, s), 4.56 (2H, s), 6.95-7.19 (8H, m), 7.50 (1H, dd, J=9.2, 2.6 Hz), 8.01 (1H, d, J=2.6 Hz), 8.74 (1H, d, J=9.2 Hz), 11.7 (1H, s).

(ii) Sodium 2-(2-(2-(bis(4-fluorobenzyl)amino)-2-oxoethoxy)acetamido)-5-chlorobenzoate 0.62 g (1.2 mmol) of methyl 2-(2-(2-(bis(4-fluorobenzyl)amino)-2-oxoethoxy)acetamido)-5-chlorobenzoate was dissolved in 6.2 ml of THF. Subsequently, a 1N aqueous sodium hydroxide solution was added and the mixture was stirred at 50 for 1 hour. After cooling, THF was distilled off under reduced pressure, and water was added to wash the residue. The obtained residue was washed with IPE to give the titled sodium 2-(2-(2-(bis(4-fluorobenzyl)amino)-2-oxoethoxy)acetamido)-5-chlorobenzoate (yield: 85.7%).

$^1$H-NMR (DMSO-d$_6$) δ: 4.14 (2H, s), 4.45 (2H, s), 4.45 (4H, s), 7.10-7.36 (9H, m), 7.94 (1H, d, J=2.7 Hz), 8.52 (1H, d, J=8.8 Hz), 14.5 (1H, s).

Example 74

Preparation of 2-(2-(2-(3,5-bis(trifluoromethyl)phenylamino)-2-oxoethoxy)acetamido)-5-chlorobenzoic acid The titled compound was prepared according to Steps (i) and (ii) described below.

(i) Methyl 2-(2-(2-(3,5-bis(trifluoromethyl)phenylamino)-2-oxoethoxy)acetamido)-5-chlorobenzoate 1.21 g (4.0 mmol) of 2-(2-(4-chloro-2-(methoxycarbonyl)phenylamino)-2-oxoethoxy)acetic acid obtained in Example 29-(i), 32 mg (0.44 mmol) of DMF, and 0.41 ml (4.8 mmol) of oxalyl chloride were stirred in 12 ml of THF at 0 for 30 minutes. After completion of the reaction, the solvent was distilled off under reduced pressure and dried. 1.10 g (4.8 mmol) of 3,5-bis(trifluoromethyl)aniline and 1.67 ml (9.6 mmol) of N,N-diisopropylethylamine were added to this residue, and the mixture was stirred in 8.4 ml of THF at room temperature overnight. After completion of the reaction, an aqueous sodium hydrogen carbonate solution was added, and the mixture was extracted with ethyl acetate. The extract was washed with a saturated sodium chloride solution. After the obtained organic layer was dried over anhydrous sodium sulfate, the solvent was distilled off under reduced pressure. The obtained crude product was separated and purified by silica gel column chromatography to give 1.19 g of methyl 2-(2-(2-(3,5-bis(trifluoromethy)phenylamino)-2-oxoethoxy)acetamido)-5-chlorobenzoate (yield: 58.0%).

$^1$H-NMR (CDCl$_3$) δ: 3.85 (3H, s), 4.29 (2H, s), 4.33 (2H, s), 7.57 (1H, dd, J=9.1, 2.6 Hz), 7.68 (1H, s), 8.07 (2H, d, J=2.6 Hz), 8.27 (1H, s), 8.77 (1H, d, J=9.1 Hz), 9.11 (1H, s), 11.8 (1H, s).

(ii) 2-(2-(2-(3,5-bis(trifluoromethyl)phenylamino)-2-oxoethoxy)acetamido)-5-chlorobenzoic acid Using the same method as in Example 67-(ii), the titled 2-(2-(2-(3,5-bis(trifluoromethyl)phenylamino)-2-oxoethoxy)acetamido)-5-chlorobenzoic acid (yield: 67.0%) was obtained using methyl 2-(2-(2-(3,5-bis(trifluoromethyl)phenylamino)-2-oxoethoxy)acetamido)-5-chlorobenzoate.

$^1$H-NMR (CDCl$_3$) δ: 4.32 (2H, s), 4.39 (2H, s), 7.71 (1H, dd, J=9.1, 2.7 Hz), 7.81 (1H, s), 7.97 (1H, d, J=2.7 Hz), 8.39 (2H, s), 8.69 (1H, d, J=9.1 Hz), 10.5 (1H, s), 11.9 (1H, s), 13.9 (1H, br).

Example 75

Preparation of sodium 2-(2-(2-(4-benzhydrylpiperazin-1-yl)-2-oxoethoxy)acetamido)-4-chlorobenzoate The titled compound was prepared according to Steps (i) to (iii) described below.

(i) 2-(2-(5-chloro-2-(methoxycarbonyl)phenylamino)-2-oxoethoxy)acetic acid 5.0 g (26.9 mmol) of methyl 2-amino-4-chlorobenzoate and 3.44 g (29.6 mmol) of diglycolic anhydride were heated in 35 ml of THF under reflux for 5 hours. After cooling, the reaction mixture was concentrated, the residue was collected by filtration, washed with IPE, and dried to give 7.65 g of 2-(2-(5-chloro-2-(methoxycarbonyl)phenylamino)-2-oxoethoxy)acetic acid (yield: 94.2%).

$^1$H-NMR (DMSO-d$_6$) δ: 3.89 (3H, s), 4.23 (2H, s), 4.28 (2H, s), 7.29 (1H, dd, J=8.6, 2.0 Hz), 8.00 (1H, d, J=8.6 Hz), 8.71 (1H, d, J=2.0 Hz), 11.5 (1H, s), 12.9 (1H, br).

(ii) Methyl 2-(2-(2-(4-benzhydrylpiperazin-1-yl)-2-oxoethoxy)acetamido)-4-chlorobenzoate 0.91 g (3.0 mmol) of 2-(2-(5-chloro-2-(methoxycarbonyl)phenylamino)-2-oxoethoxy)acetic acid, 0.76 g (3.0 mmol) of 1-benzhydrylpiperazine, 0.69 g (3.6 mmol) of 1-ethyl-3-(3-dimethylaminopropyl)carbodiimide hydrochloride, and 0.49 g (3.6 mmol) of 1-hydroxybenzotriazole were stirred in 6.4 ml of DMA for 2 hours. After completion of the reaction, the reaction solution was poured into an aqueous sodium hydrogen carbonate solution. The solid was separated by filtration and washed with city water to give 1.55 of methyl 2-(2-(2-(4-benzhydrylpiperazin-1-yl)-2-oxoethoxy)acetamido)-4-chlorobenzoate (yield: 96.3%).

$^1$H-NMR (CDCl$_3$) δ: 2.39-2.48 (4H, m), 3.52-3.65 (4H, m), 3.80 (3H, s), 4.22 (2H, s), 4.22 (1H, s), 4.34 (2H, s), 7.08 (1H, dd, J=8.6, 2.0 Hz), 7.14-7.42 (10H, m), 7.95 (1H, d, J=8.6 Hz), 8.86 (1H, d, J=2.0 Hz), 11.8 (1H, s).

(iii) Sodium 2-(2-(2-(4-benzhydrylpiperazin-1-yl)-2-oxoethoxy)acetamido)-4-chlorobenzoate 1.53 g (2.85 mmol) of methyl 2-(2-(2-(4-benzhydrylpiperazin-1-yl)-2-oxoethoxy)acetamido)-4-chlorobenzoate was dissolved in 15.3 ml of THF. Subsequently, a 1N aqueous sodium hydroxide solution was added and the mixture was stirred at 50 for 1 hour. After cooling, THF was distilled off under reduced pressure, and the residue was washed with water. The obtained residue was washed with IPE to give the titled sodium 2-(2-(2-(4-benzhydrylpiperazin-1-yl)-2-oxoethoxy)acetamido)-4-chlorobenzoate (yield: 67.7%).

$^1$H-NMR (DMSO-d$_6$) δ: 2.28-2.38 (4H, m), 3.37-3.52 (4H, m), 4.08 (2H, s), 4.30 (2H, s), 4.30 (1H, s), 7.00 (1H, dd, J=8.3, 2.1 Hz), 7.18-7.44 (10H, m), 7.98 (1H, d, J=8.3 Hz), 8.59 (1H, d, J=2.1 Hz), 14.6 (1H, s).

Example 76

Preparation of sodium 2-(2-(2-(4-benzhydrylpiperazin-1-yl)-2-oxoethoxy)acetamido)-4-bromobenzoate The titled compound was prepared according to Steps (i) to (iii) described below.

(i) 2-(2-(5-bromo-2-(methoxycarbonyl)phenylamino)-2-oxoethoxy)acetic acid

Using the same method as in Example 29 (i), methyl 2-amino-4-bromobenzoate was reacted with diglycolic anhydride to give 2-(2-(5-bromo-2-(methoxycarbonyl)phenylamino)-2-oxoethoxy)acetic acid (yield: 88.9%).

$^1$H-NMR (DMSO-d$_6$) δ: 3.89 (3H, s), 4.22 (2H, s), 4.28 (2H, s), 7.42 (1H, dd, J=8.6, 2.2 Hz), 7.92 (1H, d, J=8.6 Hz), 8.86 (1H, d, J=2.2 Hz), 11.5 (1H, s), 12.9 (1H, br).

(ii) Methyl 2-(2-(2-(4-benzhydrylpiperazin-1-yl)-2-oxoethoxy)acetamido)-4-bromobenzoate Using the same method as in Example 67 (i), 2-(2-(5-bromo-2-(methoxycarbonyl)phenylamino)-2-oxoethoxy)acetic acid was reacted with 1-benzhydrylpiperazine to quantitatively obtain methyl 2-(2-(2-(4-benzhydrylpiperazin-1-yl)-2-oxoethoxy)acetamido)-4-bromobenzoate.

$^1$H-NMR (CDCl$_3$) δ: 2.37-2.45 (4H, m), 3.50-3.68 (4H, m), 3.80 (3H, s), 4.21 (2H, s), 4.34 (1H, s), 4.34 (2H, s), 7.14-7.41 (11H, m), 7.87 (1H, d, J=8.6 Hz), 9.02 (1H, d, J=2.0 Hz), 11.7 (1H, s).

(iii) Sodium 2-(2-(2-(4-benzhydrylpiperazin-1-yl)-2-oxoethoxy)acetamido)-4-bromobenzoate Using the same method as in Example 73-(ii), the titled sodium 2-(2-(2-(4-benzhydrylpiperazin-1-yl)-2-oxoethoxy)acetamido)-4-bromobenzoate (yield: 78.8%) was obtained using 2-(2-(2-(4-benzhydrylpiperazin-1-yl)-2-oxoethoxy)acetamido)-4-bromobenzoate.

$^1$H-NMR (DMSO-d$_6$) δ: 2.27-2.39 (4H, m), 3.30-3.51 (4H, m), 4.08 (2H, s), 4.30 (2H, s), 4.30 (1H, s), 7.13-7.44 (11H, m), 7.92 (1H, d, J=8.3 Hz), 8.74 (1H, d, J=2.2 Hz), 14.6 (1H, s).

Example 77

Preparation of 2-(2-(2-(4-benzhydrylpiperazin-1-yl)-2-oxoethoxy)acetamido)-4-(pyridin-4-yl)benzoic acid The titled compound was prepared according to Steps (i) and (ii) described below.

(i) Methyl 2-(2-(2-(4-benzhydrylpiperazin-1-yl)-2-oxoethoxy)acetamido)-4-(pyridin-4-yl)benzoate 1.16 g (2.0 mmol) of methyl 2-(2-(2-(4-benzhydrylpiperazin-1-yl)-2-oxoethoxy)acetamido)-4-bromobenzoate obtained in Example 76-(ii), 0.62 g (3.0 mmol) of 4-(4,4,5,5-tetramethyl-1,3,2-dioxaborolan-2-yl)pyridine, 0.23 g (0.2 mmol) of tetrakis(triphenylphosphine)palladium (0), and 0.98 g (3.0 mmol) of cesium carbonate were heated in 97 ml of THF under reflux for 8 hours. After completion of the reaction, THF was distilled off under reduced pressure. After ethyl acetate was added and the solid was separated by filtration, the organic layer was washed with a saturated sodium chloride solution, and dried over anhydrous sodium sulfate. The solvent was then distilled off under reduced pressure. The obtained crude product was separated and purified by silica gel column chromatography to quantitatively obtain methyl 2-(2-(2-(4-benzhydrylpiperazin-1-yl)-2-oxoethoxy)acetamido)-4-(pyridin-4-yl)benzoate.

$^1$H-NMR (CDCl$_3$) δ: 2.38-2.43 (4H, m), 3.41-3.65 (4H, m), 3.85 (3H, s), 4.23 (1H, s), 4.26 (2H, s), 4.38 (2H, s), 7.15-7.73 (13H, m), 8.13 (1H, d, J=8.2 Hz), 8.67-8.71 (2H, m), 9.14 (1H, d, J=1.9 Hz), 11.8 (1H, s).

(ii) 2-(2-(2-(4-benzhydrylpiperazin-1-yl)-2-oxoethoxy)acetamido)-4-(pyridin-4-yl)benzoic acid 1.16 g (2.0 mmol) of methyl 2-(2-(2-(4-benzhydrylpiperazin-1-yl)-2-oxoethoxy)acetamido)-4-(pyridin-4-yl)benzoate was dissolved in 11.6 ml of THF. Subsequently, a 1N aqueous sodium hydroxide solution was added and the mixture was stirred at 50° C. for 1 hours. After cooling, THF was distilled off under reduced pressure, and the residue was neutralized with a 1N aqueous HCl solution, and washed with water. The obtained residue was washed with IPE to give the titled 2-(2-(2-(4-benzhydrylpiperazin-1-yl)-2-oxoethoxy)acetamido)-4-(pyridin-4-yl)benzoic acid (yield: 67.0%).

$^1$H-NMR (DMSO-d$_6$) δ: 2.29-2.38 (4H, m), 3.38-3.57 (4H, m), 4.17 (2H, s), 4.31 (1H, s), 4.38 (2H, s), 7.14-7.43 (10H, m), 7.58 (1H, dd, J=8.3, 1.7 Hz), 7.68 (2H, d, J=6.1 Hz), 8.13 (1H, d, J=8.3 Hz), 8.70 (1H, d, J=6.1 Hz), 9.07 (1H, d, J=1.7 Hz), 12.1 (1H, s).

Example 78

Preparation of 3-(2-(2-(4-benzhydrylpiperazin-1-yl)-2-oxoethoxy)acetamido)-4'-fluorobiphenyl-4-carboxylic acid The titled compound was prepared according to Steps (i) and (ii) described below.

(i) Methyl 3-(2-(2-(4-benzhydrylpiperazin-1-yl)-2-oxoethoxy)acetamido)-4'-fluorobiphenyl-4-carboxylate Using the same method as in Example 77 (i), 2-(2-(2-(4-benzhydrylpiperazin-1-yl)-2-oxoethoxy)acetamido)-4-bromobenzoate was reacted with 4-(4,4,5,5-tetramethyl-1,3,2-dioxaborolan-2-yl)fluorobenzene to give methyl 3-(2-(2-(4-benzhydrylpiperazin-1-yl)-2-oxoethoxy)acetamido)-4'-fluorobiphenyl-4-carboxylate (yield: 76.5%).
$^1$H-NMR (CDCl$_3$) δ: 2.37-2.42 (4H, m), 3.53-3.67 (4H, m), 3.82 (3H, s), 4.22 (1H, s), 4.25 (2H, s), 4.37 (2H, s), 7.10-7.42 (13H, m), 7.61-7.68 (2H, m), 8.08 (1H, d, J=8.4 Hz), 9.03 (1H, d, J=1.9 Hz), 11.8 (1H, s).

(ii) 3-(2-(2-(4-Benzhydrylpiperazin-1-yl)-2-oxoethoxy)acetamido)-4'-fluorobiphenyl-4-carboxylic acid Using the same method as in Example 77 (ii), the titled 3-(2-(2-(4-benzhydrylpiperazin-1-yl)-2-oxoethoxy)acetamido)-4'-fluorobiphenyl-4-carboxylic acid (yield: 64.8%) was obtained using methyl 3-(2-(2-(4-benzhydrylpiperazin-1-yl)-2-oxoethoxy)acetamido)-4'-fluorobiphenyl-4-carboxylate.
$^1$H-NMR (DMSO-d$_6$) δ: 2.21-2.39 (4H, m), 3.38-3.61 (4H, m), 4.16 (2H, s), 4.31 (1H, s), 4.37 (2H, s), 7.15-7.50 (13H, m), 7.70-7.77 (2H, m), 8.08 (1H, d, J=8.3 Hz), 8.98 (1H, d, J=1.7 Hz), 11.9 (1H, s).

Example 79

Preparation of 2-(2-(benzhydrylamino)-2-oxoacetamido)-5-chlorobenzoic acid

The titled compound was prepared according to Steps (i) and (ii) described below.

(i) Methyl 2-(2-(benzhydrylamino)-2-oxoacetamido)-5-chlorobenzoate 0.73 g (3.91 mmol) of methyl 2-amino-5-chlorobenzoate, 1.0 g (3.91 mmol) of 2-(benzhydrylamino)-2-oxoacetic acid, 1.78 g (4.69 mmol) of O-(benzotriazol-1-yl)-N,N,N',N'-tetramethyluronium hexafluorophosphate, and 1.63 ml (9.38 mmol) of N,N-diisopropylethylamine were stirred in 5 ml of DMA overnight. After completion of the reaction, ethyl acetate was added. The mixture was washed with an aqueous sodium hydrogen carbonate solution and with city water, and dried over anhydrous sodium sulfate. IPE was added to the concentrated residue, and the mixture was formed into a powder to give 0.48 g of methyl 2-(2-(benzhydrylamino)-2-oxoacetamido)-5-chlorobenzoate (yield: 29.1%).
$^1$H-NMR (CDCl$_3$) δ: 3.97 (3H, s), 6.27 (1H, d, J=8.6 Hz), 7.16-7.52 (11H, m), 7.56 (1H, dd, J=8.9, 2.4 Hz), 8.05 (1H, d, J=2.4 Hz), 8.10 (1H, d, J=8.6 Hz), 8.67 (1H, d, J=8.9 Hz).

(ii) 2-(2-(Benzhydrylamino)-2-oxoacetamido)-5-chlorobenzoic acid 0.48 g (1.14 mmol) of methyl 2-(2-(benzhydrylamino)-2-oxoacetamido)-5-chlorobenzoate was dissolved in 4.8 ml of THF. Subsequently, a 1N aqueous sodium hydroxide solution was added, and the mixture was stirred at 50° C. for 1 hour. After cooling, THF was distilled off under reduced pressure, and the residue was neutralized with a 1N aqueous HCl solution, and washed with water. The obtained residue was washed with IPE to give the titled 2-(2-(benzhydrylamino)-2-oxoacetamido)-5-chlorobenzoic acid (yield: 66.0%).
$^1$H-NMR (DMSO-d$_6$) δ: 6.25 (1H, d, J=9.1 Hz), 7.26-7.42 (10H, m), 7.75 (1H, dd, J=9.1, 2.7 Hz), 7.98 (1H, d, J=2.7 Hz), 8.67 (1H, d, J=9.1 Hz), 9.85 (1H, d, J=9.1 Hz), 12.7 (1H, s).

Example 80

Preparation of 2-(5-(4-benzhydrylpiperazin-1-yl)-5-oxopentanamido)-5-chlorobenzoic acid The titled compound was prepared according to Steps (i) to (iii) described below.

(i) 5-(4-chloro-2-(methoxycarbonyl)phenylamino)-5-oxopentanoic acid 5.0 g (26.9 mmol) of 2-amino-4-chlorobenzoate methyl and 3.38 g (29.6 mmol) of glutaric anhydride were heated in 35 ml of THF under reflux for 8 hours. After cooling, the reaction mixture was concentrated, the residue was collected by filtration, and washed with IPE, and dried to give 4.88 g of 5-(4-chloro-2-(methoxycarbonyl)phenylamino)-5-oxopentanoic acid (yield: 60.5%).
$^1$H-NMR (DMSO-d$_6$) δ: 1.82 (2H, q, J=7.3 Hz), 2.30 (2H, t, J=7.3 Hz), 2.42 (2H, t, J=7.3 Hz), 3.85 (3H, s), 7.66 (1H, dd, J=9.0, 2.6 Hz), 7.83 (1H, d, J=2.6 Hz), 8.18 (1H, d, J=9.0 Hz), 10.5 (1H, s), 12.1 (1H, br).

(ii) Methyl 2-(5-(4-benzhydrylpiperazin-1-yl)-5-oxopentanamido)-5-chlorobenzoate 0.90 g (3.0 mmol) of 5-(4-chloro-2-(methoxycarbonyl)phenylamino)-5-oxopentanoic acid, 0.76 g (3.0 mmol) of 1-benzhydrylpiperazine, 0.69 g (3.6 mmol) of 1-ethyl-3-(3-dimethylaminopropyl)carbodiimide hydrochloride, and 0.49 g (3.6 mmol) of 1-hydroxybenzotriazole were stirred in 6.3 ml of DMA for 2 hours. After completion of the reaction, the reaction solution was poured into an aqueous sodium hydrogen carbonate solution, and the solid was separated by filtration, and washed with city water to give 1.40 g of methyl 2-(5-(4-benzhydrylpiperazin-1-yl)-5-oxopentanamido)-5-chlorobenzoate (yield: 87.5%).
$^1$H-NMR (CDCl$_3$) δ: 2.06 (2H, q, J=7.1 Hz), 2.34-2.56 (8H, m), 3.45-3.64 (4H, m), 3.92 (3H, s), 4.21 (1H, s), 7.14-7.43 (10H, m), 7.47 (1H, dd, J=9.0, 2.6 Hz), 7.99 (1H, d, J=2.6 Hz), 8.67 (1H, d, J=9.0 Hz), 11.0 (1H, s).

(iii) 2-(5-(4-benzhydrylpiperazin-1-yl)-5-oxopentanamido)-5-chlorobenzoic acid 1.39 g (2.6 mmol) of methyl 2-(5-(4-benzhydrylpiperazin-1-yl)-5-oxopentanamido)-5-chlorobenzoate was dissolved in 13.9 ml of THF. Subsequently, a 1N aqueous sodium hydroxide solution was added, and the mixture was stirred at 50° C. for 1 hours. After cooling, THF was distilled off under reduced pressure. The residue was neutralized with a 1N aqueous HCl solution, and water was added. The obtained solid was washed with IPE to give the titled 2-(5-(4-benzhydrylpiperazin-1-yl)-5-oxopentanamido)-5-chlorobenzoic acid (yield: 92.6%).
$^1$H-NMR (DMSO-d$_6$) δ: 1.76-1.92 (2H, m), 2.34-2.54 (8H, m), 3.41-3.62 (4H, m), 4.43 (1H, s), 7.17-7.48 (10H, m), 7.63 (1H, dd, J=9.0, 2.7 Hz), 7.92 (1H, d, J=2.7 Hz), 8.48 (1H, d, J=9.0 Hz), 11.1 (1H, s).

Example 81

Preparation of sodium 2-(2-(2-(4-benzhydrylpiperazin-1-yl)-2-oxoethoxy)acetamido)-5-(2,4-dimethylthiazol-5-yl)benzoate The titled compound was prepared according to Steps (i) and (ii) described below.

(i) Methyl 2-(2-(2-(4-benzhydrylpiperazin-1-yl)-2-oxoethoxy)acetamido)-5-(2,4-dimethylthiazole 5-yl)benzoate Using the same method as in Example 44-(iii), methyl 2-(2-(2-(4-benzhydrylpiperazin-1-yl)-2-oxoethoxy)acetamido)-5-bromobenzoate obtained in Example 44-(ii) was reacted with 2,4-dimethyl-5-(4,4,5,5-tetramethyl-1,3,2-dioxaborolan-2-yl)-1,3-thiazole to quantitatively obtain methyl 2-(2-(2-(4-benzhydrylpiperazin-1-yl)-2-oxoethoxy)acetamido)-5-(2,4-dimethylthiazole 5-yl)benzoate.

$^1$H-NMR (CDCl$_3$) δ: 2.35-2.44 (4H, m), 2.44 (3H, s), 2.69 (3H, s), 3.38-3.70 (4H, m), 3.82 (3H, s), 4.22 (1H, s), 4.24 (2H, s), 4.36 (2H, s), 7.13-7.74 (11H, m), 8.06 (1H, d, J=2.2 Hz), 8.81 (1H, d, J=8.8 Hz), 11.7 (1H, s).

(ii) Sodium 2-(2-(2-(4-benzhydrylpiperazin-1-yl)-2-oxoethoxy)acetamido)-5-(2,4-dimethylthiazol-5-yl)benzoate Using the same method as in Example 44-(iv), the titled sodium 2-(2-(2-(4-benzhydrylpiperazin-1-yl)-2-oxoethoxy)acetamido)-5-(2,4-dimethylthiazole 5-yl)benzoate (yield: 33%) was obtained using methyl 2-(2-(2-(4-benzhydrylpiperazin-1-yl)-2-oxoethoxy)acetamido)-5-(2,4-dimethylthiazol-5-yl)benzoate.

$^1$H-NMR (DMSO-d$_6$) δ: 2.17-2.33 (4H, m), 2.37 (3H, s), 2.61 (3H, s), 3.30-3.52 (4H, m), 4.09 (2H, s), 4.27 (1H, s), 4.34 (2H, s), 7.12-7.47 (11H, m), 8.08 (1H, d, J=2.2 Hz), 8.61 (1H, d, J=8.5 Hz), 14.0 (1H, s).

Example 82

Preparation of 2-(2-(2-(benzhydrylamino)-2-oxoethoxy)acetamido)-5-methyl-4-phenylthiophene-3-carboxylic acid The titled compound was prepared according to Steps (i) and (ii) described below.

(i) tert-Butyl 2-(2-(2-(benzhydrylamino)-2-oxoethoxy)acetamido)-5-methyl-4-phenylthiophene-3-carboxylate Using the same method as in Example 13-(iii), 2-(2-(3-(tert-butoxycarbonyl-)-5-methyl-4-phenylthiophen-2-ylamino)-2-oxoethoxy)acetic acid obtained in Example 15-(i) was reacted with diphenylmethylamine to give tert-butyl 2-(2-(2-(benzhydrylamino)-2-oxoethoxy)acetamido)-5-methyl-4-phenylthiophene-3-carboxylate (yield: 57%).

$^1$H-NMR (CDCl$_3$) δ: 1.06 (9H, s), 2.08 (3H, s), 4.28 (2H, s), 4.35 (2H, s), 6.19 (1H, d, J=8.6 Hz), 7.10-7.48 (15H, m), 8.80 (1H, d, J=8.6 Hz), 11.5 (1H, s).

(ii) 2-(2-(2-(benzhydrylamino)-2-oxoethoxy)acetamido)-5-methyl-4-phenylthiophene-3-carboxylic acid 1.0 g (1.7 mmol) of tert-butyl 2-(2-(2-(benzhydrylamino)-2-oxoethoxy)acetamido)-5-methyl-4-phenylthiophen-3-carboxylate and 5 ml of TFA were stirred in 10 ml of chloroform as a solvent at room temperature for 5 hours. After the reaction solution was concentrated, ethyl acetate was added. The precipitate was obtained by filtration, washed with ethyl acetate, and dried to give the titled 2-(2-(2-(benzhydrylamino)-2-oxoethoxy)acetamido)-5-methyl-4-phenylthiophen-3-carboxylic acid (yield: 82%).

$^1$H-NMR (DMSO-d$_6$) δ: 2.09 (3H, s), 4.26 (2H, s), 4.34 (2H, s), 6.19 (1H, d, J=8.7 Hz), 7.13-7.43 (15H, m), 8.82 (1H, d, J=8.7 Hz), 11.9 (1H, s), 12.7 (1H, bs).

Example 83

Preparation of sodium 5-chloro-2-(2-(2-(diphenylamino)-2-oxoethoxy)acetamido)benzoate The titled compound was prepared according to Steps (i) and (ii) described below.

(i) Methyl 5-chloro-2-(2-(2-(diphenylamino)-2-oxoethoxy)acetamido)benzoate

Using the same method as in Example 29-(ii), 2-(2-(4-chloro-2-(methoxycarbonyl)phenylamino)-2-oxoethoxy) acetic acid obtained in Example 29-(i) was reacted with diphenylamine to give a crude product of methyl 5-chloro-2-(2-(2-(diphenylamino)-2-oxoethoxy)acetamido)benzoate. The crude product was used in the subsequent step without being purified.

$^1$H-NMR (CDCl$_3$) δ: 3.92 (3H, s), 4.22 (2H, s), 4.25 (2H, s), 7.24-7.48 (10H, m), 7.48 (1H, dd, J=9.0, 2.6 Hz), 8.00 (1H, d, J=2.6 Hz), 8.72 (1H, d, J=9.0 Hz), 11.6 (1H, s).

(ii) Sodium 5-chloro-2-(2-(2-(diphenylamino)-2-oxoethoxy)acetamido)benzoate

Using the same method as in Example 29-(iii), the titled sodium 5-chloro-2-(2-(2-(diphenylamino)-2-oxoethoxy)acetamido)benzoate (yield from step (i): 34%) was obtained using the crude product of methyl 5-chloro-2-(2-(2-(diphenylamino)-2-oxoethoxy)acetamido)benzoate obtained above.

$^1$H-NMR (DMSO-d$_6$) δ: 4.12 (2H, s), 4.14 (2H, s), 7.15-7.60 (10H, m), 7.29 (1H, dd, J=8.9, 2.8 Hz), 7.92 (1H, d, J=2.8 Hz), 8.51 (1H, d, J=8.9 Hz), 14.3 (1H, s).

Example 84

Preparation of 5-chloro-2-(2-(2-(2,2-diphenylethylamino)-2-oxoethoxy)acetamido)benzoic acid The titled compound was prepared according to Steps (i) and (ii) described below.

(i) Methyl 5-chloro-2-(2-(2-(2,2-diphenylethylamino)-2-oxoethoxy)acetamido)benzoate Using the same method as in Example 67 (i), 2-(2-(4-chloro-2-(methoxycarbonyl)phenylamino)-2-oxoethoxy) acetic acid obtained in Example 29-(i) was reacted with 2,2-diphenylethylamine to quantitatively obtain methyl 5-chloro-2-(2-(2-(2,2-diphenylethylamino)-2-oxoethoxy)acetamido) benzoate.

$^1$H-NMR (CDCl$_3$) δ: 3.19 (3H, s), 4.02 (2H, s), 4.02 (2H, dd, J=7.6, 6.1 Hz), 4.06 (2H, s), 4.31 (1H, t, J=7.6), 7.06-7.30

(11H, m), 7.54 (1H, dd, J=9.0, 2.6 Hz), 8.04 (1H, d, J=2.6 Hz), 8.72 (1H, d, J=9.0 Hz), 11.6 (1H, s).

(ii) 5-Chloro-2-(2-(2-(2,2-diphenylethylamino)-2-oxoethoxy)acetamido)benzoic acid Using the same method as in Example 34-(ii), the titled 5-chloro-2-(2-(2-(2,2-diphenylethylamino)-2-oxoethoxy) acetamido)benzoic acid was obtained using methyl 5-chloro-2-(2-(2-(2,2-diphenylethylamino)-2-oxoethoxy)acetamido) benzoate (yield: 84%).

$^1$H-NMR (DMSO-d$_6$) δ: 3.83 (2H, dd, J=7.8, 5.8 Hz), 4.00 (2H, s), 4.01 (2H, s), 4.33 (1H, t, J=7.8 Hz), 7.09-7.36 (10H, m), 7.70 (1H, dd, J=9.0, 2.7 Hz), 7.80 (1H, t, J=5.8 Hz), 8.00 (1H, d, J=2.7 Hz), 8.64 (1H, d, J=9.0 Hz), 11.8 (1H, s).

Example 85

Preparation of 2-(2-(2-((3S*,5R*)-4-benzhydryl-3,5-dimethyl piperazin-1-yl)-2-oxoethoxy)acetamido)-5-chlorobenzoic acid hydrochloride The titled compound was prepared according to Steps (i) to (iv) described below.

(i) tert-Butyl cis-4-benzhydryl-3,5-dimethylpiperazine-1-carboxylate 3.46 g (16.1 mmol) of cis-1-Boc-3,5-dimethylpiperazine, 3.99 g (16.1 mmol) of α-bromodiphenylmethane, and 2.23 g (16.1 mmol) of potassium carbonate were stirred in 15 ml of DMF at room temperature for 40 hours. After the reaction mixture was filtered, the solvent was distilled off under reduced pressure. The obtained crude product was separated and purified by silica gel column chromatography to give 0.58 g of tert-butyl cis-4-benzhydryl-3,5-dimethylpiperazine-1-carboxylate (yield: 9%).

$^1$H-NMR (CDCl$_3$) (DMSO-d$_6$) δ: 0.99 (6H, d, J=7.1 Hz), 1.44 (9H, s), 2.90-3.20 (4H, m), 3.60-3.90 (2H, m), 4.89 (1H, s), 7.18-7.52 (10H, m).

(ii) cis-1-Benzhydryl-2,6-dimethylpiperazine 10 ml of 4N hydrochloric acid/dioxane solution was added to 0.58 g (1.65 mmol) of tert-butyl cis-4-benzhydryl-3,5-dimethylpiperazine-1-carboxylate, and the mixture was stirred at room temperature for 5 hours. After concentrating the reaction mixture, the residue was dissolved in a chloroform-methanol mixture, and alkalized with a 1N aqueous sodium hydroxide solution. The solvent was distilled off under reduced pressure. After water was added to the residue, the residue was filtered and dried to give 0.41 g of cis-1-benzhydryl-2,6-dimethylpiperazine (yield: 89%).

$^1$H-NMR (DMSO-d$_6$) δ: 1.10 (6H, d, J=7.1 Hz), 2.90-3.30 (7H, m), 5.07 (1H, s), 7.10-7.60 (10H, m).

(iii) Methyl 2-(2-(2-((3S*,5R*)-4-benzhydryl-3,5-dimethylpiperazin-1-yl)-2-oxoethoxy)acetamido)-5-chlorobenzoate Using the same method as in Example 67-(i), 2-(2-(4-chloro-2-(methoxycarbonyl)phenylamino)-2-oxoethoxy) acetic acid obtained in Example 29-(i) was reacted with cis-1-benzhydryl-2,6-dimethylpiperazine to give methyl 2-(2-(2-(3S*,5R*)-4-benzhydryl-3,5-dimethylpiperazine-1-yl)-2-oxoethoxy)acetamido)-5-chlorobenzoate (yield: 71%).

$^1$H-NMR (CDCl$_3$) δ: 1.01 (3H, d, J=6.6 Hz), 1.04 (3H, d, J=6.6 Hz), 2.90-3.25 (3H, m), 3.30-3.60 (2H, m), 3.88 (3H, s), 4.10-4.30 (1H, m), 4.24 (2H, s), 4.39 (2H, s), 4.90 (1H, s), 7.21-7.54 (11H, m), 8.00 (1H, d, J=2.7 Hz), 8.74 (1H, d, J=9.0 Hz), 11.7 (1H, s).

(iv) 2-(2-(2-((3S*,5R*)-4-benzhydryl-3,5-dimethylpiperazin-1-yl)-2-oxoethoxy)acetamido)-5-chlorobenzoic acid Hydrochloride 0.54 g (0.97 mmol) of methyl 2-(2-(2-(3S*,5R*)-4-benzhydryl-3,5-dimethylpiperazine-1-yl)-2-oxoethoxy)acetamido)-5-chlorobenzoate was dissolved in 4 ml of THF. Subsequently, 5 ml of 1N aqueous sodium hydroxide solution was added and the mixture was stirred at 60° C. for 4 hours. After cooling, the resulting mixture was acidified with a 1N aqueous hydrochloric acid, and the solvent was then distilled off under reduced pressure. After addition of water, the residue was filtered and dried. After the obtained crude product was separated and purified by silica gel column chromatography, the resulting product was acidified with hydrochloric acid to give the titled 2-(2-(2-((3S*,5R*-4-benzhydryl-3,5-dimethylpiperazin-1-yl)-2-oxoethoxy)acetamido)-5-chlorobenzoic acid hydrochloride (yield: 66%).

$^1$H-NMR (DMSO-d) δ: 0.60-1.60 (6H, m), 2.60-4.60 (6H, m), 4.19 (2H, s), 4.40 (2H, s), 5.00 (1H, bs), 7.00-8.40 (10H, m), 7.69 (1H, dd, J=9.0, 2.6 Hz), 7.95 (1H, d, J=2.6 Hz), 8.67 (1H, d, J=9.0), 11.8 (1H, s).

Example 86

Preparation of sodium 2-(2-(2-(4-benzhydrylpiperazin-1-yl)-2-oxoethoxy)acetamido)-5-(benzyloxy) benzoate The titled compound was prepared according to Steps (i) to (iii) described below.

(i) 2-(2-(4-(benzyloxy)-2-(methoxycarbonyl)phenylamino)-2-oxoethoxy)acetic acid

Using the same method as in Example 29-(i), methyl 2-amino-5-(benzyloxy)benzoate was reacted with diglycolic anhydride to give 2-(2-(4-(benzyloxy)-2-(methoxycarbonyl) phenylamino)-2-oxoethoxy)acetic acid (yield: 84%).

$^1$H-NMR (DMSO-d$_6$) δ: 3.88 (3H, s), 4.17 (2H, s), 4.26 (2H, s), 5.14 (2H, s), 7.28-7.51 (6H, m), 7.56 (1H, d, J=3.2 Hz), 8.49 (1H, d, J=9.3 Hz), 11.1 (1H, s).

(ii) Methyl 2-(2-(2-(4-benzhydrylpiperazin-1-yl)-2-oxoethoxy)acetamido)-5-(benzyloxy)benzoate Using the same method as in Example 29-(ii), 2-(2-(4-(benzyloxy)-2-(methoxycarbonyl)phenylamino)-2-oxoethoxy)acetic acid was reacted with 1-benzhydrylpiperazine to give methyl 2-(2-(2-(4-benzhydrylpiperazin-1-yl)-2-oxoethoxy)acetamido)-5-(benzyloxy)benzoate (yield: 72%).

$^1$H-NMR (CDCl$_3$) δ: 2.34-2.44 (4H, m), 3.49-3.69 (4H, m), 3.79 (3H, s), 4.20 (2H, s), 4.21 (1H, s), 4.34 (2H, s), 5.07 (2H, s), 7.13-7.48 (16H, m), 7.62 (1H, d, J=2.9 Hz), 8.67 (1H, d, J=9.2 Hz), 11.5 (1H, s).

(iii) Sodium 2-(2-(2-(4-benzhydrylpiperazin-1-yl)-2-oxoethoxy)acetamido)-5-(benzyloxy)benzoate Using the same method as in Example 29-(iii), the titled sodium 2-(2-(2-(4-benzhydrylpiperazin-1-yl)-2-oxoethoxy)

acetamido)-5-(benzyloxy)benzoate (yield: 81%) was obtained using methyl 2-(2-(2-(4-benzhydrylpiperazin-1-yl)-2-oxoethoxy)acetamido)-5-(benzyloxy)benzoate.

¹H-NMR (DMSO-d₆) δ: 2.20-2.35 (4H, m), 3.33-3.53 (4H, m), 4.03 (2H, s), 4.29 (2H, s), 4.31 (1H, s), 5.06 (2H, s), 6.94 (1H, dd, J=8.9, 3.2 Hz), 7.13-7.49 (15H, m), 7.64 (1H, d, J=3.2 Hz), 8.44 (1H, d, J=8.9 Hz), 14.1 (1H, s).

Example 87

Preparation of sodium 2-(2-(2-(4-benzhydrylpiperazin-1-yl)-2-oxoethoxy)acetamido)-5-isobutoxybenzoate The titled compound was prepared according to Steps (i) to (v) described below.

(i) Methyl 2-acetamido-5-isobutoxybenzoate 2.09 g (10.0 mmol) of methyl 2-acetamido-5-hydroxybenzoate, 4.11 g (30.0 mmol) of isobutyl bromide, and 7.08 g (51.3 mmol) of potassium carbonate were suspended in 65 ml of acetone, and the mixture was heated under reflux for 33 hours. After the reaction mixture was cooled to room temperature, the mixture was filtered. The filtrate was concentrated, and the obtained crude product was separated and purified by silica gel column chromatography to give 1.91 g of methyl 2-acetamido-5-isobutoxybenzoate (yield: 72%).

¹H-NMR (CDCl₃) δ: 1.03 (6H, d, J=6.8 Hz), 1.96-2.19 (1H, m), 2.21 (3H, s), 3.71 (2H, d, J=6.6 Hz), 3.93 (3H, s), 7.10 (1H, dd, J=9.2, 3.1 Hz), 7.50 (1H, d, J=3.1 Hz), 8.60 (1H, d, J=9.2 Hz), 10.8 (1H, s).

(ii) Methyl 2-amino-5-isobutoxybenzoate 75 ml of a saturated solution of hydrogen chloride in methanol was added to 1.87 g (7.05 mmol) of methyl 2-acetamido-5-isobutoxybenzoate, and the mixture was heated under reflux for 2 hours. After cooling the reaction mixture, the solvent was distilled off under reduced pressure. The obtained residue was diluted with ethyl acetate, washed with saturated sodium hydrogen carbonate, and dried over anhydrous sodium sulfate to give 1.41 g of methyl 2-amino-5-isobutoxybenzoate (yield: 90%).

¹H-NMR (CDCl₃) δ: 1.01 (6H, d, J=6.6 Hz), 1.93-2.15 (1H, m), 3.66 (2H, d, J=6.6 Hz), 3.88 (3H, s), 5.30 (2H, bs), 6.63 (1H, d, J=9.0 Hz), 6.96 (1H, dd, J=9.0, 2.9 Hz), 7.34 (1H, d, J=2.9 Hz).

(iii) 2-(2-(4-Isobutoxy-2-(methoxycarbonyl)phenylamino)-2-oxoethoxy)acetic acid

Using the same method as in Example 29-(i), methyl 2-amino-5-isobutoxybenzoate was reacted with diglycolic anhydride to quantitatively obtain 2-(2-(4-isobutoxy-2-(methoxycarbonyl)phenylamino)-2-oxoethoxy)acetic acid.

¹H-NMR (DMSO-d₆) δ: 0.98 (6H, d, J=6.6 Hz), 1.89-2.13 (1H, m), 3.76 (2H, d, J=6.3 Hz), 3.88 (3H, s), 4.17 (2H, s), 4.26 (2H, s), 7.31 (1H, dd, J=9.0, 3,2 Hz), 7.45 (1H, d, J=3.2 Hz), 8.48 (1H, d, J=9.0 Hz), 11.1 (1H, s), 12.9 (1H, bs).

(iv) Methyl 2-(2-(2-(4-benzhydrylpiperazin-1-yl)-2-oxoethoxy)acetamido)-5-isobutoxybenzoate Using the same method as in Example 29-(ii), 2-(2-(4-isobutoxy-2-(methoxycarbonyl)phenylamino)-2-oxoethoxy) acetic acid was reacted with 1-benzhydrylpiperazine to give methyl 2-(2-(2-(4-benzhydrylpiperazin-1-yl)-2-oxoethoxy)acetamido)-5-isobutoxybenzoate (yield: 70%).

¹H-NMR (CDCl₃) δ: 1.03 (6H, d, J=6.8 Hz), 1.97-2.19 (1H, m), 2.34-2.45 (4H, m), 3.50-3.69 (4H, m), 3.73 (2H, d, J=6.4 Hz), 3.79 (3H, s), 4.20 (2H, s), 4.21 (1H, s), 4.35 (2H, s), 7.12 (1H, dd, J=9.2, 3.1 Hz), 7.15-7.43 (10H, m), 7.51 (1H, d, J=3.1 Hz), 8.65 (1H, d, J=9.2 Hz), 11.4 (1H, s).

(v) Sodium 2-(2-(2-(4-benzhydrylpiperazin-1-yl)-2-oxoethoxy)acetamido)-5-isobutoxybenzoate Using the same method as in Example 29-(iii), the titled sodium 2-(2-(2-(4-benzhydrylpiperazin-1-yl)-2-oxoethoxy) acetamido)-5-isobutoxybenzoate (yield: 88%) was obtained using methyl 2-(2-(2-(4-benzhydrylpiperazin-1-yl)-2-oxoethoxy)acetamido)-5-isobutoxybenzoate.

¹H-NMR (DMSO-d₆) δ: 0.97 (6H, d, J=6.6 Hz), 1.88-2.11 (1H, m), 2.20-2.36 (4H, m), 3.34-3.52 (4H, m), 3.69 (2H, d, J=6.3 Hz), 4.02 (2H, s), 4.28 (2H, s), 4.31 (1H, s), 6.84 (1H, dd, J=9.0, 3.1 Hz), 7.12-7.48 (10H, m), 7.54 (1H, d, J=3.1 Hz), 8.42 (1H, d, J=9.0 Hz), 14.1 (1H, s).

Example 88

Preparation of 2-(2-(4-benzhydrylpiperazin-1-yl)-2-oxoethoxy)-N-(4-chloro-2-(1H-tetrazol-5-yl)phenyl) acetamide The titled compound was prepared according to Steps (i) to (iii) described below.

(i) 2-(2-(4-chloro-2-cyanophenylamino)-2-oxoethoxy)acetic acid

Using the same method as in Example 29-(i), 2-amino-5-chlorobenzonitrile was reacted with diglycolic anhydride to quantitatively obtain 2-(2-(4-chloro-2-cyanophenylamino)-2-oxoethoxy)acetic acid.

¹H-NMR (DMSO-d₆) δ: 4.24 (2H, s), 4.26 (2H, s), 7.76 (1H, d, J=0.7 Hz), 7.78 (1H, d, J=2.2 Hz), 8.04 (1H, dd, J=2.2, 0.7 Hz), 10.1 (1H, s), 12.9 (1H, bs).

(ii) 2-(2-(4-Benzhydrylpiperazin-1-yl)-2-oxoethoxy)-N-(4-chloro-2-cyanophenyl)acetamido Using the same method as in Example 29-(ii), 2-(2-(4-chloro-2-cyanophenylamino)-2-oxoethoxy)acetic acid was reacted with 1-benzhydrylpiperazine to give 2-(2-(4-benzhydrylpiperazin-1-yl)-2-oxoethoxy)-N-(4-chloro-2-cyanophenyl)acetamido (yield: 71%).

¹H-NMR (CDCl₃) δ: 2.20-2.40 (4H, m), 3.25-3.60 (4H, m), 4.22 (2H, s), 4.33 (1H, s), 4.40 (2H, s), 7.10-7.50 (10H, m), 7.78 (1H, d, J=2.0 Hz), 7.78 (1H, d, J=1.8 Hz), 8.02 (1H, dd, J=2.0, 1.8 Hz), 10.5 (1H, s).

(iii) 2-(2-(4-Benzhydrylpiperazin-1-yl)-2-oxoethoxy)-N-(4-chloro-2-(1H-tetrazol-5-yl)phenyl)acetamide 0.83 g (1.65 mmol) of 2-(2-(4-benzhydrylpiperazin-1-yl)-2-oxoethoxy)-N-(4-chloro-2-cyanophenyl)acetamide, 0.12 g (1.83 mmol) of sodium azide, 0.41 g (1.81 mmol) of zinc bromide, 20 ml of water, 10 ml of isopropanol, and 10 ml of THF were added, and the mixture was heated under reflux for 26.5 hours. After cooling the reaction mixture, THF was distilled off under reduced pressure. The residue was acidified with a 1N aqueous hydrochloric acid, and then extracted with ethyl acetate. After the extract was dried over anhydrous sodium sulfate, the solvent was distilled off under reduced pressure. The obtained crude product was separated and purified by silica gel column chromatography to give the titled 2-(2-(4-benzhydrylpiperazin-1-yl)-2-oxoethoxy)-N-(4-chloro-2-(1H-tetrazol-5-yl)phenyl)acetamide (yield: 33%).

$^1$H-NMR (DMSO-d$_d$) δ: 2.22-2.37 (4H, m), 3.20-3.70 (4H, m), 4.18 (2H, s), 4.31 (1H, s), 4.40 (2H, s), 7.12-7.47 (11H, m), 8.17 (1H, d, J=2.7 Hz), 8.65 (1H, d, J=9.0 Hz), 12.7 (1H, s).

Example 89

Preparation of 2-(2-(4-benzhydrylpiperazin-1-yl)-2-oxoethoxy)-N-(4-chloro-2-(5-oxo-4,5-dihydro-1,2,4-oxadiazol-3-yl)phenyl)acetamide The titled compound was prepared according to Steps (i) and (ii) described below.

(i) 2-(2-(4-Benzhydrylpiperazin-1-yl)-2-oxoethoxy)-N-(4-chloro-2-(N'-hydroxycarbamimidoyl)phenyl)acetamide 1.0 g (1.99 mmol) of 2-(2-(4-benzhydrylpiperazin-1-yl)-2-oxoethoxy)-N-(4-chloro-2-cyanophenyl)acetamide obtained in Example 88-(ii), 0.28 g (3.98 mmol) of hydroxylamine hydrochloride, and 0.41 g (2.98 mmol) of potassium carbonate were suspended in ethanol, and the mixture was heated under reflux for 11.5 hours. The reaction mixture was diluted with chloroform, washed with water, and dried over anhydrous sodium sulfate. The solvent was then distilled off under reduced pressure. The obtained crude product was separated and purified by silica gel column chromatography to give 0.27 g of 2-(2-(4-benzhydrylpiperazin-1-yl)-2-oxoethoxy)-N-(4-chloro-2-(N'-hydroxycarbamimidoyl)phenyl)acetamide (yield: 25%).

$^1$H-NMR (CDCl$_3$) δ: 2.29 (1H, bs), 2.32-2.49 (4H, m), 3.45-3.75 (4H, m), 4.24 (1H, s), 4.47 (2H, s), 5.09 (2H, s), 7.14-7.45 (11H, m), 7.48 (1H, dd, J=8.8, 2.2 Hz), 7.75 (1H, d, J=8.8 Hz), 8.19 (1H, d, J=2.2 Hz), 8.62 (2H, bs).

(ii) 2-(2-(4-Benzhydrylpiperazin-1-yl)-2-oxoethoxy)-N-(4-chloro-2-(5-oxo-4,5-dihydro-1,2,4-oxadiazol-3-yl)phenyl)acetamide 0.27 g (0.53 mmol) of 2-(2-(4-benzhydrylpiperazin-1-yl)-2-oxoethoxy)-N-(4-chloro-2-(N'-hydroxycarbamimidoyl)phenyl)acetamide, 0.20 g (1.25 mmol) of CDI, and 0.08 g (0.54 mmol) of DBU were dissolved in 5 ml of THF. The mixture was heated under reflux for 13 hours. The reaction mixture was diluted with chloroform, and washed with a 1N aqueous hydrochloric acid solution. The organic layer was then dried over anhydrous sodium sulfate, and the solvent was distilled off under reduced pressure. The obtained crude product was separated and purified by silica gel column chromatography to give the titled 2-(2-(4-benzhydrylpiperazin-1-yl)-2-oxoethoxy)-N-(4-chloro-2-(5-oxo-4,5-dihydro-1,2,4-oxadiazol-3-yl)phenyl)acetamide (yield: 58%).

$^1$H-NMR (DMSO-d$_6$) δ: 2.26-2.43 (4H, m), 3.30-3.60 (4H, m), 4.14 (2H, s), 4.36 (2H, s), 4.41 (1H, s), 7.14-7.50 (10H, m), 7.66 (1H, dd, J=9.0, 2.4 Hz), 7.79 (1H, d, J=2.4 Hz), 8.40 (1H, d, J=9.0 Hz), 11.7 (1H, s).

Example 90

Preparation of 2-(2-(4-benzhydrylpiperazin-1-yl)-2-oxoethoxy)-N-(5-methyl-4-phenyl-3-(1H-tetrazol-5-yl)thiophen-2-yl)acetamide The titled compound was prepared according to Steps (i) to (iv) described below.

(i) 2-Amino-5-methyl-4-phenylthiophen-3-carbonitrile

Using the same method as in Example 7-(i), propiophenone was reacted with malononitrile and sulfur to give 2-amino-5-methyl-4-phenylthiophen-3-carbonitrile (yield: 59%).

$^1$H-NMR (CDCl$_3$) δ: 2.24 (3H, s), 4.71 (2H, bs), 7.29-7.49 (5H, m).

(ii) 2-(2-(3-Cyano-5-methyl-4-phenylthiophen-2-ylamino)-2-oxoethoxy)acetic acid

Using the same method as in Example 29 (i), 2-amino-5-methyl-4-phenylthiophen-3-carbonitrile was reacted with diglycolic anhydride to give a crude product of 2-(2-(3-cyano-5-methyl-4-phenylthiophen-2-ylamino)-2-oxoethoxy) acetic acid. The crude product was used in the subsequent step without being purified.

$^1$H-NMR (CDCl$_3$) δ: 2.29 (3H, s), 4.22 (2H, s), 4.40 (2H, s), 7.34-7.57 (5H, m), 11.5 (1H, s).

(iii) 2-(2-(4-Benzhydrylpiperazin-1-yl)-2-oxoethoxy)-N-(3-cyano-5-methyl-4-phenylthiophen-2-yl)acetamide Using the same method as in Example 67-(i), the crude product of 2-(2-(3-cyano-5-methyl-4-phenylthiophen-2-ylamino)-2-oxoethoxy)acetic acid obtained above was reacted with 1-benzhydrylpiperazine. The reaction mixture was separated and purified by silica gel column chromatography, and then recrystallized with ethyl acetate-hexane to give 2-(2-(4-benzhydrylpiperazin-1-yl)-2-oxoethoxy)-N-(3-cyano-5-methyl-4-phenylthiophen-2-yl)acetamide (yield from step (ii): 27%).

$^1$H-NMR (CDCl$_3$) δ: 2.33 (3H, s), 2.36-2.46 (4H, m), 3.27-3.38 (2H, m), 3.60-3.72 (2H, m), 4.26 (1H, s), 4.30 (2H, s), 4.35 (2H, s), 7.13-7.50 (15H, m), 11.2 (1H, s).

(iv) 2-(2-(4-Benzhydrylpiperazin-1-yl)-2-oxoethoxy)-N-(5-methyl-4-phenyl-3-(1H-tetrazol-5-yl)thiophen-2-yl)acetamide 0.36 g (0.64 mmol) of 2-(2-(4-benzhydrylpiperazin-1-yl)-2-oxoethoxy)-N-(3-cyano-5-methyl-4-phenylthiophen-2-yl) acetamide, 0.73 g (6.38 mmol) of trimethylsilylazide, and 15.8 mg (0.06 mmol) of dibutyltin oxide were suspended in 3 ml of toluene, and stirred at 90° C. for 41 hours. After cooling the reaction mixture, the solvent was distilled off under reduced pressure. The residue was separated and purified by silica gel column chromatography to give the titled 2-(2-(4-benzhydrylpiperazin-1-yl)-2-oxoethoxy)-N-(5-methyl-4-phenyl-3-(1H-tetrazol-5-yl)thiophen-2-yl)acetamide (yield: 33%).

¹H-NMR (DMSO-d₆) δ: 2.21-2.34 (4H, m), 2.25 (3H, s), 3.20-3.60 (4H, m), 4.22 (2H, s), 4.32 (1H, s), 4.35 (2H, s), 7.03-7.47 (15H, m), 11.7 (1H, s).

Example 91

Preparation of 2-(2-((2-(benzhydrylamino)-2-oxoethyl)(methyl)amino)acetamido)-5-chlorobenzoic acid hydrochloride The titled compound was prepared according to Steps (i) and (ii) described below.

(i) Methyl 2-(2-((2-(benzhydrylamino)-2-oxoethyl)(methyl)amino)acetamido)-5-chlorobenzoate Using the same method as in Example 67-(i), 2-((2-(4-chloro-2-(methoxycarbonyl)phenylamino)-2-oxoethyl)(methyl)amino)acetic acid obtained in Example 25-(i) was reacted with diphenylmethylamine to give methyl 2-(2-((2-(benzhydrylamino)-2-oxoethyl)(methyl)amino)acetamido)-5-chlorobenzoate (yield: 74%).

¹H-NMR (CDCl₃) δ: 2.41 (3H, s), 3.28 (2H, s), 3.34 (3H, s), 3.37 (2H, s), 6.45 (1H, d, J=9.3 Hz), 7.09-7.28 (10H, m), 7.52 (1H, dd, J=9.0, 2.6 Hz), 7.93 (1H, d, J=2.6 Hz), 8.23 (1H, d, J=9.3 Hz), 8.79 (1H, d, J=9.0 Hz), 12.1 (1H, s).

(ii) 2-(2-((2-(Benzhydrylamino)-2-oxoethyl)methyl)(amino)acetamido)-5-chlorobenzoic acid hydrochloride 0.54 g (1.13 mmol) of methyl 2-(2-((2-(benzhydrylamino)-2-oxoethyl)(methyl)amino)acetamido)-5-chlorobenzoate was dissolved in 3 ml of THF. Subsequently, a 1N aqueous sodium hydroxide solution was added, and the mixture was stirred at room temperature for 1 hour. THF was then distilled off under reduced pressure. After adding water to the residue the mixture was acidified with a 1N aqueous hydrochloric acid and filtered to give the titled 2-(2-((2-(benzhydrylamino)-2-oxoethyl)(methyl)amino)acetamido)-5-chlorobenzoic acid hydrochloride (yield: 91%).

¹H-NMR (DMSO-d₆) δ: 2.48 (3H, s), 3.48 (4H, s), 6.16 (1H, d, J=8.6 Hz), 7.15-7.31 (10H, m), 7.67 (1H, dd, J=9.0, 2.6 Hz), 7.93 (1H, d, J=2.6 Hz), 8.60 (1H, d, J=9.0 Hz), 8.72 (1H, d, J=8.6 Hz), 12.0 (1H, s).

Example 92

Preparation of 2-(2-(2-(4-benzhydrylpiperazin-1-yl)-2-oxoethylthio)acetamido)-5-chlorobenzoic acid hydrochloride The titled compound was prepared according to Steps (i) to (iii) described below.

(i) 2-(2-(4-Chloro-2-(methoxycarbonyl)phenylamino)-2-oxoethylthio)acetic acid

Using the same method as in Example 25-(i), 2,2'-thiodiglycolic acid was reacted with acetic anhydride and then with methyl 2-amino-5-chlorobenzoate to give 2-(2-(4-chloro-2-(methoxycarbonyl)phenylamino)-2-oxoethylthio)acetic acid (yield: 91%).

¹H-NMR (DMSO-d₆) δ: 3.38 (2H, s), 3.56 (2H, s), 3.88 (3H, s), 7.68 (1H, dd, J=9.0, 2.7 Hz), 7.87 (1H, d, J=2.7 Hz), 8.33 (1H, d, J=9.0 Hz), 11.1 (1H, s), 12.7 (1H, bs).

(ii) Methyl 2-(2-(2-(4-benzhydrylpiperazin-1-yl)-2-oxoethylthio)acetamido)-5-chlorobenzoate Using the same method as in Example 67-(i), 2-(2-(4-chloro-2-(methoxycarbonyl)phenylamino)-2-oxoethylthio)acetic acid was reacted with 1-benzhydrylpiperazine. The reaction mixture was separated and purified by silica gel column chromatography to give methyl 2-(2-(2-(4-benzhydrylpiperazin-1-yl)-2-oxoethylthio)acetamido)-5-chlorobenzoate (yield: 77%).

¹H-NMR (CDCl₃) δ: 2.28-2.46 (4H, m), 3.43-3.63 (4H, m), 3.46 (2H, s), 3.52 (2H, s), 3.90 (3H, s), 4.18 (1H, s), 7.13-7.43 (10H, m), 7.49 (1H, dd, J=9.0, 2.7 Hz), 8.01 (1H, d, J=2.7 Hz), 8.69 (1H, J=9.0 Hz), 11.5 (1H, s).

(iii) 2-(2-(2-(4-Benzhydrylpiperazin-1-yl)-2-oxoethylthio)acetamido)-5-chlorobenzoic acid Hydrochloride Using the same method as in Example 91-(ii), the titled 2-(2-(2-(4-benzhydrylpiperazin-1-yl)-2-oxoethylthio)acetamido)-5-chlorobenzoic acid hydrochloride (yield: 90%) was obtained using methyl 2-(2-(2-(4-benzhydrylpiperazin-1-yl)-2-oxoethylthio)acetamido)-5-chlorobenzoate.

¹H-NMR (DMSO-d₆) δ: 2.60-4.20 (8H, m), 3.56 (2H, s), 3.60 (2H, s), 5.30 (1H, bs), 7.26-7.90 (10H, m), 7.68 (1H, dd, J=9.0, 2.7 Hz), 7.94 (1H, d, J=2.7 Hz), 8.51 (1H, d, J=9.0 Hz), 11.5 (1H, s).

Example 93

Preparation of 2-(2-(1-(2-(4-benzhydrylpiperazin-1-yl)-2-oxoethyl)cyclohexyl)acetamido)-5-chlorobenzoic acid Hydrochloride The titled compound was prepared according to Steps (i) to (iii) described below.

(i) 2-(1-(2-(4-Chloro-2-(methoxycarbonyl)phenylamino)-2-oxoethyl)cyclohexyl)acetic acid Using the same method as in Example 25-(i), 1,1-cyclohexane diacetic acid was reacted with acetic anhydride and then with methyl 2-amino-5-chlorobenzoate to give 2-(1-(2-(4-chloro-2-(methoxycarbonyl)phenylamino)-2-oxoethyl)cyclohexyl)acetic acid (yield: 60%).

¹H-NMR (DMSO-d₆) δ: 1.30-1.40 (10H, m), 2.43 (2H, s), 2.56 (2H, s), 3.85 (3H, s), 7.65 (1H, dd, J=9.0, 2.6 Hz), 7.83 (1H, d, J=2.6 Hz), 8.23 (1H, d, J=9.0 Hz), 10.5 (1H, s), 12.1 (1H, bs).

(ii) Methyl 2-(2-(1-(2-(4-benzhydrylpiperazin-1-yl)-2-oxoethyl)cyclohexyl)acetamido)-5-chlorobenzoate Using the same method as in Example 67-(i), 2-(1-(2-(4-chloro-2-(methoxycarbonyl)phenylamino)-2-oxoethyl)cyclohexyl)acetic acid was reacted with 1-benzhydrylpiperazine to quantitatively obtain methyl 2-(2-(1-(2-(4-benzhydrylpiperazin-1-yl)-2-oxoethyl)cyclohexyl)acetamido)-5-chlorobenzoate.

¹H-NMR (CDCl₃) δ: 1.20-1.60 (10H, m), 2.20-2.40 (4H, m), 2.49 (2H, s), 2.73 (2H, s), 3.45-3.70 (4H, m), 3.92 (3H, s), 4.08 (1H, s), 7.12-7.45 (10H, m), 7.46 (1H, dd, J=9.0, 2.7 Hz), 7.99 (1H, d, J=2.7 Hz), 8.62 (1H, d, J=9.0 Hz), 10.9 (1H, s).

(iii) 2-(2-(1-(2-(4-Benzhydrylpiperazin-1-yl)-2-oxo-ethyl)cyclohexyl)acetamido)-5-chlorobenzoic acid hydrochloride Using the same method as in Example 91-(ii), the titled 2-(2-(1-(2-(4-benzhydrylpiperazin-1-yl)-2-oxoethyl)cyclohexyl)acetamido)-5-chlorobenzoic acid hydrochloride (yield: 59%) was obtained using methyl 2-(2-(1-(2-(4-benzhydrylpiperazin-1-yl)-2-oxoethyl)cyclohexyl)acetamido)-5-chlorobenzoate.

$^1$H-NMR (DMSO-d$_6$) δ: 1.10-1.70 (10H, m), 2.04-2.20 (4H, m), 2.40 (2H, s), 2.60 (2H, s), 3.35-3.52 (4H, m), 4.03 (1H, s), 7.13-7.43 (10H, m), 7.67 (1H, dd, J=9.0, 2.6 Hz), 7.96 (1H, d, J=2.6 Hz), 8.49 (1H, d, J=9.0 Hz), 11.0 (1H, s).

Example 94

Preparation of 2-((1S*,2S*)-2-(4-benzhydrylpiperazine-1-carbonyl)cyclohexanecarboxamido)-5-chlorobenzoic acid hydrochloride The titled compound was prepared according to Steps (i) to (iii) described below.

(i) (1S*,2S*)-2-(4-chloro-2-(methoxycarbonyl)phenylcarbamoyl)cyclohexanecarboxylic acid 3.0 g (16.2 mmol) of methyl 2-amino-4-chlorobenzoate, 2.74 g (17.8 mmol) of (3aS*,7aS*)-hexahydroisobenzofuran-1,3-dione were heated in 21 ml of THF under reflux for 8 hours. After cooling, the reaction mixture was concentrated. The residue was collected by filtration, washed with IPE, and dried to give 4.79 g of (1S*,2S*)-2-(4-chloro-2-(methoxycarbonyl)phenylcarbamoyl)cyclohexanecarboxylic acid (yield: 87.1%).

$^1$H-NMR (CDCl$_3$) δ: 1.35-2.13 (8H, m), 2.53-2.81 (2H, m), 3.94 (3H, s), 7.45 (1H, dd, J=9.3, 2.4 Hz), 7.98 (1H, d, J=2.4 Hz), 8.65 (1H, d, J=9.3 Hz), 11.1 (1H, s).

(ii) Methyl 2-((1S*,2S*)-2-(4-benzhydrylpiperazine-1-carbonyl)cyclohexanecarboxamido)-5-chlorobenzoate 1.02 g (3.0 mmol) of (1S*,2S*)-2-(4-chloro-2-(methoxycarbonyl)phenylcarbamoyl)cyclohexanecarboxylic acid, 0.76 g (3.0 mmol) of 1-benzhydrylpiperazine, 0.69 g (3.6 mmol) of 1-ethyl-3-(3-dimethylaminopropyl)carbodiimide hydrochloride, and 0.49 g (3.6 mmol) of 1-hydroxybenzotriazole were stirred in 7.1 ml of DMA for 2 hours. After completion of the reaction, ethyl acetate was added. The mixture was washed with an aqueous sodium hydrogen carbonate solution and a saturated sodium chloride solution, and dried over anhydrous sodium sulfate. The solvent was then distilled off under reduced pressure. The obtained crude product was separated and purified by silica gel column chromatography to give 0.32 g of methyl 2-((1S*,2S*-2-(4-benzhydrylpiperazine-1-carbonyl)cyclohexanecarboxamido)-5-chlorobenzoate (yield: 18.6%).

$^1$H-NMR (CDCl$_3$) δ: 1.31-1.58 (4H, m), 1.70-1.92 (4H, m), 2.24-2.42 (4H, m), 2.73-2.97 (2H, m), 3.54-3.64 (4H, m), 3.92 (3H, s), 4.14 (1H, s), 7.14-7.41 (10H, m), 7.46 (1H, dd, J=9.2, 2.6 Hz), 7.98 (1H, d, J=2.6 Hz), 8.66 (1H, d, J=9.2 Hz), 11.0 (1H, s).

(iii) 2-((1S*,2S*)-2-(4-benzhydrylpiperazine-1-carbonyl)cyclohexanecarboxamido)-5-chlorobenzoic acid hydrochloride 0.31 g (0.54 mmol) of methyl 2-((1S*,2S*)-2-(4-benzhydrylpiperazine-1-carbonyl)cyclohexanecarboxamido)-5-chlorobenzoate was dissolved in 3.1 ml of THF. Subsequently, a 1N aqueous sodium hydroxide solution was added, and the mixture was stirred at 50° C. for 1 hour. After cooling, THF was distilled off under reduced pressure, and the residue was washed with water. The obtained residue was washed with IPE to give the titled 2-(1S*,2S*)-2-(4-benzhydrylpiperazine-1-carbonyl)cyclohexanecarboxamido)-5-chlorobenzoic acid hydrochloride (yield: 34.4%).

$^1$H-NMR (DMSO-d$_6$) δ: 1.09-1.57 (4H, m), 1.61-1.83 (3H, m), 1.93-2.02 (1H, m), 2.05-2.73 (5H, m), 2.78-3.00 (1H, m), 3.20-3.83 (4H, m), 4.39 (1H, s), 7.18-7.58 (10H, m), 7.68 (1H, dd, J=8.8, 2.7 Hz), 7.93 (1H, d, J=2.7 Hz), 8.48 (1H, d, J=8.8 Hz), 11.1 (1H, s).

Example 95

Preparation of 2-((1S*,2R*)-2-(4-benzhydrylpiperazine-1-carbonyl)cyclohexanecarboxamido)-5-chlorobenzoic acid hydrochloride The titled compound was prepared according to Steps (i) to (iii) described below.

(i) (1R*,2S*)-2-(4-Chloro-2-(methoxycarbonyl)phenylcarbamoyl)cyclohexanecarboxylic acid Using the same method as in Example 94-(i), methyl 2-amino-4-chlorobenzoate was reacted with (3aR*,7aS*)-hexahydroisobenzofuran-1,3-dione to give (1R*,2S*)-2-(4-chloro-2-(methoxycarbonyl)phenylcarbamoyl)cyclohexanecarboxylic acid (yield: 96.0%).

$^1$H-NMR (CDCl$_3$) δ: 1.43-2.22 (8H, m), 2.86-3.00 (2H, m), 3.93 (3H, s), 7.45 (1H, dd, J=9.1, 2.5 Hz), 7.98 (1H, d, J=2.5 Hz), 8.69 (1H, d, J=9.1 Hz), 11.2 (1H, s).

(ii) Methyl 2-((1S,2R)-2-(4-benzhydrylpiperazine-1-carbonyl)cyclohexanecarboxamido)-5-chlorobenzoate Using the same method as in Example 94-(ii), (1R*,2S*)-2-(4-chloro-2-(methoxycarbonyl)phenylcarbamoyl)cyclohexanecarboxylic acid was reacted with 1-benzhydrylpiperazine to give methyl 2-((1S*,2R*)-2-(4-benzhydrylpiperazine-1-carbonyl) cyclohexanecarboxamido)-5-chlorobenzoate (yield: 7.19%).

$^1$H-NMR (CDCl$_3$) δ: 1.41-1.63 (4H, m), 1.99-2.53 (10H, m), 3.42-2.54 (4H, m), 3.54 (3H, s), 4.18 (1H, s), 7.14-7.38 (10H, m), 7.45 (1H, dd, J=9.2, 2.4 Hz), 7.98 (1H, d, J=2.4 Hz), 8.75 (1H, d, J=9.2 Hz), 11.1 (1H, s).

(iii) 2-(1S*,2R*)-2-(4-Benzhydrylpiperazine-1-carbonyl)cyclohexanecarboxamido)-5-chlorobenzoic acid hydrochloride Using the same method as in Example 94-(iii), the titled 2-((1S*,2R*)-2-(4-benzhydrylpiperazine-1-carbonyl)cyclohexanecarboxamido)-5-chlorobenzoic acid hydrochloride (yield: 83.3%) was obtained using methyl 2-(1S*,2R*)-2-(4-benzhydrylpiperazine-1-carbonyl)cyclohexanecarboxamido)-5-chlorobenzoate.

$^1$H-NMR (DMSO-$d_6$) δ: 1.21-1.68 (4H, m), 1.68-2.00 (2H, m), 2.18-2.69 (6H, m), 3.23-3.80 (6H, m), 4.62 (1H, s), 7.25-7.56 (10H, m), 7.65 (1H, dd, J=9.0, 2.7 Hz), 7.94 (1H, d, J=2.7 Hz), 8.63 (1H, d, J=9.0 Hz), 11.2 (1H, s).

Test Example

PAI-1 Inhibitory Activity Assay

The compounds (1) to (95) prepared in the above Examples 1 to 95 were assayed and evaluated for inhibitory action on human PAI-1 (product of Molecular Innovation Inc. USA, hereinafter referred to the same).

More specifically, human-derived PAI-1 was added to a 0.1% Tween 80-containing 100 mM Tris-HCl (pH 8) solution containing each of the above test compounds in a given concentration (20 µM, 50 µM or 100 µM), and incubated at 37° C. for 15 minutes. Subsequently, human-derived tissue plasminogen activator (t-PA)(product of American Diagonostica, Inc. USA, hereinafter referred to the same), adjusted to 0.3 µmol/µL, was added thereto, and further incubated at 37° C. for 15 minutes. Added thereto was 1.25 mM of S-2288 synthesized substrate (product of Chromogenixs, Italy, hereinafter referred to the same), a chromogenic substrate. The final mixed solution contains 100 mM Tris-HCl(pH 8), 30 mM NaCl, 1% DMSO, 0.1% Tween 80, 67 nM PAI-1, 9.8 nMt-PA, 1 mM S-2288 synthesized substrate, and each of the test compounds (100 µM, 50 µM or 20 µM), respectively.

Free radical p-nitrile removed from the chromogenic substrate (S-2288) by t-PA action was measured using a spectrophotometer at an absorbance of 405 nm, every 5 minutes, for 30 minutes. A system that did not contain a test compound was similarly evaluated, and the PAI-1 activity of this system after 30 minutes was taken as 100%, to evaluate the PAI-1 activity of the system to which a test compound was added. The results are together shown in FIGS. 4 to 13.

Reference Test Example 1

2-[3-(3'-Carboxy-4'-phenylthiophen-2'-ylcarbamoyl)-pentanoylamino]-4-phenylthiophen-3-carboxylic acid (hereinafter referred to as "compound a"), and 2-[3-(3'-carboxy-4'-thienylthiophen-2'-ylcarbamoyl)-pentanoylamino]-4-thienylthiophen-3-carboxylic acid (hereinafter referred to as "compound b") were each evaluated for (1) PAI-1 inhibitory activity, (2) fibrinolytic action, and (3) preventive or therapeutic effect on bleomycin-induced pulmonary fibrosis.

(1) PAI-1 Inhibitory Activity Assay

The compounds a and b (test compounds) were evaluated for inhibitory action on human PAI-1 (product of Molecular Innovations Inc., USA, hereinafter referred to the same). More specifically, human PAI-1 was added to a 0.1% Tween 80-containing 100 mM Tris-HCl (pH 8) solution each containing the above compound respectively in a given concentration (20, 35, 50 and 100 µM), and incubated at 37° C. for 15 minutes. Subsequently, added thereto was human tissue plasminogen activator (t-PA) (product of American Diagnostica, Inc., USA, hereinafter referred to the same), adjusted to 0.53 µmol/µL, and further incubated at 37° C. for 15 minutes. Then, 1.25 mM of S-2288 synthesized substrate (product of Chromogenix, Italy, hereinafter referred to as the same), a chromogenic substrate, was added thereto. The final mixed solution contained 100 mM Tris-HCl (pH 8), 30 mM NaCl, 1% DMSO, 0.1% Tween 80, 67 mM PAI-1, 9.8 nM t-PA, 1 mM S-2288 and the test compound a or b (20, 35, 50 or 100 µM).

Free radical p-nitroanilide removed from the chromogenic substrate (S-2288) by t-PA action was measured using a spectrophotometer at an absorbance of 405 nm, every 5 minutes, for 30 minutes. A system that did not contain a test compound was similarly evaluated, and PAI-1 activity of this system (control system) after 30 minutes was taken as 100% to evaluate the PAI-1 activity of the systems to which each of the test compounds was added.

Comparative tests were carried out in the same manner, using, in place of the above test compounds, a compound (tiplextinin) of the formula below used as an antithrombotic drug in US clinical trials (provided that the given concentrations were 20, 35, 50 µM).

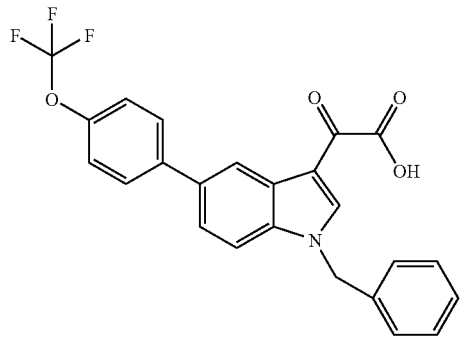

The results are shown in FIGS. 14 (A) to (C). FIGS. 14 (A), (B) and (C) each show PAI-1 activity (%) when the compound a (20, 35, 50, and 100 µM), the compound b (20, 35, 50, 100 µM), and tiplaxtinin (comparative compound) (20, 35, 50 µM), are added, respectively. The results reveal that the compounds a and b have higher PAI-1 activity inhibitory action at concentrations of 35 µM and 50 µM than tiplaxtinin (comparative compound) (PAI-1 inhibitory activity).

(2) Fibrinolytic Action Assay

The compounds a and b were evaluated for fibrinolytic action in accordance with the method disclosed in the document (Matsuo, O. et al., Haemostasis 16, 43-50 (1986)).

More specifically, an aqueous solution (25 mM barbital sodium, 50 mM NaCl, and 25 mM $CaCl_2$) containing a concentration of 1.5 mg/ml of fibrinogen (product of Organon Teknica) was added on a 9 cm-plate to thrombin (10NIH U/ml: product of Mochida Pharmaceutical Co., Ltd.) dissolved in a 0.2 ml physiological saline, and the mixture was allowed to stand for 2 hours at room temperature. Using this mixture, fibrinolysis assay was conducted.

Namely, a mixture of PAI-1, t-PA and a test compound were dropped onto the above-mentioned plate, and incubated for 18 hours at room temperature. Fibrinolysis due to the plasminogen activation was assayed in terms of the lysed area on the plate. The results demonstrate that the compounds a and b inhibit the fibrinolysis suppression caused by PAI-1.

(3) Evaluation of Effects on Bleomycin-Induced Pulmonary Fibrosis

To evaluate antifibrotic action in vivo of the compound b having PAI-1 inhibitory activity, an experiment was carried out using an animal (mouse) model with pulmonary fibrosis artificially induced by bleomycin.

A C57BL/6 mouse (male, body weight 19 to 21 g) was intraperitoneally anesthetized with pentobarbital, and an incision was made on the cervical organ. Ten mice were used as controls. The control mice (n=10) were endotracheally administered with bleomycin (product of Nippon Kayaku Co., Ltd.) (1.5 U/kg), lysed in physiological saline, twice a day for 14 days. On the other hand, the test mice were subjected to forcible oral administration with the compound b (200 mg/kg), suspended in a 0.5% carboxymethyl cellulose aqueous solution, twice a day for 14 days, in addition to the above endotracheal administration. Then, the lung tissues taken from these control mice and the test mice were analyzed, and further assayed for hydroxyproline levels. The hydroxyproline levels in the lung tissues were assayed in terms of the level in the hydrolysate of the lung tissues as described in the method of Kivirikko et al (Anal. Biochem. 19, 249-255 (1967)). Pulmonary fibrosis levels (severity) were scored from 0 to 8, based on the method of Ashcort et al (J. Clin. Pathol. 41, 467-470, (1988)). Further, the control mice and test mice were assayed for plasma PAI-1 activity (ng/ml). The results of lung tissue analysis were shown in FIG. 15 (a represents fibrosis score and b is a set of histological stain images). The hydroxyproline levels (n=10, mean±SE) and plasma PAI-1 activity (n=10, mean±SE) are shown in the following table.

| Treatment | Hydroxyproline Level in Lung Tissue (µg/lung) | Plasma PAI-1 Activity (ng/ml) |
|---|---|---|
| Control (Untreated) | 140.2 ± 4.8 | 0.8 ± 0.1 |
| Bleomycin + Vehicle (0.5% CMC) | 232.9 ± 8.5[a] | 1.7 ± 0.2[a] |
| Bleomycin + Compound b (0.5% CMC) (200 mg/kg, p.o., twice/day) | 204.2 ± 9.5[b] | 1.2 ± 0.1[b] |

[a] $P < 0.001$ vs. control by Mann Whitney U test
[b] $P < 0.05$ vs. control by Mann Whitney U test The results reveal that the hydroxyproline level in the lung tissues, notably elevated by the administration of bleomycin, significantly decreases by the administration of the compound b. The results further demonstrate that the plasma PAI-1 activity, remarkably elevated by the bleomycin administration, significantly decreases by the compound b administration.

As clearly shown in FIG. 15, pulmonary fibrosis induced by the administered bleomycin (fibrosis score: 4.7±0.17, Control group: 0.5±0.17, P<0.001) is significantly ameliorated by the administration of the compound b (fibrosis score: 2.9±0.42, P<0.01). These results agree with the results of the above PAI-1 activity.

These results suggest that the compound b and other compounds having PAI-1 inhibitory action have properties that prevent the process of pulmonary fibrosis, in addition to a fibrinolytic system promoting action. Eitzman et at. has already documented the strong correlation between collagen accumulation extent and PAI-1 expression level in the lung tissues of mice that either overexpressed or were completely deficient in murine PAI-1 gene (J. Clin. Invest. 97, 232-237 (1996)). The above results, indicating pulmonary fibrosis improvement by the compound b having strong PAI-1 inhibitory activity, suggest that PAI-1 is not a simply an indicator of pulmonary fibrosis, but is the primary factor thereof. Fibril formation occurs in many tissues and organs such as the heart, blood vessels, liver, kidneys, etc., in addition to lungs. For this reason, this finding is critical. Namely, various fibrosis-related diseases, such as heart diseases, hepatic cirrhosis, kidney diseases, and radiation injury, are thought to be prevented or treated by inhibiting PAI-1 activity.

The invention claimed is:
1. A compound represented by formula (I), or a salt or solvate thereof

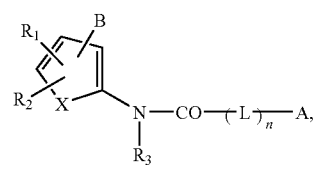

wherein
— $R_1$ and $R_2$, the same or different, each represent a hydrogen atom, halogen atom, alkyl, cycloalkyl, cycloalkylalkyl, alkenyl, cycloalkenyl, alkynyl, hydroxyl, alkoxy, cycloalkoxy, alkenyloxy, cycloalkenyloxy, aryloxy, aralkyl, aralkyloxy, heterocyclic group, heterocyclic-alkyl, or heterocyclic-alkyloxy group; or substituted or unsubstituted aryl group; or amino, carbamoyl, cyano, carboxy or alkoxycarbonyl group that may be substituted or unsubstituted with 1 to 2 substituents; and may adjoin with each other to form a ring;
— $R_3$ is a hydrogen atom; or substituted or unsubstituted alkyl, alkenyl, alkynyl, cycloalkyl, aryl or aralkyl group;
— X is a sulfur atom or —$C(R_5)$=$C(R_6)$—, wherein $R_5$ and $R_6$ each represent a hydrogen atom, halogen atom, or substituted or unsubstituted alkyl or alkoxy group;
— B is a carboxy, alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl group;
-L is substituted or unsubstituted alkylene (some carbon atoms in the alkylene may form a cycloalkyl ring), alkenylene, alkynylene, cycloalkylene, alkyleneoxyalkylene, alkylenethioalkylene, alkylene-SO-alkylene or alkylene-$SO_2$-alkylene, or alkylene-$N(R_9)$-alkylene group, wherein $R_9$ is a hydrogen atom, or a substituted or unsubstituted alkyl group;
-n is an integer of 0 or 1;
-A is —$COR_{10}$
wherein
$R_{10}$ is $N(R_{14})(R_{15})$, wherein $R_{14}$ and $R_{15}$, the same or different, each represent a hydrogen atom, a substituted or unsubstituted alkyl, alkenyl, cycloalkenyl, alkynyl, bicycloalkyl, bicycloalkenyl, adamanthyl, aryl, heterocyclic ring, aralkyl (including diphenylalkyl) or heterocyclic-alkyl group, or $R_{10}$ is a group represented by the following formula:

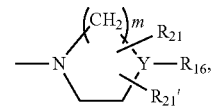

wherein m is an integer of 1 to 4, Y represents a nitrogen atom, CH, $C(R_{16}')$—, $C(OH)$— or CH—O—; $R_{16}$ and $R_{16}'$, the same or different, each represent a hydrogen atom, a substituted or unsubstituted alkyl, cycloalkyl, alkenyl, cycloalkenyl, alkynyl, bicycloalkyl, bicycloalkenyl, adamanthyl, aryl or aralkyl group (including diphenylalkyl); and $R_{21}$ and $R_{21}'$, the same or different, each represent a hydrogen atom, a substituted or unsubstituted alkyl, or phenyl group.

2. The compound according to claim 1 excluding thiophene compounds represented by formula (I'), or a salt thereof:

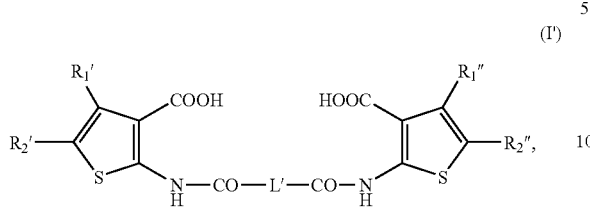

(I')

wherein $R_1'$ and $R_1''$, the same or different, each represent a hydrogen atom, substituted or unsubstituted phenyl or thienyl group, or $C_{1-6}$ straight- or branched-chain alkyl group; $R_2'$ and $R_2''$, the same or different, each represent a hydrogen atom, substituted or unsubstituted phenyl group, $C_{1-6}$ straight- or branched-chain alkyl group, or a halogen atom; $R_1'$ and $R_2'$, and $R_1''$ and $R_2''$, may join together to form a 5- or 6-membered ring; and L' represents a $C_{1-7}$ straight- or branched-chain alkylene, alkenylene or alkynylene group, or $C_{3-8}$ cycloalkylene group.

3. The compound or salt or solvate thereof according to claim 1, wherein the compound is a thiophen-3-carboxylic acid represented by formula (II), or a bioisoster thereof:

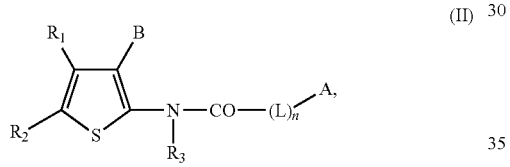

(II)

wherein $R_1$, $R_2$, $R_3$, L, B, n and A are defined as in claim 1.

4. The compound or salt or solvate thereof according to claim 1, wherein the compound is a benzoic acid represented by formula (III), or a bioisoster thereof:

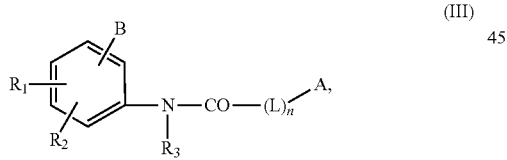

(III)

wherein $R_1$, $R_2$, $R_3$, L, B, n and A are defined as in claim 1.

5. A compound, or salt or solvate thereof, wherein the compound is selected from the group consisting of compounds (1) to (91):
(1) 2-(6-(3-(tert-butoxycarbonyl)-4-phenylthiophen-2-ylamino)-6-oxo-hexanamido)benzoic acid,
(2) 2-(6-(3-(tert-butoxycarbonyl)-4-phenylthiophen-2-ylamino)-6-oxo-hexanamido)-5-chlorobenzoic acid,
(3) 2-(6-oxo-6-(4-phenylthiophen-2-ylamino)hexanamido)benzoic acid,
(4) 2-(6-(2-carboxy-4-chlorophenylamine)-6-oxo-hexanamido)-4-phenylthiophen-3-carboxylic acid,
(5) 2-(6-oxo-6-(4-phenylpiperidin-1-yl)hexanamido)-4-phenylthiophen-3-carboxylic acid,
(6) 2-(6-(4-chlorophenylamino)-6-oxo-hexanamido)-4-phenylthiophen-3-carboxylic acid,
(7) 2,2'-(oxybis((1-oxo-2,1-ethanediyl)imino))bis(5-methyl-4-phenylthiophen-3-carboxylic acid),
(8) 2,2'-(oxybis((1-oxo-2,1-ethanediyl)imino))bis(5-phenylthiophen-3-carboxylic acid),
(9) 2,2'-(oxybis((1-oxo-2,1-ethanediyl)imino))bis(4-phenylthiophen-3-carboxylic acid),
(10) 2-(2-(2-(3-(tert-butoxycarbonyl)-5-methyl-4-phenylthiophen-2-ylamino)-2-oxoethoxy)acetamido)-5-methyl-4-phenylthiophen-3-carboxylic acid,
(11) 2-(6-(3-(tert-butoxycarbonyl)-4-isopropylthiophen-2-ylamino)-6-oxo-hexanamido)benzoic acid,
(12) 2-(6-(4-isopropylthiophen-2-ylamino)-6-oxo-hexanamido)benzoic acid,
(13) 2-(2-(2-(4-benzhydryl piperazin-1-yl)-2-oxoethoxy)acetamido)-5-methyl-4-(pyridin-4-yl)thiophen-3-carboxylic acid,
(14) 2-(2-(2-(4-benzhydryl piperazin-1-yl)-2-oxoethoxy)acetamido)-5-methyl-4-(pyridin-3-yl)thiophen-3-carboxylic acid,
(15) 2-(2-(2-(4-benzhydryl piperazin-1-yl)-2-oxoethoxy)acetamido)-5-methyl-4-phenylthiophen-3-carboxylic acid,
(16) 2-(2-(benzyloxycarbonylamino)-5-(4-chlorophenylamino)-5-oxopentanamido)-5-chlorobenzoic acid,
(17) 2-(2-(benzyloxycarbonylamino)-5-((4-chlorophenyl)(methyl)amino)-5-oxopentanamido)-5-chlorobenzoic acid,
(18) 2-(2-(benzyloxycarbonylamino)-5-oxo-5-(4-phenylpiperazin-1-yl)pentanamido)-5-chlorobenzoic acid,
(19) 2-(5-(4-benzhydryl piperazin-1-yl)-2-(benzyloxycarbonylamino)-5-oxopentanamido)-5-chlorobenzoic acid,
(20) 2-(5-(4-benzhydryl piperazin-1-yl)-4-(benzyloxycarbonylamino)-5-oxopentanamido)-5-chlorobenzoic acid,
(21) 2-(5-(4-benzhydryl piperazin-1-yl)-2-(tert-butoxycarbonylamino)-5-oxopentanamido)-5-chlorobenzoic acid,
(22) 2-(2-amino-5-(4-benzhydryl piperazin-1-yl)-5-oxopentanamido)-5-chlorobenzoic acid,
(23) 5-chloro-2-(2-((2-(4-chlorophenylamino)-2-oxoethyl)(methyl)amino)acetamido)benzoic acid,
(24) 2-(2-((2-(4-benzhydryl piperazine-1-yl)-2-oxoethyl)(methyl)amino)acetamido)-5-chlorobenzoic acid,
(25) 5-chloro-2-(6-(4-chlorophenylamin)-6-oxo-hexanamido)benzoic acid,
(26) 2-(2-(2-(4-benzhydryl piperazin-1-yl)-2-oxoethoxy)acetamido)-5-methoxybenzoic acid,
(27) 5-chloro-2-(2-(2-(4-(4-chlorophenyl)piperazin-1-yl)-2-oxoethoxy)acetamido)benzoic acid,
(28) 2-(2-(2-(4-benzhydryl piperazin-1-yl)-2-oxoethoxy)acetamido)-5-chlorobenzoic acid,
(29) 2-(2-(2-(4-benzhydryloxy)piperidin-1-yl)-2-oxoethoxy)acetamido-5-chlorobenzoic acid,
(30) 5-chloro-2-(2-(2-(4,4-diphenylpiperidin-1-yl)-2-oxoethoxy)acetamido)benzoic acid,
(31) 2-(2-(2-(4-chloro-2-(methoxycarbonyl)phenylamino)-2-oxoethoxy)acetamido)-5-methyl-4-phenylthiophen-3-carboxylic acid,
(32) 2-(2-(2-(4-(bis(4-fluorophenyl)methyl)piperazin-1-yl)-2-oxoethoxy)acetamido)-5-chlorobenzoic acid,
(33) 2-(2-(2-(1-adamantylamino)-2-oxoethoxy)acetamido)-5-chlorobenzoic acid,
(34) 2-(2-(2-(4-(9H-fluoren-9-yl)piperazin-1-yl)-2-oxoethoxy)acetamido)-5-chlorobenzoic acid,
(35) 2-(2-(2-(benzhydrylamino)-2-oxoethoxy)acetamido)-5-chlorobenzoic acid,

(36) 2-(2-(2-(3-(tert-butoxycarbonyl)-5-methyl-4-phenylthiophen-2-ylamino)-2-oxoethoxy)acetamido)-5-chlorobenzoic acid,
(37) 5-chloro-2-(2-(2-(4-chlorophenylamino)-2-oxoethoxy)acetamido)benzoic acid,
(38) 2-(2-(2-(2-benzoyl-4-chlorophenylamino)-2-oxoethoxy)acetamido)-5-chlorobenzoic acid,
(39) 2-(2-(2-(4-benzhydryl piperazin-1-yl)-2-oxoethoxy)acetamido)-5-fluorobenzoic acid,
(40) 3-(2-(2-(4-benzhydryl piperazin-1-yl)-2-oxoethoxy)acetamido)benzoic acid,
(41) 4-(2-(2-(4-benzhydryl piperazin-1-yl)-2-oxoethoxy)acetamido)-3-chlorobenzoic acid,
(42) 4-(2-(2-(4-benzhydryl piperazin-1-yl)-2-oxoethoxy)acetamido)-4'-fluorobiphenyl-3-carboxylic acid,
(43) 4-(2-(2-(4-benzhydryl piperazin-1-yl)-2-oxoethoxy)acetamido)-2',4'-difluorobiphenyl-3-carboxylic acid,
(44) 4-(2-(2-(4-benzhydryl piperazin-1-yl)-2-oxoethoxy)acetamido)-4'-cyano biphenyl-3-carboxylic acid,
(45) 4-(2-(2-(4-benzhydryl piperazin-1-yl)-2-oxoethoxy)acetamido)-4'-(dimethylamino)biphenyl-3-carboxylic acid,
(46) 4-(2-(2-(4-benzhydryl piperazin-1-yl)-2-oxoethoxy)acetamido)-4'-methoxybiphenyl-3-carboxylic acid,
(47) 4-(2-(2-(4-benzhydryl piperazin-1-yl)-2-oxoethoxy)acetamido)-4'-morpholinobiphenyl-3-carboxylic acid,
(48) 2-(2-(2-(4-benzhydryl piperazin-1-yl)-2-oxoethoxy)acetamido)-5-(pyridine-4-yl)benzoic acid,
(49) 2-(2(2-(4-benzhydryl piperazin-1-yl)-2-oxoethoxy)acetamido)-5-bromobenzoic acid,
(50) 2-(2-(2-benzhydrylamino)-2-oxoethoxy)acetamido-5-(pyridine-4-yl)benzoic acid,
(51) 2-(2-(2-(4-benzhydryl piperazin-1-yl)-2-oxoethoxy)acetamido)-5-(pyridin-3-yl)benzoic acid,
(52) 2-(2-(2-(4-benzhydryl piperazin-1-yl)-2-oxoethoxy)acetamido)-5-(pyridine-4-yl)benzoic acid,
(53) 2-(2-(2-(4-benzhydryl piperazin-1-yl)-2-oxoethoxy)acetamido)-5-(1-methyl-1H-pyrazol-4-yl)benzoic acid,
(54) 2-(2-(2-(4-benzhydryl piperazin-1-yl)-2-oxoethoxy)acetamido)-5-benzylbenzoic acid,
(55) 4-(2-(2-(4-benzhydryl piperazin-1-yl)-2-oxoethoxy)acetamido)biphenyl-3-carboxylic acid,
(56) 4-(2-(2-(4-chlorophenylamino)-2-oxoethoxy)acetamido) biphenyl-3-carboxylic acid,
(57) 2,2'-(oxybis((1-oxo-2,1-ethanediyl)imino))bis(5-phenylbenzen-1-carboxylic acid),
(58) 2-(2-(2-(4-benzhydrylpiperazin-1-yl)-2-oxoethoxy)acetamido)-5-isobutyl benzoic acid,
(59) 2-(2-(2-(4-benzhydrylpiperazin-1-yl)-2-oxoethoxy)acetamido)-5-(1H-pirazol-4-yl)benzoic acid,
(60) 2-(2-(2-(4-benzhydrylpiperazin-1-yl)-2-oxoethoxy)acetamido)-5-(quinolin-3-yl)benzoic acid,
(61) 2-(2-(2-(4-benzhydrylpiperazin-1-yl)-2-oxoethoxy)acetamido)-5-(benzo[b]thiophen-2-yl)benzoic acid,
(62) 4-(2-(2-(benzhydrylamino)-2-oxoethoxy)acetamido)-4'-fluorobiphenyl-3-carboxylic acid,
(63) 5-chloro-2-(2-(2-(2,6-diisopropylphenylamino)-2-oxoethoxy)acetamido)benzoic acid,
(64) 5-chloro-2-(2-(2-(1-(naphthalen-1-yl)ethylamino)-2-oxoethoxy)acetamido)benzoic acid,
(65) 5-chloro-2-(2-(2-(5-isopropyl-2-methylphenylamino)-2-oxoethoxy)acetamido)benzoic acid,
(66) 5-chloro-2-(2-(2-(2-oxo-2-(4-phenylbutylamino)ethoxy)acetamido)benzoic acid,
(67) 2-(2-(2-(bis(4-fluorophenyl)methyl)amino-2-oxoethoxy)acetamido)-5-chlorobenzoic acid,
(68) 2-(2-(2-(bis(4-(trifluoromethyl)benzyl)amino)-2-oxoethoxy)acetamido)-5-chlorobenzoic acid,
(69) 2-(2-(2-(bis(4-fluorobenzyl)amino)-2-oxoethoxy)acetamido)-5-chlorobenzoic acid,
(70) 2-(2-(2-(3,5-bis(trifluoromethyl)phenylamino)-2-oxoethoxy)acetamido)-5-chlorobenzoic acid,
(71) 2-(2-(2-(4-benzhydrylpiperazin-1-yl)-2-oxoethoxy)acetamido)-4-chlorobenzoic acid,
(72) 2-(2-(2-(4-benzhydrylpiperazin-1-yl)-2-oxoethoxy)acetamido)-4-bromobenzoic acid,
(73) 2-(2-(2-(4-benzhydrylpiperazin-1-yl)-2-oxoethoxy)acetamido)-4-(pyridin-4-yl)benzoic acid,
(74) 3-(2-(2-(4-benzhydrylpiperazin-1-yl)-2-oxoethoxy)acetamido)-4'-fluorobiphenyl-4-carboxylic acid,
(75) 2-(2-(benzhydrylamino)-2-oxoacetamido)-5-chlorobenzoic acid,
(76) 2-(5-(4-benzhydrylpiperazin-1-yl)-5-oxopentanamido)-5-chlorobenzoic acid,
(77) 2-(2-(2-(4-benzhydrylpiperazin-1-yl)-2-oxoethoxy)acetamido)-5-(2,4-dimethylthiazol-5-yl)benzoic acid,
(78) 2-(2-(2-(benzhydrylamino)-2-oxoethoxy)acetamido)-5-methyl-4-phenylthiophen-3-carboxylic acid,
(79) 5-chloro-2-(2-(2-(diphenylamino)-2-oxoethoxy)acetamido)benzoic acid,
(80) 5-chloro-2-(2-(2-(2,2-diphenylethylamino)-2-oxoethoxy)acetamido)benzoic acid,
(81) 2-(2-(2-((3S*,5R*)-4-benzhydryl-3,5-dimethylpiperazin-1-yl)-2-oxoethoxy)acetamido)-5-chlorobenzoic acid,
(82) 2-(2-(2-(4-benzhydrylpiperazin-1-yl)-2-oxoethoxy)acetamido)-5-(benzyloxy)benzoic acid,
(83) 2-(2-(2-(4-benzhydrylpiperazin-1-yl)-2-oxoethoxy)acetamido)-5-isobutoxybenzoic acid,
(84) 2-(2-(4-benzhydrylpiperazin-1-yl)-2-oxoethoxy)-N-(4-chloro-2-(1H-tetrazol-5-yl)phenyl)acetamide,
(85) 2-(2-(4-benzhydrylpiperazin-1-yl)-2-oxoethoxy)-N-(4-chloro-2-(5-oxo-4,5-dihydro-1,2,4-oxadiazol-3-yl)phenyl)acetamide,
(86) 2-(2-(4-benzhydrylpiperazin-1-yl)-2-oxoethoxy)-N-(5-methyl-4-phenyl-3-(1H-tetrazol-5-yl)thiophen-2-yl)acetamide,
(87) 2-(2-((2-(benzhydrylamino)-2-oxoethyl)(methyl)amino)acetamido)-5-chlorobenzoic acid,
(88) 2-(2-(2-(4-benzhydrylpiperazin-1-yl)-2-oxoethylthio)acetamido)-5-chlorobenzoic acid,
(89) 2-(2-(1-(2-(4-benzhydrylpiperazin-1-yl)-2-oxyethyl)cyclohexyl)acetamido)-5-chlorobenzoic acid,
(90) 2-((1S*,2S*)-2-(4-benzhydrylpiperazine-1-carbonyl)cyclohexanecarboxamido)-5-chlorobenzoic acid, and
(91) 2-((1S*,2R*)-2-(4-benzhydrylpiperazine-1-carbonyl)cyclohexanecarboxamido)-5-chlorobenzoic acid.

6. A method for producing an aromatic or heterocyclic carboxylic acid represented by formula (Ic), comprising the following steps (c), (d) and (x):
(c) a step of reacting the compound (1) and an intramolecular anhydride of dicarboxylic acid (5) to form an ester carboxylic acid compound (6a), represented by the formulae below,
(d) a step of reacting the ester carboxylic acid (6a) formed in the above step (c) and a compound (7) to form an ester compound (4c), and
(x) a step of removing the $R_{17}$ group from the ester compound (4c) formed in the above step (d) to produce an aromatic or heterocyclic carboxylic acid (Ic);

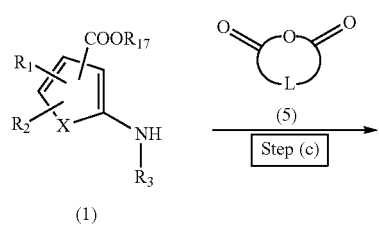

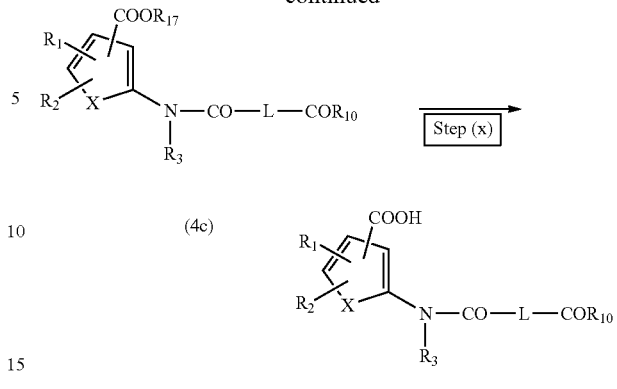

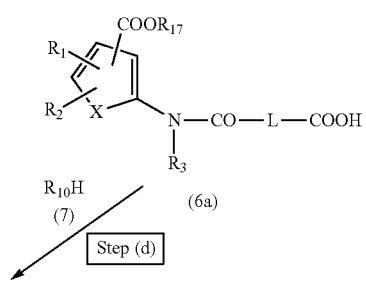

wherein $R_1$, $R_2$, $R_3$, $R_{10}$, L and X are defined as in claim 1, and $R_{17}$ is alkyl, aryl or aralkyl.

7. A pharmaceutical composition comprising a compound, or a salt or solvate thereof, according to any one of claims 1 to 5, and a pharmaceutically acceptable carrier or additive.

8. The pharmaceutical composition according to claim 7, the composition being in a form for oral administration.

\* \* \* \* \*